(12) United States Patent
Wood et al.

(10) Patent No.: US 7,728,118 B2
(45) Date of Patent: Jun. 1, 2010

(54) SYNTHETIC NUCLEIC ACID MOLECULE COMPOSITIONS AND METHODS OF PREPARATION

(75) Inventors: Keith V. Wood, Mt. Horeb, WI (US);
Monika G. Wood, Mt. Horeb, WI (US);
Brian Almond, Fitchburg, WI (US);
Aileen Paguio, Madison, WI (US);
Frank Fan, Madison, WI (US)

(73) Assignee: Promega Corporation, Madison, WI (US)

( * ) Notice: Subject to any disclaimer, the term of this patent is extended or adjusted under 35 U.S.C. 154(b) by 538 days.

(21) Appl. No.: 10/943,508

(22) Filed: Sep. 17, 2004

(65) Prior Publication Data

US 2006/0068395 A1 Mar. 30, 2006

(51) Int. Cl.
*C07H 21/02* (2006.01)
*C07H 21/04* (2006.01)
*C12N 15/00* (2006.01)
*C12Q 1/68* (2006.01)
*C12P 19/34* (2006.01)

(52) U.S. Cl. .................. 536/23.1; 536/23.2; 536/23.4; 536/23.7; 435/320.1

(58) Field of Classification Search .............. None
See application file for complete search history.

(56) References Cited

U.S. PATENT DOCUMENTS

| | | | |
|---|---|---|---|
| 4,412,001 A | 10/1983 | Baldwin et al. |
| 4,503,142 A | 3/1985 | Berman et al. |
| 4,581,335 A | 4/1986 | Baldwin |
| 4,968,613 A | 11/1990 | Masuda et al. |
| 5,096,825 A | 3/1992 | Barr et al. |
| 5,168,062 A | 12/1992 | Stinski |
| 5,182,202 A | 1/1993 | Kajiyama et al. |
| 5,196,524 A | 3/1993 | Gustafson et al. |
| 5,219,737 A | 6/1993 | Kajiyama et al. |
| 5,221,623 A | 6/1993 | Legocki et al. |
| 5,229,285 A | 7/1993 | Kajiyama et al. |
| 5,283,179 A | 2/1994 | Wood |
| 5,292,658 A | 3/1994 | Cormier et al. |
| 5,330,906 A | 7/1994 | Kajiyama et al. |
| 5,352,598 A | 10/1994 | Kajiyama et al. |
| 5,418,155 A | 5/1995 | Cormier et al. |
| 5,567,862 A | 10/1996 | Adang et al. |
| 5,583,024 A | 12/1996 | McElroy et al. |
| 5,604,123 A | 2/1997 | Kazami et al. |
| 5,641,641 A | 6/1997 | Wood |
| 5,650,289 A | 7/1997 | Wood |
| 5,670,356 A | 9/1997 | Sherf et al. |
| 5,674,713 A | 10/1997 | McElroy et al. |
| 5,700,673 A | 12/1997 | McElroy et al. |
| 5,744,320 A | 4/1998 | Sherf et al. |
| 5,786,464 A | 7/1998 | Seed |
| 5,795,737 A | 8/1998 | Seed et al. |
| 5,814,471 A | 9/1998 | Wood |
| 5,874,304 A | 2/1999 | Zolotukhin et al. |
| 5,952,547 A | 9/1999 | Cornelissen et al. |
| 5,968,750 A | 10/1999 | Zolotukhin et al. |
| 5,976,796 A | 11/1999 | Szalay et al. |
| 6,020,192 A | 2/2000 | Muzyczka et al. |
| 6,074,859 A | 6/2000 | Hirokawa et al. |
| 6,114,148 A | 9/2000 | Seed et al. |
| 6,130,313 A | 10/2000 | Li et al. |
| 6,169,232 B1 | 1/2001 | Hey et al. |
| 6,306,600 B1 | 10/2001 | Kain et al. |
| 6,602,677 B1 | 8/2003 | Wood et al. |
| 6,700,038 B1 | 3/2004 | Dasgputa et al. |
| 6,878,531 B1 * | 4/2005 | Seyfang ............... 435/91.2 |
| 2002/0100076 A1 | 7/2002 | Garcon et al. |
| 2003/0157643 A1 | 8/2003 | Almond et al. |
| 2006/0127988 A1 | 6/2006 | Wood et al. |
| 2008/0070299 A1 | 3/2008 | Wood et al. |
| 2008/0090291 A1 | 4/2008 | Wood et al. |
| 2009/0191622 A1 | 7/2009 | Almond et al. |

FOREIGN PATENT DOCUMENTS

| | | |
|---|---|---|
| EP | 0337349 A2 | 10/1989 |
| EP | 0364707 A1 | 4/1990 |
| EP | 0524448 A1 | 1/1993 |
| EP | 0353464 B1 | 10/1993 |
| JP | 08-510837 | 11/1996 |
| JP | 2000-503536 | 3/2000 |
| WO | WO-90/01542 A1 | 2/1990 |
| WO | WO-91/16432 A1 | 10/1991 |
| WO | WO-92/15673 A1 | 9/1992 |
| WO | WO-95/18853 A1 | 7/1995 |
| WO | WO-9518853 A1 | 7/1995 |

(Continued)

OTHER PUBLICATIONS

GenBank Accession No. AF081957.1, "Synthetic construct aminoglycoside 3'-phosphotransferase mutant (mNeo) gene, complete cds", Aug. 1999.*
GenBank Accession No. U19276.1, "Cloning vector pGFP-1 green fluorescent protein, complete cds", Jul. 1995.*
CloneTech Catalog, p. 96 (1996/97).*
CloneTech document PT2038-5, p. 1-2 (1996/97).*
GenBank Accession No. AAD50549, "Aminoglycoside 3'-phosphotransferase mutant [synthetic construct]." Aug. 1999.*
GenBank Accession No. AAA69543, "Neomycin phosphotransferase" Jul. 1995.*
Wells, K.D. et al., "Codon optimization, genetic insulation, and an rtTA reporter improve performance of the tetracycline swittch", Transgenic Research, vol. 8, p. 371-381 (1999).*
Shim, J. et al., "Canonical 3'-deoxyribonucleotides as a chain terminator for HCV NS5B RNA-dependent RNA polymerase", Antiviral Research, vol. 58, pp. 243-251 (May 2003).*

(Continued)

*Primary Examiner*—Teresa E Strzelecka
(74) *Attorney, Agent, or Firm*—Michael Best & Friedrich LLP

(57) ABSTRACT

A method to prepare synthetic nucleic acid molecules having reduced inappropriate or unintended transcriptional characteristics when expressed in a particular host cell.

36 Claims, 2 Drawing Sheets

FOREIGN PATENT DOCUMENTS

| WO | WO-95/25798 A1 | 9/1995 |
|---|---|---|
| WO | WO-96/22376 A1 | 7/1996 |
| WO | WO-97/08320 A1 | 3/1997 |
| WO | WO-97/26333 A1 | 7/1997 |
| WO | WO-97/26366 A1 | 7/1997 |
| WO | WO-97/47358 A1 | 12/1997 |
| WO | WO-99/14336 A2 | 3/1999 |
| WO | WO-01/23541 A2 | 4/2001 |
| WO | WO-01/27150 A2 | 4/2001 |
| WO | WO-02/16944 A2 | 2/2002 |
| WO | WO-02016944 A2 | 2/2002 |
| WO | WO-02090535 A1 | 11/2002 |
| WO | WO-2004/025264 A2 | 3/2004 |
| WO | WO-2004/042010 A2 | 5/2004 |
| WO | WO-2006/034061 A2 | 3/2006 |

OTHER PUBLICATIONS

BIOBASE, www.gene-regulation.com/pub/databases/html; printed Jul. 31, 2007.*
Leclerc, G.M., Biotechniques, vol. 29, pp. 590, 591, 594, 596, 598, 600, 601 (2000).*
"Cloning Vector pGL3—Control", *NCBI Sequence Accession No. U47296*, 4 pgs.
"Cloning Vector psiSTRIKE Puromycin, Complete Sequence", *NCBI Sequence Accession No. AY497507*, 3 pgs.
"Sequence of pcdna3.1/Hygro", http://www.invitrogen.com/content/sfs/vectors/pcdna3.1hygro_seq.txt, 2 pgs.
"Sequence 1 from Patent WO9529245", *NCBI Sequence Accession No. A47120*, 2 pgs.
Aota, S., "Codon Usage Tabulated from the GenBank Genetic Sequence Data", *Nucleic Acids Research, 16 (Supplement)*, (1988), r315-r402.
Bachmair, A., "In vivo Half-Life of a Protein is a Function of its Amino Terminal Residue", *Science*, 234(4773), (1986), 179-186.
Batt, D. B., "Polyadenylation and Transcription Termination in Gene Constructs Containing Multiple Tandem Polyadenylation Signals", *Nucleic Acids Research*, 22(14), (Jul. 15, 1994), 2811-2816.
Benzakour, O., "Evaluation of the Use of the Luciferase-Reporter-Gene System for Gene-Regulation Studies Involving Cyclic AMP-Elevating Agents", *The Biochemical Journal*, 309 (Pt 2), (1995), 385-387.
Bernardi, G., "Codon Usage and Genome Composition", *Journal of Moleular Biology*, 22(4), (1985),363-365.
Bonin, A. L., "*Photinus pyralis* luciferase: Vectors that Contain a Modified *luc* Coding Sequence Allowing Convenient Transfer into Other Systems", *Gene*, 141(1), (1994),75-77.
Bronstein, I., "Chemiluminescent and Bioluminescent Reporter Gene Assays", *Analytical Biochemistry* 219(2), (1994), 169-181.
Bulmer, M , "Codon Usage and Secondary Structure of MS2 Phage RNA", *Nucleic Acids Res.*, 17(5), (1989), 1839-1843.
Bulmer, M , "Coevolution of Codon Usage and Transfer RNA Abundance", *Nature*, 325(6106), (1987), 728-730.
Chen, H., "Gene Transfer and Expression in Oligodendrocytes Under the Control of Myelin Basic Protein Transcriptional Control Region Mediated by Adeno-Associated Virus", *Gene Therapy*, 5(1), (1998), 50-58.
Coker, G T., "8-Br-cAMP Inhibits the Transient Expression of Firefly Luciferase", *FEBS Letters*, 249, (1989), 183-185.
De Wet, J. R., "Cloning of Firefly Luciferase cDNA and the Expression of Active Luciferase in *Escherichia coli*", *Proc. Natl. Acad. Sci. USA*, 82(23), (1985), 7870-7873.
De Wet, J. R., "Firefly Luciferase Gene: Structure and Expression in Mammalian Cells", *Molecular and Cellular Biology*, 7(2), (1987), 725-737.
Dean, C., "mRNA Transcripts of Several Plant Genes are Polyadenylated at Multiple Sites in vivo", *Nucleic Acids Research*, vol. 14(5), (1986), 2229-2240.
Dementieva, E. I., "Physicochemical Properties of Recombinant *Luciola mingrelica* Luciferase and its Mutant Forms", *Biochemistry*, 61(1), (1996), 115-119.

Faisst, S., "Compilation of Vertebrate-Encoded Transcription Factors", *Nucleic Acids Research*, 20(1), (Jan. 11, 1992), 3-26.
Ferbitz, L., "A Synthetic Gene Coding for Renilla luciferase is a versatile expression marker in green algae", *NCBI Sequence Accession No. AAF93166* (Aug. 8, 2000), 1 pg.
Fiers, W , "On Codon Usage (letter)", *Nature*, 277(5694), (1979), 328.
Fleer, R., "High-Level Secretion of Correctly Processed Recombinant Human Interleukin-1β in *Kluyveromyces lactis*", *Gene*, 107(2), (1991), 285-295.
Fuerst, T. R., "Structure and Stability of mRNA Synthesized by Vaccinia Virus-Encoded Bacteriophage T7 RNA Polymerase in Mammalian Cells—Importance of the 5' untranslated leader", *Journal of Molecular Biology*, 206, (1989), 333-348.
Gould, S. J., "A Conserved Tripeptide Sorts Proteins to Peroxisomes", *The Journal of Cell Biology*, 108(5), (1989), 1657-1664.
Gould, S. J., "Antibodies Directed Against the Peroxisomal Targeting Signal of Firefly Luciferase Recognize Multiple Mammalian Peroxisomal Proteins", *The Journal of Cell Biology*, 110(1), (1990), 27-34.
Gould, S. J., "Identification and Characterization of a Peroxisomal Targeting Signal", *Dissertation Abstracts International*, vol. 50/07-B, (1989), 2766, 2 pgs.
Gouy, M., "Codon Usage in Bacteria: Correlation With Gene Expressivity", *Nucleic Acids Research*, 10(22), (1982),7055-7074.
Green, Pamela J., "Control of mRNA Stability in Higher Plants", *Plant Physiology*, 102(4), (1993),1065-1070.
Gruber, M G., "Design Strategy for Synthetic Luciferase Reporter Genes", (Abstract Only), *11th International Symposium on Bioluminescence and Chemiluminescence*, (May 2000), 1 pg.
Henning, K. A., "Humanizing the yeast telomerase template", *Proceedings of the National Academy of Sciences of USA*, 95(10), (May 12, 1998), 5667-5671.
Holm, L , "Codon Usage and Gene Expression", *Nucleic Acids Research*, 14(7), (1986),3075-3087.
Iannacone, R., "Specific Sequence Modifications of a *cry*3B Endotoxin Gene Result in High Levels of Expression and Insect Resistance", *Plant Molecular Biology* 34, (1997), 485-496.
Ikemura, T., "Codon Usage and tRNA Content in Unicellular and Multicellular Organisms", *Molecular Biology and Evolution*, 2(1), (1985), 13-34.
Johnson, L. R., "Role of the Transcription Factor Sox-2 in the Expression of the FGF-4 Gene in Embryonal Carcinoma Cells", *Molecular Reproduction and Development.*, 50(4), (1998), 377-386.
Jones, P L., "Tumor Necrosis Factor Alpha and linterleukin-1β Regulate the Murine Manganese Superoxide Dismutase Gene Through a Complex Intronic Enhancer Involving C/EBP-β and NF-κB", *Molecular and Cellular Biology*, 17(12), (1997), 6970-6981.
Keller, G.-A. , "Firefly Luciferase is Targeted to Peroxisomes in Mammalian Cells", *Proc. Natl. Acad. Sci. USA*, 84(10), (1987), 3264-3268.
Kim, C. H., "Codon Optimization for High-Level Expression of Human Erythropoietin (EPO) in Mammalian Cells", *Gene*, 199( 1-2), (1997), 293-301.
Kuprash, D V., "Conserved κB Element Located Downstream of the Tumor Necrosis Factor α Gene: Distinct NF-κB Binding Pattern and Enhancer Activity in LPS Activated Murine Macrophages", *Oncogene*, 11(1), (1995), 97-106.
Lamb, K. A., "Effects of Differentiation on the Transcriptional Regulation of the FGF-4 Gene: Critical Roles Played by a Distal Enhancer", *Molecular Reproduction and Development*, 51(2), (1998), 218-224.
Liljenström, H., "Translation Rate Modification by Preferential Codon Usage: Intragenic Position Effects", *Journal of Theoretical Biology*, 124(1), (1987), 43-55.
Liu, J., "Improved Assay Sensitivity of an Engineered Secreted *Renilla* Luciferase", *Gene*, 237(1), (1999), 153-159.
Magari, S. R., "Pharmacologic Control of a Humanized Gene Therapy System Implanted into Nude Mice", *Journal of Clinical Investigation*, 100(11), (1997), 2865-2872.
Malter, J. S., "Identification of an AUUUA-Specific Messenger RNA Binding Protein", *Science*, 246(4930), (1989), 664-666.

Murray, E. E., "Codon Usage in Plant Genes", *Nucleic Acids Research*, 17(2), (Jan. 25, 1989), 477-498.

Nibu, Y., "A Cell Type-Dependent Enhancer Core Element is Located in Exon 5 of the Human Angiotensinogen Gene", *Biochemical and Biophysical Research Communications*, 205(2), (1994), 1102-1108.

Pan, W., "Vaccine Candidate MSP-1 from *Plasmodium falciparum*:: a Redesigned 4917 bp Polynucleotide Enables Synthesis and Isolation of Full-Length Protein from *Escherichia coli* and Mammalian Cells", *Nucleic Acids Research*, 27(4) (1999),1094-1103.

Peers, B , "Regulatory Elements Controlling Pituitary-Specific Expression of the Human Prolactin Gene", *Molecular and Cellular Biology*, 10(9), (Sep. 1990),4690-4700.

Perlak, Frederick J., "Modification of the coding sequence enhances plant expression of insect control protein genes", *Proc. Natl. Acad. Sci.USA*, 88(8), (1991), 3324-3328.

Reese, M. G., "Large Scale Sequencing Specific Neural Networks for Promoter and Splice Site Recognition", (Abstract Only), *Biocomputing: Proceedings of the 1996 Pacific Symposium*, Lawrence Hunter et al., ed., World Publishing Co., Singapore, (1996), 1 pg.

Reese, M. G., et al., "New Neural Network Algorithms for Improved Eukaryotic Promoter Site Recognition", *The Seventh International Genome Sequencing and Analysis Conference*, Hilton Head Island, South Carolina, (Abstract Only),(1995), 1 pg.

Robinson, M , "Codon Usage Can Affect Efficiency of Translation of Genes in *Escherichia colii*", *Nucleic Acids Res.*, 12(17), (1984),6663-6671.

Saisanit, S., "A Novel Enhancer, the Pro-B Enhancer, Regulates Id1 Gene Expression in Progenitor B Cells", *Mol. Cell. Biol.*, 15(3), (1995), 1513-1521.

Sala-Newby, G., "Engineering a Bioluminescent Indicator for Cyclic AMP-Dependent Protein Kinase", *The Biochemical Journal*, 279(Part 3), (1991), 727-732.

Sala-Newby, G., "Engineering Firefly Luciferase as an Indicator of Cyclic AMP-Dependent Protein Kinase in Living Cells", *FEBS Letters*, 307 (2), (Jul. 1992),pp. 241-244.

Sala-Newby, G. B., "Stepwise Removal of the C-Terminal 12 Amino Acids of Firefly Luciferase Results in Graded Loss of Activity", *Biochimica et Biophysica Acta (BBA)—Protein Structure and Molecular Enzymology*, 1206, (1994), 155-160.

Schatt, M D., "A Single DNA-Binding Transcription Factor is Sufficient for Activation From a Distant Enhancer and/or From a Promoter Position", *The EMBO Journal*, 9(2), (1990), 481-487.

Sharp, P M., "Codon usage patterns in *Escherichia coli, Bacillus subtilis, Saccharomyces cerevisiae, Schizosaccharomyces pombe, Drosophila melanogaster* and *Homo sapiens*; a Review of the Considerable Within-Species Diversity", *Nucleic Acids Research*, 16(17), (Sep. 12, 1988),8207-8211.

Sharp, P M., "The Codon Adaptation Index—A Measure of Directional Synonymous Codon Usage Bias, and Its Potential Applications", *Nucleic Acids Research*, 15(3), (1987), 1281-95.

Shaw, G., "A Conserved AU Sequence from the 3' Untranslated Region of GM-CSF mRNA Mediates Selective mRNA Degradation", *Cell*, 46(5), (1986), 659-667.

Sherf, B A., "Firefly Luciferase Engineered for Improved Genetic Reporting", *Promega Notes Magazine*, No. 14,(1994), 8 pgs.

Simpson, C. G., "Efficient Splicing of an AU-Rich Antisense Intron Sequence", *Plant Molecular Biology*, 21(2), (1993), 205-211.

Sommer, J. M., "In vivo Import of Firefly Luciferase into the Glycosomes of *Trypanosoma brucei* and Mutational Analysis of the C-Terminal Targeting Signal", *Molecular Biology of the Cell*, 3(7), (1992), 749-759.

Sørensen, M A., "Codon Usage Determines Translation Rate in *Escherichia coli*", *Journal of Molecular Biology*, 207(2), (1989), 365-377.

Tanaka, M , "Synonymous Codon Usage and Cost of Genetic Information", *Bulletin of the Osaka Medical College*, 34(1-2), (1988), 3-12.

Ticher, A , "Nucleic acid Compositions, Codon Usage, and the Rate of Synonymous Substitution in Protein-Coding Genes", *Journal of Molecular Evolution*, 28(4), (1989), 286-298.

Türkel, S , "GCR-1-Dependent Transcriptional Activation of Yeast Retrotransposon Ty2-917", *Yeast*, 13(10), (1997), 917-930.

Van Aarssen, R., "*CTY* IA(b) Transcript Formation in Tobacco is Inefficient", *Plant Molecular Biology*, 28(3), (1995), 513-524.

Viviani, V. R., "Bioluminescence Color Determinants of *Phrixothrix* Railroad-Worm Luciferases: Chimeric Luciferases, Site-Directed Mutagenesis of Arg 215 and Guanidine Effect", *Photochemistry and Photobiology*, 72(2), (2000), 267-271.

Wada, K., "Codon Usage Tabulated from GenBank Genetic Sequence Data", *Nucleic Acids Research*, 18 (Suppl), (1990), 2367-2411.

Wain-Hobson, S., "Preferential Codon Usage in Genes", *Gene*, 13(4), (1981),355-364.

Wilson, T., "Removal of poly(A) and Consequence Degradation of c-*fos* mRNA Facilitated by 3' AU-Rich Sequences", *Nature*, vol. 336, (1988), 396-399.

Wood, K. V., "Bioluminescent Click Beetles Revisited", *Journal of Bioluminescence and Chemiluminescence*, 4(1), (1989), 31-39.

Wood, K. V., "Complementary DNA Coding Click Beetle Luciferases can Elicit Bioluminescence of Different Colors", *Science*, 244(4905), (1989), 700-702.

Wood, K. V., "Introduction to Beetle Luciferases and Their Applications", *Journal of Bioluminescence and Chemiluminescence*, 4(1), (1989), 289-301.

Wood, K V., "*Luc* Genes: Introduction of Colour Into Bioluminescence Assays", *Journal of Bioluminescence and Chemiluminescence*, 5(2), (1990), 107-114.

Wood, K. V., "Photographic Detection of Luminescence in *Escherichia coli* Containing the Gene for Firefly Luciferase", *Analytical Biochemistry*, 161(2), (1987), 501-507.

Wood, K. V., "The Chemical Mechanism and Evolutionary Development of Beetle Bioluminescence", *Photochemistry and Photobiology*, 62, (1995), 662-673.

Yanai, K , "A *cis*-acting DNA Element Located Between TATA Box and Transcription Initiation Site is Critical in Response to Regulatory Sequences in Human Angiotensinogen Gene", *The Journal of Biological Chemistry*, 271(27), (1996), 15981-15986.

Yang, J K., "Human Dihydrofolate Reductase Gene Organization. Extensive Conservation of the G + C-rich 5' Non-Coding Sequence and Strong Intron Size Divergence from Homologous Mammalian Genes", *Journal of Molecular Biology*, 176(2), (1984), 169-187.

"Partial International Search Report for corresponding PCT Application No. PCT/US2005/033218", Jan. 12, 2006, 1 pg.

"International Search Report for corresponding PCT Application No. PCT/US2005/033218", (Mar. 31, 2006), 9 pgs.

Groskreutz, D. J., et al., "Cloning Vector pGL3-Basic, Complete sequence", *Database EMBL Online*, (Accession No. EMBL:U47295),(Mar. 1, 1996), 3 pgs.

Zhuang, Y. , et al., "Co-Reporter vector phRG-B, complete sequence", *Database EMBL Online*, (Accession No. EMBL:AF362550),(May 15, 2001), 3 pgs.

"U.S. Appl. No. 11/316,042, Preliminary Amendment filed Dec. 22, 2005", 8 pgs.

"U.S. Appl. No. 11/786,785, Preliminary Amendment filed Apr. 12, 2007", 11 pgs.

"U.S. Appl. No. 11/825,304, Preliminary Amendment filed Jul. 5, 2007", 7 pgs.

"Australian Patent Application No. 2003297293, Response filed May 30, 2007 to Examiner's First Report mailed Oct. 5, 2006", 19 pgs.

"Australian Patent Application No. 2001285278, Examiner's First Report mailed Oct. 16, 2006", 4 pgs.

"Australian Patent Application No. 2003297293, Examiner's Report No. 2 mailed Jun. 18, 2006", 2 pgs.

"Australian Patent Application No. 2003297293, Examiner's First Report mailed Oct. 5, 2006".

Australian Patent Application No. 2003297293, Response filed Aug. 29, 2007 to Examiner's Report No. 2 mailed Jun. 18, 2007, 27 pgs.

"Dual-Luciferase™ Reporter Assay System", (1998),2 pgs.

"EP Application No. 01964425.1, Communication Pursuant to Article 96(2) EPC mailed Nov. 23, 2006", 13 pgs.

"EP Application No. 01964425.1, Communication Pursuant to Article 96(2) EPC mailed Jun. 27, 2005", 12 pgs.

"EP Application No. 01964425.1, Response filed Apr. 6, 2006 to Communication mailed Jun. 27, 2005", 20 pgs.

"EP Application No. 01964425.1, Communication Noting Loss of Rights (R. 69(1) EPC mailed Feb. 10, 2006", 1 pg.
"EP Application No. 03819255.5, Communication Pursuant to Article 96(2) EPC mailed May 18, 2007", 5 pgs.
"Luciferase Reporter Gene Technology", (1996),4 pgs.
"PCT Application No. PCT/US03/37117, International Preliminary Examination Report mailed Mar. 15, 2007", 10 pgs.
"PCT Application No. PCT/US03/37117, International Search Report mailed Oct. 31, 2005", 5 pgs.
"PCT Application No. PCT/US2005/033218, International Preliminary Report on Patentability mailed Mar. 29, 2007", 10 pgs.
"Promega Technical Bulletin No. 161—Luciferase Assay System With Reporter Lysis Buffer", (Mar. 1998),9 pgs.
"Promega Technical Bulletin No. 101—Luciferase Assay System", (Mar. 1998),9 pgs.
"Promega Technical Manual—Dual-Luciferase™ Reporter Assay System", (Feb. 1999),26 pgs.
"Promega Technical Manual—Steady-Glo™ Luciferase Assay System", (Oct. 1998),19 pgs.
"Prosecution File History for U.S. Appl. No. 10/314,827" (as of Nov. 5, 2007), 765 pgs.
"Prosecution File History for U.S. Appl. No. 09/645,706", (as of Nov. 5, 2007),1047 pgs.
"Prosecution File History for U.S. Patent No. 5,670,356", 105 pgs.
Alam, J., et al., "Reporter Genes: Application to the Study of Mammalian Gene Transcription", *Analytical Biochemistry*, 188(2), (1990),245-254.
Andrews, E. M., et al., "Hierarchy of Polyadenylation Site Usage by Bovine Papillomavirus in Transformed Mouse Cells", *Journal of Virology*, 67(12), (1993), 7705-7710.
Bouthors, A.-T., et al., "Site-Directed Mutagenesis of Residues 164, 170, 171, 179, 220, 237 and 242 in PER-1 β-Lactamase Hydrolysing Expanded-Spectrum Cephalosporins", *Protein Engineering*, 12(4), (Apr. 1999), 313-318.
Carswell, S., et al., "Efficiency of Utilization of the Simian Virus 40 Late Polyadenylation Site: Effects of Upstream Sequences", *Molecular and Cellular Biology*, 9(10), (1989), 4248-4258.
Cheng, X., et al., "Agrobacterium-transformed Rice Plants Expressing Synthetic crylA(b) and CrylA(c) Genes are Highly Toxic to Striped Stem Borer and Yellow Stem Borer", *Proceedings of the National Academy of Sciences of the USA*, 95(6), (Mar. 17, 1998), 2767-2772.
Frampton, J., et al., "Synergy Between the NF-E1 Erythroid-Specific Transcription Factor and the CACCC Factor in the Erythroid-Specific Promotor of the Human Porphobilinogen Deaminase Gene", *Molecular and Cellular Biology*, 10(7), (1990),3838-3842.
Jensen, P. R., et al., "The Sequence of Spacers Between the Consensus Sequences Modulates the Strength of Prokaryotic Promoters", *Applied and Environmental Microbiology*, 64(1), (1998),82-87.
Kappel, C. A., et al., "Regulating Gene Expression in Transgenic Animals", *Current Opinion in Biotechnology*, 3, (1992),548-553.
Kimura, A, et al., "Detailed analysis of the mouse H-2K$^b$ promoter: enhancer-like sequences and their role in the regulation of class I gene expression", *Cell*, 44(2), (Jan. 31, 1986),261-272.
Labas, Y. A., et al., "Diversity and evolution of the green fluorescent protein family", *AY037769—Database Genbank*,(2002), 2 pgs.
Lesser, M. P., et al., "Green Fluorescent Proteins in Caribbean scleractinian corals", *AF401282—Database Genbank*, (Aug. 2001), 2 pgs.
Lesser, M. P., et al., "Green Fluorescent Proteins in Caribbean scleractinian corals", *AF406766—Database Genbank*, (Sep. 2001), 2 pgs.
Lewis, M. K., et al., "Efficient Site Directed in vitro Mutagenesis Using Ampicillin Selection", *Nucleic Acids Research*, 18(12), (1990),3439-3443.
Maranville, E., et al., "Assessment of Amino-Acid Substutions at Tryptophan 16 in α-galactosidase", *European Journal of Biochemistry*, 267(5), (2000),1495-1501.
Matsumura, I., et al., "Directed Evolution of the surface Chemistry of the Reporter Enzyme β-glucuronidase", *Nature Biotechnology*, 17(7), (1999),696-701.
Matz, M.V., et al., "Diversity and evolution of GFP-like fluorescent proteins", *AY037768—Database Genbank*, (May 2002), 2 pgs.

McWherter, C. A., et al., "Scanning Alanine Mutagenesis and De-Peptidization of a *Candida albicans* Myristoyl-CoA: Protein N-Myristoyltransferase Octapeptide Substrate Reveals Three Elements Critical for Molecular Recognition", *Journal of Biological Chemistry*, 272(18), (1997), 11874-11880.
Mount, S. M., "Genomic Sequence, Splicing, and Gene Annotation", *American Journal of Human Genetics*, 67(4), (2000),788-792.
Mullins, J. J., et al., "Transgenesis in Nonmurine Species", *Hypertension*, 22(4), (1993), 630-633.
Mullins, L. J., et al., "Transgenesis in the Rat and Larger Mammals", *Journal of Clinical Investigation*, 97(7), (Apr. 1996),1557-1560.
Riggs, J., et al., "Common Factor 1 Is a Transcriptional Activator Which Binds in the c-myc Promoter, the Skeletal alpha-Actin Provider, and the Immunoglobulin Heavy-Chain Enhancer", *Molecular and Cellular Biology*, 11(3), (1991),1765-1769.
Senapathy, P., et al., "Splice Junctions, Branch Point Sites, and Exons: Sequence Statistics, Identification, and Applications to Genome Project", *Methods in Enzymology*, 183, (1990),252.
Sherf, B. A., et al., "Dual-Luciferase™ Reporter Assay: An Advanced Co-Reporter Technology Integrating Firefly and *Renilla* Luciferase Assays", *Promega Notes Magazine*, No. 57, (1996),7 pgs.
Sirot, D., et al., "A Complex Mutant of TEM-1 Beta-Lactamase With Mutations Encountered in Both IRT-4 and Extended-Spectrum TEM-15, Produced by *Escherichia coli* Clinical Isolate", *Antimicrobial Agents and Chemotherapy*, 41(6), (Jun. 1997),1322-1325.
Stapleton, P. D., et al., "Construction and Characterization of Mutants of the TEM-1 β-Lactamase Containing Amino Acid Substitutions Associated With Both Extended-Spectrum Resistance and Resistance to β-Lactamase Inhibitors", *Antimicrobial Agents and Chemotherapy*, 43(8), (Aug. 1999),1881-1887.
Strauss, E. C., et al., "In Vivo Protein-DNA Interactions of Hypersensitive Site 3 of the Human β-Globin Locus Control Region", *Proc. Natl. Acad. Sci. USA*, 89(13), (Jul. 1992),5809-5813.
Voladri, R. K., et al., "Structure-Function Relationships Among Wild-Type Variants of *Staphylococcus aureus* β-Lactamase: Importance of Amino Acids 128 and 216", *Journal of Bacteriology*, 178(24), (Dec. 1996),7248-7253.
Wada, K.-N., et al., "Codon Usage Tabulated From the GenBank Genetic Sequence Data", *Nucleic Acids Research*, 20(Suppl.), (1992),2111-2118.
"U.S. Appl. No. 09/645,706, Examiner's Answer mailed Dec. 12, 2007", 67 pgs.
"U.S. Appl. No. 09/645,706, Reply Brief filed Feb. 12, 2008", 17 pgs.
"U.S. Appl. No. 11/316,042, Response to Restriction Requirement filed Apr. 15, 2008 to Restriction Requirement mailed Mar. 18, 2008", 7.
"Monstastrea cavernosa mcavFP_6 mRNa, complete cds", Accession: AY037769 (gl: 19982568),, (Apr. 5, 2001).
"Montastraea cavernosa clone 7.7 green fluorescent protein-like protein mRNA, Complete cds", Accession: AY037768 (gi: 21303777), (May 31, 2001).
"Montastraea cavernosa green fluorescent proten mRNA, complete cds", Accession: AF406766 (gi: 15425964), (Sep. 2, 2001).
"Montastraea faveolata green fluorescent protein mRNA, complete cds", Accession: AF401282 (gi: 15081471), (Aug. 5, 2001).
"Prosecution File History for U.S. Appl. No. 09/645,706", (as of Nov. 5, 2007),387 pgs.
Franklin, S., et al., "Development of a GFP reporter gene for Chlamydomonas reinhardtii chloroplast", *The Plant Journal*, 30(6), (Jun. 2002),733-744.
Lesser, M. P., et al., GenBank Accession No. AF401282, (Aug. 5, 2001).
Lesser, M. P., et al., GenBank Accession No. AF406766, (Sep. 4, 2001).
Matz, M. V., et al., GenBank Accession No. AY037768, (May 31, 2002).
Matz, M. V., et al., GenBank Accession No. AY037769, (Apr. 5, 2002).
Voss, S. D., et al., "The Role of Enhancers in the Regulation of Cell-Type-Specific Transcriptional Control", *Trends Biochem. Sci.*, 11, (1986),287-289.
Yang, F., et al., "The Molecular Structure of Green Fluorescent Protein", *Nature Biotech*, 14(10), (1996),1246-1251.

"Japanese Application Serial No. 2005-513754, Final Office Action mailed May 13, 2008", FOAR-MISC,4.

"U.S. Appl. No. 11/316,042, Non-Final Office Action mailed Jun. 11, 2008", OARN,18 pgs.

"U.S. Appl. No. 09/645,706, Final Office Action mailed Feb. 3, 2009", 24 pgs.

"U.S. Appl. No. 09/645,706, Record of Oral Hearing held Aug. 13, 2008", 15 pgs.

"U.S. Appl. No. 09/645,706, Decision on Appeal mailed Sep. 3, 2008", 26 pgs.

"U.S. Appl. No. 09/645,706, Request to Reopen Prosecution filed Nov. 3, 2008", 21 pgs.

"Australian Patent Application No. 2001285278, Examiner's Second Report mailed Dec. 19, 2007", 2 pgs.

"Australian Patent Application No. 2001285278, Response filed Apr. 21, 2008 to Examiner's Report mailed Dec. 19, 2007", 34 pgs.

"Australian Patent Application No. 2001285278, Response filed Dec. 10, 2007 to Examiner's First Report mailed Oct. 16, 2006", 31 pgs.

"Canadian Application Serial No. 2,420,328, Office Action mailed Feb. 4, 2008", 3 pgs.

"Canadian Application Serial No. 2,420,328, Response filed Jul. 31, 2008 to Office Action mailed Feb. 4, 2008", 77 pgs.

"Canadian Application Serial No. 2,525,582, Examiner's Report mailed 01-022008", 5 pgs.

"Canadian Application Serial No. 2,525,582, Response filed Jun. 20, 2008 to Examiner's Report mailed Jan. 2, 2008", 21 pgs.

"Japanese Application Serial No. 2005-513754, Argument and Amendment filed Feb. 29, 2008 to Office Action mailed Nov. 13, 2007", (w/ English Translation), 33 pgs.

"Japanese Application Serial No. 2005-513754, Office Action mailed Nov. 13, 2007", (w/ English Translation),7 pgs.

"Japanese Patent Application No. 2002-521985, Notice of Appeal filed Jun. 13, 2007 to Final Offiice Action mailed Mar. 16, 2007", 3 pgs.

"Japanese Patent Application No. 2002-521985, Amendment and Appeal Brief filed Jul. 12, 2007", (w/ English Translation),27 pgs.

"Japanese Patent Application No. 2002-521985, Final Offiice Action mailed Mar. 16, 2007", 4 pgs.

"Japanese Patent Application No. 2002-521985, Notice of Reasons for Rejection mailed Jun. 7, 2006", (English Translation),6 pgs.

"Japanese Patent Application No. 2002-521985, Official Action on Formalities mailed Jul. 19, 2007", 3 pgs.

"Japanese Patent Application No. 2002-521985, Response filed Oct. 23, 2006 to Notice of Reasons for Rejection mailed Jun. 7, 2006", (w/ English Translation), 54 pgs.

"U.S. Appl. No. 10/314,827, Amendment filed Nov. 25, 2008 to Office Communication mailed Oct. 28, 2008", 6 pgs.

"U.S. Appl. No. 10/314,827, Communication mailed Aug. 5, 2008 including Transcript of Oral Hearing held Jun. 17, 2008", 23 pgs.

"U.S. Appl. No. 10/314,827, Decision on Appeal dated Jul. 22, 2008", 23 pgs.

"U.S. Appl. No. 10/314,827, Office Communication mailed Oct. 28, 2008", 15 pgs.

"U.S. Appl. No. 10/314,827, Request to Reopen Prosecution and Amendment filed Sep. 22, 2008", 21 pgs.

"U.S. Appl. No. 11/316,042, Restriction Requirement mailed Mar. 18, 2008", 5 pgs.

"U.S. Appl. No. 11/316,042, Response filed Dec. 11, 2008 to Non-Final Office Action mailed Jun. 11, 2008", 14 pgs.

"U.S. Appl. No. 12/323,270, Preliminary Amendment filed Dec. 2, 2008", 10 pgs.

"European Application No. 03819255.5, Response filed Nov. 27, 2007 to Communication mailed May 18, 2007", 12 pgs.

"European Application Serial No. 01964425.1, Office Action mailed Jun. 9, 2008", 9 pgs.

"European Application Serial No. 01964425.1, Response filed Oct. 20, 2008 to Office Action mailed Jun. 9, 2008", 25 pgs.

"Japanese Application Serial No. 2005-513754, Reasons for Appeal filed on Sep. 5, 2008", (w/ English Translation), 30 pgs.

"Japanese Application Serial No. 2006-288147 Office Action Mailed Dec. 3, 2008", 3 pgs.

Kim, C. H., et al., "Codon optimization for high-level expression of human erythropoietin (EPO) in mammalian cells", *Gene*, 199(1-2), (1997), 293-301.

Pan, W., et al., "Vaccine candidate MSP-1 from Plasmodium falciparum: a redesigned 4917 bp polynucleotide enables synthesis and isolation of full-length protein from *Escherichia coli* and mammalian cells", *Nucleic Acid Research*, 27(4), (Feb. 15, 1999), 1094-1103.

"Cloning Vector pGL3 - Control", *NCBI Sequence Accession No.* U47296, 4 pgs. Apr. 2002.

"Cloning Vector psiSTRIKE Puromycin, CompleteSequence", *NCBI Sequence Accession No.* AY497507, 3 pgs. Jan. 2004.

"Sequence 1 from Patent WO9529245", *NCBI Sequence Accession No.* A47120, 2 pgs. Mar. 1997.

"U.S. Appl. No. 11-316,042, Final Office Action mailed Apr. 2, 2009", 8 pgs.

"European Application Serial No. 03819255.5, Office Action mailed on Mar. 17, 2009", 4 pgs.

"European Application No. 05797929.6, Office Action mailed Apr. 2, 2009", 4 pgs.

"U.S. Appl. No. 09/645,706, Final Office Action mailed Sep. 3, 2009", 13 pgs.

"U.S. Appl. No. 09/645,706, Final Office Action mailed Sep. 3, 2009", 13 pgs.

"U.S. Appl. No. 09/645,706, Response filed Jul. 31, 2009 to Final Office Action mailed Feb. 3, 2009", 10 pgs.

"U.S. Appl. No. 10/314,827, Notice of Allowance mailed Jul. 13, 2009", 21 Pgs.

"U.S. Appl. No. 11/316,042 , Final Office Action mailed Sep. 4, 2009", 15 pgs.

"U.S. Appl. No. 11/316,042, Response filed Aug. 3, 2009 to Final Office Action mailed Apr. 2, 2009", 11 pgs.

"U.S. Appl. No. 11/786,785, Non Final Office Action mailed Aug. 4, 2009", 16 pgs.

"U.S. Appl. No. 11/786,785, Response filed Jun. 25, 2009 to Restriction Requirement mailed May 26, 2009", 10 pgs.

"U.S. Appl. No. 11/786,785, Restriction Requirement mailed May 26, 2009", 10 pgs.

"Chinese Application Serial No. 200580039282.5, First Office Action mailed Aug. 7, 2009", (English Translation), 4 pgs.

"European Application Serial No. 01964425.1, Response filed Nov. 16, 2007 to Office Action mailed Nov. 23, 2006", 27 pgs.

"European Application Serial No. 05797929.6, Response filed Aug. 12, 2009 to Office Action mailed Apr. 2, 2009", 22 pgs.

"Japanese Application Serial No. 2006-288147, Response filed Jun. 3, 2009 to Office Action Mailed Dec. 3, 2008", 8 pgs.

* cited by examiner

Figure 1

| Amino Acid | Codon |
|---|---|
| Phe | UUU, UUC |
| Ser | UCU, UCC, UCA, UCG, AGU, AGC |
| Tyr | UAU, UAC |
| Cys | UGU, UGC |
| Leu | UUA, UUG, CUU, CUC, CUA, CUG |
| Trp | UGG |
| Pro | CCU, CCC, CCA, CCG |
| His | CAU, CAC |
| Arg | CGU, CGC, CGA, CGG, AGA, AGG |
| Gln | CAA, CAG |
| Ile | AUU, AUC, AUA |
| Thr | ACU, ACC, ACA, ACG |
| Asn | AAU, AAC |
| Lys | AAA, AAG |
| Met | AUG |
| Val | GUU, GUC, GUA, GUG |
| Ala | GCU, GCC, GCA, GCG |
| Asp | GAU, GAC |
| Gly | GGU, GGC, GGA, GGG |
| Glu | GAA, GAG |

SYNTHETIC NUCLEIC ACID MOLECULE COMPOSITIONS AND METHODS OF PREPARATION

BACKGROUND

Transcription, the synthesis of an RNA molecule from a sequence of DNA is the first step in gene expression. Sequences which regulate DNA transcription include promoter sequences, polyadenylation signals, transcription factor binding sites and enhancer elements. A promoter is a DNA sequence capable of specific initiation of transcription and consists of three general regions. The core promoter is the sequence where the RNA polymerase and its cofactors bind to the DNA. Immediately upstream of the core promoter is the proximal promoter which contains several transcription factor binding sites that are responsible for the assembly of an activation complex that in turn recruits the polymerase complex. The distal promoter, located further upstream of the proximal promoter also contains transcription factor binding sites. Transcription termination and polyadenylation, like transcription initiation, are site specific and encoded by defined sequences. Enhancers are regulatory regions, containing multiple transcription factor binding sites, that can significantly increase the level of transcription from a responsive promoter regardless of the enhancer's orientation and distance with respect to the promoter as long as the enhancer and promoter are located within the same DNA molecule. The amount of transcript produced from a gene may also be regulated by a post-transcriptional mechanism, the most important being RNA splicing that removes intervening sequences (introns) from a primary transcript between splice donor and splice acceptor sequences.

Natural selection is the hypothesis that genotype-environment interactions occurring at the phenotypic level lead to differential reproductive success of individuals and therefore to modification of the gene pool of a population. Some properties of nucleic acid molecules that are acted upon by natural selection include codon usage frequency, RNA secondary structure, the efficiency of intron splicing, and interactions with transcription factors or other nucleic acid binding proteins. Because of the degenerate nature of the genetic code, these properties can be optimized by natural selection without altering the corresponding amino acid sequence.

Under some conditions, it is useful to synthetically alter the natural nucleotide sequence encoding a polypeptide to better adapt the polypeptide for alternative applications. A common example is to alter the codon usage frequency of a gene when it is expressed in a foreign host cell. Although redundancy in the genetic code allows amino acids to be encoded by multiple codons, different organisms favor some codons over others. It has been found that the efficiency of protein translation in a non-native host cell can be substantially increased by adjusting the codon usage frequency but maintaining the same gene product (U.S. Pat. Nos. 5,096,825, 5,670,356, and 5,874,304).

However, altering codon usage may, in turn, result in the unintentional introduction into a synthetic nucleic acid molecule of inappropriate transcription regulatory sequences. This may adversely effect transcription, resulting in anomalous expression of the synthetic DNA. Anomalous expression is defined as departure from normal or expected levels of expression. For example, transcription factor binding sites located downstream from a promoter have been demonstrated to effect promoter activity (Michael et al., 1990; Lamb et al., 1998; Johnson et al., 1998; Jones et al., 1997). Additionally, it is not uncommon for an enhancer element to exert activity and result in elevated levels of DNA transcription in the absence of a promoter sequence or for the presence of transcription regulatory sequences to increase the basal levels of gene expression in the absence of a promoter sequence.

Thus, what is needed is a method for making synthetic nucleic acid molecules with altered codon usage without also introducing inappropriate or unintended transcription regulatory sequences for expression in a particular host cell.

SUMMARY OF THE INVENTION

The invention provides an isolated nucleic acid molecule (a polynucleotide) comprising a synthetic nucleotide sequence having reduced, for instance, 90% or less, e.g., 80%, 78%, 75%, or 70% or less, nucleic acid sequence identity relative to a parent nucleic acid sequence, e.g., a wild-type nucleic acid sequence, and having fewer regulatory sequences such as transcription regulatory sequences. In one embodiment, the synthetic nucleotide sequence has fewer regulatory sequences than would result if the sequence differences between the synthetic nucleotide sequence and the parent nucleic acid sequence, e.g., optionally the result of differing codons, were randomly selected. In one embodiment, the synthetic nucleotide sequence encodes a polypeptide that has an amino acid sequence that is at least 85%, 90%, 95%, or 99%, or 100%, identical to the amino acid sequence of a naturally-occurring (native or wild-type) corresponding polypeptide (protein). Thus, it is recognized that some specific amino acid changes may also be desirable to alter a particular phenotypic characteristic of a polypeptide encoded by the synthetic nucleotide sequence. Preferably, the amino acid sequence identity is over at least 100 contiguous amino acid residues. In one embodiment of the invention, the codons in the synthetic nucleotide sequence that differ preferably encode the same amino acids as the corresponding codons in the parent nucleic acid sequence.

Hence, in one embodiment, the invention provides an isolated nucleic acid molecule comprising a synthetic nucleotide sequence having a coding region for a selectable or screenable polypeptide, wherein the synthetic nucleotide sequence has 90%, e.g., 80%, or less nucleic acid sequence identity to a parent nucleic acid sequence encoding a corresponding selectable or screenable polypeptide, and wherein the synthetic nucleotide sequence encodes a selectable or screenable polypeptide with at least 85% amino acid sequence identity to the corresponding selectable or screenable polypeptide encoded by the parent nucleic acid sequence. The decreased nucleotide sequence identity may be a result of different codons in the synthetic nucleotide sequence relative to the codons in the parent nucleic acid sequence. The synthetic nucleotide sequence of the invention has a reduced number of regulatory sequences relative to the parent nucleic acid sequence, for example, relative to the average number of regulatory sequences resulting from random selections of codons or nucleotides at the sequences which differ between the synthetic nucleotide sequence and the parent nucleic acid sequence. In one embodiment, a nucleic acid molecule may include a synthetic nucleotide sequence which together with other sequences encodes a selectable or screenable polypeptide. For instance, a synthetic nucleotide sequence which forms part of an open reading frame for a selectable or screenable polypeptide may include at least 100, 150, 200, 250, 300 or more nucleotides of the open reading, which nucleotides have reduced nucleic acid sequence identity relative to corresponding sequences in a parent nucleic acid sequence. In one embodiment, the parent nucleic acid sequence is SEQ ID NO:1, SEQ ID NO:6, SEQ ID NO:15 or SEQ ID NO:41, the complement thereof, or a sequence that has 90%, 95% or 99% nucleic acid sequence identity thereto.

In one embodiment, the nucleic acid molecule of the invention comprises sequences which have been optimized for expression in mammalian cells, and more preferably, in human cells (see, e.g., WO 02/16944 which discloses methods to optimize sequences for expression in a cell of interest). For instance, nucleic acid molecules may be optimized for expression in eukaryotic cells by introducing a Kozak sequence and/or one or more introns or decreasing the number of other regulatory sequences, and/or altering codon usage to codons employed more frequently in one or more eukaryotic organisms, e.g., codons employed more frequently in an eukaryotic host cell to be transformed with the nucleic acid molecule.

In one embodiment, the synthetic nucleotide sequence is present in a vector, e.g., a plasmid, and such a vector may include other optimized sequences. In one embodiment, the synthetic nucleotide sequence encodes a polypeptide comprising a selectable polypeptide, which synthetic nucleotide sequence has at least 90% or more nucleic acid sequence identity to an open reading frame in a sequence comprising, for example, SEQ ID NO:5, SEQ ID NO:9, SEQ ID NO:10, SEQ ID NO:11, SEQ ID NO:30, SEQ ID NO:38, SEQ ID NO:39, SEQ ID NO:42, SEQ ID NO:44, SEQ ID NO:70, SEQ ID NO:71, SEQ ID NO:72, SEQ ID NO:73, SEQ ID NO:74, SEQ ID NO:80, SEQ ID NO:81, SEQ ID NO:82, SEQ ID NO:83, SEQ ID NO:84, the complement thereof, or a fragment thereof that encodes a polypeptide with substantially the same activity as the corresponding full-length and optionally wild-type (functional) polypeptide, e.g., a polypeptide encoded by SEQ ID NO:1, SEQ ID NO:6, SEQ ID NO:15 or SEQ ID NO:41, or a portion thereof which together with other parent or wild-type sequences encodes a polypeptide with substantially the same activity as the corresponding full-length and optionally wild-type polypeptide. As used herein, "substantially the same activity" is at least about 70%, e.g., 80%, 90% or more, the activity of a corresponding full-length and optionally wild-type (functional) polypeptide. In one embodiment, an isolated nucleic acid molecule encodes a fusion polypeptide comprising a selectable polypeptide.

Also provided is an isolated nucleic acid molecule comprising a synthetic nucleotide sequence having a coding region for a firefly luciferase, wherein the nucleic acid sequence identity of the synthetic nucleic acid molecule is 90% or less, e.g., 80%, 78%, 75% or less, compared to a parent nucleic acid sequence encoding a firefly luciferase, e.g., a parent nucleic acid sequence having SEQ ID NO:14 or SEQ ID NO:43, which synthetic nucleotide sequence has fewer regulatory sequences including transcription regulatory sequences than would result if the sequence differences, e.g., differing codons, were randomly selected. Preferably, the synthetic nucleotide sequence encodes a polypeptide that has an amino acid sequence that is at least 85%, preferably 90%, and most preferably 95% or 99% identical to the amino acid sequence of a naturally-occurring or parent polypeptide. Thus, it is recognized that some specific amino acid changes may be desirable to alter a particular phenotypic characteristic of the luciferase encoded by the synthetic nucleotide sequence. Preferably, the amino acid sequence identity is over at least 100 contiguous amino acid residues. In one embodiment, the synthetic nucleotide sequence encodes a polypeptide comprising a firefly luciferase, which synthetic nucleotide sequence has at least 90% or more nucleic acid sequence identity to an open reading frame in a sequence comprising, for example, SEQ ID NO:21, SEQ ID NO:22, SEQ ID NO:23, the complement thereof, or a fragment thereof that encodes a polypeptide with substantially the same activity as the corresponding full-length and optionally wild-type (functional) polypeptide, e.g., a polypeptide encoded by SEQ ID NO:14 or SEQ ID NO:43, or a portion thereof which together with other sequences encodes a firefly luciferase. For instance, a synthetic nucleotide sequence which forms part of an open reading frame for a firefly luciferase may include at least 100, 150, 200, 250, 300 or more nucleotides of the open reading, which nucleotides have reduced nucleic acid sequence identity relative to corresponding sequences in a parent nucleic acid sequence.

In another embodiment, the invention provides an isolated nucleic acid molecule comprising a synthetic nucleotide sequence which does not include an open reading frame encoding a peptide or polypeptide of interest, e.g., the synthetic nucleotide sequence may have an open reading frame but it does not include sequences that encode a functional or desirable peptide or polypeptide, but may include one or more stop codons in one or more reading frames, one or more poly(A) adenylation sites, and/or a contiguous sequence for two or more restriction endonucleases (restriction enzymes), i.e., a multiple cloning region (also referred to as a multiple cloning site, "MCS"), and which is generally at least 20, e.g., at least 30, nucleotides in length and up to 1000 or more nucleotides, e.g., up to 10,000 nucleotides, which synthetic nucleotide sequence has fewer regulatory sequences such as transcription regulatory sequences relative to a corresponding parent nucleic acid sequence. In one embodiment, the synthetic nucleotide sequence which does not encode a peptide or polypeptide has 90% or less, e.g., 80%, or less nucleic acid sequence identity to a parent nucleic acid sequence, wherein the decreased sequence identity is a result of a reduced number of regulatory sequences in the synthetic nucleotide sequence relative to the parent nucleic acid sequence.

The regulatory sequences which are reduced in the synthetic nucleotide sequence include, but are not limited to, any combination of transcription factor binding sequences, intron splice sites, poly(A) adenylation sites (poly(A) sequences or poly(A) sites hereinafter), enhancer sequences, promoter modules, and/or promoter sequences, e.g., prokaryotic promoter sequences. Generally, a synthetic nucleic acid molecule lacks at least 10%, 20%, 50% or more of the regulatory sequences, for instance lacks substantially all of the regulatory sequences, e.g., 80%, 90% or more, for instance, 95% or more, of the regulatory sequences, present in a corresponding parent or wild-type nucleotide sequence. Regulatory sequences, e.g., transcription regulatory sequences, are well known in the art. The synthetic nucleotide sequence may also have a reduced number of restriction enzyme recognition sites, and may be modified to include selected sequences, e.g., sequences at or near the 5' and/or 3' ends of the synthetic nucleotide sequence such as Kozak sequences and/or desirable restriction enzyme recognition sites, for instance, restriction enzyme recognition sites useful to introduce a synthetic nucleotide sequence to a specified location, e.g., in a multiple cloning region 5' and/or 3' to a nucleic acid sequence of interest.

In one embodiment, the synthetic nucleotide sequence of the invention has a codon composition that differs from that of the parent or wild-type nucleic acid sequence. Preferred codons for use in the invention are those which are employed more frequently than at least one other codon for the same amino acid in a particular organism and/or those that are not low-usage codons in that organism and/or those that are not low-usage codons in the organism used to clone or screen for the expression of the synthetic nucleotide sequence (for example, *E. coli*). Moreover, codons for certain amino acids (i.e., those amino acids that have three or more codons), may include two or more codons that are employed more frequently than the other (non-preferred) codon(s). The presence of codons in a synthetic nucleotide sequence that are employed more frequently in one organism than in another organism results in a synthetic nucleotide sequence which, when introduced into the cells of the organism that employs those codons more frequently, has a reduced risk of aberrant expression and/or is expressed in those cells at a level that may be greater than the expression of the wild type (unmodified) nucleic acid sequence in those cells under some conditions. For example, a synthetic nucleic acid molecule of the invention which encodes a selectable or screenable polypeptide may be expressed at a level that is greater, e.g., at least about 2, 3, 4, 5, 10-fold or more relative to that of the parent or wild-type (unmodified) nucleic acid sequence in a cell or cell extract under identical conditions (such as cell culture conditions, vector backbone, and the like). In one embodiment, the synthetic nucleotide sequence of the invention has a codon composition that differs from that of the parent or wild-type nucleic acid sequence at more than 10%, 20% or more, e.g., 30%, 35%, 40% or more than 45%, e.g., 50%, 55%, 60% or more of the codons.

In one embodiment of the invention, the codons that are different are those employed more frequently in a mammal, while in another embodiment the codons that are different are those employed more frequently in a plant. A particular type of mammal, e.g., human, may have a different set of preferred codons than another type of mammal. Likewise, a particular type of plant may have a different set of preferred codons than another type of plant. In one embodiment of the invention, the majority of the codons which differ are ones that are preferred codons in a desired host cell and/or are not low usage codons in a particular host cell. Preferred codons for mammals (e.g., humans) and plants are known to the art (e.g., Wada et al., 1990). For example, preferred human codons include, but are not limited to, CGC (Arg), CTG (Leu), AGC (Ser), ACC (Thr), CCC (Pro), GCC (Ala), GGC (Gly), GTG (Val), ACT (Ile), AAG (Lys), AAC (Asn), CAG (Gln), CAC (His), GAG (Glu), GAC (Asp), TAC (Tyr), TGC (Cys) and TTC (Phe) (Wada et al., 1990). Thus, synthetic nucleotide sequences of the invention have a codon composition which differs from a wild type nucleic acid sequence by having an increased number of preferred human codons, e.g. CGC, CTG, TCT, AGC, ACC, CCC, GCC, GGC, GTG, ACT, AAG, AAC, CAG, CAC, GAG, GAC, TAC, TGC, TTC, or any combination thereof. For example, the synthetic nucleotide sequence of the invention may have an increased number of AGC serine-encoding codons, CCC proline-encoding codons, and/or ACC threonine-encoding codons, or any combination thereof, relative to the parent or wild-type nucleic acid sequence. Similarly, synthetic nucleotide sequences having an increased number of codons that are employed more frequently in plants, have a codon composition which differs from a wild-type nucleic acid sequence by having an increased number of the plant codons including, but not limited to, CGC (Arg), CTT (Leu), TCT (Ser), TCC (Ser), ACC (Thr), CCA (Pro), CCT (Pro), GCT (Ser), GGA (Gly), GTG (Val), ATC (Ile), ATT (Ile), AAG (Lys), AAC (Asn), CAA (Gln), CAC (His), GAG (Glu), GAC (Asp), TAC (Tyr), TGC (Cys), TTC (Phe), or any combination thereof (Murray et al., 1989). Preferred codons may differ for different types of plants (Wada et al., 1990).

The nucleotide substitutions in the synthetic nucleic acid sequence may be influenced by many factors such as, for example, the desire to have an increased number of nucleotide substitutions such as those resulting in a silent nucleotide substitution (encodes the same amino acid) and/or decreased number of regulatory sequences. Under some circumstances (e.g., to permit removal of a transcription factor binding site) it may be desirable to replace a non-preferred codon with a codon other than a preferred codon or a codon other than the preferred codon in order to decrease the number of regulatory sequences.

The invention also provides an expression cassette or vector. The expression cassette or vector of the invention comprises a synthetic nucleotide sequence of the invention operatively linked to a promoter that is functional in a cell or comprises a synthetic nucleotide sequence, respectively. Preferred promoters are those functional in mammalian cells and those functional in plant cells. Optionally, the expression cassette may include other sequences, e.g., one or more restriction enzyme recognition sequences 5' and/or 3' to an open reading frame for a selectable polypeptide or luciferase and/or a Kozak sequence, and be a part of a larger polynucleotide molecule such as a plasmid, cosmid, artificial chromosome or vector, e.g., a viral vector, which may include a multiple cloning region for other sequences, e.g., promoters, enhancers, other open reading frames and/or poly(A) sites. In one embodiment, a vector of the invention includes SEQ ID NO:88, SEQ ID NO:89, SEQ ID NO:90, the complement thereof, or a sequence which has at least 80% nucleic acid sequence identity thereto and encodes a selectable and/or screenable polypeptide.

In one embodiment, the synthetic nucleotide sequence encoding a selectable or screenable polypeptide is introduced into a vector backbone, e.g., one which optionally has a poly(A) site 3' to the synthetic nucleotide sequence, a gene useful for selecting transformed prokaryotic cells which optionally is a synthetic sequence, a gene useful for selecting transformed eukaryotic cells which optionally is a synthetic sequence, a noncoding region for decreasing transcription and/or translation into adjacent linked desirable open reading frames, and/or a multiple cloning region 5' and/or 3' to the synthetic nucleotide sequence encoding a selectable or screenable polypeptide which optionally includes one or more protein destabilization sequences (see U.S. application Ser. No. 10/664,341, filed Sep. 16, 2003, the disclosure of which is incorporated by reference herein). In one embodiment, the vector having a synthetic nucleotide sequence encoding a selectable or screenable polypeptide may lack a promoter and/or enhancer which is operably linked to that synthetic sequence. In another embodiment, the invention provides a vector comprising a promoter, e.g., a prokaryotic or eukaryotic promoter, operably linked to a synthetic nucleotide sequence encoding a selectable or screenable polypeptide. Such vectors optionally include one or more multiple cloning regions, such as ones that are useful to introduce an additional open reading frame and/or a promoter for expression of the open reading frame which promoter optionally is different than the promoter for the selectable or screenable polypeptide, and/or a prokaryotic origin of replication. A "vector backbone" as used herein may include sequences (open reading frames) useful to identify cells with those sequences, e.g., in prokaryotic cells, their promoters, an origin of replication for vector maintenance, e.g., in prokaryotic cells, and optionally one or more other sequences including multiple cloning regions e.g., for insertion of a promoter and/or open reading frame of interest, and sequences which inhibit transcription and/or translation.

Also provided is a host cell comprising the synthetic nucleotide sequence of the invention, an isolated polypeptide (e.g., a fusion polypeptide encoded by the synthetic nucleotide sequence of the invention), and compositions and kits comprising the synthetic nucleotide sequence of the invention, a polypeptide encoded thereby, or an expression cassette or vector comprising the synthetic nucleotide sequence in suitable container means and, optionally, instruction means. The host cell may be an eukaryotic cell such as a plant or vertebrate cell, e.g., a mammalian cell, including but not limited to a human, non-human primate, canine, feline, bovine, equine, ovine or rodent (e.g., rabbit, rat, ferret, hamster, or mouse) cell or a prokaryotic cell.

The invention also provides a method to prepare a synthetic nucleotide sequence of the invention by genetically altering a parent, e.g., a wild-type or synthetic, nucleic acid sequence. The method comprises altering (e.g., decreasing or eliminating) a plurality of regulatory sequences in a parent nucleic acid sequence, e.g., one which encodes a selectable or screenable polypeptide or one which does not encode a peptide or polypeptide, to yield a synthetic nucleotide sequence which has a decreased number of regulatory sequences and, if the synthetic nucleotide sequence encodes a polypeptide, it preferably encodes the same amino acids as the parent nucleic acid molecule. The transcription regulatory sequences which are reduced include but are not limited to any of transcription factor binding sequences, intron splice sites, poly(A) sites, enhancer sequences, promoter modules, and/or promoter sequences. Preferably, the alteration of sequences in the synthetic nucleotide sequence does not result in an increase in regulatory sequences. In one embodiment, the synthetic nucleotide sequence encodes a polypeptide that has at least 85%, 90%, 95% or 99%, or 100%, contiguous amino acid sequence identity to the amino acid sequence of the polypeptide encoded by the parent nucleic acid sequence.

Thus, in one embodiment, a method to prepare a synthetic nucleic acid molecule comprising an open reading frame is provided. The method includes altering the codons and/or regulatory sequences in a parent nucleic acid sequence which encodes a reporter protein such, as a firefly luciferase or a selectable polypeptide such as one encoding resistance to ampicillin, puromycin, hygromycin or neomycin, to yield a synthetic nucleotide sequence which encodes a corresponding reporter polypeptide and which has for instance at least 10% or more, e.g., 20%, 30%, 40%, 50% or more, fewer regulatory sequences relative to the parent nucleic acid sequence. The synthetic nucleotide sequence has 90%, e.g., 85%, 80%, or 78%, or less nucleic acid sequence identity to the parent nucleic acid sequence and encodes a polypeptide with at least 85% amino acid sequence identity to the polypeptide encoded by the parent nucleic acid sequence. The regulatory sequences which are altered include transcription factor binding sequences, intron splice sites, poly(A) sites, promoter modules, and/or promoter sequences. In one embodiment, the synthetic nucleic acid sequence hybridizes under medium stringency hybridization but not stringent conditions to the parent nucleic acid sequence or the complement thereof. In one embodiment, the codons which differ encode the same amino acids as the corresponding codons in the parent nucleic acid sequence.

Also provided is a synthetic (including a further synthetic) nucleotide sequence prepared by the methods of the invention, e.g., a further synthetic nucleotide sequence in which introduced regulatory sequences or restriction endonuclease recognition sequences are optionally removed. Thus, the method of the invention may be employed to alter the codon usage frequency and/or decrease the number of regulatory sequences in any open reading frame or to decrease the number of regulatory sequences in any nucleic acid sequence, e.g., a noncoding sequence. Preferably, the codon usage frequency in a synthetic nucleotide sequence which encodes a selectable or screenable polypeptide is altered to reflect that of the host organism desired for expression of that nucleotide sequence while also decreasing the number of potential regulatory sequences relative to the parent nucleic acid molecule.

Also provided is a method to prepare a synthetic nucleic acid molecule which does not code for a peptide or polypeptide. The method includes altering the nucleotides in a parent nucleic acid sequence having at least 20 nucleotides which optionally does not code for a functional or desirable peptide or polypeptide and which optionally may include sequences which inhibit transcription and/or translation, to yield a synthetic nucleotide sequence which does not include an open reading frame encoding a peptide or polypeptide of interest, e.g., the synthetic nucleotide sequence may have an open reading frame but it does not include sequences that encode a functional or desirable peptide or polypeptide, but may include one or more stop codons in one or more reading frames, one or more poly(A) adenylation sites, and/or a contiguous sequence for two or more restriction endonucleases, i.e., a multiple cloning region. The synthetic nucleotide sequence is generally at least 20, e.g., at least 30, nucleotides in length and up to 1000 or more nucleotides, e.g., up to 10,000 nucleotides, and has fewer regulatory sequences such as transcription regulatory sequences relative to a corresponding parent nucleic acid sequence which does not code for a peptide or polypeptide, e.g., a parent nucleic acid sequence which optionally includes sequences which inhibit transcription and/or translation. The nucleotides are altered to reduce one or more regulatory sequences, e.g., transcription factor binding sequences, intron splice sites, poly(A) sites, enhancer sequences, promoter modules, and/or promoter sequences, in the parent nucleic acid sequence.

The invention also provides a method to prepare an expression vector. The method includes providing a linearized plasmid having a nucleic molecule including a synthetic nucleotide sequence of the invention which encodes a selectable or screenable polypeptide which is flanked at the 5' and/or 3' end by a multiple cloning region. The plasmid is linearized by contacting the plasmid with at least one restriction endonuclease which cleaves in the multiple cloning region. The linearized plasmid and an expression cassette having ends compatible with the ends in the linearized plasmid are annealed, yielding an expression vector. In one embodiment, the plasmid is linearized by cleavage by at least two restriction endonucleases, only one of which cleaves in the multiple cloning region.

Also provided is a method to clone a promoter or open reading frame. The method includes comprising providing a linearized plasmid having a multiple cloning region and a synthetic sequence of the invention which encodes a selectable or screenable polypeptide and/or a synthetic sequence of the invention which does not encode a peptide or polypeptide, which is plasmid is linearized by contacting the plasmid with at least two restriction endonucleases at least one of which cleaves in the multiple cloning region; and annealing the linearized plasmid with DNA having a promoter or an open reading frame with ends compatible with the ends of the linearized plasmid.

Exemplary methods to prepare synthetic sequences for firefly luciferase and a number of selectable polypeptide nucleic acid sequences, as well as non-coding regions present in a vector backbone, are described hereinbelow. For instance, the methods may produce synthetic selectable polypeptide nucleic acid molecules which exhibit similar or significantly enhanced levels of mammalian expression without negatively effecting other desirable physical or biochemical properties and which were also largely devoid of regulatory elements.

Clearly, the present invention has applications with many genes and across many fields of science including, but not limited to, life science research, agrigenetics, genetic therapy, developmental science and pharmaceutical development.

BRIEF DESCRIPTION OF THE FIGURES

FIG. 1. Codons and their corresponding amino acids.

DETAILED DESCRIPTION OF THE INVENTION

Definitions

Figure 2:
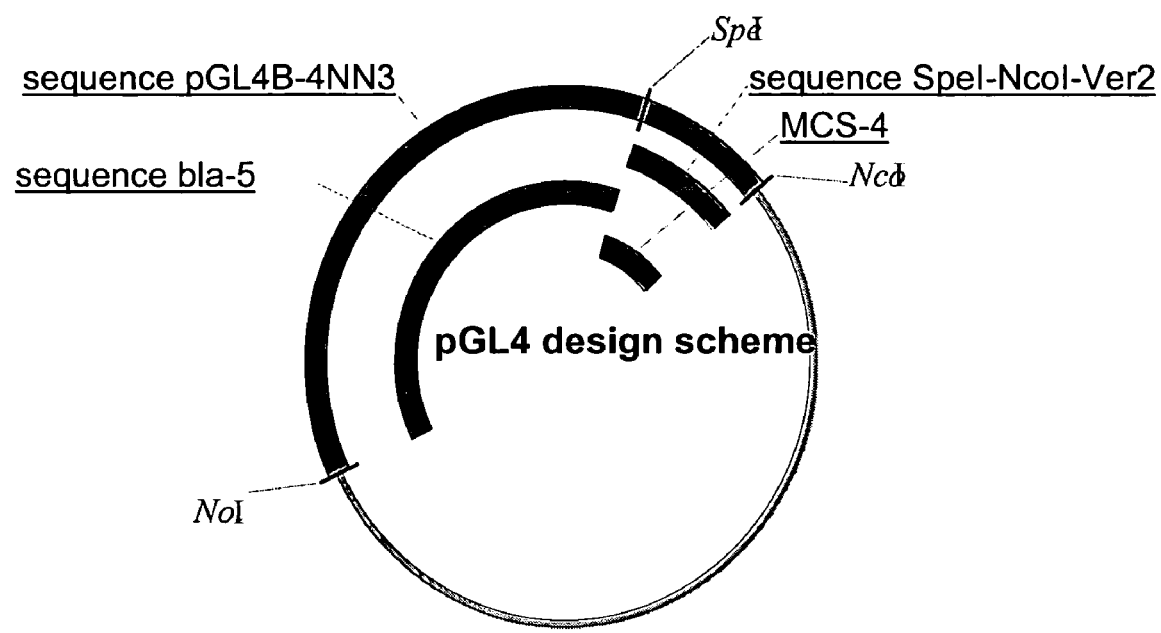
FIG. 2. Design scheme for the pGL4 vector.

The term "nucleic acid molecule" or "nucleic acid sequence" as used herein, refers to nucleic acid, DNA or RNA, that comprises noncoding or coding sequences. Coding sequences are necessary for the production of a polypeptide or protein precursor. The polypeptide can be encoded by a full-length coding sequence or by any portion of the coding sequence, as long as the desired protein activity is retained. Noncoding sequences refer to nucleic acids which do not code for a polypeptide or protein precursor, and may include regulatory elements such as transcription factor binding sites, poly(A) sites, restriction endonuclease sites, stop codons and/or promoter sequences.

A "synthetic" nucleic acid sequence is one which is not found in nature, i.e., it has been derived using molecular biological, chemical and/or informatic techniques.

A "nucleic acid", as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence, i.e., a linear order of nucleotides. A "polynucleotide", as used herein, is a nucleic acid containing a sequence that is greater than about 100 nucleotides in length. An "oligonucleotide" or "primer", as used herein, is a short polynucleotide or a portion of a polynucleotide. An oligonucleotide typically contains a sequence of about two to about one hundred bases. The word "oligo" is sometimes used in place of the word "oligonucleotide".

Nucleic acid molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a polynucleotide at which a new linkage would be to a 5' carbon is its 5' terminal nucleotide. The end of a polynucleotide at which a new linkage would be to a 3' carbon is its 3' terminal nucleotide. A terminal nucleotide, as used herein, is the nucleotide at the end position of the 3'- or 5'-terminus.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring.

As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. Typically, promoter and enhancer elements that direct transcription of a linked gene (e.g., open reading frame or coding region) are generally located 5' or upstream of the coding region. However, enhancer elements can exert their effect even when located 3' of the promoter element and the coding region. Transcription termination and polyadenylation signals are located 3' or downstream of the coding region.

The term "codon" as used herein, is a basic genetic coding unit, consisting of a sequence of three nucleotides that specify a particular amino acid to be incorporation into a polypeptide chain, or a start or stop signal. The term "coding region" when used in reference to structural genes refers to the nucleotide sequences that encode the amino acids found in the nascent polypeptide as a result of translation of a mRNA molecule. Typically, the coding region is bounded on the 5' side by the nucleotide triplet "ATG" which encodes the initiator methionine and on the 3' side by a stop codon (e.g., TAA, TAG, TGA). In some cases the coding region is also known to initiate by a nucleotide triplet "TTG".

By "protein", "polypeptide" or "peptide" is meant any chain of amino acids, regardless of length or post-translational modification (e.g., glycosylation or phosphorylation). The nucleic acid molecules of the invention may also encode a variant of a naturally-occurring protein or a fragment thereof. Preferably, such a variant protein has an amino acid sequence that is at least 85%, preferably 90%, and most preferably 95% or 99% identical to the amino acid sequence of the naturally-occurring (native or wild-type) protein from which it is derived.

Polypeptide molecules are said to have an "amino terminus" (N-terminus) and a "carboxy terminus" (C-terminus) because peptide linkages occur between the backbone amino group of a first amino acid residue and the backbone carboxyl group of a second amino acid residue. The terms "N-terminal" and "C-terminal" in reference to polypeptide sequences refer to regions of polypeptides including portions of the N-terminal and C-terminal regions of the polypeptide, respectively. A sequence that includes a portion of the N-terminal region of a polypeptide includes amino acids predominantly from the N-terminal half of the polypeptide chain, but is not limited to such sequences. For example, an N-terminal sequence may include an interior portion of the polypeptide sequence including bases from both the N-terminal and C-terminal halves of the polypeptide. The same applies to C-terminal regions. N-terminal and C-terminal regions may, but need not, include the amino acid defining the ultimate N-terminus and C-terminus of the polypeptide, respectively.

The term "wild-type" as used herein, refers to a gene or gene product that has the characteristics of that gene or gene product isolated from a naturally occurring source. A wild-type gene is that which is most frequently observed in a population and is thus arbitrarily designated the "wild-type" form of the gene. In contrast, the term "mutant" refers to a gene or gene product that displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

The term "fusion polypeptide" refers to a chimeric protein containing a protein of interest (e.g., luciferase) joined to a heterologous sequence (e.g., a non-luciferase amino acid or protein).

The terms "cell," "cell line," "host cell," as used herein, are used interchangeably, and all such designations include progeny or potential progeny of these designations. By "transformed cell" is meant a cell into which (or into an ancestor of which) has been introduced a nucleic acid molecule of the invention, e.g., via transient transfection. Optionally, a nucleic acid molecule synthetic gene of the invention may be introduced into a suitable cell line so as to create a stably-transfected cell line capable of producing the protein or polypeptide encoded by the synthetic gene. Vectors, cells, and methods for constructing such cell lines are well known in the art. The words "transformants" or "transformed cells" include the primary transformed cells derived from the originally transformed cell without regard to the number of transfers. All progeny may not be precisely identical in DNA content, due to deliberate or inadvertent mutations. Nonetheless, mutant progeny that have the same functionality as screened for in the originally transformed cell are included in the definition of transformants.

Nucleic acids are known to contain different types of mutations. A "point" mutation refers to an alteration in the sequence of a nucleotide at a single base position from the wild type sequence. Mutations may also refer to insertion or deletion of one or more bases, so that the nucleic acid sequence differs from the wild-type sequence.

The term "homology" refers to a degree of complementarity between two or more sequences. There may be partial homology or complete homology (i.e., identity). Homology is often measured using sequence analysis software (e.g., EMBOSS, the European Molecular Biology Open Software Suite URL is available at www.hgmp.mrc.ac.uk/Software/EMBOSS/overview/html. Such software matches similar sequences by assigning degrees of homology to various substitutions, deletions, insertions, and other modifications. Conservative substitutions typically include substitutions within the following groups: glycine, alanine; valine, isoleucine, leucine; aspartic acid, glutamic acid, asparagine, glutamine; serine, threonine; lysine, arginine; and phenylalanine, tyrosine.

The term "isolated" when used in relation to a nucleic acid, as in "isolated oligonucleotide" or "isolated polynucleotide" refers to a nucleic acid sequence that is identified and separated from at least one contaminant with which it is ordinarily associated in its source. Thus, an isolated nucleic acid is present in a form or setting that is different from that in which it is found in nature. In contrast, non-isolated nucleic acids (e.g., DNA and RNA) are found in the state they exist in nature. For example, a given DNA sequence (e.g., a gene) is found on the host cell chromosome in proximity to neighboring genes; RNA sequences (e.g., a specific mRNA sequence encoding a specific protein), are found in the cell as a mixture with numerous other mRNAs that encode a multitude of proteins. However, isolated nucleic acid includes, by way of example, such nucleic acid in cells ordinarily expressing that nucleic acid where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide contains at a minimum, the sense or coding strand (i.e., the oligonucleotide may be single-stranded), but may contain both the sense and anti-sense strands (i.e., the oligonucleotide may be double-stranded).

The term "isolated" when used in relation to a polypeptide, as in "isolated protein" or "isolated polypeptide" refers to a polypeptide that is identified and separated from at least one contaminant with which it is ordinarily associated in its source. Thus, an isolated polypeptide is present in a form or setting that is different from that in which it is found in nature. In contrast, non-isolated polypeptides (e.g., proteins and enzymes) are found in the state they exist in nature.

The term "purified" or "to purify" means the result of any process that removes some of a contaminant from the component of interest, such as a protein or nucleic acid. The percent of a purified component is thereby increased in the sample.

The term "operably linked" as used herein refer to the linkage of nucleic acid sequences in such a manner that a nucleic acid molecule capable of directing the transcription of a given gene and/or the synthesis of a desired protein molecule is produced. The term also refers to the linkage of sequences encoding amino acids in such a manner that a functional (e.g., enzymatically active, capable of binding to a binding partner, capable of inhibiting, etc.) protein or polypeptide is produced.

The term "recombinant DNA molecule" means a hybrid DNA sequence comprising at least two nucleotide sequences not normally found together in nature.

The term "vector" is used in reference to nucleic acid molecules into which fragments of DNA may be inserted or cloned and can be used to transfer DNA segment(s) into a cell and capable of replication in a cell. Vectors may be derived from plasmids, bacteriophages, viruses, cosmids, and the like.

The terms "recombinant vector" and "expression vector" as used herein refer to DNA or RNA sequences containing a desired coding sequence and appropriate DNA or RNA sequences necessary for the expression of the operably linked coding sequence in a particular host organism. Prokaryotic expression vectors include a promoter, a ribosome binding site, an origin of replication for autonomous replication in a host cell and possibly other sequences, e.g. an optional operator sequence, optional restriction enzyme sites. A promoter is defined as a DNA sequence that directs RNA polymerase to bind to DNA and to initiate RNA synthesis. Eukaryotic expression vectors include a promoter, optionally a polyadenlyation signal and optionally an enhancer sequence.

A polynucleotide having a nucleotide sequence encoding a protein or polypeptide means a nucleic acid sequence comprising the coding region of a gene, or in other words the nucleic acid sequence encodes a gene product. The coding region may be present in either a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc. may be placed in close proximity to the coding region of the gene if needed to permit proper initiation of transcription and/or correct processing of the primary RNA transcript. Alternatively, the coding region utilized in the expression vectors of the present invention may contain endogenous enhancers/promoters, splice junctions, intervening sequences, polyadenylation signals, etc. In further embodiments, the coding region may contain a combination of both endogenous and exogenous control elements.

The term "regulatory element" or "regulatory sequence" refers to a genetic element or sequence that controls some aspect of the expression of nucleic acid sequence(s). For example, a promoter is a regulatory element that facilitates the initiation of transcription of an operably linked coding region. Other regulatory elements include, but are not limited to, transcription factor binding sites, splicing signals, polyadenylation signals, termination signals and enhancer elements.

Transcriptional control signals in eukaryotes comprise "promoter" and "enhancer" elements. Promoters and enhancers consist of short arrays of DNA sequences that interact specifically with cellular proteins involved in transcription. Promoter and enhancer elements have been isolated from a variety of eukaryotic sources including genes in yeast, insect and mammalian cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types. For example, the SV40 early gene enhancer is very active in a wide variety of cell types from many mammalian species and has been widely used for the expression of proteins in mammalian cells. Two other examples of promoter/enhancer elements active in a broad range of mammalian cell types are those from the human elongation factor 1 gene (Uetsuki et al., 1989; Kim et al., 1990; and Mizushima and Nagata, 1990) and the long terminal repeats of the Rous sarcoma virus (Gorman et al., 1982); and the human cytomegalovirus (Boshart et al., 1985).

The term "promoter/enhancer" denotes a segment of DNA containing sequences capable of providing both promoter and enhancer functions (i.e., the functions provided by a promoter element and an enhancer element as described above). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques) such that transcription of the gene is directed by the linked enhancer/promoter.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook et al., 1989). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides-in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly (A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly(A) signal. The SV40 poly(A) signal is contained on a 237 bp BamH I/Bcl I restriction fragment and directs both termination and polyadenylation (Sambrook et al., 1989).

Eukaryotic expression vectors may also contain "viral replicons" or "viral origins of replication." Viral replicons are viral DNA sequences which allow for the extrachromosomal replication of a vector in a host cell expressing the appropriate replication factors. Vectors containing either the SV40 or polyoma virus origin of replication replicate to high copy number (up to $10^4$ copies/cell) in cells that express the appropriate viral T antigen. In contrast, vectors containing the replicons from bovine papillomavirus or Epstein-Barr virus replicate extrachromosomally at low copy number (about 100 copies/cell).

The term "in vitro" refers to an artificial environment and to processes or reactions that occur within an artificial environment. In vitro environments include, but are not limited to, test tubes and cell lysates. The term "in vivo" refers to the natural environment (e.g., an animal or a cell) and to processes or reactions that occur within a natural environment.

The term "expression system" refers to any assay or system for determining (e.g., detecting) the expression of a gene of interest. Those skilled in the field of molecular biology will understand that any of a wide variety of expression systems may be used. A wide range of suitable mammalian cells are available from a wide range of sources (e.g., the American Type Culture Collection, Rockland, Md.). The method of transformation or transfection and the choice of expression vehicle will depend on the host system selected. Transformation and transfection methods are described, e.g., in Ausubel et al., 1992. Expression systems include in vitro gene expression assays where a gene of interest (e.g., a reporter gene) is linked to a regulatory sequence and the expression of the gene is monitored following treatment with an agent that inhibits or induces expression of the gene. Detection of gene expression can be through any suitable means including, but not limited to, detection of expressed mRNA or protein (e.g., a detectable product of a reporter gene) or through a detectable change in the phenotype of a cell expressing the gene of interest. Expression systems may also comprise assays where a cleavage event or other nucleic acid or cellular change is detected.

All amino acid residues identified herein are in the natural L-configuration. In keeping with standard polypeptide nomenclature, abbreviations for amino acid residues are as shown in the following Table of Correspondence.

| TABLE OF CORRESPONDENCE | | |
| --- | --- | --- |
| 1-Letter | 3-Letter | AMINO ACID |
| Y | Tyr | L-tyrosine |
| G | Gly | L-glycine |
| F | Phe | L-phenylalanine |
| M | Met | L-methionine |
| A | Ala | L-alanine |
| S | Ser | L-serine |
| I | Ile | L-isoleucine |
| L | Leu | L-leucine |
| T | Thr | L-threonine |
| V | Val | L-valine |

-continued

TABLE OF CORRESPONDENCE

| 1-Letter | 3-Letter | AMINO ACID |
|---|---|---|
| P | Pro | L-proline |
| K | Lys | L-lysine |
| H | His | L-histidine |
| Q | Gln | L-glutamine |
| E | Glu | L-glutamic acid |
| W | Trp | L-tryptophan |
| R | Arg | L-arginine |
| D | Asp | L-aspartic acid |
| N | Asn | L-asparagine |
| C | Cys | L-cysteine |

The terms "complementary" or "complementarity" are used in reference to a sequence of nucleotides related by the base-pairing rules. For example, for the sequence 5' "A-G-T" 3', is complementary to the sequence 3' "T-C-A" 5'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon hybridization of nucleic acids.

When used in reference to a double-stranded nucleic acid sequence such as a cDNA or a genomic clone, the term "substantially homologous" refers to any probe which can hybridize to either or both strands of the double-stranded nucleic acid sequence under conditions of low stringency as described herein.

"Probe" refers to an oligonucleotide designed to be sufficiently complementary to a sequence in a denatured nucleic acid to be probed (in relation to its length) and is bound under selected stringency conditions.

"Hybridization" and "binding" in the context of probes and denatured nucleic acids are used interchangeably. Probes that are hybridized or bound to denatured nucleic acids are base paired to complementary sequences in the polynucleotide. Whether or not a particular probe remains base paired with the polynucleotide depends on the degree of complementarity, the length of the probe, and the stringency of the binding conditions. The higher the stringency, the higher must be the degree of complementarity and/or the longer the probe.

The term "hybridization" is used in reference to the pairing of complementary nucleic acid strands. Hybridization and the strength of hybridization (i.e., the strength of the association between nucleic acid strands) is impacted by many factors well known in the art including the degree of complementarity between the nucleic acids, stringency of the conditions involved such as the concentration of salts, the Tm (melting temperature) of the formed hybrid, the presence of other components (e.g., the presence or absence of polyethylene glycol), the molarity of the hybridizing strands and the G:C content of the nucleic acid strands.

The term "stringency" is used in reference to the conditions of temperature, ionic strength, and the presence of other compounds, under which nucleic acid hybridizations are conducted. With "high stringency" conditions, nucleic acid base pairing will occur only between nucleic acid fragments that have a high frequency of complementary base sequences. Thus, conditions of "medium" or "low" stringency are often required when it is desired that nucleic acids that are not completely complementary to one another be hybridized or annealed together. The art knows well that numerous equivalent conditions can be employed to comprise medium or low stringency conditions. The choice of hybridization conditions is generally evident to one skilled in the art and is usually guided by the purpose of the hybridization, the type of hybridization (DNA-DNA or DNA-RNA), and the level of desired relatedness between the sequences (e.g., Sambrook et al., 1989; Nucleic Acid Hybridization, A Practical Approach, IRL Press, Washington D.C., 1985, for a general discussion of the methods).

The stability of nucleic acid duplexes is known to decrease with increasing numbers of mismatched bases, and further to be decreased to a greater or lesser degree depending on the relative positions of mismatches in the hybrid duplexes. Thus, the stringency of hybridization can be used to maximize or minimize stability of such duplexes. Hybridization stringency can be altered by: adjusting the temperature of hybridization; adjusting the percentage of helix destabilizing agents, such as formamide, in the hybridization mix; and adjusting the temperature and/or salt concentration of the wash solutions. For filter hybridizations, the final stringency of hybridizations often is determined by the salt concentration and/or temperature used for the post-hybridization washes.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"Low stringency conditions" comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100 g/ml denatured salmon sperm DNA followed by washing in a solution comprising 5×SSPE, 0.1% SDS at 42° C. when a probe of about 500 nucleotides in length is employed.

The term "$T_m$" is used in reference to the "melting temperature". The melting temperature is the temperature at which 50% of a population of double-stranded nucleic acid molecules becomes dissociated into single strands. The equation for calculating the $T_m$ of nucleic acids is well-known in the art. The Tm of a hybrid nucleic acid is often estimated using a formula adopted from hybridization assays in 1 M salt, and commonly used for calculating Tm for PCR primers: [(number of A+T)×2° C.+(number of G+C)×4° C.]. (C. R. Newton et al., PCR, 2nd Ed., Springer-Verlag (New York, 1997), p. 24). This formula was found to be inaccurate for primers longer than 20 nucleotides. (Id.) Another simple estimate of the $T_m$ value may be calculated by the equation: $T_m=81.5+0.41$ (% G+C), when a nucleic acid is in aqueous solution at 1 M NaCl. (e.g., Anderson and Young, Quantitative Filter Hybridization, in *Nucleic Acid Hybridization*, 1985). Other more sophisticated computations exist in the art which take structural as well as sequence characteristics into account for the calculation of $T_m$. A calculated $T_m$ is merely an estimate; the optimum temperature is commonly determined empirically.

The term "promoter/enhancer" denotes a segment of DNA containing sequences capable of providing-both promoter and enhancer functions (i.e., the functions provided by a promoter element and an enhancer element as described above). For example, the long terminal repeats of retroviruses contain both promoter and enhancer functions. The enhancer/promoter may be "endogenous" or "exogenous" or "heterologous." An "endogenous" enhancer/promoter is one that is naturally linked with a given gene in the genome. An "exogenous" or "heterologous" enhancer/promoter is one that is placed in juxtaposition to a gene by means of genetic manipulation (i.e., molecular biological techniques) such that transcription of the gene is directed by the linked enhancer/promoter.

The term "sequence homology" means the proportion of base matches between two nucleic acid sequences or the proportion of amino acid matches between two amino acid sequences. When sequence homology is expressed as a percentage, e.g., 50%, the percentage denotes the proportion of matches over the length of sequence from one sequence that is compared to some other sequence. Gaps (in either of the two sequences) are permitted to maximize matching; gap lengths of 15 bases or less are usually used, 6 bases or less are preferred with 2 bases or less more preferred. When using oligonucleotides as probes or treatments, the sequence homology between the target nucleic acid and the oligonucleotide sequence is generally not less than 17 target base matches out of 20 possible oligonucleotide base pair matches (85%); preferably not less than 9 matches out of 10 possible base pair matches (90%), and more preferably not less than 19 matches out of 20 possible base pair matches (95%).

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 100 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, 1972, volume 5, National Biomedical Research Foundation, pp. 101-110, and Supplement 2 to this volume, pp. 1-10. The two sequences or parts thereof are more preferably homologous if their amino acids are greater than or equal to 85% identical when optimally aligned using the ALIGN program.

The following terms are used to describe the sequence relationships between two or more polynucleotides: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing, or may comprise a complete cDNA or gene sequence. Generally, a reference sequence is at least 20 nucleotides in length, frequently at least 25 nucleotides in length, and often at least 50 or 100 nucleotides in length. Since two polynucleotides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity.

A "comparison window", as used herein, refers to a conceptual segment of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences.

Methods of alignment of sequences for comparison are well known in the art. Thus, the determination of percent identity between any two sequences can be accomplished using a mathematical algorithm. Preferred, non-limiting examples of such mathematical algorithms are the algorithm of Myers and Miller (1988); the local homology algorithm of Smith and Waterman (1981); the homology alignment algorithm of Needleman and Wunsch (1970); the search-for-similarity-method of Pearson and Lipman (1988); the algorithm of Karlin and Altschul (1990), modified as in Karlin and Altschul (1993).

Computer implementations of these mathematical algorithms can be utilized for comparison of sequences to determine sequence identity. Such implementations include, but are not limited to: ClustalW (see the URL available at www.e-bi.ac.uk/clustalw/; the ALIGN program (Version 2.0) and GAP, BESTFIT, BLAST, FASTA, and TFASTA in the Wisconsin Genetics Software Package, Version 8. Alignments using these programs can be performed using the default parameters. The CLUSTAL program is well described by Higgins et al. (1988); Higgins et al. (1989); Corpet et al. (1988); Huang et al. (1992); and Pearson et al. (1994). The ALIGN program is based on the algorithm of Myers and Miller, supra. The BLAST programs of Altschul et al. (1990), are based on the algorithm of Karlin and Altschul supra. To obtain gapped alignments for comparison purposes, Gapped BLAST (in BLAST 2.0) can be utilized as described in Altschul et al. (1997). Alternatively, PSI-BLAST (in BLAST 2.0) can be used to perform an iterated search that detects distant relationships between molecules. See Altschul et al., supra. When utilizing BLAST, Gapped BLAST, PSI-BLAST, the default parameters of the respective programs (e.g. BLASTN for nucleotide sequences, BLASTX for proteins) can be used. See the URL at www.ncbi.nlm.nih.gov. Alignment may also be performed manually by inspection The term "sequence identity" means that two polynucleotide sequences are identical (i.e., on a nucleotide-by-nucleotide basis) over the window of comparison. The term "percentage of sequence identity" means that two polynucleotide sequences are identical (i.e., on a nucleotide-by-nucleotide basis) for the stated proportion of nucleotides over the window of comparison. The term "percentage of sequence identity" is calculated by comparing two optimally aligned sequences over the window of comparison, determining the number of positions at which the identical nucleic acid base (e.g., A, T, C, G, U, or I) occurs in both sequences to yield the number of matched positions, dividing the number of matched positions by the total number-positions in the window of comparison (i.e., the window size), and multiplying the result by 100 to yield the percentage of sequence identity.

The terms "substantial identity" as used herein denote a characteristic of a polynucleotide sequence, wherein the polynucleotide comprises a sequence that has at least 60%, preferably at least 65%, more preferably at least 70%, up to about 85%, and even more preferably at least 90 to 95%, more usually at least 99%, sequence identity as compared to a reference sequence over a comparison window of at least 20 nucleotide positions, frequently over a window of at least 20-50 nucleotides, and preferably at least 300 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

As applied to polypeptides, the term "substantial identity" means that two peptide sequences, when optimally aligned, such as by the programs GAP or BESTFIT using default gap weights, share at least about 85% sequence identity, preferably at least about 90% sequence identity, more preferably at least about 95% sequence identity, and most preferably at least about 99% sequence identity.

Synthetic Nucleotide Sequences and Methods of the Invention

The invention provides compositions comprising synthetic nucleotide sequences, as well as methods for preparing those sequences which yield synthetic nucleotide sequences that are efficiently expressed as a polypeptide or protein with desirable characteristics including reduced inappropriate or unintended transcription characteristics, or do not result in inappropriate or unintended transcription characteristics, when present in a particular cell type.

Natural selection is the hypothesis that genotype-environment interactions occurring at the phenotypic level lead to differential reproductive success of individuals and hence to modification of the gene pool of a population. It is generally accepted that the amino acid sequence of a protein found in nature has undergone optimization by natural selection. However, amino acids exist within the sequence of a protein that do not contribute significantly to the activity of the protein and these amino acids can be changed to other amino acids with little or no consequence. Furthermore, a protein may be useful outside its natural environment or for purposes that differ from the conditions of its natural selection. In these circumstances, the amino acid sequence can be synthetically altered to better adapt the protein for its utility in various applications.

Likewise, the nucleic acid sequence that encodes a protein is also optimized by natural selection. The relationship between coding DNA and its transcribed RNA is such that any change to the DNA affects the resulting RNA. Thus, natural selection works on both molecules simultaneously. However, this relationship does not exist between nucleic acids and proteins. Because multiple codons encode the same amino acid, many different nucleotide sequences can encode an identical protein. A specific protein composed of 500 amino acids can theoretically be encoded by more than $10^{150}$ different nucleic acid sequences.

Natural selection acts on nucleic acids to achieve proper encoding of the corresponding protein. Presumably, other properties of nucleic acid molecules are also acted upon by natural selection. These properties include codon usage frequency, RNA secondary structure, the efficiency of intron splicing, and interactions with transcription factors or other nucleic acid binding proteins. These other properties may alter the efficiency of protein translation and the resulting phenotype. Because of the redundant nature of the genetic code, these other attributes can be optimized by natural selection without altering the corresponding amino acid sequence.

Under some conditions, it is useful to synthetically alter the natural nucleotide sequence encoding a protein to better adapt the protein for alternative applications. A common example is to alter the codon usage frequency of a gene when it is expressed in a foreign host. Although redundancy in the genetic code allows amino acids to be encoded by multiple codons, different organisms favor some codons over others. The codon usage frequencies tend to differ most for organisms with widely separated evolutionary-histories. It has been found that when transferring genes between evolutionarily distant organisms, the efficiency of protein translation can be substantially increased by adjusting the codon usage frequency (see U.S. Pat. Nos. 5,096,825, 5,670,356 and 5,874,304).

In one embodiment, the sequence of a reporter gene is modified as the codon usage of reporter genes often does not correspond to the optimal codon usage of the experimental cells. In another embodiment, the sequence of a reporter gene is modified to remove regulatory sequences such as those which may alter expression of the reporter gene or a linked gene. Examples include β-galactosidase (β-gal) and chloramphenicol acetyltransferase (cat) reporter genes that are derived from *E. coli* and are commonly used in mammalian cells; the β-glucuronidase (gus) reporter gene that is derived from *E. coli* and commonly used in plant cells; the firefly luciferase (luc) reporter gene that is derived from an insect and commonly used in plant and mammalian cells; and the *Renilla* luciferase, and green fluorescent protein (gfp) reporter genes which are derived from coelenterates and are commonly used in plant and mammalian cells. To achieve sensitive quantitation of reporter gene expression, the activity of the gene product must not be endogenous to the experimental host cells. Thus, reporter genes are usually selected from organisms having unique and distinctive phenotypes. Consequently, these organisms often have widely separated evolutionary histories from the experimental host cells.

Previously, to create genes having a more optimal codon usage frequency but still encoding the same gene product, a synthetic nucleic acid sequence was made by replacing existing codons with codons that were generally more favorable to the experimental host cell (see U.S. Pat. Nos. 5,096,825, 5,670,356 and 5,874,304.) The result was a net improvement in codon usage frequency of the synthetic gene. However, the optimization of other attributes was not considered and so these synthetic genes likely did not reflect genes optimized by natural selection.

In particular, improvements in codon usage frequency are intended only for optimization of a RNA sequence based on its role in translation into a protein. Thus, previously described methods did not address how the sequence of a synthetic gene affects the role of DNA in transcription into RNA. Most notably, consideration had not been given as to how transcription factors may interact with the synthetic DNA and consequently modulate or otherwise influence gene transcription. For genes found in nature, the DNA would be optimally transcribed by the native host cell and would yield an RNA that encodes a properly folded gene product. In contrast, synthetic genes have previously not been optimized for transcriptional characteristics. Rather, this property has been ignored or left to chance.

This concern is important for all genes, but particularly important for reporter genes, which are most commonly used to quantitate transcriptional behavior in the experimental host cells, and vector backbone sequences for genes. Hundreds of transcription factors have been identified in different cell types under different physiological conditions, and likely more exist but have not yet been identified. All of these transcription factors can influence the transcription of an introduced gene or sequences linked thereto. A useful synthetic reporter gene or vector backbone of the invention has a minimal risk of influencing or perturbing intrinsic transcriptional characteristics of the host cell because the structure of that gene or vector backbone has been altered. A particularly useful synthetic reporter gene or vector backbone will have desirable characteristics under a new set and/or a wide variety of experimental conditions. To best achieve these characteristics, the structure of the synthetic gene or synthetic vector backbone should have minimal potential for interacting with transcription factors within a broad range of host cells and physiological conditions. Minimizing potential interactions between a reporter gene or vector backbone and a host cell's endogenous transcription factors increases the value of a reporter gene or vector backbone by reducing the risk of inappropriate transcriptional characteristics of the gene or vector backbone within a particular experiment, increasing applicability of the gene or vector backbone in various environments, and increasing the acceptance of the resulting experimental data.

In contrast, a reporter gene comprising a native nucleotide sequence, based on a genomic or cDNA clone from the original host organism, or a vector backbone comprising native sequences found in one or a variety of different organisms, may interact with transcription factors when present in an exogenous host. This risk stems from two circumstances. First, the native nucleotide sequence contains sequences that were optimized through natural selection to influence gene transcription within the native host organism. However, these sequences might also influence transcription when the sequences are present in exogenous hosts, i.e., out of context, thus interfering with its performance as a reporter gene or vector backbone. Second, the nucleotide sequence may inadvertently interact with transcription factors that were not present in the native host organism, and thus did not participate in its natural selection. The probability of such inadvertent interactions increases with greater evolutionary separation between the experimental cells and the native organism of the reporter gene or vector backbone.

These potential interactions with transcription factors would likely be disrupted when using a synthetic reporter gene having alterations in codon usage frequency. However, a synthetic reporter gene sequence, designed by choosing codons based only on codon usage frequency, or randomly replacing sequences or randomly juxtaposing sequences in a vector backbone, is likely to contain other unintended transcription factor binding sites since the resulting sequence has not been subjected to the benefit of natural selection to correct inappropriate transcriptional activities. Inadvertent interactions with transcription factors could also occur whenever an encoded amino acid sequence is artificially altered, e.g., to introduce amino acid substitutions. Similarly, these changes have not been subjected to natural selection, and thus may exhibit undesired characteristics.

Thus, the invention provides a method for preparing synthetic nucleotide sequences that reduce the risk of undesirable interactions of the nucleotide sequence with transcription factors and other trans-acting factors when expressed in a particular host cell, thereby reducing inappropriate or unintended characteristics. Preferably, the method yields synthetic genes containing improved codon usage frequencies for a particular host cell and with a reduced occurrence of regulatory sequences such as transcription factor binding sites and/or vector backbone sequences with a reduced occurrence of regulatory sequences. The invention also provides a method of preparing synthetic genes containing improved codon usage frequencies with a reduced occurrence of transcription factor binding sites and additional beneficial-structural attributes. Such additional attributes include the absence of inappropriate RNA splicing junctions, poly(A) addition signals, undesirable restriction enzyme recognition sites, ribosomal binding sites, and/or secondary structural motifs such as hairpin loops.

In one embodiment, a parent nucleic acid sequence encoding a polypeptide is optimized for expression in a particular cell. For example, the nucleic acid sequence is optimized by replacing codons in the wild-type sequence with codons which are preferentially employed in a particular (selected) cell, which codon replacement also reduces the number of regulatory sequences. Preferred codons have a relatively high codon usage frequency in a selected cell, and preferably their introduction results in the introduction of relatively few regulatory sequences such as transcription factor binding sites, and relatively few other undesirable structural attributes. Thus, the optimized nucleotide sequence may have an improved level of expression due to improved codon usage frequency, and a reduced risk of inappropriate transcriptional behavior due to a reduced number of undesirable transcription regulatory sequences. In another embodiment, a parent vector backbone sequence is altered to remove regulatory sequences and optionally restriction endonuclease sites, and optionally retain or add other desirable characteristics, e.g., the presence of one or more stop codons in one or more reading frames, one or more poly(A) sites, and/or restriction endonuclease sites.

The invention may be employed with any nucleic acid sequence, e.g., a native sequence such as a cDNA or one that has been manipulated in vitro. Exemplary genes include, but are not limited to, those encoding lactamase (β-gal), neomycin resistance (Neo), hygromycin resistance (Hyg), puromycin resistance (Puro), ampicillin resistance (Amp), CAT, GUS, galactopyranoside, GFP, xylosidase, thymidine kinase, arabinosidase, luciferase and the like. As used herein, a "reporter gene" is a gene that imparts a distinct phenotype to cells expressing the gene and thus permits cells having the gene to be distinguished from cells that do not have the gene. Such genes may encode either a selectable or screenable polypeptide, depending on whether the marker confers a trait which one can 'select' for by chemical means, i.e., through the use of a selective agent (e.g., a herbicide, antibiotic, or the like), or whether it is simply a "reporter" trait that one can identify through observation or testing, i.e., by 'screening'. Included within the terms selectable or screenable marker genes are also genes which encode a "secretable marker" whose secretion can be detected as a means of identifying or selecting for transformed cells. Examples include markers that encode a secretable antigen that can be identified by antibody interaction, or even-secretable enzymes which can be detected by their catalytic activity. Secretable proteins fall into a number of classes, including small, diffusible proteins detectable, e.g., by ELISA, and proteins that are inserted or trapped in the cell membrane.

Elements of the present disclosure are exemplified in detail through the use of particular genes and vector backbone sequences. Of course, many examples of suitable genes and vector backbones are known to the art and can be employed in the practice of the invention. Therefore, it will be understood that the following discussion is exemplary rather than exhaustive. In light of the techniques disclosed herein and the general recombinant techniques that are known in the art, the present invention renders possible the alteration of any gene or vector backbone sequence.

Exemplary genes include, but are not limited to, a neo gene, a puro gene, an amp gene, a β-gal gene, a gus gene, a cat gene, a gpt gene, a hyg gene, a hisD gene, a ble gene, a mprt gene, a bar gene, a nitrilase gene, a mutant acetolactate synthase gene (ALS) or acetoacid synthase gene (AAS), a methotrexate-resistant dhfr gene, a dalapon dehalogenase gene, a mutated anthranilate synthase gene that confers resistance to 5-methyl tryptophan (WO 97/26366), an R-locus gene, a β-lactamase gene, a xylE gene, an α-amylase gene, a tyrosinase gene, a luciferase (luc) gene (e.g., a *Renilla reniformis* luciferase gene, a firefly luciferase gene, or a click beetle luciferase (*Pyrophorus plagiophthalamus* gene), an aequorin gene, or a fluorescent protein gene.

The method of the invention can be performed by, although it is not limited to, a recursive process. The process includes assigning preferred codons to each amino acid in a target molecule, e.g., a native nucleotide sequence, based on codon usage in a particular species, identifying potential transcription regulatory sequences such as transcription factor binding sites in the nucleic acid sequence having preferred codons, e.g., using a database of such binding sites, optionally identifying other undesirable sequences, and substituting an alternative codon (i.e., encoding the same amino acid) at positions where undesirable transcription factor binding sites or other sequences occur. For codon distinct versions, alternative preferred codons are substituted in each version. If necessary, the identification and elimination of potential transcription factor or other undesirable sequences can be repeated until a nucleotide sequence is achieved containing a maximum number of preferred codons and a minimum number of undesired sequences including transcription regulatory sequences or other undesirable sequences. Also, optionally, desired sequences, e.g., restriction enzyme recognition sites, can be introduced. After a synthetic nucleotide sequence is designed and constructed, its properties relative to the parent nucleic acid sequence can be determined by methods well known to the art. For example, the expression of the synthetic and target nucleic acids in a series of vectors in a particular cell can be compared.

Thus, generally, the method of the invention comprises identifying a target nucleic acid sequence, and a host cell of interest, for example, a plant (dicot or monocot), fungus, yeast or mammalian cell. Preferred host cells are mammalian host cells such as CHO, COS, 293, Hela, CV-1 and NIH3T3 cells. Based on preferred codon usage in the host cell(s) and, optionally, low codon usage in the host cell(s), e.g., high usage mammalian codons and low usage *E. coli* and mammalian codons, codons to be replaced are determined. Concurrent, subsequent or prior to selecting codons to be replaced, desired and undesired sequences, such as undesired transcriptional regulatory sequences, in the target sequence are identified. These sequences, including transcriptional regulatory sequences and restriction endonuclease sites, can be identified using databases and software such as TRANSFAC® (Transcription Factor Database, see the URL available at www.gene-regulation.com), Match™ (see the URL available at www.gene-regulation.com), MatInspector (Genomatix, see the URL available at www.genomatix.de), EPD (Eukaryotic Promoter Database, see the URL available at www.epd.isb-sib.ch), REBASE® (Restriction Enzyme Database, NEB, see the URL available at rebase.neb.com), TESS (Transcription Element Search System, see the URL available at www.cbil.upenn.edu/tess/), MAR-Wiz (Futuresoft, see the URL available at www.futuresoft.org), Lasergene® (DNASTAR, see the URL available at www.dnastar.com), Vector NTI™ (Invitrogen, see the URL available at www.invitrogen.com), and Sequence Manipulation Suite (see the URL available at www.bioinformatics.org/SMS/index.html). Links to other databases and sequence analysis software are listed at see the URL available at www.expasy.org/alinks.html. After one or more sequences are identified, the modification(s) may be introduced. Once a desired synthetic nucleotide sequence is obtained, it can be prepared by methods well known to the art (such as nucleic acid amplification reactions with overlapping primers), and its structural and functional properties compared to the target nucleic acid sequence, including, but not limited to, percent homology, presence or absence of certain sequences, for example, restriction sites, percent of codons changed (such as an increased or decreased usage of certain codons) and/or expression rates.

As described below, the method was used to create synthetic reporter genes encoding firefly luciferases and selectable polypeptides, and synthetic sequences for vector backbones. Synthetic sequences may support greater levels of expression and/or reduced aberrant expression than the corresponding native or parent sequences for the protein. The native and parent sequences may demonstrate anomalous transcription characteristics when expressed in mammalian cells, which are likely not evident in the synthetic sequences.

Exemplary Uses of the Synthetic Nucleotide Sequences

The synthetic genes of the invention preferably encode the same proteins as their native counterpart (or nearly so), but have improved codon usage while being largely devoid of regulatory elements in the coding (it is recognized that a small number of amino acid changes may be desired to enhance a property of the native counterpart protein, e.g. to enhance luminescence of a luciferase) and noncoding regions. This increases the level of expression of the protein the synthetic gene encodes and reduces the risk of anomalous expression of the protein. For example, studies of many important events of gene regulation, which may be mediated by weak promoters, are limited by insufficient reporter signals from inadequate expression of the reporter proteins. Also, the use of some selectable markers may be limited by the expression of that marker in an exogenous cell. Thus, synthetic selectable marker genes which have improved codon usage for that cell, and have a decrease in other undesirable sequences, (e.g., transcription factor binding sites), can permit the use of those markers in cells that otherwise were undesirable as hosts for those markers.

Promoter crosstalk is another concern when a co-reporter gene is used to normalize transfection efficiencies. With the enhanced expression of synthetic genes, the amount of DNA containing strong promoters can be reduced, or DNA containing weaker promoters can be employed, to drive the expression of the co-reporter. In addition, there may be a reduction in the background expression from the synthetic reporter genes of the invention. This characteristic makes synthetic reporter genes more desirable by minimizing the sporadic expression from the genes and reducing the interference resulting from other regulatory pathways.

The use of reporter genes in imaging systems, which can be used for in vivo biological studies or drug screening, is another use for the synthetic genes of the invention. Due to their increased level of expression, the protein encoded by a synthetic gene is more readily detectable by an imaging system. In fact, using a synthetic *Renilla* luciferase gene, luminescence in transfected CHO cells was detected visually without the aid of instrumentation.

In addition, the synthetic genes may be used to express fusion proteins, for example fusions with secretion leader sequences or cellular localization sequences, to study transcription in difficult-to-transfect cells such as primary cells, and/or to improve the analysis of regulatory pathways and genetic elements. Other uses include, but are not limited to, the detection of rare events that require extreme sensitivity (e.g., studying RNA recoding), use with IRES, to improve the efficiency of in vitro translation or in vitro transcription-translation coupled systems such as TnT (Promega Corp., Madison, Wis.), study of reporters optimized to different host organisms (e.g., plants, fungus, and the like), use of multiple genes as co-reporters to monitor drug toxicity, as reporter molecules in multiwell assays, and as reporter molecules in drug screening with the advantage of minimizing possible interference of reporter signal by different signal transduction pathways and other regulatory mechanisms.

Additionally, uses for the synthetic nucleotide sequences of the invention include fluorescence activated cell sorting (FACS), fluorescent microscopy, to detect and/or measure the level of gene expression in vitro and in vivo, (e.g., to determine promoter strength), subcellular localization or targeting (fusion protein), as a marker, in calibration, in a kit (e.g., for dual assays), for in vivo imaging, to analyze regulatory pathways and genetic elements, and in multi-welling formats.

Further, although reporter genes are widely used to measure transcription events, their utility can be limited by the fidelity and efficiency of reporter expression. For example, in U.S. Pat. No. 5,670,356, a firefly luciferase gene (referred to as luc+) was modified to improve the level of luciferase expression. While a higher level of expression was observed, it was not determined that higher expression had improved regulatory control.

The invention will be further described by the following nonlimiting examples. In particular, the synthetic nucleic acid molecules of the invention may be derived by other methods as well as by variations on the methods described herein.

EXAMPLE 1

Synthetic Click Beetle (RD and GR) Luciferase Nucleic Acid Molecules

LucPp/YG is a wild-type click beetle luciferase that emits yellow-green luminescence (Wood, 1989). A mutant of LucPpIYG named YG#81-6G01 was envisioned. YG#81-6G01 lacks a peroxisome targeting signal, has a lower KM for luciferin and ATP, has increased signal stability and increased temperature stability when compared to the wild type (PCT/WO9914336). YG #81-6G01 was mutated to emit green luminescence by changing Ala at position 224 to Val (A224V is a green-shifting mutation), or to emit red luminescence by simultaneously introducing the amino acid substitutions A224H, S247H, N346I, and H348Q (red-shifting mutation set) (PCT/WO9518853)

Using YG #81-6G01 as a parent gene, two synthetic gene sequences were designed. One codes for a luciferase emitting green luminescence (GR) and one for a luciferase emitting red luminescence (RD). Both genes were designed to 1) have optimized codon usage for expression in mammalian cells, 2) have a reduced number of transcriptional regulatory sites including mammalian transcription factor binding sites, splice sites, poly(A) sites and promoters, as well as prokaryotic (*E. coli*) regulatory sites, 3) be devoid of unwanted restriction sites, e.g., those which are likely to interfere with standard cloning procedures, and 4) have a low DNA sequence identity compared to each other in order to minimize genetic rearrangements when both are present inside the same cell. In addition, desired sequences, e.g., a Kozak sequence or restriction enzyme recognition sites, may be identified and introduced.

Not all design criteria could be met equally well at the same time. The following priority was established for reduction of transcriptional regulatory sites: elimination of transcription factor (TF) binding sites received the highest priority, followed by elimination of splice sites and poly(A) sites, and finally prokaryotic regulatory sites. When removing regulatory sites, the strategy was to work from the lesser important to the most important to ensure that the most important changes were made last. Then the sequence was rechecked for the appearance of new lower priority sites and additional changes made as needed. Thus, the process for designing the synthetic GR and RD gene sequences, using computer programs described herein, involved 5 optionally iterative steps that are detailed below 1. Optimized codon usage and changed A224V to create GRver1, separately changed A224H, S247H, H348Q and N346I to create RDver1. These particular amino acid changes were maintained throughout all subsequent manipulations to the sequence.
2. Removed undesired restriction sites, prokaryotic regulatory sites, splice sites, poly(A) sites thereby creating GRver2 and RDver2.
3. Removed transcription factor binding sites (first pass) and removed any newly created undesired sites as listed in step 2 above thereby creating GRver3 and RDver3.
4. Removed transcription factor binding sites created by step 3 above (second pass) and removed any newly created undesired sites as listed in step 2 above thereby creating GRver4 and RDver4.
5. Removed transcription factor binding sites created by step 4 above (third Pass) and confirmed absence of sites listed in step 2 above thereby creating GRver5 and RDver5.
6. Constructed the actual genes by PCR using synthetic oligonucleotides corresponding to fragments of GRver5 and RDver5 designed sequences thereby creating GR6 and RD7. GR6, upon sequencing was found to have the serine residue at amino acid position 49 mutated to an asparagine and the proline at amino acid position 230 mutated to a serine (S49N, P230S). RD7, upon sequencing was found to have the histidine at amino acid position 36 mutated to a tyrosine (H36Y). These changes occurred during the PCR process.
4. The mutations described in step 6 above (S49N, P230S for GR6 and H36Y for RD7) were reversed to create GRver5.1 and RDver5.1.
5. RDver5.1 was further modified by changing the arginine codon at position 351 to a glycine codon (R351 G) thereby creating RDver5.2 with improved spectral properties compared to RDver5.1.
6. RDver5.2 was further mutated to increase luminescence intensity thereby creating RD 156-1H9 which encodes four additional amino acid changes (M21, S349T, K488T, E538V) and three silent single base changes (see U.S. application Ser. No. 09/645,706, filed Aug. 24, 2000, the disclosure of which is incorporated by reference herein).

1. Optimize Codon Usage and Introduce Mutations Determining Luminescence Color

The starting gene sequence for this design step was YG #81-6G01.

a) Optimize Codon Usage:

The strategy was to adapt the codon usage for optimal expression in human cells and at the same time to avoid *E. coli* low-usage codons. Based on these requirements, the best two codons for expression in human cells for all amino acids with more than two codons were selected (see Wada et al., 1990). In the selection of codon pairs for amino acids with six codons, the selection was biased towards pairs that have the largest number of mismatched bases to allow design of GR and RD genes with minimum sequence identity (codon distinction):

| | | |
|---|---|---|
| Arg: CGC/CGT | Leu: CTG/TTG | Ser: TCT/AGC |
| Thr: ACC/ACT | Pro: CCA/CCT | Ala: GCC/GCT |
| Gly: GGC/GGT | Val: GTC/GTG | Ile: ATC/ATT |

Based on this selection of codons, two gene sequences encoding the YG#81-6G01 luciferase protein sequence were computer generated. The two genes were designed to have minimum DNA sequence identity and at the same time closely similar codon usage. To achieve this, each codon in the two genes was replaced by a codon from the limited list described above in an alternating fashion (e.g., $Arg_{(n)}$ is CGC in gene 1 and CGT in gene 2, $Arg_{(n+1)}$ is CGT in gene 1 and CGC in gene 2).

For subsequent steps in the design process it was anticipated that changes had to be made to this limited optimal codon selection in order to meet other design criteria, however, the following low-usage codons in mammalian cells were not used unless needed to meet criteria of higher priority:

| | | |
|---|---|---|
| Arg: CGA | Leu: CTA | Ser: TCG |
| Pro: CCG | Val: GTA | Ile: ATA |

Also, the following low-usage codons in *E. coli* were avoided when reasonable (note that 3 of these match the low-usage list for mammalian cells):

| | | |
|---|---|---|
| Arg: CGA/CGG/AGA/AGG | | |
| Leu: CTA | Pro: CCC | Ile: ATA | b) Introduce Mutations Determining Luminescence Color:

Into one of the two codon-optimized gene sequences was introduced the single green-shifting mutation and into the other were introduced the 4 red-shifting mutations as described above.

The two output sequences from this first design step were named GRver1 (version 1 GR) and RDver1 (version 1 RD). Their DNA sequences are 63% identical (594 mismatches), while the proteins they encode differ only by the 4 amino acids that determine luminescence color (see FIGS. 2 and 3 for an alignment of the DNA and protein sequences).

Tables 1 and 2 show, as an example, the codon usage for valine and leucine in human genes, the parent gene YG#81-6G01, the codon-optimized synthetic genes GRver1 and RDver1, as well as the final versions of the synthetic genes after completion of step 5 in the design process (GRver5 and RDver5).

TABLE 1

| | | | Valine | | | |
|---|---|---|---|---|---|---|
| Codon | Human | Parent | GR ver1 | RD ver1 | GR ver5 | RD ver5 |
| GTA | 4 | 13 | 0 | 0 | 1 | 1 |
| GTC | 13 | 4 | 25 | 24 | 21 | 26 |
| GTG | 24 | 12 | 25 | 25 | 25 | 17 |
| GTT | 9 | 20 | 0 | 0 | 3 | 5 |

TABLE 2

| | | | Leucine | | | |
|---|---|---|---|---|---|---|
| Codon | Human | Parent | GR ver1 | RD ver1 | GR ver5 | RD ver5 |
| CTA | 3 | 5 | 0 | 0 | 0 | 0 |
| CTC | 12 | 4 | 0 | 1 | 12 | 11 |
| CTG | 24 | 4 | 28 | 27 | 19 | 18 |
| CTT | 6 | 12 | 0 | 0 | 1 | 1 |
| TTA | 3 | 17 | 0 | 0 | 0 | 0 |
| TTG | 6 | 13 | 27 | 27 | 23 | 25 |

2. Remove Undesired Restriction Sites, Prokaryotic Regulatory Sites, Splice Sites and Poly(A) Sites The starting gene sequences for this design step were GRver1 and RDver1.

a) Remove Undesired Restriction Sites:

To check for the presence and location of undesired restriction sites, the sequences of both synthetic genes were compared against a database of restriction enzyme recognition sequences (REBASE ver.712, see the URL available at www.neb.com/rebase) using standard sequence analysis software (GenePro ver 6.10, Riverside Scientific Ent.).

Specifically, the following restriction enzymes were classified as undesired:
 BamH I, Xho I, Sfi I, Kpn I, Sac I, Mlu I, Nhe I, Sma I, Xho I, Bgl II, Hind III, Nco I, Nar I, Xba I, Hpa I, Sal I,
 other cloning sites commonly used: EcoR I, EcoR V, Cla I,
 eight-base cutters (commonly used for complex constructs),
 BstE II (to allow N-terminal fusions),
 Xcm I (can generate A/T overhang used for T-vector cloning).

To eliminate undesired restriction sites when found in a synthetic gene, one or more codons of the synthetic gene sequence were altered in accordance with the codon optimization guidelines described in 1a above.

b) Remove Prokaryotic (*E. coli*) Regulatory Sequences:

To check for the presence and location of prokaryotic regulatory sequences, the sequences of both synthetic genes were searched for the presence of the following consensus sequences using standard sequence analysis software (GenePro):
 TATAAT (−10 Pribnow box of promoter)
 AGGA or GGAG (ribosome binding site; only considered if paired with a methionine codon 12 or fewer bases downstream).

To eliminate such regulatory sequences when found in a synthetic gene, one or more codons of the synthetic gene at sequence were altered in accordance with the codon optimization guidelines described in 1a above.

c) Remove Splice Sites:

To check for the presence and location of splice sites, the DNA strand corresponding to the primary RNA transcript of each synthetic gene was searched for the presence of the following consensus sequences (see Watson et al., 1983) using standard sequence analysis software (GenePro):

splice donor site: AG|GTRAGT (exon|intron), the search was performed for AGGTRAG and the lower stringency GGTRAGT;

splice acceptor site: (Y)$_n$NCAG|G (intron|exon), the search was performed with n=1.

To eliminate splice sites found in a synthetic gene, one or more codons of the synthetic gene sequence were altered in accordance with the codon optimization guidelines described in 1a above. Splice acceptor sites were generally difficult to eliminate in one gene without introducing them into the other gene because they tended to contain one of the two only Gln codons (CAG); they were removed by placing the Gln codon CAA in both genes at the expense of a slightly increased sequence identity between the two genes.

d) Remove Poly(A) Sites:

To check for the presence and location of poly(A) sites, the sequences of both synthetic genes were searched for the presence of the following consensus sequence using standard sequence analysis software (GenePro):

AATAAA.

To eliminate each poly(A) addition site found in a synthetic gene, one or more codons of the synthetic gene sequence were altered in accordance with the codon optimization guidelines described in 1a above. The two output sequences from this second-design step were named GRver2 and RDver2. Their DNA sequences are 63% identical (590 mismatches).

3. Remove Transcription Factor (TF) Binding Sites, then Repeat Steps 2 a-d

The starting gene sequences for this design step were GRver2 and RDver2.

To check for the presence, location and identity of potential TF binding sites, the sequences of both synthetic genes were used as query sequences to search a database of transcription factor binding sites (TRANSFAC v3.2). The TRANSFAC database (see the URL available at transfac.gbf.de/TRANSFAC/index.html) holds information on gene regulatory DNA sequences (TF binding sites) and proteins (TFs) that bind to and act through them. The SITE table of TRANSFAC Release 3.2 contains 4,401 entries of individual (putative) TF binding sites (including TF binding sites in eukaryotic genes, in artificial sequences resulting from mutagenesis studies and in vitro selection procedures based on random oligonucleotide mixtures or specific theoretical considerations, and consensus binding sequences (from Faisst and Meyer, 1992).

The software tool used to locate and display these TF binding sites in the synthetic gene sequences was TESS (Transcription Element Search Software, http://agave.humgen.upenn.edu/tess/index.html). The filtered string-based search option was used with the following user-defined search parameters:

Factor Selection Attribute: Organism Classification
Search Pattern: Mammalia
Max. Allowable Mismatch %: 0
Min. element length: 5
Min. log-likelihood: 10

This parameter selection specifies that only mammalian TF binding sites (approximately 1,400 of the 4,401 entries in the database) that are at least 5 bases long will be included in the search. It further specifies that only TF binding sites that have a perfect match in the query sequence and a minimum log likelihood (LLH) score of 10 will be reported. The LLH scoring method assigns 2 to an unambiguous match, 1 to a partially ambiguous match (e.g., A or T match W) and 0 to a match against 'N'. For example, a search with parameters specified above would-result in a "hit" (positive result or match) for TATAA (SEQ ID NO:50) (LLH=10), STRATG (SEQ ID NO:51) (LLH=10), and MTTNCNNMA (SEQ ID NO:52) (LLH=10) but not for TRATG (SEQ ID NO: 53) (LLH=9) if these four TF binding sites were present in the query sequence. A lower stringency test was performed at the end of the design process to re-evaluate the search parameters.

When TESS was tested with a mock query sequence containing known TF binding sites it was found that the program was unable to report matches to sites ending with the 3' end of the query sequence. Thus, an extra nucleotide was added to the 3' end of all query sequences to eliminate this problem.

The first search for TF binding sites using the parameters described above found about 100 transcription factor binding sites (hits) for each of the two synthetic genes (GRver2 and RDver2). All sites were eliminated by changing one or more codons of the synthetic gene sequences in accordance with the codon optimization guidelines described in 1a above. However, it was expected that some these changes created new TF binding sites, other regulatory sites, and new restriction sites. Thus, steps 2 a-d were repeated as described, and 4 new restriction sites and 2 new splice sites were removed. The two output sequences from this third design step were named GRver3 and RDver3. Their DNA sequences are 66% identical (541 mismatches).

4. Remove New Transcription Factor (TF) Binding Sites then Repeat Steps 2 a-d

The starting gene sequences for this design step were GRver3 and RDver3.

This fourth step is an iteration of the process described in step 3. The search for newly introduced TF binding sites yielded about 50 hits for each of the two synthetic genes. All sites were eliminated by changing one or more codons of the synthetic gene sequences in general accordance with the codon optimization guidelines described in 1a above. However, more high to medium usage codons were used to allow elimination of all TF binding sites. The lowest priority was placed on maintaining low sequence identity between the GR and RD genes. Then steps 2 a-d were repeated as described. The two output sequences from this fourth design step were named GRver4 and RDver4. Their DNA sequences are 68% identical (506 mismatches).

5. Remove New Transcription Factor (TF) Binding Sites, then Repeat Steps 2 a-d

The starting gene sequences for this design step were GRver4 and RDver4.

This fifth step is another iteration of the process described in step 3 above. The search for new TF binding sites introduced in step 4 yielded about 20 hits for each of the two synthetic genes. All sites were eliminated by changing one or more codons of the synthetic gene sequences in general accordance with the codon optimization guidelines described in 1a above. However, more high to medium usage codons were used (these are all considered "preferred") to allow elimination of all TF binding sites. The lowest priority was placed on maintaining low sequence identity between the GR and RD genes. Then steps 2 a-d were repeated as described. Only one acceptor splice site could not be eliminated. As a final step the absence of all TF binding sites in both genes as specified in step 3 was confirmed. The two output sequences from this fifth and last design step were named GRver5 and RDver5. Their DNA sequences are 69% identical (504 mismatches).

Additional Evaluation of GRver5 and RDver5 a) Use Lower Stringency Parameters for TESS:

The search for TF binding sites was repeated as described in step 3 above, but with even less stringent user-defined parameters:
- setting LLH to 9 instead of 10 did not result in new hits;
- setting LLH to 0 through 8 (incl.) resulted in hits for two additional sites, MAMAG (22 hits) and CTKTK (24 hits);
- setting LLH to 8 and the minimum element length to 4, the search yielded (in addition to the two sites above) different 4-base sites for AP-1, NF-1, and c-Myb that are shortened versions of their longer respective consensus sites which were eliminated in steps 3-5 above.

It was not realistic to attempt complete elimination of these sites without introduction of new sites, so no further changes were made.

b) Search Different Database:

The Eukaryotic Promoter Database (release 45) contains information about reliably mapped transcription start sites (1253 sequences) of eukaryotic genes. This database was searched using BLASTN 1.4.11 with default parameters (optimized to find nearly identical sequences rapidly; see Altschul et al, 1990) at the National Center for Biotechnology Information site (see the URL available at www/ncbi.nlm.nih.gov/cgi-bin/BLAST). To test this approach, a portion of pGL3-Control vector sequence containing the SV40 promoter and enhancer was used as a query sequence, yielding the expected hits to SV40 sequences. No hits were found when using the two synthetic genes as query sequences.

Summary of GRver5 and RDver5 Synthetic Gene Properties

Both genes, which at this stage were still only "virtual" sequences in the computer, have a codon usage that strongly favors mammalian high-usage codons and minimizes mammalian and E. coli low-usage codons.

Both genes are also completely devoid of eukaryotic TF binding sites consisting of more than four unambiguous bases, donor and acceptor splice sites (one exception: GRver5 contains one splice acceptor site), poly(A) sites, specific prokaryotic (E. coli) regulatory sequences, and undesired restriction sites.

The gene sequence identity between GRver5 and RDver5 is only 69% (504 base mismatches) while their encoded proteins are 99% identical (4 amino acid mismatches). Their identity with the parent sequence YG#81-6G1 is 74% (GRver5) and 73% (RDver5). Their base composition is 49.9% GC (GRver5) and 49.5% GC (RDver5), compared to 40.2% GC for the parent YG#81-6G01.

Construction of Synthetic Genes

The two synthetic genes were constructed by assembly from synthetic oligonucleotides in a thermocycler followed by PCR amplification of the full-length genes (similar to Stemmer et al. (1995) *Gene.* 164, pp. 49-53). Unintended mutations that interfered with the design goals of the synthetic genes were corrected.

a) Design of Synthetic Oligonucleotides:

The synthetic oligonucleotides were mostly 40mers that collectively code for both complete strand each designed gene (1,626 bp) plus flanking regions needed for cloning (1,950 bp total for each gene). The 5' and 3' boundaries of all oligonucleotides specifying one strand were generally placed in a manner to give an average offset/overlap of 20 bases relative to the boundaries of the oligonucleotides specifying the opposite strand.

The ends of the flanking regions of both genes matched the ends of the amplification primers (pRAMtailup: 5'-gtact-gagacgacgccagcccaagcttaggcctgagtg SEQ ID NO: 54, and pRAMtaildn: 5'-ggcatgagcgtgaactgactgaactagcggccgccgag SEQ ID NO:55) to allow cloning of the genes into our *E. coli* expression vector pRAM (WO99/14336).

A total of 183 oligonucleotides were designed: fifteen oligonucleotides that collectively encode the upstream and downstream flanking sequences and 168 oligonucleotides (4×42) that encode both strands of the two genes.

All 183 oligonucleotides were run through the hairpin analysis of the OLIGO software (OLIGO 4.0 Primer Analysis Software © 1989-1991 by Wojciech Rychlik) to identify potentially detrimental intra-molecular loop formation. The guidelines for evaluating the analysis results were set according to recommendations of Dr. Sims (Sigma-Genosys Custom Gene Synthesis Department): oligos forming hairpins with $\Delta G<-10$ have to be avoided, those forming hairpins with $\Delta G \leq -7$ involving the 3' end of the oligonucleotide should also be avoided, while those with an overall $\Delta G \leq -5$ should not pose a problem for this application. The analysis identified 23 oligonucleotides able to form hairpins with a $\Delta G$ between $-7.1$ and $-4.9$. Of these, 5 had blocked or nearly blocked 3' ends (0-3 free bases) and were re-designed by removing 1-4 bases at their 3' end and adding it to the adjacent oligonucleotide.

The 40mer oligonucleotide covering the sequence complementary to the poly(A) tail had a very low complexity 3' end (13 consecutive T bases). An additional 40mer was designed with a high complexity 3' end but a consequently reduced overlap with one of its complementary oligonucleotides (11 instead of 20 bases) on the opposite-strand.

Even though the oligonucleotides were designed for use in a thermocycler-based assembly reaction, they could also be used in a ligation-based protocol for gene construction. In this approach, the oligonucleotides are annealed in a pairwise fashion and the resulting short double-stranded fragments are ligated using the sticky overhangs. However, this would require that all oligonucleotides be phosphorylated.

b) Gene Assembly and Amplification

In a first step, each of the two synthetic genes was assembled in a separate reaction from 98 oligonucleotides. The total volume for each reaction was 50 μl:
- 0.5 μM oligonucleotides (=0.25 pmoles of each oligo)
- 1.0 U Taq DNA polymerase
- 0.02 U Pfu DNA polymerase
- 2 mM MgCl$_2$
- 0.2 mM dNTPs (each)
- 0.1% gelatin
- Cycling conditions: (94° C. for 30 seconds, 52° C. for 30 seconds, and 72° C. for 30 seconds)×55 cycles.

In a second step, each assembled synthetic gene was amplified in a separate reaction. The total volume for each reaction was 50 μl:
- 2.5 l assembly reaction
- 5.0 U Taq DNA polymerase
- 0.1 U Pfu DNA polymerase
- 1 M each primer (pRAMtailup, pRAMtaildn)
- 2 mM MgCl$_2$
- 0.2 mM dNTPs (each)

Cycling conditions: (94° C. for 20 seconds, 65° C. for 60 seconds, 72° C. for 3 minutes)×30 cycles.

The assembled and amplified genes were subcloned into the pRAM vector and expressed in *E. Coli*, yielding 1-2% luminescent GR or RD clones. Five GR and five RD clones were isolated and analyzed further. Of the five GR clones, three had the correct insert size, of which one was weakly luminescent and one had an altered restriction pattern. Of the five RD clones, two had the correct size insert with an altered restriction pattern and one of those was weakly luminescent. Overall, the analysis indicated the presence of a large number of mutations in the genes, most likely the result of errors introduced in the assembly and amplification reactions.

c) Corrective Assembly and Amplification

To remove the large number of mutations present in the full-length synthetic genes we performed an additional assembly and amplification reaction for each gene using the proof-reading DNA polymerase Tli. The assembly reaction contained, in addition to the 98 GR or RD oligonucleotides, a small amount of DNA from the corresponding full-length clones with mutations described above. This allows the oligos to correct mutations present in the templates.

The following assembly reaction was performed for each of the synthetic genes. The total volume for each reaction was 50 μl:

0.5 μM oligonucleotides (=0.25 pmoles of each oligo)
0.016 pmol plasmid (mix of clones with correct insert size)
2.5 U Tli DNA polymerase
2 mM MgCl$_2$
0.2 mM dNTPs (each)
0.1% gelatin
Cycling conditions: 94° C. for 30 seconds, then (94° C. for 30 seconds, 52° C. for 30 seconds, 72° C. for 30 seconds) for 55 cycles, then 72° C. for 5 minutes.

The following amplification reaction was performed on each of the assembly reactions. The total volume for each amplification reaction was 50 μl:

1-5 μl of assembly reaction
40 pmol each primer (pRAMtailup, pRAMtaildn)
2.5 U Tli DNA polymerase
2 mM MgCl$_2$
0.2 mM dNTPs (each)
Cycling conditions: 94° C. for 30 seconds, then (94° C. for 20 seconds, 65° C. for 60 seconds and 72° C. for 3 minutes) for 30 cycles, then 72° C. for 5 minutes.

The genes obtained from the corrective assembly and amplification step were subcloned into the pRAM vecter and expressed in *E. coli*, yielding 75% luminescent GR or RD clones. Forty-four GR and 44 RD clones were analyzed with the screening robot described in WO99/14336. The six best GR and RD clones were manually analyzed and one best GR and RD clone was selected (GR6 and RD7). Sequence analysis of GR6 revealed two point mutations in the coding region, both of which resulted in an amino acid substitution (S49N and P230S). Sequence analysis of RD7 revealed three point mutations in the coding region, one of which resulted in an amino acid substitution (H36Y). It was confirmed that none of the silent point mutations introduced any regulatory or restriction sites conflicting with the overall design criteria for the synthetic genes.

d) Reversal of Unintended Amino Acid Substitutions

The unintended amino acid substitutions present in the GR6 and RD7 synthetic genes were reversed by site-directed mutagenesis to match the GRver5 and RDver5 designed sequences, thereby creating GRver5.1 and RDver5.1. The DNA sequences of the mutated regions were confined by sequence analysis.

e) Improve Spectral Properties

The RDver5.1 gene was further modified to improve its spectral properties by introducing an amino change (R351 G), thereby creating RDver5.2 pGL3 Vectors with RD and GR Genes

The parent click beetle luciferase YG#81-6G1 ("YG"), and the synthetic click beetle luciferase genes GRver5.1 ("GR"), RDver5.2 ("RD"), and RD156-1H9 were cloned into the four pGL3 reporter vectors (Promega Corp.):

pGL3-Basic=no promoter, no enhancer
pGL3-Control=SV40 promoter, SV40 enhancer
pGL3-Enhancer=SV40 enhancer (3' to luciferase coding sequences)
pGL3-Promoter=SV40 promoter.

The primers employed in the assembly of GR and RD synthetic genes facilitated the cloning of those genes into pRAM vectors. To introduce the genes into pGL3 vectors (Promega Corp., Madison, Wis.) for analysis in mammalian cells, each gene in a pRAM vector (PRAM RDver5.1, pRAM GRver5.1, and pRAM RD 156-1H9) was amplified to introduce an Nco I site at the 5' end and an Xba I site at the 3' end of the gene. The primers for pRAM RDver5.1 and pRAM GRver5.1 were:

```
                                           (SEQ ID NO:56)
GR→5' GGA TCC CAT GGT GAA GCG TGA GAA 3'
or
                                           (SEQ ID NO:57)
RD→5' GGA TCC CAT GGT-GAA-ACG-CGA 3'
and
                                           (SEQ ID NO:58)
5' CTA GCT TTT TTT TCT AGA TAA TCA TGA AGA C 3'
```

The primers for pRAM RD156-1H9 were:

```
                                           (SEQ ID NO:59)
5' GCG TAG CCA TGG TAA AGC GTG AGA AAA ATG TC 3'
and
                                           (SEQ ID NO:60)
5' CCG ACT CTA GAT TAG TAA CCG CCG CCC TTC ACC 3'
```

The PCR included:
100 ng DNA plasmid
1 μM primer upstream
1 μM primer downstream
0.2 mM dNTPs
1× buffer (Promega Corp.)
5 units Pfu DNA polymerase (Promega Corp.)
Sterile nanopure H$_2$O to 50 μl The cycling parameters were: 94° C. for 5 minutes; (94° C. for 30 seconds; 55° C. for 1 minute; and 72° C. for 3 minutes)×15 cycles. The purified PCR product was digested with Nco I and Xba I, ligated with pGL3-control that was also digested with Nco I and Xba I, and the ligated products introduced to *E. coli*. To insert the luciferase genes into the other pGL3 reporter vectors (basic, promoter and enhancer), the pGL3-control vectors containing each of the luciferase genes was digested with Nco I and Xba I, ligated with other pGL3 vectors that also were digested with Nco I and Xba I, and the ligated products introduced to *E. coli*. Note that the polypeptide encoded by GRver5.1 and RDver5.1 (and RD156-1H9, see below) nucleic acid sequences in pGL3 vectors has an amino acid substitution at position 2 to valine as a result of the Nco I site at the initiation codon in the oligonucleotide.

Because of internal Nco I and Xba I sites, the native gene in YG #81-6G01 was amplified from a Hind III site upstream to a Hpa I site downstream of the coding region and which included flanking sequences found in the GR and RD clones. The upstream primer (5'-CAA AAA GCT TGG CAT TCC GGT ACT GTT GGT AAA GCC ACC ATG GTG AAG CGA GAG-3'; SEQ ID NO:61) and a downstream primer (5'-CAA-TTG TTG TTG TTA ACT TGT TTA TT-3'; SEQ ID NO:62) were mixed with YG#81-6G01 and amplified using the PCR conditions above. The purified PCR product was digested with Nco I and Xba I, ligated with pGL3-control that was also digested with Hind III and Hpa I, and the ligated products introduced into E. coli. To insert YG#81-6G01 into the other pGL3 reporter vectors (basic, promoter and enhancer), the pGL3-control vectors containing YG#81-6G01 were digested with Nco I and Xba I, ligated with the other pGL3 vectors that also were digested with Nco I and Xba I, and the ligated products introduced to E. coli. Note that the clone of YG#81-6G01 in the pGL3 vectors has a C instead of an A at base 786, which yields a change in the amino acid sequence at residue 262 from Phe to Leu. To determine whether the altered amino acid at position 262 affected the enzyme biochemistry, the clone of YG#81-6G01 was mutated to resemble the original sequence. Both clones were then tested for expression in E. coli, physical stability, substrate binding, and luminescence output kinetics. No significant differences were found.

Partially purified enzymes expressed from the synthetic genes and the parent gene were employed to determine Km for luciferin and ATP (see Table 3).

TABLE 3

| Enzyme | $K_M(LH_2)$ | $K_M(ATP)$ |
| --- | --- | --- |
| YG parent | 2 µM | 17 µM |
| GR | 1.3 µM | 25 µM |
| RD | 24.5 µM | 46 µM |

In vitro eukaryotic transcription/translation reactions were also conducted using Promega's TNT T7 Quick system according to manufacturer's instructions. Luminescence levels were 1 to 37-fold and 1 to 77-fold higher (depending on the reaction time) for the synthetic GR and RD genes, respectively, compared to the parent gene (corrected for luminometer spectral sensitivity).

To test whether the synthetic click beetle luciferase genes and the wild type click beetle gene have improved expression in mammalian cells, each of the synthetic genes and the parent gene was cloned into a series of pGL3 vectors and introduced into CHO cells (Table 8). In all cases, the synthetic click beetle genes exhibited a higher expression than the native gene. Specifically, expression of the synthetic GR and RD genes was 1900-fold and 40-fold higher, respectively, than that of the parent (transfection efficiency normalized by comparison to native Renilla luciferase gene). Moreover, the data (basic versus control vector) show that the synthetic genes have reduced basal level transcription.

Further, in experiments with the enhancer vector where the percentage of activity in reference to the control is compared between the native and synthetic gene, the data showed that the synthetic genes have reduced risk of anomalous transcription characteristics. In particular, the parent gene appeared to contain one or more internal transcriptional regulatory sequences that are activated by the enhancer in the vector, and thus is not suitable as a reporter gene while the synthetic GR and RD genes showed a clean reporter response (transfection efficiency normalized by comparison to native Renilla luciferase gene). See Table 8.

EXAMPLE 2

Synthetic Renilla Luciferase Nucleic Acid Molecule

The synthetic Renilla luciferase genes prepared include 1) an introduced Kozak sequence, 2) codon usage optimized for mammalian (human) expression, 3) a reduction or elimination of unwanted restriction sites, 4) removal of prokaryotic regulatory sites (ribosome binding site and TATA box), 5) removal of splice sites and poly(A) sites, and 6) a reduction or elimination of mammalian transcriptional factor binding sequences.

The process of computer-assisted design of synthetic Renilla luciferase genes by iterative rounds of codon optimization and removal of transcription factor binding sites and other regulatory sites as well as restriction sites can be described in three steps:

1. Using the wild type Renilla luciferase gene as the parent gene, codon usage was optimized, one amino acid was changed (T→A) to generate a Kozak consensus sequence, and undesired restriction sites were eliminated thereby creating synthetic gene Rlucver1.
2. Remove prokaryotic regulatory sites, splice sites, poly(A) sites and transcription factor (TF) binding sites (first pass). Then remove newly created TF binding sites. Then remove newly created undesired restriction enzyme sites, prokaryotic regulatory sites, splice sites, and poly(A) sites without introducing new TF binding sites. This thereby created Rlucver2.
3. Change 3 bases of Rlucver2 thereby creating Rluc-final.
4. The actual gene was then constructed from synthetic oligonucleotides corresponding to the Rluc-final designed sequence. All mutations resulting from the assembly or PCR process were corrected. This gene is Rluc-final.

Codon Selection

Starting with the Renilla reniformis luciferase sequence in Genbank (Accession No. M63501), codons were selected based on codon usage for optimal expression in human cells and to avoid E. coli low-usage codons. The best codon for expression in human cells (or the best two codons if found at a similar frequency) was chosen for all amino acids with more than one codon (Wada et al., 1990):

| | |
| --- | --- |
| Arg: CGC | Lys: AAG |
| Leu: CTG | Asn: AAC |
| Ser: TGT/AGC | Gln: CAG |
| Thr: ACC | His: CAC |
| Pro: CCA/CCT | Glu: GAG |
| Ala: GCC | Asp: GAC |
| Gly: GGC | Tyr: TAC |
| Val: GTG | Cys: TGC |
| Ile: ATC/ATT | Phe: TTC |

In cases where two codons were selected for one amino acid, they were used in an alternating fashion. To meet other criteria for the synthetic gene, the initial optimal codon selection was modified to some extent later. For example, introduction of a Kozak sequence required the use of GCT for Ala at amino acid position 2 (see below).

The following low-usage codons in mammalian cells were not used unless needed: Arg: CGA, CGU; Leu: CTA, UUA; Ser: TCG; Pro: CCG; Val: GTA; and Ile: ATA. The following low-usage codons in *E. coli* were also avoided when reasonable (note that 3 of these match the low-usage list for mammalian cells): Arg: CGA/CGG/AGA/AGG, Leu: CTA; Pro: CCC; Ile: ATA.

Introduction of Kozak Sequences

The Kozak sequence: 5' aaccATGGCT 3' (SEQ ID NO: 63) (the Nco I site is underlined, the coding region is shown in capital letters) was introduced to the synthetic *Renilla* luciferase gene. The introduction of the Kozak sequence changes the second amino acid from Thr to Ala (GCT).

Removal of Undesired Restriction Sites

REBASE ver. 808 (updated Aug. 1, 1998; Restriction Enzyme Database; www.neb.com/rebase) was employed to identify undesirable restriction sites as described in Example 1. The following undesired restriction sites (in addition to those described in Example 1) were removed according to the process described in Example 1: EcoICR I, NdeI, NsiI, SphI, SpeI, XmaI, PstI.

The version of *Renilla* luciferase (Rluc) which incorporates all these changes is Rlucver1.

Removal of Prokaryotic (*E. coli*) Regulatory Sequences, Splice Sites, and Poly(A) Sites The priority and process for eliminating transcription regulation sites was as described in Example 1.

Removal of TF Binding Sites

The same process, tools, and criteria were used as described in Example 1, however, the newer version 3.3 of the TRANSFAC database was employed.

After removing prokaryotic regulatory sequences, splice sites and poly(A) sites from Rlucver1, the first search for TF binding sites identified about 60 hits. All sites were eliminated with the exception of three that could not be removed without altering the amino acid sequence of the synthetic *Renilla* gene:

1. site at position 63 composed of two codons for W (TGGTGG), for CAC-binding protein T00076;
2. site at position 522 composed of codons for KMV (AANATGGTN), for myc-DF1 T00517;
3. site at position 885 composed of codons for EMG (GARATGGGN), for myc-DF 1 T00517.

The subsequent second search for (newly introduced) TF binding sites yielded about 20 hits. All new sites were eliminated, leaving only the three sites described above. Finally, any newly introduced restriction sites, prokaryotic regulatory sequences, splice sites and poly(A) sites were removed without introducing new TF binding sites if possible.

Rlucver2 was obtained.

As in Example 1, lower stringency search parameters were specified for the TESS filtered string search to further evaluate the synthetic *Renilla* gene.

With the LLH reduced from 10 to 9 and the minimum element length reduced from 5 to 4, the TESS filtered string search did not show any new hits. When, in addition to the parameter changes listed above, the organism classification was expanded from "mammalia" to "chordata", the search yielded only four more TF binding sites. When the Min LLH was further reduced to between 8 and 0, the search showed two additional 5-base sites (MAMAG and CTKTK) which combined had four matches in Rlucver2, as well as several 4-base sites. Also as in Example 1, Rlucver2 was checked for hits to entries in the EPD (Eukaryotic Promoter Database, Release 45). Three hits were determined one to *Mus musculus* promoter H-2L^d (*Cell*, 44, 261 (1986)), one to Herpes Simplex Virus type 1 promoter b'g'2.7 kb, and one to *Homo sapiens* DHFR promoter (*J. Mol. Biol.*, 176, 169 (1984)). However, no further changes were made to Rlucver2.

Summary of Properties for Rlucver2

All 30 low usage codons were eliminated. The introduction of a Kozak sequence changed the second amino acid from Thr to Ala;

base composition: 55.7% GC (*Renilla* wild-type parent gene: 36.5%);

one undesired restriction site could not be eliminated: EcoR V at position 488;

the synthetic gene had no prokaryotic promoter sequence but one potentially functional ribosome binding site (RBS) at positions 867-73 (about 13 bases upstream of a Met codon) could not be eliminated;

all poly(A) sites were eliminated;

splice sites: 2 donor splice sites could not be eliminated (both share the amino acid sequence MGK);

TF sites: all sites with a consensus of >4 unambiguous bases were eliminated (about 280 TF binding sites were removed) with 3 exceptions due to the preference to avoid changes to the amino acid sequence.

When introduced into pGL3, Rluc-final has a Kozak sequence (CACCATGGCT; SEQ ID NO:65). The changes in Rluc-final relative to Rlucver2 were introduced during gene assembly. One change was at position 619, a C to an A, which eliminated a eukaryotic promoter sequence and reduced the stability of a hairpin structure in the corresponding oligonucleotide employed to assemble the gene. Other changes included a change from CGC to AGA at positions 218-220 (resulted in a better oligonucleotide for PCR).

Gene Assembly Strategy

The gene assembly protocol employed for the synthetic *Renilla* luciferase was similar to that described in Example 1.

```
Sense Strand primer:
                                        (SEQ ID NO:66)
5' AACCATGGCTTCCAAGGTGTACGACCCCGAGCAACGCAAA 3'

Anti-sense Strand primer:
                                        (SEQ ID NO:67)
5' GCTCTAGAATTACTGCTCGTTCTTCAGCACGCGCTCCACG 3'
```

The resulting synthetic gene fragment was cloned into a pRAM vector using Nco I and Xba I. Two clones having the correct size insert were sequenced. Four to six mutations were found in the synthetic gene from each clone. These mutations were fixed by site-directed mutagenesis (Gene Editor from Promega Corp., Madison, Wis.) and swapping the correct regions between these two genes. The corrected gene was confirmed by sequencing.

Other Vectors

To prepare an expression vector for the synthetic *Renilla* luciferase gene in a pGL-3 control vector backbone, 5 µg of pGL3-control was digested with Nco I and Xba I in 50 µl final volume with 2 µl of each enzyme and 5 µl 10× buffer B (nanopure water was used to fill the volume to 50 µl). The digestion reaction was incubated at 37° C. for 2 hours, and the whole mixture was run on a 1% agarose gel in 1×TAE. The desired vector backbone fragment was purified using Qiagen's QIAquick gel extraction kit.

The native *Renilla* luciferase gene fragment was cloned into pGL3-control vector using two oligonucleotides, Nco I-RL-F and Xba I-RL-R, to PCR amplify native *Renilla* luciferase gene using pRL-CMV as the template. The sequence for Nco I-RL-F is 5'-CGCTAGCCATGGCTTC-GAAAGTTTATGATCC-3' (SEQ ID NO:68); the sequence for Xba I-RL-R is 5' GGCCAGTAACTCTAGAATTAT-TGTT-3' (SEQ ID NO:69). The PCR reaction was carried out as follows:

Reaction Mixture (for 100 µl):

| | |
|---|---|
| DNA template (Plasmid) | 1.0 µl (1.0 ng/µl final) |
| 10 X Rec. Buffer | 10.0 µl (Stratagene Corp.) |
| dNTPs (25 mM each) | 1.0 µl (final 250 µM) |
| Primer 1 (10 µM) | 2.0 µl (0.2 µM final) |
| Primer 2 (10 µM) | 2.0 µl (0.2 µM final) |
| Pfu DNA Polymerase | 2.0 µl (2.5 U/µl, Stratagene Corp.) |
| | 82.0 µl double distilled water |

PCR Reaction: heat 94° C. for 2 minutes; (94° C. for 20 seconds; 65° C. for 1 minute; 72° C. for 2 minutes; then 72° C. for 5 minutes)×25 cycles, then incubate on ice. The PCR amplified fragment was cut from a gel, and the DNA purified and stored at −20° C.

To introduce native *Renilla* luciferase gene fragment into pGL3-control vector, 5 µg of the PCR product of the native *Renilla* luciferase gene (RAM-RL-synthetic) was digested with Nco I and Xba I. The desired *Renilla* luciferase gene fragment was purified and stored at −20° C.

Then 100 ng of insert and 100 ng of pGL3-control vector backbone were digested with restriction enzymes Nco I and Xba I and ligated together. Then 2 µl of the ligation mixture was transformed into JM109 competent cells. Eight ampicillin resistance clones were picked and their DNA isolated. DNA from each positive clone of pGL3-control-native and pGL3-control-synthetic was purified. The correct sequences for the native gene and the synthetic gene in the vectors were confined by DNA sequencing.

To determine whether the synthetic *Renilla* luciferase gene has improved expression in mammalian cells, the gene was cloned into the mammalian expression vector pGL3-control vector under the control of SV40 promoter and SV40 early enhancer. The native *Renilla* luciferase gene was also cloned into the pGL-3 control vector so that the expression from synthetic gene and the native gene could be compared. The expression vectors were then transfected into four common mammalian cell lines (CHO, NIH3T3, Hela and CV-1; Table 9), and the expression levels compared between the vectors with the synthetic gene versus the native gene. The amount of DNA used was at two different levels to ascertain that expression from the synthetic gene is consistently increased at different expression levels. The results show a 70-600 fold increase of expression for the synthetic *Renilla* luciferase gene in these cells (Table 4).

TABLE 4

| Cell Type | Amount Vector | Fold Expression Increase |
|---|---|---|
| CHO | 0.2 µg | 142 |
| | 2.8 µg | 145 |
| NIH3T3 | 0.2 µg | 326 |
| | 2.0 µg | 593 |
| HeLa | 0.2 µg | 185 |
| | 1.0 µg | 103 |
| CV-1 | 0.2 µg | 68 |
| | 2.0 µg | 72 |

One important advantage of luciferase reporter is its short protein half-life. The enhanced expression could also result from extended protein half-life and, if so, this gives an undesired disadvantage of the new gene. This possibility is ruled out by a cycloheximide chase ("CHX Chase") experiment, which demonstrated that there was no increase of protein half-life resulted from the humanized *Renilla* luciferase gene.

To ensure that the increase in expression is not limited to one expression vector backbone, is promoter specific and/or cell specific, a synthetic *Renilla* gene (Rluc-final) as well as native *Renilla* gene were cloned into different vector backbones and under different promoters. The synthetic gene always exhibited increased expression compared to its wild-type counterpart (Table 5).

TABLE 5

| Vector | NIH-3T3 | HeLa | CHO |
|---|---|---|---|
| pRL-tk, native | 3,834.6 | 922.4 | 7,671.9 |
| pRL-tk, synthetic | 13,252.5 | 9,040.2 | 41,743.5 |
| pRL-CMV, native | 168,062.2 | 842,482.5 | 153,539.5 |
| pRL-CMV, synthetic | 2,168,129 | 8,440,306 | 2,532,576 |
| pRL-SV40, native | 224,224.4 | 346,787.6 | 85,323.6 |
| pRL-SV40, synthetic | 1,469,588 | 2,632,510 | 1,422,830 |
| pRL-null, native | 2,853.8 | 431.7 | 2,434 |
| pRL-null, synthetic | 9,151.17 | 2,439 | 28,317.1 |
| pRGL3b, native | 12 | 21.8 | 17 |
| pRGL3b, synthetic | 130.5 | 212.4 | 1,094.5 |
| pRGL3-tk, native | 27.9 | 155.5 | 186.4 |
| pRGL3-tk, synthetic | 6,778.2 | 8,782.5 | 9,685.9 |
| pRL-tk no intron, native | 31.8 | 165 | 93.4 |
| pRL-tk no intron, synthetic | 6,665.5 | 6,379 | 21,433.1 |

TABLE 6

| | Percent of control vector | | |
|---|---|---|---|
| Vector | CHO cells | NIH3T3 cells | HeLa cells |
| pRL-control native | 100 | 100 | 100 |
| pRL-control synthetic | 100 | 100 | 100 |
| pRL-basic native | 4.1 | 5.6 | 0.2 |
| pRL-basic synthetic | 0.4 | 0.1 | 0.0 |
| pRL-promoter native | 5.9 | 7.8 | 0.6 |
| pRL-promoter synthetic | 15.0 | 9.9 | 1.1 |
| pRL-enhancer native | 42.1 | 123.9 | 52.7 |
| pRL-enhancer synthetic | 2.6 | 1.5 | 5.4 |

With reduced spurious expression the synthetic gene should exhibit less basal level transcription in a promoterless vector. The synthetic and native *Renilla* luciferase genes were cloned into the pGL3-basic vector to compare the basal level of transcription. Because the synthetic gene itself has increased expression efficiency, the activity from the promoterless vector cannot be compared directly to judge the difference in basal transcription, rather, this is taken into consideration by comparing the percentage of activity from the promoterless vector in reference to the control vector (expression from the basic vector divided by the expression in the fully functional expression vector with both promoter and enhancer elements). The data demonstrate that the synthetic *Renilla* luciferase has a lower level of basal transcription than the native gene in mammalian cells (Table 6).

It is well known to those skilled in the art that an enhancer can substantially stimulate promoter activity. To test whether the synthetic gene has reduced risk of inappropriate transcriptional characteristics, the native and synthetic gene were introduced into a vector with an enhancer element (pGL3-enhancer vector). Because the synthetic gene has higher expression efficiency, the activity of both cannot be compared directly to compare the level of transcription in the presence of the enhancer, however, this is taken into account by using the percentage of activity from enhancer vector in reference to the control vector (expression in the presence of enhancer divided by the expression in the fully functional expression vector with both promoter and enhancer elements). Such results show that when native gene is present, the enhancer alone is able to stimulate transcription from 42-124% of the control, however, when the native gene is replaced by the synthetic gene in the same vector, the activity only constitutes 1-5% of the value when the same enhancer and a strong SV40 promoter are employed. This clearly demonstrates that synthetic gene has reduced risk of spurious expression (Table 6).

The synthetic *Renilla* gene (Rluc-final) was used in in vitro systems to compare translation efficiency with the native gene. In a T7 quick coupled transcription/translation system (Promega Corp., Madison, Wis.), pRL-null native plasmid (having the native *Renilla* luciferase gene under the control of the T7 promoter) or the same amount of pRL-null-synthetic plasmid (having the synthetic *Renilla* luciferase gene under the control of the T7 promoter) was added to the TNT reaction mixture and luciferase activity measured every 5 minutes up to 60 minutes. Dual Luciferase assay kit (Promega Corp.) was used to measure *Renilla* luciferase activity. The data showed that improved expression was obtained from the synthetic gene. To further evidence the increased translation efficiency of the synthetic gene, RNA was prepared by an in vitro transcription system, then purified. pRL-null (native or synthetic) vectors were linearized with BamHI. The DNA was purified by multiple phenol-chloroform extraction followed by ethanol precipitation. An in vitro T7 transcription system was employed by prepare RNAs. The DNA template was removed by using RNase-free DNase, and RNA was purified by phenol-chloroform extraction followed by multiple isopropanol precipitations. The same amount of purified RNA, either for the synthetic gene or the native gene, was then added to a rabbit reticulocyte lysate or wheat germ lysate. Again, the synthetic *Renilla* luciferase gene RNA produced more luciferase than the native one. These data suggest that the translation efficiency is improved by the synthetic sequence. To determine why the synthetic gene was highly expressed in wheat germ, plant codon usage was determined. The lowest usage codons in higher plants coincided with those in mammals.

Reporter gene assays are widely used to study transcriptional regulation events. This is often carried out in co-transfection experiments, in which, along with the primary reporter construct containing the testing promoter, a second control reporter under a constitutive promoter is transfected into cells as an internal control to normalize experimental variations including transfection efficiencies between the samples. Control reporter signal, potential promoter cross talk between the control reporter and primary reporter, as well as potential regulation of the control reporter by experimental conditions, are important aspects to consider for selecting a reliable co-reporter vector.

As described above, vector constructs were made by cloning synthetic *Renilla* luciferase gene into different vector backbones under different promoters. All the constructs showed higher expression in the three mammalian cell lines tested (Table 5). Thus, with better expression efficiency, the synthetic *Renilla* luciferase gives out higher signal when transfected into mammalian cells.

Because a higher signal is obtained, less promoter activity is required to achieve the same reporter signal, this reduced risk of promoter interference. CHO cells were transfected with 50 ng pGL3-control (firefly luc+) plus one of 5 different amounts of native pRL-TK plasmid (50, 100, 500, 1000, or 2000 ng) or synthetic pRL-TK (5, 10, 50, 100, or 200 ng). To each transfection, pUC19 carrier DNA was added to a total of 3 µg DNA. 10 fold less pRL-TK DNA gave similar or more signal as the native gene, with reduced risk of inhibiting expression from the primary reporter pGL3-control.

Experimental treatment sometimes may activate cryptic sites within the gene and cause induction or suppression of the co-reporter expression, which would compromise its function as co-reporter for normalization of transfection efficiencies. One example is that TPA induces expression of co-reporter vectors harboring the wild-type gene when transfecting MCF-7 cells. 500 ng pRL-TK (native), 5 µg native and synthetic pRG-B, 2.5 µg native and synthetic pRG-TK were transfected per well of MCF-7 cells. 100 ng/well pGL3-control (firefly luc+) was co-transfected with all RL plasmids. Carrier DNA, pUC 19, was used to bring the total DNA transfected to 5.1 µg/well. 15.3 ttl TransFast Transfection Reagent (Promega Corp., Madison, Wis.) was added per well. Sixteen hours later, cells were trypsinized, pooled and split into six wells of a 6-well dish and allowed to attach to the well for 8 hours. Three wells were then treated with the 0.2 nM of the tumor promoter, TPA (phorbol-12-myristate-13-acetate, Calbiochem #524400-S), and three wells were mock treated with 20 µl DMSO. Cells were harvested with 0.4 ml Passive Lysis Buffer 24 hours post TPA addition. The results showed that by using the synthetic gene, undesirable change of co-reporter expression by experimental stimuli can be avoided (Table 7). This demonstrates that using synthetic gene can reduce the risk of anomalous expression.

TABLE 7

| Vector | Rlu | Fold Induction |
| --- | --- | --- |
| pRL-tk untreated (native) | 184 | |
| pRL-tk TPA treated (native) | 812 | 4.4 |
| pRG-B untreated (native) | 1 | |
| pRG-B TPA treated (native) | 8 | 8.0 |
| pRG-B untreated (final) | 132 | |
| pRG-B TPA treated (final) | 195 | 1.47 |
| pRG-tk untreated (native) | 44 | |
| pRG-tk TPA treated (native) | 192 | 4.36 |
| pRG-tk untreated (final) | 12,816 | |
| pRG-tk TPA treated (final) | 11,347 | 0.88 |

EXAMPLE 3

Synthetic Firefly Luciferase Genes

The luc+gene (U.S. Pat. No. 5,670,356) was optimized using two approaches. In the first approach (Strategy A), regulatory sequences such as codons were optimized and consensus transcription factor binding sites (TFBS) were removed (see Example 4, although different versions of programs and databases were used). The sequences obtained for the first approach include hluc+ver2AF1 through hluc+ver2AF8 (designations with an "F" indicate the construct included flanking sequences). hluc+ver2AF1 is codon-optimized, hluc+ver2AF2 is a sequence obtained after a first round of removal of identified undesired sequences including transcription factor binding sites, hluc+ver2AF3 was obtained after a second round of removal of identified undesired sequences including transcription factor binding sites, hluc+ver2AF4 was obtained after a third round of removal of identified undesired sequences including transcription factor binding sites, hluc+ver2AF5 was obtained after a fourth round of removal of identified undesired sequences including transcription factor binding sites, hluc+ver2AF6 was obtained after removal of promoter modules and RBS, hluc+ ver2AF7 was obtained after further removal of identified undesired sequences including transcription factor binding sites, and hluc+ver2AF8 was obtained after modifying a restriction enzyme recognition site. Pairwise DNA identity of different *P. pyralis* luciferase gene versions:

TABLE 8

|  | luc | luc+ | hluc+ | hluc + ver2A1 | hluc + ver2B1 | hluc + ver2A6 | hluc + ver2B6 |
|---|---|---|---|---|---|---|---|
| luc | 100 | 95 | 76 | 73 | 77 | 74 | 75 |
| luc+ |  | 100 | 78 | 76 | 78 | 75 | 77 |
| hluc+ |  |  | 100 | 91 | 81 | 87 | 81 |
| hluc + ver2A1 |  |  |  | 100 | 74 | 91 | 78 |
| hluc + ver2B1 |  |  |  |  | 100 | 74 | 85 |
| hluc + ver2A6 |  |  |  |  |  | 100 | 80 |
| hluc + ver2B6 |  |  |  |  |  |  | 100 | luc+ has the following sequence:

(SEQ ID NO:43)
atggaagacgccaaaaacataaagaaaggcccggcgccattctatccgct
ggaagatggaaccgctggagagcaactgcataaggctatgaagagatacg
ccctggttcctggaacaattgcttttacagatgcacatatcgaggtggac
atcacttacgctgagtacttcgaaatgtccgttcggttggcagaagctat
gaaacgatatgggctgaatacaaatcacagaatcgtcgtatgcagtgaaa
actctcttcaattctttatgccggtgttgggcgcgttatttatcggagtt
gcagttgcgcccgcgaacgacatttataatgaacgtgaattgctcaacag
tatgggcatttcgcagcctaccgtggtgttcgtttccaaaaaggggttgc
aaaaaattttgaacgtgcaaaaaaagctcccaatcatccaaaaaattatt
atcatggattctaaaacggattaccagggatttcagtcgatgtacacgtt
cgtcacatctcatctacctcccggttttaatgaatacgattttgtgccag
agtccttcgatagggacaagacaattgcactgatcatgaactcctctgga
tctactggtctgcctaaaggtgtcgctctgcctcatagaactgcctgcgt
gagattctcgcatgccagagatcctattttggcaatcaaatcattccgg
atactgcgatttaagtgttgttccattccatcacggttttggaatgtttt
actacactcggatatttgatatgtggatttcgagtcgtcttaatgtatag
atttgaagaagagctgtttctgaggagccttcaggattacaagattcaaa
gtgcgctgctggtgccaaccctattctccttcttcgccaaaagcactctg
attgacaaatacgatttatctaatttacacgaaattgcttctggtggcgc
tcccctctctaaggaagtcggggaagcggttgccaagaggttccatctgc
caggtatcaggcaaggatatgggctcactgagactacatcagctattctg
attacacccgagggggatgataaaccgggcgcggtcggtaaagttgttcc
attttttgaagcgaaggttgtggatctggataccgggaaaacgctgggcg
ttaatcaaagaggcgaactgtgtgtgagaggtcctatgattatgtccggt
tatgtaaacaatccggaagcgaccaacgccttgattgacaaggatggatg
gctacattctggagacatagcttactgggacgaagacgaacacttcttca tcgttgaccgcctgaagtctctgattaagtacaaaggctatcaggtggct
cccgctgaattggaatccatcttgctccaacaccccaacatcttcgacgc
aggtgtcgcaggtcttcccgacgatgacgccggtgaacttcccgccgccg
ttgttgttttggagcacggaaagacgatgacggaaaaagagatcgtggat
tacgtcgccagtcaagtaacaaccgcgaaaaagttgcgcggaggagttgt
gtttgtggacgaagtaccgaaaggtcttaccggaaaactcgacgcaagaa
aaatcagagagatcctcataaaggccaagaagggcggaaagatcgccgtg
taa and hluc+ has the following sequence:

(SEQ ID NO: 14)
atggccgatgctaagaacattaagaagggccctgctcccttctaccctct
ggaggatggcaccgctggcgagcagctgcacaaggccatgaagaggtatg
ccctggtgcctggcaccattgccttcaccgatgcccacattgaggtggac
atcacctatgccgagtacttcgagatgtctgtgcgcctggccgaggccat
gaagaggtacggcctgaacaccaaccaccgcatcgtggtgtgctctgaga
actctctgcagttcttcatgccagtgctgggcgccctgttcatcggagtg
gccgtggcccctgctaacgacatttacaacgagcgcgagctgctgaacag
catgggcatttctcagcctaccgtggtgttcgtgtctaagaagggcctgc
agaagatcctgaacgtgcagaagaagctgcctatcatccagaagatcatc
atcatggactctaagaccgactaccagggcttccagagcatgtacacatt
cgtgacatctcatctgcctcctggcttcaacgagtacgacttcgtgccag
agtctttcgacagggacaaaaccattgccctgatcatgaacagctctggg
tctaccggcctgcctaagggcgtggccctgcctcatcgcaccgcctgtgt
gcgcttctctcacgcccgcgaccctattttcggcaaccagatcatccccg
acaccgctattctgagcgtggtgccattccaccacggcttcggcatgttc
accaccctgggctacctgatttgcggctttcgggtggtgctgatgtaccg
cttcgaggaggagctgttcctgcgcagcctgcaagactacaaaattcagt
ctgccctgctggtgccaacctgttcagcttcttcgctaagagcaccctg
atcgacaagtacgacctgtctaacctgcacgagattgcctctggcggcgc
cccactgtctaaggaggtgggcgaagccgtggccaagcgctttcatctgc
caggcatccgccagggctacggcctgaccgagacaaccagcgccattctg
attccccagagggcgacgacaagcctggcgccgtgggcaaggtggtgcc
attcttcgaggccaaggtggtggacctggacaccggcaagaccctgggag
tgaaccagcgcggcgagctgtgtgtgcgcggccctatgattatgtccggc
tacgtgaataaccctgaggccacaaacgccctgatcgacaaggacggctg
gctgcactctggcgacattgcctactgggacgaggacgagcacttcttca
tcgtggaccgcctgaagtctctgatcaagtacaagggctaccaggtggcc
ccagccgagctggagtctatcctgctgcagcaccctaacattttcgacgc
cggagtggccggcctgcccgacgacgatgccggcgagctgcctgccgccg -continued
tcgtcgtgctggaacacggcaagaccatgaccgagaaggagatcgtggac tatgtggccagccaggtgacaaccgccaagaagctgcgcggcggagtggt gttcgtggacgaggtgcccaagggcctgaccggcaagctggacgcccgca agatccgcgagatcctgatcaaggctaagaaaggcggcaagatcgccgtg taa.

TABLE 9

Percent Identity

|  |  | hluc + ver2A8 | hluc + ver2B10 | luc+ | hluc+ |
|---|---|---|---|---|---|
| Divergence | hluc + ver2A8 |  | 79.6 | 74 | 86.6 |
|  | hluc + ver2B10 | 22.9 |  | 75.9 | 80.1 |
|  | luc+ | 30.4 | 27.8 |  | 77.4 |
|  | hluc+ | 14.7 | 22.5 | 25.7 |  |

TABLE 10

**Composition statistics of different *P.pyralis* luciferase gene versions**

|  | GC content | CG di-nucleotides |
|---|---|---|
| *H. sapiens* | 53% | — |
| luc | 45% | 99 |
| luc+ | 47% | 97 |
| hluc+ | 60% | 111 |
| hluc+ver2A1 | 66% | 151 |
| hluc+ver2B1 | 46% | 1 |
| hluc+ver2A6 | 58% | 133 |
| hluc+ver2B6 | 49% | 53 | hluc+ver2A1-hluc+ver2A5 have the following sequences (SEQ ID Nos.16-20):

```
hluc+ver2A1
AAAGCCACCATGGAGGACGCCAAGAACATCAAGAAGGGCCCCGCCCCTT
CTACCCCCTGGAGGACGGCACCGCCGGCGAGCAGCTGCACAAGGCCATGA
AGCGCTACGCCCTGGTGCCCGGCACCATCGCCTTCACCGACGCCCACATC
GAGGTGGACATCACCTACGCCGAGTACTTCGAGATGAGCGTGCGCCTGGC
CGAGGCCATGAAGCGCTACGGCCTGAACACGAACCACCGCATCGTGGTGT
GCAGCGAGAACAGCCTGCAGTTCTTCATGCCCGTGCTGGGCGCCCTGTTC
ATCGGCGTGGCCGTGGCCCCCGCCAACGACATCTACAACGAGCGCGAGCT
GCTGAACAGCATGGGCATCAGCCAGCCCACCGTGGTGTTCGTGAGCAAGA
AGGGCCTGCAGAAGATCCTGAACGTGCAGAAGAAGCTGCCCATCATCCAG
AAGATCATCATCATGGACAGCAAGACCGACTACCAGGGCTTCCAGAGCAT
GTACACCTTCGTGACCAGCCACCTGCCCGCCGGCTTCAACGAGTACGACT
TCGTGCCCGAGAGCTTCGACCGCGACAAGACCATCGCCCTGATCATGAAC
AGCAGCGGCAGCACCGGCCTGCCCAAGGGCGTGGCCCTGCCCCACCGCAC
CGCCTGCGTGCGCTTCAGCCACGCCCGCGACCCCATCTTCGGCAACCAGA
TCATCCCCGACACCGCCATCCTGAGCGTGGTGCCCTTCCACCACGGCTTC
GGCATGTTCACCACCCTGGGCTACCTGATCTGCGGCTTCCGCGTGGTGCT
GATGTACCGCTTCGAGGAGGAGCTGTTCCTGCGCAGCCTGCAGGACTACA
AGATCCAGAGCGCCCTGCTGGTGCCCACCCTGTTCAGCTTCTTCGCCAAG
AGCACCCTGATCGACAAGTACGACCTGAGCAAGCTCCACGAGATCGCCAG
CGGGGGCGCCCCCCTGAGCAAGGAGGTGGGCGAGGCCGTGGCCAAGCGCT
TCCACCTGCCCGGCATCCGCCAGGGCTACGGCCTGACCGAGACCACCAGC
GCCATCCTGATCACCCCCGAGGGCGACGACAAGCCCGGCGCCGTGGGCAA
GGTGGTGCCCTTCTTCGAGGCCAAGGTGGTGGACCTGGACACCGGCAAGA
CCCTGGGCGTGAACCAGCGCGGCGAGCTGTGCGTGCGCGGCCCCATGATC
ATCAGCGGCTACGTGAACAACCCCGAGGCCACCAACGCCCTGATCGACAA
GGACGGCTGGCTGCACAGCGGCGACATCGCCTACTGGGACGAGGACGAGC
ACTTCTTCATCGTGGACCGCCTGAAGAGCCTGATCAAGTACAAGGGCTAC
CAGGTGGCCCCCGCCGAGCTGGAGAGCATCCTGCTGCAGCACCCCAACAT
CTTCGACGCCGGCGTGGCCGGCCTGCCCGACGACGACGCCGGCGAGCTGC
CCGCCGCCGTGGTGGTGCTGGAGCACGGCAAGACCATGACCGAGAAGGAG
ATGGTGGACTACGTGGCCAGCCAGGTGACCACCGCCAAGAAGCTGCGCGG
CGGCGTGGTGTTCGTGGACGAGGTGCCCAAGGGCCTGACCGGCAAGCTGG
ACGCCCGCAAGATCCGCGAGATCCTGATCAAGGCCAAGAAGGGCGGCAAG
ATCGCCGTGTAATAATTCTAGA hluc+ver2A2
AAAGCCACCATGGAGGACGCCAAGAACATCAAGAAGGGCCCCAGCGCCATC
TACCCCCTGGAGGACGGCACCGCCGGCGAGCAGCTGCACAAGGCCATGAA
GCGCTACGCCCTGGTGCCCGGCACCATCGCCTTCACCGACGCACATATCG
AGGTGGACATCACCTACGCCGAGTACTTCGAGATGAGCGTTCGGCTGGCA
GAGGCTATGAAGCGCTATGGGCTGAACACCAACCATCGCATCGTGGTGTG
CAGCGAGAACAGCTTGCAGTTCTTCATGCCCGTGTTGGGTGCCCTGTTCA
TCGGCGTGGCTGTGGCCCCAGCTAACGACATCTACAACGAGCGCGAGCTG
CTGAACAGCATGGGCATCAGCCAGCCCACCGTCGTATTCGTGAGCAAGAA
AGGGCTGCAAAAGATCCTGAACGTGCAAAAGAAGCTGCCCATCATCCAAA
AGATCATCATCATGGACAGCAAGACCGACTACCAGGGCTTCCAAAGCATG
TACACCTTCGTGACCAGCCATTTGCCGCCCGGCTTCAACGAGTACGACTT
CGTGCCCGAGAGCTTCGACCGCGACAAGACCATCGCCCTGATCATGAACA
GTAGTGGCAGTACCGGCTTACCTAAGGGCGTGGCCCTAGCGCACCGCACC
GCCTGTGTCCGATTCAGTCATGCCCGCGACCCCATCTTCGGCAACCAGAT
CATCCCCGACACCGCTATCCTGAGCGTGGTGCCATTTCACCACGGCTTCG
GCATGTTCACCACCCTGGGCTACTTGATCTGCGGCTTCCGGGTCGTGCTG
ATGTACCGCTTCGAGGAGGAGCTATTTCTTGCGCAGCTTGCAAGACTACA
AGATTCAAAGCGCCCTGCTGGTGCCCACCCTGTTCAGTTTCTTCGCCAAG
AGCACCCTGATCGACAAGTACGACCTGAGCAACCTGCACGAGATCGCCAG
CGGCGGCGCCCCCGCTCAGCAAGGAGGTGGGCGAGGCCGTGGCCAAGCGCT
TCCACCTGCCCAGGCATCCGCCAGGGCTACGGCCTGACCGAGACAACCAGC
```

```
GCCATTCTGATCACCCCCGAGGGGACGACAAGCCTGGCGCAGTAGGCAA
GGTGGTGCGCTTCTTCGAGGCTAAGGTGGTGGACCTGGACACCGGTAAA
CCCTGGGTGTGAACCAGCGCGGCGAGCTGTGCGTCCGTGGCCCCATGATC
ATGAGCGGCTACGTTAACAACCCCGAGGCTACAAACGCCCTGATCGACAA
GGACGGCTGGCTGCACAGCGGCGACATCGCCTACTGGGACGAGGACGAGC
ACTTCTTCATCGTGGACCGGCTGAAGAGCCTGATCAAATACAAGGGCTAC
CAGGTAGCCCCAGCGGAACTGGAGAGCATCCTGCTGCAGCACCCCAACAT
CTTTCGACGCCGGGTCGCCGGCCTGCCCGACGACGATGCCGGCGAGCTG
CCCGCCGCAGTCGTGGTGCTGGAGCACGGTAAAACCATGACCGAGAAGGA
GATCGTGGACTATGTGGCCAGCCAGGTTACAACCGCCAAGAAGCTGCGCG
GCGGCGTGGTGTTCGTGGACGAGGTGCCTAAAGGCCTGACGGGCAAGTT
GGACGCCCGCAAGATCCGCGAGATTCTGATCAAGGCCAAGAAGGGCGGCA
AGATCGCCGTGTAATAATTTCTAGA
hluc+ver2A3
AAAGCCACCATGGAAGATGCCAAAAACATTAAGAAGGGCCCAGCGCCAT
TCTACCCACTCGAGGACGGCACCGCCGGCGAGCAGCTGCACAAAGCCATG
AAGCGCTACGCCCTGGTGCCCGGCACCATCGCCTTTACCGACGCACATAT
CGAGGTGGACATCACCTACGCCGAGTACTTCGAGATGAGCGTTCGGCTGG
CAGAGGCTATGAAGCGCTATGGGCTGAATACCAACCATCGCATCGTGGTG
TGCAGCGAGAATAGCTTGCAGTTCTTCATGCCCGTGTTGGGTGGCCTGT
TCATCGGTGTGGCTGTGGGCCCAGCTAACGACATCTACAACGAGCGCGAG
CTGCTGAACAGCATGGGCATCAGCCAGCCCACCGTCGTATTCGTGAGCAA
GAAAGGGCTGCAAAAGATCCTCAACGTGCAAAAGAAGCTACCGATCATAC
AAAAGATCATCATCATGGATAGCAAGACCGACTACCAGGGCTTCCAAAGC
ATGTACACCTTCGTGACCAGCCATTTGCCACCCGGCTTCAACGAGTACGA
CTTCGTGCCCGAGAGCTTCGACCGGGACAAAACCATCGCCCTGATCATGA
ACAGTAGTGGCAGTACCGGATTGCCCAAGGGCGTAGCCCTACCGCACCGC
ACCGCCTGTGTCCGATTCAGTCATGCCCGGGACCCCATCTTCGGCAACCA
GATCATCCCCGACACCGCTATCCTCAGCGTGGTGCCATTTCACCACGGCT
TCGGCATGTTCACCACGCTGGGCTACTTGATCTGCGGGTTTCGGGTCGTG
CTCATGTACCGCTTCGAGGAGGAGCTATTCTTGCGCAGCTTGCAAGACTA
TAAGATTCAAAGCGCCCTGCTGGTGCCCACACTGTTCAGCTTGTTCGCCA
AGAGCACTCTCATCGACAAGTACGACCTGAGCAACCTGCACGAGATCGCG
AGCGGCGGGGCGCCGCTCAGCAAGGAGGTGGGCGAGGCCGTGGCCAAGCG
CTTCCACCTACCAGGCATCCGCCAGGGCTACGGCCTGAGAGAAACAACCA
GCGCCATTCTGATCACCCCCGAAGGGGACGACAAGCCTGGCGCAGTAGGC
AAGGTGGTGCCCTTCTTCGAGGCTAAGGTGGTGGACTTGGACACCGGTAA
GACCCTGGGTGTGAACCAGCGCGGCGAGCTGTGCGTCCGTGGCCCCATGA
TCATGAGCGGCTAGGTTAACAACCCCGAGGCTACAAACGCTCTCATCGAG
AAGGACGGCTGGCTGCACAGCGGCGACATCGCCTAGTGGGACGAGGACGA GCACTTCTTCATCGTGGACCGGCTGAAGAGCCTGATCAAATACAAGGGCT
ACCAGGTAGCCCCAGCCGAACTGGAGAGCATCCTGCTGCAACACCCCAAC
ATCTTCGACGCCGGGGTCGCCGGCCTGCCCGAGGACGATGCCGGCGAGCT
GCCCGCCGCAGTCGTCGTGCTGGAGCACGGTAAAACCATGACCGAGAAGG
AGATCGTGGACTATGTGGCCAGCCAGGTTACAACCGCCAAGAAGCTGCGC
GGTGGTGTTGTGTTCGTGGACGAGGTGCCTAAAGGCCTGACGGGCAAGTT
GGACGCCCGCAAGATCCGGGAGATTCTCATTAAGGCCAAGAAGGGCGGCA
AGATCGCCGTGTAATAATTTCTAGA
hluc+ver2A4
AAAGCCACCATGGAAGATGGCAAAAAGATTAAGAAGGGCCCAGCGCCATT
TCTACCCACTCGAAGACGGCACCGCCGGCGAGCAGGTGCAGAAAGCCATG
AAGCGCTACGCCCTGGTGCCCGGCACCATCGCCTTTACCGACGCACATAT
CGAGGTGGACATTACCTACGCCGAGTACTTTCGAGATGAGCGTTCGGCTG
GCAGAAGCTATGAAGCGCTATGGGCTGAAGACCAACCATCGCATCGTGGT
GTGCAGCGAGAATAGCTTGCAGTTCTTTCATGCCCGTGTTGGGTGCCCTG
TTTCATCGGTGTGGCTGTGGCCCCAGCTAACGACATCTACAACGAGCGCG
AGCTGCTGAACAGCATGGGCATCAGCCAGCCGACCGTCGTATTCGTGAGC
AAGAAAGGGCTGCAAAAGATCCTCAACGTGCAAAAGAAGCTACCGATCAT
ACAAAAGATCATCATCATGGATAGCAAGACCGACTACCAGGGCTTCCAAA
GCATGTACACCTTCGTGACTTCCCATTTGCCACCCGGCTTCAACGAGTAC
GACTTCGTGCCCGAGAGCTTCGACCGGGACAAAACCATCGCCCTGATCAT
GAACAGTAGTGGCAGTACCGGATTGCCCAAGGGCGTAGCCCTACCGCACC
GCACCGCTTTGTGTCCGATTCAGTCATGCCCGCGACCCCATCTTCGGCAA
CCAGATCATCCCCGACACCGCTATCCTCAGCGTGGTGCCATTTCACCACG
GCTTCGGCATGTTCACCACGCTGGGCTACTTTGATCTGCGGCTTTCGGGT
CGTGCTCATGTACCGCTTCGAGGAGGAGCTATTCTTGCGCAGCTTGCAAG
ACTATAAGATTCAAAGCGCCCTGCTGGTGCCCACACTGTTCAGTTTCTTC
GCCAAGAGCACTCTCATCGACAAGTACGACCTAAGCAACTTGCACGAGAT
CGCCAGCGGCGGGGCGCCGCTCAGCAAGGAGGTGGGCGAGGCCGTGGGCA
AACGCTTCCACCTACCAGGCATCCGCCAGGGCTACGGCCTGACAGAAACA
ACCAGCGCCATTCTGATCACCCCCGAAGGGGACGAGAAGCCTGGCGCAGT
AGGCAAGGTGGTGCCCTTCTTCGAGGCTAAGGTGGTGGACTTGGACACCG
GTAAGACACTGGGTGTGAACCAGCGCGGCGAGCTGTGCGTCCGTGGCCCC
ATGATCATGAGCGGCTACGTTAACAACCCCGAGGCTACAAACGCTCTCAT
CGACAAGGACGGCTGGCTGCACAGCGGCGACATCGCCTACTGGGACGAGG
ACGAGCACTTCTTCATCGTGGACCGGCTGAAGAGCCTGATCAAATACAAG
GGCTACCAGGTAGCCCCAGGCGAACTGGAGAGCATCCTGCTGCAACACCC
CAACATGTTCGACGCCGGGGTCGCGGGCCTGCCCGACGACGATGCCGGCG
AGCTGCCCGCCGCAGTCGTCGTGCTGGAACACGGTAAAACCATGACCGAG
AAGGAGATCGTGGACTATGTGGCCAGCCAGGTAACAACCGCCAAGAAGCT
```

-continued

```
GCGCGGTGGTGTTGTGTTCGTGGACGAGGTGCCTAAAGGCCTGACGGGCA
AGTTGGACGCCCGCAAGATCCGCGAGATTCTCATTAAGGCCAAGAAGGGC
GGCAAGATCGCCGTGTAATAATTCTAGA
``` hluc+ver2A5

```
AAAGCCACCATGGAAGATGCCAAAAACATTAAGAAGGGCCCAGCGGCATT
CTACCCACTCGAAGACGGCACGGCCGGCGAGCAGCTGCAGAAAGCCATGA
AGCGCTACGCCCTGGTGCCCGGCAGCATCGCCTTTACCGACGCACATATC
GAGGTGGACATTACCTAGGCCGAGTACTTCGAGATGAGCGTTCGGCTGGC
AGAAGCTATGAAGCGCTATGGGCTGAACACCAACCATGGGATCGTGGTGT
GCAGCGAGAATAGCTTGCAGTTCTTCATGCCCGTGTTGGGTGCCCTGTTC
ATCGGTGTGGCTGTGGGCCCAGCTAACGACATCTACAACGAGCGCGAGCT
GCTGAACAGCATGGGCATCAGCCAGCCCACCGTCGTATTGGTGAGCAAGA
AAGGGCTGCAAAAGATCCTCAACGTGCAAAAGAAGCTACCGATGATACAA
AAGATCATCATCATGGATAGCAAGACCGACTAGCAGGGCTTCCAAAGCAT
GTAGACCTTCGTGACTTCCCATTTGCCACCCGGCTTCAACGAGTACGACT
TCGTGCCCGAGAGCTTCGACCGGGACAAAACGATCGCCCTGATCATGAAC
AGTAGTGGCAGTACCGGATTTGGCCAAGGGCGTAGCCCTACCGGACCGCA
CCGCTTGTGTCCGATTGAGTCATGCCCGGGACCCGATCTTCGGCAACCAG
ATCATCCGCGAGACCGCTATCCTCAGCGTGGTGCGATTTTGAGCACGGGT
TTCGGCATGTTCACCACGCTGGGCTACTTGATCTGCGGCTTTCGGGTCGT
GCTGATGTACCGCTTCGAGGAGGAGCTATTCTTGCGGAGCTTGGAAGACT
ATAAGATTTCAAAGCGCCTGCTGGTGCCCACACTGTTCAGATTCTTCGC
TAAGAGCACTCTCATCGACAAGTACGAGGTAAGCAACTTTGCAGGAGATC
GGGAGCGGCGGGGCGCCGCTCAGCAAGGAGGTGGGCGAGGCCGTGGCCAA
ACGCTTTCCACGTACCAGGCATCCGCCAGGGCTACGGCCTGACAGAAACA
ACCAGCGCCATTCTGATCACCCCCGAAGGGGACGACAAGCCTGGCGCAGT
AGGCAAGGTGGTGCCCTTCTTCGAGGCTAAGGTGGTGGACTTGGACACCG
GTAAGACAGTGGGTGTGAACCAGCGCGGCGAGCTGTGCGTCCGTGGCCCC
ATGATCATGAGCGGCTAGGTTAACAACCCCGAGGCTACAAACGCTCTCAT
CGACAAGGAGGCTGGCTGCACAGCGGCGACATCGCCTACTGGGACGAGG
ACGAGCACTTCTTCATCGTGGACCGGCTGAAGAGCCTGATCAAATACAAG
GGCTACCAGGTAGCCCCAGCCGAACTGGAGAGCATCCTGCTGCAACACCC
CAACATCTTTCGACGCCGGGGTCGCCGGCCTGCCCGACGACGATGCCGGC
GAGGTGCCCGCCGCAGTCGTCGTGCTGGAAGACGGTAAAAGCATGACGGA
GAAGGAGATCGTGGACTATGTGGCCAGCCAGGTTACAACCGCCAAGAAGC
TGCGCGGTGGTGTTGTGTTCGTGGACGAGGTGCCTAAAGGCCTGACGGGC
AAGTTGGACGCCCGCAAGATCCGCGAGATTCTCATTAAGGCCAAGAAGGG
CGGCAAGATCGCCGTGTAATAATTCTAGA
``` hluc+ver2A6 has the following sequence (SEQ ID NO:21)
```
AAAGCCACCATGGAaGAtGCCAAaAACATtAAGAAGGGCCCaGCgCCaTT
CTACCCaCTCGAaGACGGCACCGCCGGCGAGCAGCTGCACAAaGCCATGA
AGCGCTACGCCCTGGTGCCCGGCACCATCGCCTTtACCGACGCaCAtATC
GAGGTGGACATtACCTACGCCGAGTACTTCGAGATGAGCGTtCGgCTGGC
aGAaGCtATGAAGCGCTAtGGgCTGAAtACaAACCAtCGgATCGTGGTGT
GCAGCGAGAAtAGCtTGCAGTTCTTTCATGCCCGTGtTGGGtGCCCTGTT
CATCGGtGTGGCtGTGGCCCCaGCtAACGACATCTACAACGAGCGCGAGC
TGCTGAACAGCATGGGCATCAGCCAGCCCACCGTCGTaTTCGTGAGCAAG
AAaGGgCTGCAaAAGATCCTCAACGTGCAaAAGAAGCTaCCgATCATaCA
aAAGATCATCATCATGGAtAGCAAGACCGACTACCAGGGCTTCCAaAGCA
TGTACACCTTCGTGACttCCCAttTGCCaCCCGGCTTCAACGAGTACGAC
TTCGTGCCCGAGAGCTTCGACCGgGACAAaACCATCGCCCTGATCATGAA
CAGtAGtGGCAGtACCGGatTgCCCAAGGGCGTaGCCCTaGCgCACCGCA
CCGCtTGtGTcCGatPTCAGtCAtGCGCGCGACCCCATCTTCGGCAACCA
GATCATCCCCGACACCGCtATCCTcAGCGTGGTGCCaTTtCACCACGGCT
TTCGGCATGTTCACCACgCTGGGCTACtTGATCTGCGGCTTtCGgGTcGT
GCTcATGTACCGCTTCGAGGAGGAGCTaTTCtTGCGCAGCtTGCAaGAGT
AtAAGATtCAaAGCGCCCTGCTGGTGCCCACaCTGTTCAGtTTTCTTCGC
tAAGAGCACtCTcATCGACAAGTACGACCTaAGCAACtTGCACGAGATCG
CCAGCGGCGGgGCgCCgTcAGCAAGGAGGTaGGtGAGGCCGTGGCCAAa
GGGTTTCCACCTaCCaGGCATCCGCCAGGGCTACGGCCTGACaGAaACaA
CCAGCGCCATtCTGATCACCCCCGAaGGgGACGACAAGCCtGGCGCaGTa
GGCAAGGTGGTGCCCTTCTTCGAGGCtAAGGTGGTGGACtTGGACACCGG
tAAgACaCTGGGtGTGAACCAGCGCGGCGAGCTGTGCGTcCGtGGGCCCA
TGATGATGAGCGGCTAGGTtAACAACCCCGAGGCtACaAACGCtCTcATC
GACAAGGACGCTGGCTGCACAGCGGCGACATGGCCTACTGGGACGAGGA
CGAGCACTTCTTCATCGTGGACCGgCTGAAGAGGCTGATCAAaTACAAGG
GCTAGCAGGTaGCGCCaGCCGAaGTGGAGAGGATCCTGCTGCAaCACCGC
AACATCTTGGACGCCGGgGTcGCCGGCGTGCCCGACGAGGAtGCCGGCGA
GCTGCCCGCGGCaGTcGTcGTGGTGGAaCACGGtAAaAGCATGACCGAGA
AGGAGATCGTGGACTAtGTGGCCAGCCAGGTtACaACCGCCAAGAAGCTG
CGCGGtGGtGTtGTGTTCGTGGAGGAGGTGCCtAAaGGCCTGACgGGCAA
GtTGGACGCCGGCAAGATCCGCGAGATtCTcATtAAGGCCAAGAAGGGGG
GCAAGATCGCCGTGTAATAATTTCTAGA.
```

The hluc+ver2A6 sequence was modified yielding hluc+ver2A7:

(SEQ ID NO:22)
```
AAAGCCACCATGGAaGAtGCCAAaAACATtAAGAAGGGCCCaGCgCCaTT
TCTACGGaCTcGAaGACGGgACCGCCGGCGAGGAGCTGCACAAaGCCATG
AAGCGCTACGCCCTGGTGCCCGGGACCATCGCCThACCGACGCaCAtATC
GAGGTGGACATtACCTACGCCGAGTACTTCGAGATGAGCGTtCGgCTGGC
aGAaGCtATGAAGCGCTAtGGgCTGAAtACaAACCAtCGgATCGTGGTGT
GCAGCGAGAAtAGCtTGCAGTTCTTCATGCCCGTGtTGGGtGCCCTGTTC
ATCGGtGTGGCIGTGGCCCCaGCtAACGACATCTACAACGAGCGCGAGCT
GCTGAACAGCATGGGCATCAGCCAGCCCACCGTcGTaTTCGTGAGCAAGA
AaGGgCTGCAaAAGATCCTcAACGTGCAaAAGAAGCTaCCgATCATaCAa
AAGATCATCATCATGGAtAGCAAGACCGAGTACCAGGGCTTCCAaAGCAT
GTAGACCTTCGTGACttcCCAttTGCCaCCCGGCTTCAACGAGTACGAGT
TGGTGCCCGAGAGCTTCGACCGgGACAAaACCATCGCCCTGATCATGAAC
AGtAGtGGCAGtACCGGatTgGGcAAGGGCGTaGCCCTaCCgCACCGCAC
CGCtTGtGTcCGaTTCAGtCAtGCCCGGGACCCCATCTTCGGCAACCAGA
TCATCCCCGACACCGCtATCCTcAGGGTGGTGCCaTTtCACCACGGCTTC
GGCATGTTCACCACgCTGGGCTACtTGATCTGCGGCTTTtCGgGTcGTGC
TcATGTACCGCTTCGAGGAGGAGCTaTTCtTGCGGAGCtTGCAaGACTAt
AAGATtCAatctGCCCTGCTGGTGCCCACaCTaTTtAGcTTCTTCGCtAA
GAGCACtCTcATCGACAAGTACGACCTaAGCAACtTGCACGAGATCGCCA
GCGGCGGgGCgCCgGTcAGCAAGGAGGTaGGtGAGGcCGTGGCCAAaCGC
TTTCCACCTaCCaGGCATCCGCCAGGGCTACGGCCTGACaGAaACaACCA
GCGCCATtGTGATCACCCCCGAaGGgGACGACAAGCCtGGCGCaGTaGGC
AAGGTGGTGCCCTTCTTCGAGGCtAAGGTGGTGGACtTGGACACCGGtAA
gACaCTGGGtGTGAACCAGCGCGGCGAGCTGTGCGTcCGtGGCCGCATGA
TGATGAGCGGCTACGTtAACAACCCCGAGGCtACaAACGCtCTcATCGAC
AAGGAGGGCTGGCTGCACAGCGGCGACATCGCCTACTGGGACGAGGACGA
GCACTTCTTTCATCGTGGACCGgGTGAAGAGCCTGATCAAaTACAAGGGC
TACCAGGTaGCCCCaGCCGAaCTGGAGAGCATCCTGCTGCAacACCCCAA
CATCTTCGACGCCGGgGTcGCGGGCCTGCCCGACGACGAtGCCGGCGAGC
TGcccGccGCaGTcGTcGTGCTGGAaCACGGtAAaACCATGAGCGAGAAG
GAGATCGTGGACTAtGTGGCCAGCCAGGTtACaACCGCCAAGAAGCTGCG
CGGtGGtGTtGTGTTCGTGGACGAGGTGCCtAAaGGCGTGACgGGCAAGt
TGGACGCCCGCAAGATCCGCGAGATtCTCATtAAGGCCAAGAAGGGCGGC
AAGATCGCCGTGTAATAATTCTAGA.
```

For vectors with a BglI site in the multiple cloning region, the BglI site present in the firefly sequence can be removed. The luciferase gene from hluc+ver2AF8, which lacks a BglI site, displays an average of a 7.2-fold increase in expression when assayed in four mammalian cell lines, i.e., NIH3T3, CHO, HeLa and HEK293 cells.

hluc+ver2A8 has the following sequence:

(SEQ ID.NO:23)
```
AAAGCCACCATGGAaGAtGCCAAaAACATtAAGAAGGGCCCaGCgCCaTT
CTACCCaCTcGAaGACGGgACCGCCGGCGAGCAGCTGcACAAaGCcATGA
AGCGCTACGCCCTGGTGCGCGGCACCATCGCCTTtACCGACGCaCAtATC
GAGGTGGACATtACCTACGCCGAGTACTrCGAGATGAGCGTtCGgCTGGC
aGAaGCtATGAAGGGCTAtGGgGTGAAtACaAACCAtCGgATcGTGGTGT
GCAGCGAGAAtAGCtTGGAGTTGTTCATGCCCGTGtTGGGtGCCCTGTTC
ATCGGtGTGGCtGTGGCCCCaGCtAACGACATCTACAACGAGCGCGAGCT
GGTGAACAGCATGGGCATCAGCCAGCCCACCGTcGTaTTCGTGAGCAAGA
AaGGgCTGCAaAAGATCCTcAACGTGCAaAAGAAGcTaccgATCATaCAa
AAGATCATGATCATGGAtAGcAAGAccGAcTAccAGGGCTTCCAaAGGAT
GTACACCTTCGTGACttcCCAttTGCCaCCCGGCTTCAACGAGTACGACT
TCGTGCCCGAGAGCTTCGACCGgGACAAaACCATCGcCCTGATCATGAAC
AGtAGtGGCAGtACCGGatTgCCcAAGGGCGTaGCCCTaCCgCACCGCAC
CGGtTGtGTcCGaTTCAGtCAtGCCCGcGACCccATcTTCGGGAACCAGA
TCATCCCCGACACCGCtATCCTcAGCGTGGTGCCaTTtCACCACGGCTTT
CGGCATGTTTCACCACgCTGGGGTACtTGATCTGcGGCTtCGgGTCGTGC
TCATGTACCGGTTCGAGGAGGAGCTaTTCtTGCGCAGCtTGCAaGACTAt
AAGATtCAatctGCCCTGCTGGTGCCCACaCTaTTtAGcTTCTTCGCtAA
GAGCACtCTCATCGACAAGTACGACCTaAGCAACtTGCACGAGATCGCCA
GCGGCGGgGCgCCgCTcAGCAAGGAGGTaGGtGAGGcCGTGGCCAAaCGC
TTGCACCTaCCaGGCATCCGCCAGGGCTACGGCCTGACaGAaACaACCAG
CGCCATtCTGATCACCCGCGAaGGgGACGAcGcCtGGCGCaGTaGGCAAG
GTGGTGCGCTTCTTCGAGGGtAAGGTGGTGGACtTGGACACCGGtAAgAC
aCTGGGtGTGAACCAGGGCGGCGAGGTGTGcGTcCGtGGCCCCATGATCA
TGAGCGGCTACGTtAACAACCCCGAGGCtACaAACGCtCTcATCGACAAG
GACGGCTGGCTGCACAGCGGCGACATCGCCTACTGGGACGAGGACGAGCA
CTTCTTCATCGTGGACCGgCTGAAGAGGGTGATCAAaTACAAGGGCTACC
AGGTaGCCCCaGCCGAaCTGGAGAGCATCCTGCTGCAaCACCCCAACATC
TTCGACGCCGGgGTcGCCGGCGTGCCCGACGACGAtGCCGGCGAGCTGCC
CGCCGCaGTcGTcGTGCTGGAaCACGGtAAaACCATGACCGAGAAGGAGA
TCGTGGACTAtGTGGCCAGCCAGGTtACaACGGCCAAGAAGCTGCGCGGt
GGtGTtGTGTTCGTGGAccccCGAGGTGCCtAAaGGaCTGACcGGCAAGtT
GGACGCCCGCAAGATCCGCGAGATtCTCATtAAGGCCAAGAAGGGCGGCA
AGATCGCCGTGTAATAATTCTAGA.
```

For the second approach, firefly luciferase luc+ codons were optimized for mammalian expression, and the number of consensus transcription factor binding site, and CG dinucleotides (CG islands, potential methylation sites) was reduced. The second approach yielded: versions hluc+ver2BF 1 through hluc+ver2BF5. hluc+ver2BF 1 is codon-optimized, hluc+ver2BF2 is a sequence obtained after a first round of removal of identified undesired sequences including transcription factor binding sites, hluc+ver2BF3 was obtained after a second round of removal of identified undesired sequences including transcription factor binding sites, hluc+ver2BF4 was obtained after a third round of removal of identified undesired sequences including transcription factor binding sites, hluc+ver2BF5 was obtained after a fourth round of removal of identified undesired sequences including transcription factor binding sites, hluc+ver2BF6 was obtained after removal of promoter modules and RBS, hluc+ver2BF7 was obtained after further removal of identified undesired sequences including transcription factor binding sites, and hluc+ver2BF8 was obtained after modifying a restriction enzyme recognition site.

hluc+ver2B1-B5 have the following sequences (SEQ ID Nos. 24-28):

```
hluc+ver2B1
AAAGCCACCATGGAGGATGCTAAGAATATTAAGAAGGGGCCTGCTCCTTT
TTATCCTCTGGAGGATGGGACAGCTGGGGAGCAGCTGCATAAGGCTATGA
AGAGATATGCTCTGGTGCCTGGGACAATTGCTTTTACAGATGCTCATATT
GAGGTGGATATTTACATATGCTGAGTATTTTTGAGATGTCTGTGAGACTG
GCTGAGGCTATGAAGAGATATGGGCTGAATACAAATCATAGAATTGTGGT
GTGTTCTGAGAATTGTTCTGCAGTTTTTTTTATGCCTGTGCTGGGGCTC
TGTTTATTGGGGTGGCTGTGGCTCCTGCTAATGATATTTATAATGAGAGA
GAGCTGCTGAATTCTATGGGGATTTCTCAGCCTACAGTGGTGTTTTGTGT
CTAAGAAGGGGCTGCAGAAGATTCTGAATGTGCAGAAGAAGCTGCCTATT
ATTCAGAAGATTATTATTATGGATTCTAAGACAGATTATCAGGGGTTTTC
AGTCTATGTATACATTTTGTGACATCTCATCTGCCTCCTGGGTTTAATGA
GTATGATTTTGTGCCTGAGTCTTTTGATAGAGATAAGACAATTGGTCTGA
TTATGAATTTCTTCTGGGTCTACAGGGCTGCCTAAGGGGTGGCTCTGCC
TCATAGAACAGCTTGTGTGAGATTTTCTCATGGTAGAGATCCTATTTTTT
GGGAATCAGATTATTCCTGATACAGCTATTCTGTCTGTGGTGCGTTTTCA
TCATGGGTTTGGGATGTTTACAACACTGGGGTATCTGATTTGTGGGTTTA
GAGTGGTGCTGATGTATAGATTTTGAGGAGGAGCTGTTTCTGAGATGTCT
GCAGGATTATAAGATTCAGTCTGGTCTGCTGGTGCCTAGACTGTTTTCTT
TTTTTGCTAAGTCTACACTGATTGATAAGTATGATCTGTCTAATCTGCAT
GAGATTGCTTCTGGGGGGGCTCCTCTGTCTAAGGAGGTGGGGGAGGCTGT
GGCTAAGAGATTTCATCTGCCTGGGATTAGACAGGGGTATGGGCTGACAG
AGACAACATCTGCTATTCTGATTACACCTGAGGGGGATGATAAGCCTGGG
GCTGTGGGGAAGGTGGTGGCTTTTTTTTTGAGGCTAAGGTGGTGGATCTG
GATACAGGGAAGACACTGGGGGTGAATCAGAGAGGGGAGCTGTGTGTGAG
AGGGCGTATGATTATGTCTGGGTATGTGAATAATCCTGAGGGTACAAATG
CTGTGATTGATAAGGATGGGTGGGTGCATTCTGGGGATATTGGTTATTGG
GATGAGGATGAGCATTTTTTTATTGTGGATAGACTGAAGTCTCTGATTAA
GTATAAGGGGTATCAGGTGGCTCCTGCTGAGCTGGAGTCTATTCTGCTGC
AGCATCCTAATATTTTTGATGCTGGGGTGGCTGGGCTGCGTGATGATGAT
GGTGGGGAGCTGCCTGCTGCTGTGGTGGTGCTGGAGCATGGGAAGACAAT
```

```
GACAGAGAAGGAGATTGTGGATTATGTGGCTTCTGAGGTGACAACAGCTA
AGAAGCTGAGAGGGGGGGTGGTGTTTGTGGATGAGGTGCCTAAGGGGCTG
ACAGGGAAGCTGGATGCTAGAAAGATTAGAGAGATTCTGATTAAGGCTAA
GAAGGGGGGAAGATTGCTGTGTAATAATTCTAGA hluc+ver2B2
AAAGCCACCATGGAAGATGCTAAAAACATTTTAAGAAGGGGCCTGCTCCT
TTTCTACCGTCTGGAGGATGGGACTGGGGGGAGCAGCTGCATAAAGCTA
TGAAGCGGTATGCTCTGGTGCCAGGCACAATTGCGTTCACGGATGCTCAC
ATTGAGGTGGACATTTACATACGCTGAGTATTTTGAGATGTCGGTGCGGC
TGGCTGAGGCTATGAAGCGATATGGGCTGAATACAAACCATAGAATTGTA
GTGTGCTCTGAGAACTCGTTGCAGTTTTTTTATGCCTGTGGTGGGGCTC
TGTTCATCGGGGTGGGTGTGGCTCCTGCTAACGAGATTTTTACAATGAGA
GAGAGCTTTTGAACTCGATGGGGATTTTTCTCAGCCTACAGTGGTGTTTT
GTGAGTAAGAAAGGGCTTCAAAAGATTTCTCAATGTGCAAAAGAAGCTGC
CTATTATTTTCAAAAGATTATTATTTTATGGACTCTAAGACAGACTACCA
GGGGTTTTCAGTCTATGTATACATTTGTGACATCTCATCTGCCTCCTGGG
TTCAACGAGTATGACTTTTGTGCCCGAGTCTTTCGACAGAGATAAGACAA
TTGCTCTGATTTATGAATTCATCTGGGTCTACCGGGCTGCCTAAGGGTGT
AGCTCTGCCACATAGAACAGCTTTGTGTGAGATTTTTCTCATGCTAGGGA
CCCTATTTTTTGGGAATCAGATTATTCCTGATACTGCTATTCTGTCGTT
TGTGCCCTTTCATCATGGGTTTTGGGATGTTTTACAACACTGGGCTACCT
GATATGTGGGTTTAGAGTGGTGCTCATGTATAGGTTTGAGGAGGAGCTTT
TTTTTTGGGCTCTCTGCAAGATTATAAGATTCAGTCTGCTCTGCTGGTGC
CTACACTGTLTTCTTTTTTTGCTAAGTCTACCCTGATCGATAAGTATGA
TCTGTCCAACCTGCACGAGATTGCTTTTCTGGGGGGGCTCCTCTGTCTAA
GGAGGTAGGTGAGGCTGTGGCTAAGCGCTTTCATCTGCCTGGAATCAGAC
AGGGGTATGGGCTAACAGAAACAACATCTGCTATTCTGATTTTACACCAG
AGGGGGATGATAAGCCCGGGGCTGTAGGGAAAGTGGTGCCCTTTTTTGAA
GCTAAAGTAGTTGATGTTGATACCGGTAAGCACTGGGGGTGAATCAGCG
AGGGGAACTGTGTGTGAGAGGGCCTATGATTATGTCGGGGTATGTGAACA
ACCCTGAGGCTACAAATGCTCTGATTGATAAGGATGGGTGGCTGCATTTC
GGGCGATATTGCTTACTGGGATGAGGATGAGCATTTCTTCATCGTGGACA
GACTGAAGTCGTTGATCAAATATAAGGGGTATCAAGTAGCTCCTGCTGAG
CTGGAGTCCATTCTGCTTCAACATCCTAACATTTTCGATGCTGGGGTGGC
TGGGGTGGCTGATGATGATGCTGGGGAGCTGCCTGCTGCTGTAGTGGTGC
TGGAGCACGGTAAGACAATGACAGAGAAGGAGTTGTGGATTTATGTGGC
TTCACAAGTGACAACAGCTAAGAAACTGAGAGGTGGCGTTGTGTTTTGTG
GATGAGGTGCCTAAAGGGCTGACAGGCAAGCTGGATGCTAGAAAAATTTT
CGAGAGATTCTGATTAAGGCTAAGAAGGGTGGAAAGATTGCTGTGTAATA
GTTCTAGA
``` hluc+ver2B3

AAAGCCACCATGGAAGATGGTAAAAACATTTAAGAAGGGGCCTGCTCCTT
TCTAGCCTCTTGAAGATGGGACTGCTGGCGAGCAACTTCACAAAGCTATG
AAGCGGTATGCTCTTTGTGCCAGGCACAATTGCGTTCACGGATGCTCACA
TTGAGGTGGACATCACATACGCTGAGTATTTTGAGATGTCGGTGCGGCTG
GCAGAAGCTATGAAGCGCTATGGGCTGAATACAAACCATAGAATTGTAGT
GTGCAGTGAGAACTCGTTTTGCAGTTCTTTATGCCCGTGCTGGGGCTCT
CTTTCATCGGGTGGCTGTGGCTGCTGCTAACGACATCTACAACGAGCGA
GAGCTGTTGAACTCGATGGGATTTCTCAGCCTACAGTGGTGTTTTGTGA
GTAAGAAAGGGCTTCAAAAGATTCTCAATGTGCAAAAGAAGCTGCCTATT
TTATTTTCAAAAGATTATTATTATGGACTCTAAGACCGACTACCAGGGGT
TTCAGTCTATGTATACATTTTGTGACATCTCATCTGCCTCCTGGCTTCAA
CGAGTACGACTTCGTGCCCGAGTCTTTCGACAGAGATAAGACAATTGCTC
TGATCATGAATTTCATCCGGGTCTACCGGGCTGCCTAAGGGTGTAGCTCT
GCCCCATAGAACAGCTTTTGTGTGAGATTTTCTCATGCTAGGGACCCTAT
TTTTTGGGAATCAGATTATTCCTGACACTGCTATTGTGTCGGTGGTGCCC
TTTCATCATGGGTTTTGGGATGTTTACAACACTGGGCTACCTAATATGTG
GGTTTTAGAGTGGTGCTCATGTATAGGTTTTGAAGAAGAGCTGTTCTTAC
GCTCTTTGCAAGATTATAAGATTCAGTCTGCTCTGCTGGTGCCAACACTA
TTCTCTTTTTTTGCTAAGTCTAGGCTCATAGACAAGTATGACTTTGTCCA
ACTTTGCACGAGATTGCTTCTGGCGGAGCAGCTCTGTCTAAGGAGGTAGG
TGAGGCTGTGGCTAAGCGCTTTTCATCTGCCTGGTATCAGACAGGGGTAT
GGGCTAACAGAAACAACATCTGCTATITCTGATTACACCAGAGGGGGATG
ATAAGCCCGGGGCTGTAGGGAAAGTGGTGCCCTTTTTTGAAGCCAAAGTA
GTTGATCTTGATACCGGTAAGACACTAGGGGTGAACCAGCGTGGTGAACT
GTGTGTGAGAGGGCCTATGATTATGTCGGGGTACGTTAACAACCCCGAAG
CTACAAATGCTCTGATTGATAAGGATGGCTGGCTGCATTCGGGCGACATT
GCTTACTGGGATGAGGATGAGCATTTTTTCATCGTGGACAGACTGAAGTC
GTTGATCAAATACAAGGGGTATCAAGTAGCTCCTGCTGAGCTGGAATCCA
TTCTGCTTCAACATCCCAACATTTTCGATGCTGGGGTGGCTGGGCTGCCT
GATGATGATGCTGGGGAGTTGCCTGCTGCTGTAGTGGTGCTTTGAGCACG
GTAAGACAATGACAGAGAAGGAGATCGTGGATTTATGTGGCTTCACAAGT
GACAACAGCTAAGAAACTGAGAGGTGGCGTTGTGTTTGTGGATGAGGTGC
CTAAAGGGCTCACTGGCAAGCTGGATGCTAGAAAAATTCGAGAGATTCTG
ATTAAGGCTAAGAAGGGTGGAAAGATTGCTGTGTAATAGTTCTAGA hluc+ver2B4

AAAGCCACCATGGAAGATGCTAAAAACATTAAGAAGGGGCCTGCTCCCTT
CTACCCTCTTGAAGATGGGACTGCTGGCGAGCAACTTCACAAAGCTATGA
AGCGGTATGCTCTTGTGCCAGGCACAATTTGCGTTCACGGATGCTCACAT
TGAGGTGGACATCACATACGCTGAGTATTTTGAGATGTCGGTGCGGCTGG
CAGAAGCTATGAAGCGCTATGGGCTGAATACAAACCATAGAATTGTAGTG
TGCAGTGAGAACTCGTTTTGCAGTTCTTTATGCCCGTGCTGGGGCTCTC
TTCATCGGGGTGGCTGTGGCTCCTGCTATTGACATCTACAACGAGCGAGA
GCTGTTGAACTCGATGGGATCTCTCAGCCTACAGTGGTGTTTGTGAGTA
AGAAAGGGCTTCAAAAGATTCTCAATGTGCAAAAGAAGCTGCCTATTATT
CAAAAGATTATTlTATTATGGACTCTAAGACAGACTACCAGGGGTTTCAG
TCCATGTATACATTTTGTGACATCTCATCTGCCTCCTGGCTTCAACGAGT
ACGACTTCGTGCCCGAGTCTTTCGACAGAGATAAGACAATTGCTCTGATC
ATGAATTCATCCGGGTCTACCGGGCTGCCTAAGGGTGTAGCTCTGCCCCA
TCGAACAGCTTGTGTGAGATTCTCTCATGCCAGGGACCCGATCTTTTTGG
AATCAGATTATTCCTGACACTGCTATTCTGTCGGTGGTGCCCTTTCATCA
TGGGTTTTGGGATGTTTACAACACTGGGATACCTAATATGTGGGTTTAGA
GTGGTGCTCATGTATAGGTTTGAAGAAGAACTGTTCTTACGCTCTTTGCA
AGATTATAAGATTCAGTCTGCTCTGCTGGTGCCAACACTATTCTCTTTTT
TTGCTAAGTCTACGCTCATAGACAAGTATGACTTGTCCAACTTGCACGAG
ATTGCTTCTGGCGGAGCACCTCTGTCTAAGGAGGTAGGTGAGGCTGTGGC
TAAGCGCTTTCATCTGCCTGGTATCAGACAGGGGTACGGGCTAACAGAAA
CAACTTCTGGTATTCTGATTACACCAGAGGGCGATGACAAGCCCGGGGCT
GTAGGGAAAGTGGTGCCCTTTTTTGAAGCCAAAGTAGTTGATCTTGATAC
CGGTAAGCACTAGGGGTGAACCAGCGTGGTGAACTGTGTGTGCGGGGCC
CTATGATTATGTCGGGGTACGTTAACAACCCCGAAGCTACAAATGCTCTT
ATTGATAAGGATGGCTGGYTGCATTCGGGCGACATTGCCTACTGGGATGA
GGATGAGCATTTCTTCATCGTGGACAGACTGAAGTCGTTTGATCAAATAC
AAGGGGTATCAAGTAGCTCCTGCTGAGCTGGAATCCATTCTGCTTCAACA
TCCAAACATTTTCGATGCTGGGGTGGCTGGGCTGCCTGATGATGATGCTG
GAGAGTTGCCTGCTGCTGTAGTAGTGCTTGAGCACGGTAAGACAATGACA
GAGAAGGAGATCGTGGATTATGTGGCTTTCACAAGTGACAACAGCTAAGA
AACTGAGAGGTGGCGYTGTGTTTGTGGATGAGGTGCCTAAAGGGCTCACT
GGCAAGCTGGATGCCAGAAAATTCGAGAGATTCTCATTAAGGCTAAGAAG
GGTGGAAGATTGCTGTGTAATAGTTTCTAGA hluc+ver2B5

AAAGCCACCATGGAAGATGCTAAAAACATTAAGAAGGGGCCTGCTCCCTT
CTACCCTCTTGAAGATGGGACTGCTGGCGAGCAACTTCACAAAGCTATGA
AGCGGTATGCTCTTGTGCCAGGCACAATTGCGTTCACGGATGCTCACATT
TGAGGTGGACATCACATACGCTGAGTATTTTGAGATGTCGGTGCGGCTGG
CAGAAGCTATGAAGCGCTATGGGCTGAATACAAACCATAGAATTGTAGTG
TGCAGTGAGAACTCGTTGCAGTTCTTTATGCCCGTGCTGGGGCTCTCTT
CATCGGGGTGGCTGTGGCTCCTGCTAACGACATCTACAACGAGCGAGAGG
TGTTGAACTCGATGGGATCTCTCAGCCTACAGTGGTGTTTGTGAGTAAG
AAAGGGCTTCAAAAGATTCTCAATGTGCAAAAGAAGCTGCCTATTATACA

AAAGATTATTATTATGGACTCTAAGAGCGACTACCAGGGGTTTCAGTCCA
TGTACACATTTGTAACCTCTCATCTGCCTCCTGGCTTCAACGAGTACGAC
TTCGTGCCCGAGTCTTTCGACAGGGACAAAACGATTTGCTCTGATCATGA
ACTCATCCGGGTCTACCGGGCTGCCTAAGGGTGTAGCTCTGCCGCATCGA
AGAGCTTGTGTGAGATTCTCTCATGCCAGGGACGCGATCTTTGGGAATCA
GATTATTCCTGACACTGCTATTCTGTCGGTGGTGCCCTTTCATCATGGGT
TTGGGATGTTCACAACACTGGGATACCTCATTTGCGGGTTTAGAGTGGTG
CTCATGTATAGGTTTGAAGAAGAACTATTCCTACGCTCTTTGCAAGATTA
TAAGATTCAGTCTGCTCTGCTGGTGCCAACACTATTCTCTTTTTTTGCTA
AGTCTACGCTCATAGACAAGTATGACTTGTCCAACTTGCACGAGATTGCT
TCTGGCGGAGCACCTCTGTCTAAGGAGGTAGGTGAGGCTGTGGCTTAAGC
GCTTTCATCTGCCTGGTATCAGACAGGGGTACGGGCTAACAGACCCTTCT
GCTATTCTGATTACACCAGAGGGCGATGACAAACCCGGGGCTGTAGGGAA
AGTGGTGCCGTTTTTTGAAGCCAAAGTAGTTGATCTTGATACCGGTAAGA
CACTAGGGGTGAACCAGCGTGGTGAACTGTGTGTGCGGGGCCCTATGATT
TATGTCGGGGTACGTTAACAACCGCGAAGCTACAAATGCTCTTATTGATA
AGGATGGCTGGTTGCATTCGGGCGACATTGCCTACTGGGATGAGGATGAG
CATTTCTTCATCGTGGACAGACTGAAGTCGTTGATCAAATACAAGGGGTA
TCAAGTAGCTCCTGCTGAGCTGGAATCCATTTCTGCTTCAACATCCTAAC
ATTTTCGATGCTGGGGTGGCTGGGCTGCCTGATGATGATGCTGGAGAGTT
GCCTGCTGCTGTAGTAGTGCTTGAGCACGGTAAGACAATGACAGAGAAGG
AGATCGTGGATTATGTGGCTTCACAAGTGACAACAGCTAAGAAACTGAGA
GGTGGCGTTGTGTTTGTGGATGAGGTGCCTAAAGGGCTGACTGGCAAGCT
GGATGCCAGAAAAATTCGAGAGATTCTCATTAAGGCTAAGAAGGGTGGAA
AGATTGCTGTGTAATAGTTCTAGA hluc+ver2B6 has the following sequence:

(SEQ ID NO:29)
AAAGCCACCATGGAaGATGCcAAaAAcATTAAGAAGGGGCCTGCTGCcTT
cTAcCCTCTtGAaGATGGGACtGCtGGcGAGCAaCTtCAcAAaGCTATGA
AGcGgTATGCTCTtGTGCCaGGcACAATTGCgTTTcACgGATGCTCAcAT
TGAaGTaGACATCACATACGCTGAGTATTTTGAGATGTCgGTGCGgCTGG
CaGAaGCTATGAAGcGcTATGGGCTGAATACAAAcCATAGAATTGTaGTG
TGcagTGAGAAcTGgtTGCAGTTcTTTATGCCcGTGCTGGGGGCTCTcTT
cATcGGGGTGGCTGTGGCTCCTGCTAAcGAcATcTAcAAcGAGcGAGAGC
TgtTGAAcTCgATGGGGATcTCTCAGCCTACNGTGGTGTTTGTGagTAAG
AAaGGGCTtGAaAAGATTTCTcAATGTGCAaAAGAAGCTGCCTATTATaC
AaAAGATTATTATTATGGACTCtAAGACCGACTACCAGGGGTTTCAGTCC
ATGTAcACATTTGTaACcTCTCATCTGCCTCCTGGcTTcAAcGAGTAcGA
cTTcGTGCCcGAGTCTTTcGAcAGgGAcAAaACgATTGCTCTGATcATGA AcagcTCcGGGTCTACcGGGCTGCCTAAGGGtGTaGCTCTGCCCcATcGA
ACAGGTTGTGTGAGATTcTCTCATGCcAGgGAcCCgATcTTtGGaAAcGA
GATcATcCCTGAcACtGCTATTCTGTCgGTgGTGCCcTTTCATCATGGGT
TTGGGATGTTcACAACACTGGGaTAccTcATtTGcGGGTTTAGAGTGGTG
CTcATGTATAGgTTTGAaGAaGAaCTaTTCCTaCGCTCTtTGCAaGATTA
TAAGATTCAGTCTGCTCTGCTGGTGCCaACACTaTTcTCTTTTTTTGCTA
AGTCTACgCTcATaGACAAGTATGACtTGTCCAACtTGCACGAGATTGCT
TCTGGCGGaGCaCCTCTGTCTAAGGAGGTaGGtGAGGCTGTGGCTAAGCG
cTTTCATCTGCCTGGtATcAGACAGGGGTAcGGGCTaACAGAaACAACtT
CTGCTATTCTGATTACACCaGAGGGcGATGAcAAaCCcGGGGCTGTaGGG
tttaGTGGTGGCCTTTTTTGAaGCCAAaGTaGTtGATCTtGATACCGGtA
AGACACTaGGGGTGAAcCAGcGtGGtGAaCTGTGTGTGcGgGGcCCTATG
ATTATGTCgGGGTAcGTtAAcAAcGCcGAaGCTACAAATGCTCTcATaGA
cAAGGAcGGgTGGcTtCATagCGGCGACATTGCCTACTGGGACGAGGATG
AGCATTTCTTcATCGTGGAcAGACTGAAGTCgtTGATcAAaTAcAAGGGG
TATCAaGTaGCTCcTGcTGAGCTGGAaTCcATTCTGCTtCAaCAcCCcAA
tATcTTcGATGCTGGGGTGGCTGGGCTGCCTGATGATGATGCTGGaGAGc
TGCCTGCTGCTGTaGTaGTGCTtGAGCACGGtAAGACAATGACAGAGAAG
GAGATCGTGGATTATGTGGGTTCaCAaGTGACAACAGCTAAGAAaCTGAG
AGGtGGcGTtGTGTTTTGTGGATGAGGTGCCTAAaGGGCTcACtGGcAAG
CTGGATGCcAGAAAaNTTcGAGAGATTCTcATTAAGGCTAAGAAGGGtGG
aAAGATTGCTGTGTAATAgTTCTAGA.

hluc+ver2BF8 was created by removing a Ptx1 consensus transcription factor binding site from hluc+ver2BF7.

hluc+ver2B7 has the following sequence:

(SEQ ID NO:94)
AAAGCCACCATGGAAGATGCCAAAAACATTAAGAAGGGGCCTGCTCGCTT
CTACGGTCTTGAAGATGGGACTGGTGGCGAGCAACTTCACAAAGCTATGA
AGCGGTATGCTCTTGTGCCAGGGACAATTGCGTTCACGGATGCTCACATT
GAAGTAGACATCACATACGCTGAGTATTTTGAGATGTCGGTGCGGCTGGC
AGAAGCTATGAAGCGCTATGGGCTGAATACAAACCATAGAATTGTAGTGT
GCAGTGAGAACTCGTTGCAGTTCTTTATGCCCGTGCTGGGGGCTGTCTTC
ATCGGGGTGGCTGTGGCTCCTGCTAACGACATCTACAACGAGCGAGAGCT
GTTGAACTCGATGGGGATCTCTCAGCCTACAGTGGTGTTTGTGAGTAAGA
AAGGGCTTCAAAAGATTCTCAATGTGCAAAAGAAGCTGCCTATTATACAA
AAGATTATTATTATGGACTCTAAGACAGACTACCAGGGGTTTCAGTGCA
TGTACACATTTGTAACCTCTCATCTGCCTCCTGGCTTCAACGAGTACGAC
TTCGTGCCCGAGTCTTTCGACAGGGACAAAAGGATTGCTCTGATCATGAA
CAGCTCCGGGTCTACCGGGTGCCTAAGGGTGTAGCTCTGCCCCATCGAA
CAGCTTGTGTGAGATTTCTCTCATGCCAGGGACCCGATCTTTGGAAACCA

```
GATCATCCCTGACACTGCTATTCTGTCGGTGGTGCGGTTTCATCATGGGT
TTGGGATGTTCACAACACTGGGATACCTCATTTGCGGGTTTAGAGTGGTG
GTCATGTATAGGTTTGAAGAAGAACTATTCCTACGCTCTTTGCAAGATTA
TAAGATTCAGTCTGCTCTGCTGGTGCGAACACTATTGTCTTTTTTTGCTA
AGTCTACGGTCATAGACAAGTATGACTTGTCCAACTTGCACGAGATTGCT
TCTGGCGGAGCACCTCTGTGTAAGGAGGTAGGTGAGGCTGTGGCTAAGCG
CTTTCATCTGCCTGGTATCAGACAGGGGTACGGGCTAACAGAAACAACTT
CTGCTATTCTGATTACACCAGAGGGCGATGACAAACCCGGGGCTGTAGGG
AAAGTGGTGCCCTTTTTTGAAGCCAAAGTAGTTGATCTTGATACCGGTA
AGACACTAGGGGTGAACCAGCGTGGTGAACTGTGTGTGCGGGGCCCTATG
ATTATGTGGGGGTACGTTAACAAGCCCGAAGCTACAAATGCTCTCATAGA
CAAGGACGGGTGGCTTCATAGCGGCGACATTGCCTACTGGGACGAGGATG
AGCATTTCTTCATCGTGGACAGACTGAAGTCGTTGATCAAATACAAGGGG
TATCAAGTAGCTCCTGCCGAGCTTGAGTCCATTCTGCTTCAACACCCCAA
TATCTTCGATGCTGGGGTGGCTGGGCTGCCTGATGATGATGCTGGAGAGC
TGCCTGCTGCTGTAGTAGTGCTTGAGCATGGTAAGACAATGACAGAGAAG
GAGATCGTGGATTATGTGGCTTCACAAGTGACAACAGCTAAGAAACTCCG
AGGTGGCGTTGTGTTTGTGGATGAGGTGCCTAAAGGGGTCACTGGCAAGC
TGGATGCGAGAAAAATTTCGAGAGATTCTCATTAAGGCTAAGAAGGGTGG
AAAGATTGCTGTGTAATAGTTCTAGA
``` hluc+ver2B8 has the following sequence (SEQ D NO:31)
```
AAAGCCACCATGGAaGATGCcAAaAAcATTAAGAAGGGGCCTGCTGCcTT
TcTAcGCTCTtGAaGATGGGAGtGCtGGcGAGCAaCTtCAcAAaGCTATG
AAGcGgTATGCTCTtGTGCCaGGgAGAATTGCgTTcACgGATGCTCAcAT
TGAaGTaGAcATcACATAcGCTGAGTAThTTGAGATGTCgGTGcGgCTGG
CaGAaGCTATGAAGcGcTATGGGCTGAATAGAAAcCATAGAATTTTGTaG
TGTGcagTGAGAAcTCgtTGCAGTTcTTTATGCCcGTGCTGGGGCTCTc
TTcATcGGGGTGGGTGTGGCTCCTGCTAAcGAcATcTAcAAcGAGcGAGA
GCTgtTGAAcTCgATGGGGATcTCTCAGGCTACAGTGGTGTTTGTGagTA
AGAAaGGGCTtCAaAAGATTGTcAATGTGGAaAAGAAGCTaCCgATcATa
CAaAAGATcATcATcATGGAt agcAAGACcGAcTAcCAGGGGTTTTCAGT
CcATGTAcACATTTGTaACcTCTCATCTGCCTCCTGGcTTcAAcGAGTAc
GAcTTcGTGCCcGAGTCTTTcGAcAGgGAcAAaACgATTGCTCTGATcAT
GAAcagcTCcGGGTCTACcGGGCTGGCTAAGGGtGTaGCTGTGCCcATc
GAACAGCTTGTGTGAGATTcTCTCATGCcAGgGAcCCgATcTTtGGaAAc
CAGATcATcCCTGAcACtGCTATTCTGTCgGTgGTGCCcTTTCATCATGG
GTTTGGGATGTTcACAACACTGGGaTAccTcATtTGcGGGTTTAGAGTGG
TGGTcATGTATAGgTTTGAaGAaGAaCTaTTTccTacGcTCTtGCAaGAa
```

-continued
```
GATTTATAAGATTTCAGTCTGCTCTGCTGGTGCCaACACTaTTcTCTTTT
TTTTGCTAAGTCTACgCTcATaGAcAAGTATGActTGTCcAActTGCAcG
AGATTGCTTCTGGcGGaGCaCCTCTGTCTAAGGAGGTaGGtGAGGCTGTG
GCTAAGcGcTTCATCTGCCTGGtATcAGACAGGGGTACGGGCTaACAGAa
ACAACtTCTGCTATTTCTGATTACACCaGAGGGcGATGAcAAaCCtGGGG
CTGTaGGGAAaGTGGTGCCcTTTTTTGAaGCcAAaGTaGTtGATCTtGAT
ACcGGtAAGACACTaGGGGTGAAcGAGcGtGGtGAaCTGTGTGTGcGgGG
cCCTATGATTATGTCgGGGTAcGTtAAcAAcCCcGAaGCTACAAATGGTC
TcATaGAcAAGGAcGGgTGGcTtCATagcGGcGAcATTTGGcTAcTGGGA
cGAGGATGAGGATTT1TcTTcATcGTGGAcAGACTGAAGTCgtTGATcAA
aTAcAAGGGGTATCAaGTaGCTCCTGCcGAGCTtGAgTCcATTCTGCTtC
AaCAcCCcAAtATcTTcGATGCTGGGGTGGCTGGGCTGCCTGATGATGAT
GCTGGaGAGcTGCCTGCTGGTGTaGTaGTGGTtGAGCAtGGtAAGACAAT
GACAGAGAAGGAGATcGTGGATTATGTGGCTTCaCAaGTGACAACAGCTA
AGAAaCTccGAGGtGGcGTtGTGTTTGTGGATGAGGTGCCTAAaGGGGTc
ACtGGcAAGCTGGATGCcAGAAAaATTcGAGAGATTCTcATTAAGGCTAA
GAAGGGtGGaAAGATTTGCTGTGTAATAgTTCTAGA.
``` hluc+ver2BF8 was modified to yield hluc+ver2BF9. hluc+ver2B9 has the following sequence (SEQ ID NO:32)
```
AAAGCCACCATGGAaGATGCcAAaAAcATTAAGAAGGGGCCTGCTCCcTT
cTAcCCTCTtGAaGATGGGACtGCtGGcGAGCAaCTtCAcAAaGCTATGA
AGcGgTATGCTCTtGTGCCaGGgACAATTGCgTTcACgGATGCTGAcATT
GAaGTaGACATCACATACGCTGAGTATTETGAGATGTCgGTGCGgCTGGC
aGAaGCTATGAAGcGcTATGGGCTGAATACAAAcCATAGAATTGTaGTGT
GcagTGAGAAcTCgtTGCAGTTcTTTATGCCcGTGCTGGGGGCTcTcTTc
ATtGGGGTGGCTGTGGCTCCTGCTAAtGAcATcTAcAAcGAGcGAGAGCT
gtTGAAcagtATGGGGATcTCTGAGCCTACAGTGGTGTTTGTGagTAAGA
aGGGCTtCAaAAGATTCTcAATGTGCAaAAGAAGCTaCCgATcATaCAaA
AGATcATcATcATGGAt agcAAGACcGAcTAcCAGGGGTTTTCAGTCcAT
GTAcACATTTGTaACcTCTCATCTGGCTCCTGGcTTcAAtGAGTAtGAcT
TcGTGCCcGAGTCTTTcGAcAGgGAcAAaACgATTGCTCTGATcATGAAc
agcagtGGGTCTAGcGGGCTGCCTAAGGGtGTaGCTCTGGGcGATcGAAC
AGCTTGTGTGAGATTcTCTCATGGcAGgGAcCCgATcTTtGGaAAcCAGA
TcATcCCTGAcACtGCTATTCTGTCgGTgGTGCCcTTTCATCATGGGTTT
GGGATGTTcACAACACTGGGaTAccTcATtTGcGGGTTTAGAGTGGTGCT
cATGTATAGgTTTGAaGAaGAaCTaTTccTacGcTCTtGCAaGATTATA
AGATTcAGTcTGGTCTGGTGGTGCCaACACTaTTcTCTTTTTTTGCTAAG
TCTACgCTcATaGACAAGTATGACtTGTCCAACtTGCACGAGATTGCTTC
TGGCGGaGCaCCTCTGTCTAAGGAGGTaGGtGAGGCTGTGGCTAAGcGcT
```

-continued
```
TTCATCTGCCTGGtATcAGACAGGGGTAcGGGCTaACAGAaACAACtTCT
GCTATTCTGATTAGACCaGAGGGcGATGAcAAaCCtGGGGCTGTaGGGAA
aGTGGTGCCcTTTTTTTGAaGCCAAaGTaGTtGATCTtGATACCGGtAAGA
CACTaGGGGTGAACCAGaGaGGtGAatTGTGTGTGaGgGGCCCTATGATT
TATGTCgGGGTACGTtAACAACCCCGAaGCTACAAATGCTCTCATaGACA
AGGACGGgTGGCTtCATagtGGaGAtATTGCCTACTGGGAtGAaGATGAG
CATTTCTTTCATCGTGGACAGACTGAAGTCgtTGATCAAaTACAAGGGGT
ATCAaGTaGCTCCTGCcGAGCTtGAgTCcATTCTGGTtCAaCAcCCcAAt
ATcTTcGATGCTGGGGTGGCTGGGGTGCCTGATGATGATGCTGGaGAGcT
GGGTGCTGCTGTaGTaGTGGTtGAGcAtGGtAAGACAATGACAGAGAAGG
AGATcGTGGATTATGTGGCTTCaCAaGTGACAACAGCTAAGAAaCTccGA
GGtGGcGTtGTGTTTTGTGGATGAGGTGCCTAAaGGGCTcACtGGcAAGC
TGGATGCcAGAAAaATTcGAGAGATTCTcATTTAAGGCTAAGAAGGGtGG
aAAGATTGCTGTGTAATAgTTCTAGA.
```

The BglI sequence in hluc+ver2BF9 was removed resulting in hluc+ver2BF10. hluc+ver2BF10 demonstrated poor expression.

hluc+ver2B10 has the following sequence

```
                                         (SEQ ID NO:33)
AAAGCCACCATGGAaGATGCcAAaAAcATTAAGAAGGGGCCTGCTCCcTT
cTAcCCTCTtGAaGATGGGACtGCtGGcGAGCAaCTtCAcAAaGCTATGA
AGcGgTATGCTCTtGTGGCaGGgACAATTGCGTTCACgGATGCTCAcATT
GAaGTaGAcATcACATAcGCTGAGTATTTGAGATGTCgGTGcGgCTGGCa
GAaGCTATGAAGcGcTATGGGCTGAATACAAAcCATAGAATTGTaGTGTG
cagTGAGAAcTCgtTGCAGTTcTTTTATGCCcGTGCTGGGGGCTGTcTTc
ATtGGGGTGGCTGTGTGGCTCCTGCTAAtGAcATcTAcAAcGAGcGAGAGCT
gtTGAAcagtATGGGGAtCTCTCAGCCTACAGTGGTGTTTGTGagTAAGA
AaGGGCTtCAaAAGATTCTcAATGTGCAaAAGAAGCTaCCgATcATaCAa
AAGATcATcATcATGGAtagcAAGACcGAcTAcCAGGGGTTTCAGTCcAT
GTAcACATTTGTaACcTCTCATCTGCCTCCTGGcTTcAAtGAGTAtGAcT
TcGTGCCcGAGTCTTTcGAcAGgGAcAAaACgATTGCTCTGATcATGAAc
agcagtGGGTCTAGcGGGCTGCCTAAGGGtGTaGCTCTGCCcCATcGAAC
AGCTTGTGTGAGATTcTCTCATGCcAGgGAcCCgAtCTTtGGaAAcCAGA
TcATcCCTGAcAGtGCTATTCTGTCgGTgGTGCCcTTTCATCATGGGTTT
GGGATGTTcACAACACTGGGaTAccTcATtTGcGGGTTTTAGAGTGGTGC
TcATGTATAGgTTTGAaGAaGAaCTaTTccTacGcTCTtTGCAaGATTAT
AAGATTCAGTCTGCTCTGCTGGTGCCaACACTaTTcTCTTTTTTTGCTAA
GTCTACgCTcATaGACAAGTATGActTGTCcAActTGCAcGAGATTGCTT
CTGGcGGaGCaCCTGTGTCTAAGGAGGTaGGtGAGGCTGTGGCTAAGcGc
TTTCATCTGCCTGGtATcAGACAGGGGGTAcGGGCTaACAGAaACAACtTC
```

-continued
```
TGCTATTCTGATTACACCaGAGGGcGATGAcAAaCCtGGGGCTGTaGGGA
AaGTGGTGCCcTTTTTTTTGAaGCcAAaGTaGTtGATCTtGATACcGGtA
AGACAGTaGGGGTGAAcCAGaGaGGtGAatTGTGTGTGaGgGGcCCTATG
ATTTATGTCgGGGTAcGTtAAcAAcCCcGAaGCTAGAAATGCTCTcATaG
AcAAGGAcGGgTGGcTtCATagtGGaGAtATTTGCcTAcTGGGAtGAaGA
TGAGCATTTTcTTrcATcGTGGAcAGACTGAAGTCgtTGATcAAaTAcAA
GGGGTATCAaGTaGCTCCTGCcGAGCTtGAgTCcATTCTGCTtCAaGAcC
CcAAtATcTTcGATGCTGGGGTGGCTGGGCTGCCTGATGATGATGCTGGa
GAGcTGCCTGCTGCTGTaGTaGTGCTtGAGGAtGGtAAGACAATGACAGA
GAAGGAGATcGTGGATTATGTGGCTTCaCAaGTGACAACAGCTAAGAAaC
TccGAGGtGGcGTtGTGTTTGTGGATGAGGTGCCTAAaGGaGTcACtGGc
AAGCTGGATGCcAGAAAaATTcGAGAGATTCTcATTAAGGCTAAGAAGGG
tGGaAAGATTGCTGTGTAATAgTTCTAGA.
```

TABLE 11

Summary of Firefly Luciferase Constructs

| Firefly luciferase Gene | Number of consensus transcription factor binding sites | Number of Promoter modules* | CG dinucleotides (possible methylation sites) |
|---|---|---|---|
| Luc+ | 287 | 7 | 97 |
| hluc+ver2AF8 | 3 | 0 | 132 |
| hluc+ver2BF10 | 3 | 0 | 43 |

*Promoter modules are defined as a composite regulatory element, with 2 TFBS separated by a spacer, which has been shown to exhibit synergistic or antagonistic function.

EXAMPLE 4

Synthetic Selectable Polypeptide Genes

Design Process

Define Sequences

Protein Sequence that Should be Maintained:
  Neo: from neo gene of pCI-neo (Promega) (SEQ ID NO:1)
  Hyg: from hyg gene of pcDNA3.1/Hygro (Invitrogen) (SEQ ID NO:6)

DNA Flanking Regions for Starting Sequence:
  5' end: Kozak sequence from neo gene of pCI-neo (GCCACCATGA; SEQ ID NO:34)), PflMI site (CCANNNTGG; SEQ ID NO:35), add Ns at end (to avoid search algorithm errors & keep ORF 1): neo/hyg: NNNNNCCAnnnnnTGGCCACC-ATG-G (SEQ ID NO:36)

Change: Replace PflMI with SbfI (CCTGCAGG)
  3' end: two stop codons (at least one TAA), PflMI site (not compatible with that at 5' end to allow directional cloning), add Ns at end (to avoid search algorithm errors): neo/hyg: TAATAACCAnnnnnTGGNNN (SEQ ID NO:37)
Change: replace PflMI with AflII (CTTAAG)

Define Codon Usage

Codon usage was obtained from the Codon Usage Database (http://www.kazusa.or.jp/codon/):

Based on: GenBank Release 131.0 [15 Aug. 2002] (Nakamura et al., 2000).

Codon Usage Tables were Downloaded for:
- HS: *Homo sapiens* [gbpri] 50,031 CDS's (21,930,294 codons)
- MM: *Mus musculus* [gbrod] 23,113 CDS's (10,345,401 codons)
- EC: *Escherichia coli* [gbbct] 11,985 CDS's (3,688,954 codons)
- EC K12: *Escherichia coli* K12 [gbbct] 4,291 CDS's (1,363,716 codons)
  - HS and MM were compared and found to be closely similar, use HS table
  - EC and EC K12 were compared and found to be closely similar, use EC K12 table Codon Selection Strategy:
Overall strategy is to adapt codon usage for optimal expression in mammalian cells while avoiding low-usage *E. coli* codons. One "best" codon was selected for each amino acid and used to back-translate the desired protein sequence to yield a starting gene sequence.

Strategy A was chosen for the design of the neo and hyg genes (see Table 12). (Strategy A: Codon bias optimized: emphasis on codons showing the highest usage frequency in HS. Best codons are those with highest usage in HS, unless a codon with slightly lower usage has substantially higher usage in *E. coli*.).

TABLE 12

| Amino acid | Codon Choices in Examples 1–2 | Codon Choices in Codon Bias Optimized Strategy A |
|---|---|---|
| Gly | GGC/GGT | GGC |
| Glu | GAG | GAG |
| Asp | GAC | GAC |
| Val | GTG/GTC | GTG |
| Ala | GCC/GCT | GCC |
| Arg | CGC/CGT | CGC |
| Ser | TCT/AGC | AGC |
| Lys | AAG | AAG |
| Asn | AAC | AAC |
| Ile | ATC/ATT | ATC |
| Thr | ACC/ACT | ACC |
| Cys | TGC | TGC |
| Tyr | TAC | TAC |
| Leu | CTG/TTG | CTG |
| Phe | TTC | TTC |
| Gln | CAG | CAG |
| His | CAC | CAC |
| Pro | CCA/CCT | CCC |

Generate Starting Gene Sequences

Use custom codon usage table in Vector NTI 8.0 (Informax) ("Strategy A")

Back-translate neo and hyg protein sequences

Neo (based on neomycin gene from Promega's pCI-neo)

(SEQ ID NO:2)
MEQDGLHAGSPAAWVERLTGYDWAQQTGCSDAAVTRLSAQGRPVLTVKTD
LSGALNELQDEAARLSWLATTGVPCAAVLDVVTEAGRDWLLLGEVPGQDL
LSSHLAPAEKVSMADAMRRLHTLDPATCPTDHQAKHRIERARTRMEAGLV
DQDDLDEEHQGLAPAELTARLKARMPDGEDLVVTHGDACLPNMVENGRTS
GTRDCGRLGVADRYQDLALATRDLAEELGGEWADRTLVLYGAAPDSQRAT
YRLLDETT and encoded by (SEQ ID NO: 1)
Atgattgaacaagatggattgcacgcaggttctccggccgcttgggtgga
gaggctattcggctatgactgggcacaacagacaatcggctgctctgatg
ccgccgtgttccggctgtcagcgcaggggcgcccggttcttttgtcaag
accgacctgtccggtgccctgaatgaactgcaggacgaggcagcgcggct
atcgtggctggccacgacgggcgtccttgcgcagctgtgctcgacgttgt
cactgaagcgggaagggactggctgctattgggcgaagtgccggggcagg
atctcctgtcatctcaccttgctcctgccgagaaagtatccatcatggct
gatgcaatgcggcggctgcatacgcttgatccggctacctgcccattcga
ccaccaagcgaaacatcgcatcgagcgagcacgtactcggatggaagccg
gtctgtcgatcaggatgatctggacgaagagcatcaggggctcgcgccag
ccgaactgttcgccaggctcaaggcgcgcatgcccgacggcgaggatctc
gtcgtgacccatggcgatgcctgcttgccgaatatcatggtggaaatggc
cgctttctggattcatcgactgtggccggctgggtgtggcggaccgctat
caggacatagcgttggctacccgtgatatgctgaagagcttggcggcgaa
tgggctgaccgcttcctcgtgctttacggtatcgccgctcccgatcgcag
cgcatcgccttctatcgccttcttgacgagttcttctga Hyg (based on hygromycin gene from Invitrogen's pcDNA3.1/Hygro)

(SEQ ID NO:7)
MKKPELTATSVEKTLWKTDSVSDLMQLSEGEESRATSTDVGGRGYVLRVN
SCADGTYKDRYVYRTASAALPTPEVLDGETSESLTYCSRRAQGVTLQDLP
ETELPAVLQPVAEAMDAAAAADLSQTSGTGPTGPQGGQYTTWPDTCALAD
PHVYHWQTVMDDTVSASVAQALDELMLWAEDCPEVRHLVHADTGSNNVLT
DNGRTAVTDWSEMATGDSQYEVANTTTWRPWLAGMEQQTRYTERRHPELA
GSPRLRAYMLRGLDQLYQSLVDGNTDDAAWAQGRCDAIVRSGAGTVGRTQ
LARRSAAVWTDGCVEVLADSGNRRPSTRPRAKE encoded by (SEQ ID NO: 6)
Atgaaaaagcctgaactcaccgcgacgtctgtcgagaagtttctgatcga
aaagttcgacagcgtctccgacctgatgcagctctcggagggcgaagaat
ctcgtgctttcagcttcgatgtaggagggcgtggatatgtcctgcgggta
aatagctgcgccgatggtttctacaaagatcgttatgtttatcggcactt
tgcatcggccgcgctcccgattccggaagtgcttgacattggggaattca
gcgagagcctgacctattgcatctcccgccgtgcacagggtgtcacgttg
caagacctgcctgaaaccgaactgcccgctgttctgcagccggtcgcgga
ggccatggatgcgatcgctgcggccgatcttagccagacgagcgggttcg
gcccattcggaccgcaaggaatcggtcaatacactacatggcgtgattca -continued
```
tatgcgcgattgctgatccccatgtgtatcactggcaaactgtgatggac gacaccgtcagtgcgtccgtcgcgcaggctctcgatgagctgatgctttg ggccgaggactgccccgaagtccggcacctcgtgcacgcggatttcggct ccaacaatgtcctgacggacaatggccgcataacagcggtcattgactgg agcgaggcgatgttcggggattcccaatacgaggtcgccaacatcttctt ctggaggccgtggttggcttgtatggagcagcagacgcgctacttcgagc ggaggcatccggagcttgcaggatcgccgcggctccgggcgtatatgctc cgcattggtcttgaccaactctatcagagcttggttgacggcaatttcga tgatgcagcttgggcgcagggtcgatgcgacgcaatcgtccgatccggag ccgggactgtcgggcgtacacaaatcgcccgcagaagcgcggccgtctgg accgatggctgtgtagaagtactcgccgatagtggaaaccgacgcccag cactcgtccgagggcaaggaat.
```

TABLE 13

Nomenclature of exemplary neo and hyg gene versions

| Gene name | Description |
| --- | --- |
| neo | from pCI-neo (Promega) |
| hneo | humanized (codon usage strategy A) ORF |
| hneo-F | humanized ORF with 5' and 3' flanking regions |
| hneo-1F | humanized ORF with 5' and 3' flanking regions after first removal of undesired sequence matches |
| hneo-2F | humanized ORF with 5' and 3' flanking regions after second removal of undesired sequence matches |
| hneo-3F | humanized ORF with 5' and 3' flanking regions after third removal of undesired sequence matches |
| hneo-3FB | Changed 5' and 3' flanking cloning sites |
| hyg | from pcDNA3.1/Hygro (Invitrogen) |
| hhyg | humanized (codon usage strategy A) ORF |
| hhyg-F | humanized ORF with 5' and 3' flanking regions |
| hhyg-1F | humanized ORF with 5' and 3' flanking regions after first removal of undesired sequence matches |
| hhyg-2F | humanized ORF with 5' and 3' flanking regions after second removal of undesired sequence matches |
| hhyg-3F | humanized ORF with 5' and 3' flanking regions after third removal of undesired sequence matches |
| hhyg-3FB | Changed 5' and 3' flanking cloning sites |

"h" indicates humanized codons, "F" indicates presence of 5' and 3' flanking sequences.

Create starting (codon-optimized) gene sequences:

hneo (humanized starting gene sequence without flanking regions in hneo-F)

(SEQ ID NO:3)
```
CCACTCAGTGGCGACCATGATCGAGCAGGACGGCCTGCACGGCGGCAGCC

CCGCCGCCTGGGTGGAGCGCCTGTTCGGCTACGACTGGGCCCAGCAGACC

ATCGGCTGCAGCGACGCCGCCGTGTTCCGCCTGAGCGCCCAGGGCCGCCC

CGTGCTGTCGTGAAGACCGACCTGAGCGGCGCCCTGAACGAGCTGCAGGA

CGAGGCCGCCCGCCTGAGCTGGCTGGCCACCACCGGCGTGCCCTGCGCCG

CCGTGCTGGACGTGGTGAGGGAGGCCGGCCGCGACTGGCTGCTGCTGGGC

GAGGTGCCCGGCCAGGACCTGCTGAGCAGCCACCTGGCCCCCGCCGAGAA
```

-continued
```
GGTGAGCATCATGGCCGACGCCATGCGCCGCCTGCACACCCTGGACCCCG

CCACCTGCCCCTTCGACCACCAGGCCAAGCACCGCATCGAGCGCGCCCGC

ACCCGCATGGAGGCCGGCCTGGTGGACGAGGACGACCTGGACGAGGAGCA

CCAGGGCCTGGCCCCCGCCGAGCTGTTCGCCCGCCTGAAGGCCCGCATGC

CCGACGGCGAGGACCTGGTGGTGACCCACGGCGACGCCTGCCTGCCCAAC

ATCATGGTGGAGAACGGCCGCTTCAGCGGCTTTCATCGACTGCGGCCGCC

TGGGCGTGGCCGACCGCTACCAGGACATCGCCCTGGCCACCCGCGACATC

GCCGAGGAGCTGGGCGGCGAGTGGGCCGACCGCTTCCTGGTGCTGTACGG

CATCGGCGCCCCCGACAGCCAGCGCATCGCCTTCTACGCCTGCTGGAGG

AGTTCTTCTAATAACCAGTCTCTGG.
``` hhyg (humanized starting gene sequence without flanking regions)

(SEQ ID NO:8)
```
CCACTCAGTGGCCACCATGAAGAAGCCCGAGCTGACCGCCACCAGCGTGG

AGAAGTTCCTGATCGAGAAGTTCGACAGGGTGAGCGACCTGATGGAGCTG

AGCGAGGGCGAGGAGAGCCGGGGCTTCAGCTTTCGAGGTGGGCGGCCGCG

GCTACGTGCTGGGCGTGAACAGCTGCGCCGAGGGCTTCTACAAGGACCGC

TAGGTGTACCGCCACTTCGCCAGGGCCGCCCTGCCCATCCCCGAGGTGCT

GGACATCGGCGAGTTCAGCGAGAGCCTGACCTACTGCATCAGCCGCCGCG

CGCAGGGCGTGACCGTGGAGGACCTGCCCGAGACCGAGCTGCCCGGCGTG

CTGCAGCCCGTGGCCGAGGCCATGGACGCCATCGCCGCCGCCGACCTGAG

CCAGACCAGCGGCTTTCGGCCCCTTCGGCCCCCAGGGCATCGGCCAGTAC

ACCACCTGGCGCGACTTCATCTGCGCCATGGCCGACCCCCACGTGTAGCA

CTGGCAGACCGTGATGGACGAGACCGTGAGCGCCAGCGTGGCCCAGGCCG

TGGACGAGCTGATGCTGTGGGCCGAGGACTGCCCCGAGGTGCGCCACCTG

GTGCACGCCGACTTCGGCAGCAACAACGTGCTGACCGACAACGGCCGCAT

CACCGCCGTGATCGACTGGAGCGAGGCCATGTTCGGCGACAGCCAGTACG

AGGTGGCCAACATCTTTCTTTCTGGCGCCCTGGCTGGCCTGCATGGAGC

AGCAGACCCGCTACTTCGAGCGCCGCCACCCCGAGCTGGCCGGCAGCCCC

CGCCTGCGCGCCTACATGCTGCGCATCGGCCTGGACCAGCTGTACCAGAG

CCTGGTGGACGGCAACTTCGAGGACGCCGCCTGGGCCCAGGGCCGCTGCG

ACGCCATCGTGCGCAGCGGCGCCGGCACCGTGGGCCGCACCCAGATCGCC

CGCCGCAGCGCCGCCGTGTGGACCGACGGCTGCGTGGAGGTGCTGGCCGA

CAGCGGCAACCGCGGCCCCAGCACCCGCCCCCGCGCCAAGGAGTAATAAC

CAGCTCTTGG.
```

Programs and Databases Used for Identification and Removal of Sequence Motifs

All from Genomatix Software GmbH (Munich, Germany, http://www.genomatix.de):

GEMS Launcher Release 3.5.2 (June 2003)
  MatInspector professional Release 6.2.1 June 2003
  Matrix Family Library Ver 3.1.2 June 2003 (incl. 318 vertebrate matrices in 128 families)
  ModelInspector professional Release 4.8 October 2002
  Model Library Ver 3.1 March 2003 (226 modules)
  SequenceShaper tool
  User Defined Matrices Sequence Motifs to Remove from Starting Gene Sequences (In Order of Priority)
  Restriction Enzyme Recognition Sequences:
  See user-defined matrix subset neo and hyg. Same as those used for design of hluc+version 2.0
  Generally includes those required for cloning (pGL4) or commonly used for cloning
  Change: also SbfI, AflI, AccIII
  Transcription Factor Binding Sequences:
  Promoter modules (2 TF binding sites with defined orientation) with default score or greater
  Vertebrate TF binding sequences with score of at least core=0.75/matrix=optimized
  Eukaryotic Transcription Regulatory Sites:
  Kozak sequence
  Splice donor/acceptor sequences in (+) strand
  PolyA addition sequences in (+) strand
  Prokaryotic Transcription Regulatory Sequences:
  E. coli promoters
  E. coli RBS (if less than 20 bp upstream of Met codon)

User-Defined Matrix Subset "neo+hvg"

Format: Matrix name (core similarity threshold/matrix similarity threshold)
  U$AatII (0.75/1.00)
  U$BamHI (0.75/1.00)
  U$BglI (0.75/1.00)
  U$BglII (0.75/1.00)
  U$BsaI (0.75/1.00)
  U$BsmAI (0.75/1.00)
  U$BsmBI (0.75/1.00)
  U$BstEII (0.75/1.00)
  U$BstXI (0.75/1.00)
  U$Csp45I (0.75/1.00)
  U$CspI (0.75/1.00)
  U$EC-P-10 (1.00/Optimized)
  U$EC-P-35 (1.00/Optimized)
  U$EC-Prom (1.00/Optimized)
  U$EC-RBS (0.75/1.00)
  U$Ecao % RI (0.75/1.00)
  U$HindIII (0.75/1.00)
  U$Kozak (0.75/Optimized)
  U$KpnI (0.75/1.00)
  U$MluI (0.75/1.00)
  U$NcoI (0.75/1.00)
  U$NdeI (0.75/1.00)
  U$NheI (0.75/1.00)
  U$NotI (0.75/1.00)
  U$NsiI (0.75/1.00)
  U$PflMI (0.75/1.00)
  U$PmeI (0.75/1.00)
  U$PolyAsig (0.75/1.00)
  U$PstI (0.75/1.00)
  U$SacI (0.75/1.00)
  U$SacII (0.75/1.00)
  U$SalI (0.75/1.00)
  U$SfiI (0.75/1.00)
  U$SgfI (0.75/1.00)
  U$SmaI (0.75/1.00)
  U$SnaBI (0.75/1.00)
  U$SpeI (0.75/1.00)
  U$Splice-A (0.75/Optimized)
  U$Splice-D (0.75/Optimized)
  U$XbaI (0.75/1.00)
  U$XcmI (0.75/1.00)
  U$XhoI (0.75/1.00)
  ALL vertebrates.lib (0.75/Optimized)

User-Defined Matrix Subset "neo+hvg-EC"

Format: Matrix name (core similarity threshold/matrix similarity threshold)
  U$AatII (0.75/1.00)
  U$BamHI (0.75/1.00)
  U$BglI (0.75/1.00)
  U$BglII (0.75/1.00)
  U$BsaI (0.75/1.00)
  U$BsmAI (0.75/1.00)
  U$BsmBI (0.75/1.00)
  U$BstEII (0.75/1.00)
  U$BstXI (0.75/1.00)
  U$Csp45I (0.75/1.00)
  U$CspI (0.75/1.00)
  U$EcoRI (0.75/1.00)
  U$HindIII (0.75/1.00)
  U$Kozak (0.75/Optimized)
  U$KpnI (0.75/1.00)
  U$MluI (0.75/1.00)
  U$NcoI (0.75/1.0).
  U$NdeI (0.75/1.00)
  U$NheI (0.75/1.00)
  U$NotI (0.75/1.00)
  U$NsiI (0.75/1.00)
  U$PflMI (0.75/1.00)
  U$PmeI (0.75/1.00)
  U$PolyAsig (0.75/1.00)
  U$PstI (0.75/1.00)
  U$SacI (0.75/1.00)
  U$SacII (0.75/1.00)
  U$SalI (0.75/1.00)
  U$SfiI (0.75/1.00)
  U$SgfI (0.75/1.00)
  U$SmaI (0.75/1.00)
  U$SnaBI (0.75/1.00)
  U$SpeI (0.75/1.00)
  U$Splice-A (0.75/Optimized)
  U$Splice-D (0.75/Optimized)
  U$XbaI (0.75/1.00)
  U$XcmI (0.75/1.00)
  U$XhoI (0.75/1.00)
  ALL vertebrates.lib (0.75/Optimized)

User-Defined Matrix Subset "pGL4-072503"

Format: Matrix name (core similarity threshold/matrix similarity threshold)
  U$AatII (0.75/1.00)
  U$AccIII (0.75/1.00)
  U$AflII (0.75/1.00)
  U$BamHI (0.75/1.00)
  U$BglI (0.75/1.00)
  U$BglII (0.75/1.00)
  U$BsaI (0.75/1.00)
  U$BsmAI (0.75/1.00)
  U$BsmBI (0.75/1.00)
  U$BstEII (0.75/1.00)
  U$BstXI (0.75/1.00)

U$Csp45I (0.75/1.00)
U$CspI (0.75/1.00)
U$EC-P-10 (1.00/Optimized)
U$EC-P-35 (1.00/Optimized)
U$EC-Prom (1.00/Optimized)
U$EC-RBS (0.75/1.00)
U$EcoRI (0.75/1.00)
U$HindIII (0.75/1.00)
U$Kozak (0.75/Optimized)
U$KpnI (0.75/1.00)
U$MluI (0.75/1.00)
U$NcoI (0.75/1.00)
U$NdeI (0.75/1.00)
U$NheI (0.75/1.00)
U$NotI (0.75/1.00)
U$NsiI (0.75/1.00)
U$PflMI (0.75/1.00)
U$PmeI (0.75/1.00)
U$PolyAsig (0.75/1.00)
U$PstI (0.75/1.00)
U$SacI (0.75/1.00)
U$SacII (0.75/1.00)
U$SalI (0.75/1.00)
U$SbfI (0.75/1.00)
U$SfiI (0.75/1.00)
U$SgfI (0.75/1.00)
U$SmaI (0.75/1.00)
U$SnaBI (0.75/1.00)
U$SpeI (0.75/1.00)
U$Splice-A (0.75/Optimized)
U$Splice-D (0.75/Optimized)
U$XbaI (0.75/1.00)
U$XcmI (0.75/1.00)
U$XhoI (0.75/1.00)
ALL vertebrates.lib Strategy for Removal of Sequence Motifs The undesired sequence motifs specified above were removed from the starting gene sequence by selecting alternate codons that allowed retention of the specified protein and flanking sequences. Alternate codons were selected in a way to conform to the overall codon selection strategy as much as possible.

General Steps:
   Identify undesired sequence matches with MatInspector using matrix family subset "neo+hyg" or "neo+hyg-EC" and with ModelInspector using default settings.
   Identify possible replacement codons to remove undesired sequence matches with SequenceShaper (keep ORF).
   Incorporate changes into a new version of the synthetic gene sequence and re-analyze with MatInspector and ModelInspector.

Specific Steps:
   First try to remove undesired sequence matches using subset "neo+hyg-EC" and SequenceShaper default remaining thresholds (0.70/Opt-0.20).
   For sequence matches that cannot be removed with this approach use lower SequenceShaper remaining thresholds (e.g. 0.70/Opt-0.05).
   For sequence matches that still cannot be removed, try different combinations of manually chosen replacement codons (especially if more than 3 base changes might be needed). If that introduces new sequence matches, try to remove those using the steps above (a different starting sequence sometimes allows a different removal solution).
   Use subset "neo+hyg" to check whether problematic *E. coli* sequence matches were introduced, and if so try to remove them using an analogous approach to that described above for non *E. coli* sequences.

Use an analogous strategy for the flanking (non-ORF) sequences. Final check with subset "pGL4-072503" after change in flanking cloning sites After codon optimizing neo and hyg, hneo and hhyg were obtained. Regulatory sequences were removed from hneo and hhyg yielding hneo-1F and hhyg-1F (the corresponding sequences without flanking regions are SEQ ID Nos. 38 and 30, respectively). Regulatory sequences were removed from hneo-1F and hhyg-1F yielding hneo-2F and hhyg-2F (the corresponding sequences without flanking regions are SEQ ID Nos. 39 and 42, respectively). Regulatory sequences were removed from hneo-2F and hhyg-2F yielding hneo-3F and hhyg-3F. Hneo-3F and hhyg-3F were further modified by altering 5' and 3' cloning sites yielding hneo-3FB and hhyg-3FB:

hneo-3 (after 3rd round of sequence removal, subset neo+hyg) has the following sequence:

```
                                                 (SEQ ID NO:4)
CCACTCcGTGGCCACCATGATCGAaCAaGAGGGCCTcCAtGCtGGCAGtC

CCGCaGCtTGGGTcGAaCGCtTGTTTCGGgTACGACTGGGCCCAGCAGAG

CATCGGaTGtAGCGAtGCgGCCGTGTTCCGtCTaAGCGCtCAaGGCCGgC

CCGTGCTGTTCGTGAAGACCGACCTGAGCGGCGCCCTGAACGAGCTtCAa

GACGAGGCtGCCCGCCTGAGCTGGCTGGGCACCACCGGtGTaCCCTGCGC

CGGtGTGtTGGAtGTtGTGACCGAaGCCGGCCGgGACTGGCTGCTGCTGG

GCGAGGTcCCtGGCCAGGAtGTGCTGAGCAGCCACCTtGCCCCCGCtGAG

AAGGTttcCATCATGGCCGAtGGaATGCGgCGCCTGCACACCGTGGACCC

CGCtACaTGCCCCTTCGACCACCAGGCtAAGCAtCGgATCGAGCGtGCtC

GgACCCGCATGGAGGCCGCCTGGTGGACCAGGACGACGTGGACGAGGAG

GAtCAGGGCCTGGCCCGCGCtGAaCTGTTCGCCCGGCTGAAaGCCGGCAT

GGCgGACGGtGAGGACCTGGTtGTGACaCAtGGtGAtGCCTGCCTcCCtA

ACATCATGGTcGAGAAtGGcCGCTTTCtcCGGCTTCATCGACTGCGGtCG

CGTaGGaGTtGGGGACCGCTACCAGGACATCGCCCTGGCCACCCGCGACA

TCGCtGAGGAGGTtGGGGGCGAGTGGGCCGACCGCTTCtTaGTCtTGTAC

GGCATCGCaGCtCGCGACAGCGAGCGCATCGCCTTCTACCGGCTGCTcGA

CGAGTTCTTtTAATGACCAGgCTCTGG;
``` hneo-3FB (change PflMI sites to SbjI at 5' end and AflII at 3' end) has the following sequence:

```
                                                 (SEQ ID NO:5)
cctgcaggCCACCATGATCGAAGAAGACGGCCTCCATGCTGGCAGTCCCG

CAGCTTGGGTCGAACGCTTGTTCGGGTACGACTGGGCCGAGCAGACCATC

GGATGTAGCGATGCGGCCGTGTTCCGTCTAAGCGCTCAAGGCCGGCCCGT

GCTGTTCGTGAAGACCGACCTGAGCGGCGCCCTGAACGAGCTTTCAAGAC

GAGGCTGCCCGCCTGAGCTGGCTGGCCACCACCGGTGTACCCTGCGCCGC
```

-continued

TGTGTTTGGATGTTGTGACCGAAGCCGGCCGGGACTGGCTGCTGGTGGC

GAGGTCCCTGGCCAGGATCTGCTGAGCAGCCAGGTTGCCCCCGCTGAGAA

GGTTTTCCATCATGGCCGATGCAATGCGGCGCCTGCACACCCTGGACCCC

GCTACATGCCCCTTCGACCACCAGGCTAAGCATCGGATCGAGCGTGCTCG

GACCCGCATGGAGGCCGGCCTGGTGGACCAGGACGACCTGGACGAGGAGC

ATCAGGGCCTGGCCCCCGGTGAACTGTTCGCCCGCCTGAAAGCCCGCATG

CCGGACGGTGAGGACCTGGTTGTGACACATGGTGATGCCTGCCTCCCTAA

CATCATGGTCGAGAATGGCCGCTTGTCCGGCTTTCATCGACTGCGGTCGC

CTAGGAGTTGCCGACCGCTAGCAGGACATCGCCCTGGCCACCCGCGACAT

GGCTGAGGAGCTTGGCGGCGAGTGGGCCGACCGCTTCTTAGTCTTGTACG

GCATCGCAGCTCCCGACAGCCAGCGCATCGCCTTCTACCGCCTGCTCGAC

GAGTTCTTTTAATGAgcttaag;

hhyg-3 (after 3rd round of sequence removal, subset neo+ hyg) has the following sequence:

(SEQ ID NO:9)
CCACTCCGTGGCCACCATGAAGAAGCCCGAGGTGACCGCtACCAGCGTtG

AaAAaTTtCTcATCGAGAAGTCGACAGtGTGAGCGACGTGATGCAGtTgt cgGAGGGCGAaGAgAGCCGaGCCTTCAGCTTCGAtGTcGGCGGaCGCGGC

TAtGTaCTGCGgGTGAAtAGCTGCGCtGAtGGCTTCTACAAaGACCGCTA

CGTGTACCGCCACTTCGCCAGCGCtGCaCTaCGCATCCCCGAaGTGtTGG

ACATCGGCGAGTTCAGGGAGAGCGTGACaTACTGCATCAGtaGaCGCGCC

CAaGGGGTtACtCTcGAaGAGCTcCCGGAaACaGAGGTGGCtGCtGTGtT aCAGGCtGTcGCGGAaGCtATGGAtGCtATtGCCGCCGCCGACCTcAGtC

AaACCAGCGGCTTCGGCCCaTTTCGGgCCCCAaGGCATCGGGGAGTACAG aACCTGGGGgGAtTTCATtTGCGCCATtGCtGAtCCCCAtGTcTACCACT

GGCAGACCGTGATGGACGACACCGTGtcCGCCAGCGTaGCtCAaGCCCTG

GACGAaCTGATGCTGTGGGCCGAaGACTGtCCCGAGGTGCGCCAcCTcGT cCAtGCCGACTTCGGCAGCAACAACGTcCTGACGGACAACGGCCGCATCA

CCGCCGTaATCGACTGGtcCGAaGCtATGTTCGGgGACAGtCAGTACGAG

GTGGGCAACATCTTCTTCTGGCGgCCCTGGGTGGCtTGCATGGAGCAGCA

GAGtCGCTACTTCGAGCGCCGgCAtCCCGAGCTGGCCGGCAGGCCtCGtC

TGCGaGCCTACATGCTGCGCATCGGCCTGGAtCAGCTcTACCAGAGCCTc

GTGGAGGGGAACTTCGACGAtGCtGCCTGGGCtGAaGGGCGCTGCGAtGC

CATCGTcCGCAGCGGgGCCGGCACCGTcGGtCGCACaCAaATCGCtCGCC

GgAGCGCCGCCGTaTGGACCGACGGCTGCGTcGAGGTGCTGGCCGACAGC

GGCAACCGCCGgCCCAGtACaCGaCCgCGCGCtAAGGAGTAgTAACCAGg ctcTGG;
and hhyg-3FB (change PflMI sites to SbfI at 5' end and AflII at 3' end) has the following sequence:

(SEQ ID NO:10)
cctgcaggGCACCATGAAGAAGCCCGAGCTGACCGGTACCAGCGTTGAAA

AATTTCTCATCGAGAAGTTCGACAGTGTGAGCGACCTGATGCAGTTGTCG

GAGGGCGAAGAGAGCCGAGCCTTCAGCTTTCGATGTCGGCGGACGCGGCT

ATGTACTGCGGGTGAATAGCTGCGCTGATGGCTTCTACAAAGACCGCTAC

GTGTACCGGGACTTCGCCAGCGCTGCACTAGCCATCCCCGAAGTGTTGGA

CATCGGCGAGTTCAGCGAGAGCCTGACATACTGGATCAGTAGACGCGCCC

AAGGCGTTACTCTCCAAGACCTCCCCGAAACAGAGCTGCCTGCTGTGTTA

CAGCCTGTCGCCGAAGCTATGGATGCTATTTGCCGCCGCCGACCTCAGTC

AAACCAGCGGCTTCGGCCCATTCGGGCCCCAAGGCATCGGCCAGTACACA

ACGTGGCGGGATTCATTTGCGCCATTGCTGATCCCCATGTCTACCACTGG

CAGACCGTGATGGACGACACCGTGTCCGCCAGCGTAGCTCAAGCCCTGGA

CGAACTGATGCTGTGGGGCGAAGACTGTCCCGAGGTGCGCCACCTCGTCC

ATGCCGACTTCGGCAGCAACAACGTCCTGACCGACAACGGCCGCATCACC

GCCGTAATCGACTGGTCCGAAGCTATGTTCGGGGACAGTCAGTACGAGGT

GGGCCAACATCTTCTTCTGGCGGCCCTGGCTGGCTTGCATGGAGCAGCAGA

CTCGCTACTTCGAGCGCCGGCATCCCGAGCTGGCCGGCAGCCCTCGTCTG

GGAGCCTACATGCTGCGCATCGGCCTGGATCAGCTCTACCAGAGCCTCGT

GGACGGCAACTTTCGACGATGCTGCCTGGGCTCAAGGCCGCTGCGATGCC

ATCGTCCGCAGCGGGGCCGGCACCGTCGGTCGCACACAAATCGCTCGCCG

GAGCGCCGCCGTATGGACCGACGGCTGCGTCGAGGTGCTGGGCGACAGCG

GCAACCGCCGGCCCAGTAGACGAGCGCGCGCTAAGGAGTAGTAActtaa g.

Analysis of hneo-3FB and hhyg-3FB hneo-3FB had no transcription factor binding sequence, including promoter module, matches (GEMS release 3.5.2 June 2003; vertebrate TF binding sequence families (core similarity: 0.75/matrix similarity: opt); and promoter modules (default parameters: optimized threshold or 80% of maximum score)), while hhyg-3FB had 4 transcription factor binding sequence matches remaining but no promoter modules (Table 10). The following transcription factor binding sequences were found in hhyg-3FB:

1) V$MINI

Family: Muscle Initiators (2 members)

Best match: Muscle Initiator Sequence 1

Ref: Laura L. Lopez & James W. Fickett "Muscle-Specific Regulation of Transcription: A Catalog of Regulatory Elements"

http://www.cbil.upenn.edu/MTIR/HomePage.html

Position in ORF: −7 to 11

2) V$PAX5

Family: PAX-5/PAX-9 B-cell-specific activating proteins (4 members)

Best match: B-cell-specific activating protein

Ref: MEDLINE 94010299

Position in ORF: 271 to 299

3) V$AREB

Family: Atp1a1 regulatory element binding (4 members)

Best match: AREB6

Ref: MEDLINE 96061934

Position in ORF: 310 to 322

4) V$VMYB

Family: AMV-viral myb oncogene (2 members)

Best match: v-Myb

Ref: MEDLINE 94147510

Position in ORF: 619 to 629

Other sequences remaining in hneo-3F included one *E. coli* RBS 8 bases upstream of Met (ORF position 334 to 337); hneo-3FB included a splice acceptor site (+) and PstI site as part of a 5' cloning site for SbfI, and one *E. coli* RBS 8 bases upstream of Met (ORF position 334 to 337); hhyg-3F had no other sequence matches; and hhyg-3FB included a splice acceptor site (+) and PstI site as part of a 5' cloning site for SbfI.

Subsequently, regulatory sequences were removed from hneo-3F and hhyg-3F yielding hneo-4 and hhyg-4. Then regulatory sequences were removed from hneo-4 yielding hneo-5.

TABLE 14

| Gene name | TF binding sequences 5' F/ORF/3' F | Promoter modules 5' F/ORF/3' F |
|---|---|---|
| Neo | —/53/— | —/0/— |
| hneo-F | 1/61/2 | 0/2/0 |
| hneo-3F | 0/0/0 | 0/0/0 |
| hneo-3FB | 0/0/0 | 0/0/0 |
| Hyg | —/74/— | —/3/— |
| hhyg-F | 1/94/1 | 0/4/0 |
| hhyg-3F | 1/3/0 | 0/0/0 |
| hhyg-3FB | 1/3/0 | 0/0/0 |

*Promoter modules are defined as a composite regulatory element, with 2 transcription factor binding sites separated by a spacer, which has been shown to exhibit synergistic or antagonistic function.

Table 15 summarizes the identity of various genes.

TABLE 15

Pairwise identity of different gene versions
Comparisons were of open reading frames (ORFs).

| | neo | hneo | hneo-3 | hneo-4 | hneo-5 | Final hNeo |
|---|---|---|---|---|---|---|
| Neo | — | 79 | 78 | 78 | 78 | 77 |
| hneo | | — | 90 | 90 | 90 | 89 |
| hneo-3 | | | — | 100 | 99 | 98 |
| hneo-4 | | | | — | 99 | 98 |
| hneo-5 | | | | | — | 99 |
| Final hNeo | | | | | | — |

| | hyg | hhyg | hhyg-3 | hHygro | hhyg-4 | Final hHyg |
|---|---|---|---|---|---|---|
| Hyg | — | 79 | 78 | 73 | 76 | 78 |
| hhyg | | — | 88 | 83 | 86 | 88 |
| hhyg-3 | | | — | 94 | 96 | 98 |
| hHygro | | | | — | 96 | 94 |
| hhyg-4 | | | | | — | 97 |
| Final hHyg | | | | | | — |

| Percent Identity | | | | |
|---|---|---|---|---|
| Divergence | 1 | 2 | | |
| 1 | | 82.2 | 1 | Synthetic puro-SEQ ID NO: 11 |
| 2 | 19.6 | | 2 | Starting puro-SEQ ID NO: 15 |
| | 1 | 2 | | |

An expression cassette (hNeo-cassette) with a synthetic neomycin gene flanked by a SV40 promoter and a synthetic poly(A) site is shown below.

(SEQ ID NO:44)
GGATCCGTTTGCGTATTGGGCGCTCTTCCGCTGATCTGCGCAGCACCATG

GCCTGAAATAACCTCTGAAAGAGGAACTTGGTTAGCTACCTTCTGAGGCG

GAAAGAACCAGCTGTGGAATGTGTGTGAGTTAGGGTGTGGAAAGTCCCCA

GGCTCCCCAGCAGGCAGAAGTATGCAAAGCATGCATCTCAATTAGTCAGC

AACGAGGTGTGGAAAGTCCCCAGGGTCCCCAGCAGGCAGAAGTATGCAAA

GCATGCATCTGAATTAGTCAGCAACGATAGTCCCGCCCCTAACTCGGCCC

ATGCCGCCCCTAACTCCGCCCAGTTCCGCCCATCTCCGCCCCATGGCTGA

CTAATTTTTTTATTTATGCAGAGGCCGAGGCCGCCTCTGCCTCTGAGCTA

TTTCCAGAAGTAGTGAGGAGGCTTTTTTGGAGGCCTAGGCTTTGCAAAAA

GCTCGATTTCTTCTGACACTAGCGCCACCATGATCGAACAAGACGGCCTC

CATGCTGGCAGTCCCGCAGCTTGGGTCGAACGCTTGTTCGGGTACGACTG

GGCCCAGCAGACCATCGGATGTAGCGATGCGGCCGTGTTCCGTCTAAGCG

CTCAAGGCCGGCCCGTGCTGTTCGTGAAGACCGACCTGAGCGGCGCCCTG

AACGAGCTTCAAGACGAGGCTGCCCGCGTGAGCTGGCTGGCCACCACCGG

CGTACCCTGCGCCGCTGTGTTGGATGTTTGTGACCGAAGCCGGCCGGGAC

TGGCTGCTGCTGGGCGAGGTCCCTGGCCAGGATCTGCTGAGCAGCCACCT

TGCCCCCGCTGAGAAGGTTTCTATCATGGCCGATGCAATGCGGCGCCTGC

ACACCCTGGACCCCGCTACCTGCCCCTTCGACCACCAGGCTAAGCATCGG

-continued

```
ATCGAGCGTGCTCGGACCCGCATGGAGGCCGGCCTGGTGGACCAGGACGA

CCTGGACGAGGAGCATCAGGGCCTGGCCCGCGCTGAACTGTTCGCCCGAC

TGAAAGCCCGCATGCCGGACGGTGAGGACCTGGTTGTCACACACGGAGAT

GCCTGCCTCCCTAACATCATGGTCGAGAATGGCCGCTTCTCCGGCTTCAT

CGACTGCGGTGGCCTAGGAGTTGCCGACCGCTACCAGGACATCGGCCTGG

CCACCCGCGACATCGCTGAGGAGCTTGGCGGCGAGTGGGCCGACCGCTTC

TTAGTCTTTGTACGGCATCGCAGCTCCCGACAGCCAGCGCATCGCCTTCT

AGCGCTTGCTCGACGAGTTCTTTTAATGATCTAGAACCGGTCATGGCCGC

AATAAAATATCTTTATTTTCATTACATCTGTGTGTTGGTTTTTTGTGTGT

TCGAACTAGATGCTGTCGAC.
```

An expression cassette (hPuro-cassette) with a synthetic puromycin gene flanked by a SV40 promoter and a synthetic poly(A) site is shown below.

(SEQ ID NO:11)
```
GGATCCGTTTGCGTATTGGGGGCTCTTCGGCTGATCTGCGCAGCACCATG

GCCTGAAATAACGTCTGAAAGAGGAACTTGGTTAGCTACCTTCTGAGGCG

GAAAGAACCAGCTGTGGAATGTGTGTCAGTTAGGGTGTGGAAAGTCCGCA

GGCTCCCCAGGAGGCAGAAGTATGCAAAGCATGCATCTCAATTAGTCAGC

AACCAGGTGTGGAAAGTCCCCAGGCTCCCCAGCAGGCAGAAGTATGCAAA

GCATGGATCTCAATTAGTCAGCAACCATAGTCGCGCCCCTAACTCCGCCC

ATCCCGCCCCTAACTCCGCCGAGTTCCGCCCATTGTCCGCCCCATGGCTG

ACTAATTTTTTTATTTTATGCAGAGGCCGAGGCCGCCTCTGCCTCTGAGG

TATTCCAGAAGTAGTGAGGAGGGTTTTTGGAGGCCTAGGCTTTTTGCAAA

AAGCTCGATTCTTCTGAGACTAGCGCCACCATGACCGAGTACAAGCCTAC

CGTGCGCCTGGCCACTCGCGATGATGTGCCCCGCGCCGTGGGCACTCTGG

CCGGCGCTTTCGCCGACTACCCCGCTACCCGGCACACCGTGGAGCCCGAC

CGGCACATCGAGCGTGTGACAGAGTTGCAGGAGCTGTTCGTGACCCGCGT

CGGGCTGGACATCGGCAAGGTGTGGGTAGCCGACGACGGCGCGGCCGTGG

CCGTGTGGACTACCCCGAGAGCGTTGAGGCCGGCGCCGTGTTCGCCGAG

ATCGGCCCCGAATGGCCGAGCTGAGCGGCAGCCGCCTGGCCGCCCAGCA

GCAAATGGAGGGCCTGCTTGCCCCCCATCGTCCCAAGGAGCCTGCCTGGT

TTCTGGCCAGTGTAGGAGTGAGCCCCGACCACCAGGGCAAGGGCTTGGGC

AGCGCCGTCGTGTTGCCCGGCGTAGAGGCCGCCGAACGCGCCGGTGTGCC

CGCCTTTCTCGAAACAAGCGCACCAAGAAACCTTCCATTCTACGAGCGCC

TGGGCTTCACCGTGACCGCCGATGTCGAGGTGCCCGAGGGACCTAGGACC

TGGTGTATGACACGAAAACCTGGCGCCTAATGATCTAGAACCGGTCATGG

CCGCAATAAAATATCTTTATTTTCATTACATCTGTGTGTTGGTTTTTTT

GTGTGTCGAACTAGATGCTGTCGAC;
``` hpuro:
(SEQ ID NO:91)
```
GGTAGCGCCACCATGACGGAGTACAAGCCGACCGTGCGCCTGGGCACCCG

CGACGACGTGCGCCGCGCCGTGCGGACCCTGGCCGCCGCCTTCGGCGACT

ACCCCGCCACCCGCCACAGGGTGGACCCCGACCGCCACATCGAGCGCGTG

ACCGAGCTGGAGGAGCTGTTCCTGACGCGCGTGGGCCTGGACATCGGCAA

GGTGTGGGTGGCCGACGACGGCGCGGCCGTGGCCGTGTGGACCACCCCG

AGAGCGTGGAGGCCGGCGCCGTGTTCGCCGAGATCGGCCCCCGCATGGCG

GAGCTGAGCGGCAGCCGCCTGGCCGCCCAGCAGCAGATGGAGGGCCTGCT

GGCCCCCCACGGCCCCAAGGAGCCCGCCTGGTTCCTGGCCACCGTGGGCG

TGAGCCCCGACCACCAGGGCAAGGGCCTGGGCAGCGCCGTGGTGCTGCCC

GGCGTGGAGGCCGCCGAGCGCGCCGGCGTGCCCGCCTTCCTGGAGACCAG

CGCCCCCCGCAACCTGCCGTTCTACGAGCGCCTGGGCTTCACCGTGACCG

CCGACGTGGAGGTGGCCGAGGGCCCCCGCACCTGGTGCATGACCCGCAAG

CCCGGCGCCTAATGATCTAGA;
``` hpuro-1:
(SEQ ID NO:92)
```
gctagcgccaccatgaccgagtacaagcctaccgtgcgcctggccactcg cgatgatgtgccccgcgccgtccgcactctggccgccgctttcgccgact accccgctacccggcacaccgtggaccccgaccggcacatcgagcgtgtg acagagttgcaggagctgttcctgacccgcgtcgggctggacatcggcaa ggtgtgggtagccgacgacggcgcggccgtggccgtgtggactaccccg agagcgttgaggccggcgccgtgttcgccgagatcggccccgaatggcc gagctgagcggcagccgcctggccgcccagcagcaaatggagggcctgct tgccccccatcgtcccaaggagcccgcctggtttctggccactgtaggag tgagccccgaccaccagggcaagggcttgggcagcgccgtcgtgttgccc ggcgtagaggccgccgaacgcgccggtgtgcccgcctttctggagacaag cgctccgcgtaaccttccattctacgagcgcctgggcttcaccgtgaccg ccgatgtcgaggtgcccgagggaccccggacctggtgcatgactcgcaag cctggcgcctaatgatctaga;
```
and hpuro-2
(SEQ ID NO:93)
```
GCTAGCGCCACCATGACGGAGTACAAGCCTACCGTGCGCCTGGCCACTCG

CGATGATGTGCCGCGCGCCGTCCGCACTCTGGCCGCCGCTTTCGCCGACT

ACCCCGCTACCCGGCACACCGTGGACCCCGACCGGCACATCGAGCGTGTG

ACAGAGTTGCAGGAGCTGTTTCCTGACCCGCGTCGGGCTGGACATCGGCA

AGGTGTGGGTAGCCGACGACGGCGCGGCCGTGGCCGTGTGGACTACCCCC

GAGAGCGTTGAGGCCGGCGCCGTGTTCGCCGAGATCGGCCCCCGAATGGC

CGAGCTGAGGGGCAGCCGCCTGGCCGCCCAGCAGCAAATGGAGGGCCTGC

TTTGCCCGCCATCGTCCCAAGGAGCCTGCGTGGTTTCTGGCCACTGTAGG

AGTGAGCCCCGACCACCAGGGCAAGGGCTTGGGCAGCGCCGTCGTGTTGC

CCGGCGTAGAGGCCGCCGAACGCGCCGGTGTGCCCGCCTTTCTCGAAACA
```

-continued
AGCGCACCAAGAAACCTTCCATTCTACGAGGGCCTGGGCTTCACCGTGAC

CGCCGATGTCGAGGTGCCCGAGGGACCTAGGACCTGGTGTATGACAGGAA

AACCTGGCGCCTAATGATCTAGA.

The starting puro sequence (from psi STRIKE) has SEQ ID NO:15

(atgaccgagt acaagcccac ggtgcgcctc gccacccgcg acgacgtccc ccgggccgta cgcaccctcg ccgccgcgtt cgccgactac cccgccacgc gccacaccgt cgaccaggac cgccacatcg agcgggtcac cgagctgcaa gaactcttcc tcacgcgcgt cgggctcgac atcggcaagg tgtgggtcgc ggacgacggc gccgcggtgg cggtctggac cacgccggag agcgtcgaag cggggcggt gttcgccgag atcggccgc gcatggccga gttgagcggt tcccggctgg ccgcgcagca acagatggaa ggcctcctgg cgccgcaccg gcccaaggag cccgcgtggt tcctggccac cgtcggcgtg tcgcccgacc accagggcaa gggtctgggc agcgccgtcg tgctccccgg agtggaggcg gccgagcgcg ccgggggtgcc cgccttcctg gagacctccg cgccccgcaa cctcccttc tacgagcggc tcggcttcac cgtcaccgcc gacgtcgagg tgcccgaagg accgcgcacc tggtgcatga cccgcaagcc cggtgcc).

Other synthetic hyg and neo genes include hneo-1:
(SEQ ID NO:38)
CCACTCAGTGGCCACCATGATCGAGCAGGACGGCCTcCAtGCtGGCAGtC CCGCaGCCTGGGTcGAGCGCtTGTTCGGgTAGGACTGGGCCCAGCAGACC ATCGGaTGtAGGGAtGCCGCaGTGTTTGCGCCTGAGCGCtGAaGGCCGgC CCGTGCTGTTCGTGAAGACGGACCTGAGCGGCGCCCTGAACGAGCTtCAa GACGAGGCtGCCCGCCTGAGCTGGCTGGCCACCACCGGtGTaCCCTGCGC CGCtGTGtTGGAtGTtGTGACCGAaGCGGGCCGCGACTGGCTGCTGCTGG GCGAGGTGCCtGGCCAGGACGTGCTGAGCAGCCACCTGGCCCCCGCtGAG AAAGGTGAGCATCATGGCCGACGCCATGCGgCGCCTGCACACCCTGGACC CGGCtACaTGCCCCTTCGACCACCAGGCtAAGCACCGCATCGAGCGgGCt CGgACCCGCATGGAGGCCGGCCTGGTGGACCAGGACGACCTGGACGAGGA GCACCAGGGCCTGGCCCCCGCtGAaCTGTTCGCCCGCCTGAAaGCCCGCA TGCCgGACGGtGAGGACCTGGTtGTGACaCACGGCGACGCGTGCCTcCCt AACATCATGGTcGAGAACGGgCGCTTCtcCGGCTTCATCGACTGCGGCCG CCTGGGCGTtGCCGACCGCTACCAGGACATCGCCCTGGCCACCGGCGACA TCGCCGAGGAGCTGGGCGGCGAGTGGGCCGAGCGGTTCCTGGTCtTGTAC GGCATCGCaGCtCCCGACAGGCAGCGCATCGCCTTCTACCGCCTGCTGGA CGAGTTCTTCTAgTAACCAGgCTCTCC;

hneo-2
(SEQ ID NO:39)
CCACTCcGTGGCCACCATGATCGAaCAaGACGGCCTcCAtGCtGGCAGtC

CCGCaGCtTGGGTcGAacGCtTGTTCGGgTACGACTGGGCCCAGCAGACC

ATCGGaTGtAGGGAtGCgGCCGTGTtCCGtCTaAGCGCtCAaGGCCGgCC

CGTGCTGTTCGTGAAGACCGACCTGAGCGGCGCCCTGAACGAGCTtCAaG

ACGAGGCtGCCCGCCTGAGCTGGCTGGCCACCACCGGtGTaCCCTGCGCC

GCtGTGtTGGAtGTtGTGACCGAaGCCGGCCGgGACTGGGTGCTGCTGGG

CGAGGTcCCtGGCCAGGAtCTGCTGAGCAGCCACCTtGCGCCCGCtGAGA

AGGTttcCATCATGGCCGAtGCaATGCGgCGCCTGCACACCCTGGACCCC

GCtACaTGCCCCTTCGACCACCAGGCtAAGCAtCGgATCGAGCGtGCtCG gACCCGCATGGAGGCCGGCCTGGTGGACCAGGAGGACCTGGAGGAGGAGC

AtCAGGGCCTGGCCCCCGCtGAaCTGTTCGCCCGCCTGAAaGCCCGCATG

GCgGACGGtGAGGACCTGGTtGTGACaCAtGGaGAtGCCTGCCTcCCtAA

CATCATGGTcGAGAAtGGcCGCTTCtcCGGCTTCATCGACTGCGGtCGCC

TaGGaGTtGCCGACCGCTACCAGGACATCGCCCTGGGCACCCGGGACATC

GCtGAGGAGCTtGGCGGCGAGTGGGCCGACCGCTTCtTaGTctTGTACGG

CATCGCaGCtCCCGACAGCCAGCGCATCGCCTTCTACGGCCTGCTcGACG

AGTTCTTtTAATGACCAGgCTCTGG;

hhyg-1
(SEQ ID NO:30)
CCACTCAGTGGCCACCATGAAGAAGCCCGAGCTGACCGCTACCAGCGTTG

AGAAGTTCCTGATCGAGAAGTTTCGACAGCGTGAGCGACCTGATGCAGTT

TAAGCGAGGGCGAGGAAAGCCGGGCGTTCAGCTTCGATGTCGGGGACGC

GGCTATGTACTGCGGGTGAATAGGTGCGCTGATGGCTTTCTACAAAGACC

GCTACGTGTACCGGCACTTCGCCAGCGCTGCACTGCCCATCCCCGAGGTG

CTGGACATCGGCGAGTTCAGCGAGAGCCTGACATACTGCATCAGCCGCCG

CGCTCAAGGCGTGACTGTCCAAGACGTGCCCGAGACAGAGCTGCCCGCTG

TGCTACAGCCTGTCGCCGAGGCTATGGACGCTATTTGCCGCCGCCGACCT

GAGCCAGACCAGCGGCTTGGGCCCATTCGGGGCCCAAGGCATCGGCCAGT

ACACCACCTGGCGCGACTTTCATCTCGCGCCATTGCTGATCCCCATGTCTA

CCACTGGCAGACCGTGATGGACGACACCGTGAGCGCCAGCGTAGCTCAAG

CCCTGGACGAGCTGATGCTGTGGGCCGAGGACTGCCCCGAGGTGCGCCAT

CTCGTCCATGCCGACTTCGGCAGCAACAACGTCCTGACCGACAACGGCCG

CATCACCGCCGTAATCGACTGGAGCGAGGGCATGTTTCGGGGACAGTCAG

TACGAGGTGGCCAACATCTTCTTCTGGCGGCCCTGGCTGGCCTGCATGGA

GCAGCAAACCCGCTACTTCGAGCGCCGCCATCCCGAGCTGGCCGGCAGCC

CCCGTCTGCGAGCCTACATGCTGCGCATCGGCCTGGATCAGCTCTACCAG

AGCCTCGTGGACGGCAACTATCGACGATGCTGCCTGGGCTCAAGGCCGCT

GCGATGCCATCGTCCGCAGCGGGGCCGGCACCGTCGGTCGCACACAAATC

-continued

```
GCTCGCCGGAGCGCCGCCGTATGGACCGACGGCTGCGTCGAGGTGCTGGC

CGACAGCGGCAACCGCCGGCCCAGTACACGACCGCGCGCTAAGGAGTAGT

AACCAGCTCTTGG;
``` hhyg-2:
(SEQ ID NO:42)
```
CCACTCCGTGGCCACCATGAAGAAGCCCGAGCTGACCGCTACCAGCGTTT

GAAAAATTTCTCATCGAGAAGTTCGACAGTGTGAGCGACCTGATGCAGTT

GTCGGAGGGCGAAGAGAGCCGAGCCTTTCAGCTTCGATGTCGGCGGACGG

GGCTATGTACTGCGGGTGAATAGCTGCGCTGATGGCTTCTACAAAGACCG

GTACGTGTACCGCCACTTGGCCAGCGCTGCACTACCCATCCCCGAAGTGT

TGGACATCGGCGAGTTCAGCGAGAGCCTGACATACTGCATCAGTAGACGC

GCCCAAGGCGTTACTCTCCAAGACCTCCCCGAAACAGAGCTGCCTGCTGT

GTTACAGCCTGTCGCCGAAGCTATGGATGCTATTGCGGCCGCCGACGTCA

GTCAAACCAGCGGCTTCGGCCCATTCGGGCCCAAGGCATCGGCCAGTAC

ACAACCTGGCGGGATTTCATTTTGCGCCATTGCTGATCCCCATGTCTACC

ACTGGCAGACCGTGATGGACGACACCGTGTCCGCCAGCGTAGCTCAAGCC

CTGGACGAACTGATGCTGTGGGCCGAAGACTGTCCCGAGGTGCGCCACCT

CGTCCATGCCGACTTCGGCAGCAACAACGTCCTGACCGACAACGGCCGCA

TCACCGCCGTAATCGACTGGAGGGAGGCTATGTTCGGGGACAGTCAGTAC

GAGGTGGCCAACATCTTCTTCTGGCGGCCCTGGCTGGCTTGCATGGAGCA

GCAGACTCGCTACTTCGAGCGCCGGCATCCCGAGCTGGCCGGGAGCCGTC

GTCTGCGAGCCTACATGCTGCGCATCGGCGTGGATGAGCTCTACCAGAGC

CTCGTGGACGGCAACTTTCGACGATGCTGCGTGGGCTCAAGGCCGCTGCG

ATGCCATCGTCCGCAGCGGGGCCGGCAGCGTCGGTGGCACACAAATCGCT

CGCCGGAGCGCCGCGGTATGGAGCGACGGCTGCGTCGAGGTGCTGGCGGA

CAGCGGCAACCGCCGGCCCAGTACAGGACCGCGCGCTAAGGAGTAGTAAC

CAGCTCTTGG;
``` hHygro (SacI site in ORF near 5' end, insert in-frame linker coding for 12 amino acids at 3' end, and SnaBI site added at 3' end in ORF)

(SEQ ID NO:70)
```
aagcttgctagcgccaccatgaagaagcccgagctcaccgctaccagcgt tgaaaaatttctcatcgagaagttcgacagtgtgagcgacctgatgcagt tgtcggagggcgaagagagccgagccttcagcttcgatgtcggcggacgc ggctatgtactgcgggtgaatagctgcgctgatggcttctacaaagaccg ctacgtgtaccgccacttcgccagcgctgcactacccatccccgaagtgt tggacatcggcgagttcagcgagagcctgacatactgcatcagtagacgc gcccaaggcgttactctccaagacctccccgaaacagagctgcctgctgt gttacagcctgtcgccgaagctatggatgctattgccgccgccgacctca gtcaaaccagcggcttcggcccattcgggcccaaggcatcggccagtac acaacctggcgggatttcatttgcgccattgctgatccccatgtctacca
```

-continued
```
ctggcagaccgtgatggacgacaccgtgtccgccagcgtagctcaagccc tggacgaactgatgctgtgggccgaagactgtcccgaggtgcgccacctc gtccatgccgacttcggcagcaacaacgtcctgaccgacaacggccgcat caccgccgtaatcgactggtccgaagctatgttcggggacagtcagtacg aggtggccaacatcttcttctggcggccctggctggcttgcatggagcag cagactcgctacttcgagcgccggcatcccgagctggccggcagccctcg tctgcgagcctacatgctgcgcatcggcctggatcagctctaccagagcc tcgtggacggcaacttcgacgatgctgcctgggctcaaggccgctgcgat gccatcgtccgcagcggggccggcaccgtcggtcgcacacaaatcgctcg ccggagcgccgccgtatggaccgacggctgcgtcgaggtgctggccgaca gcggcaaccgccggcccagtacacgaccgcgcgctaaggagggtggcgga gggagcggtggcggaggttcctacgtatagtctagactcgag;
``` hhyg-4
(SEQ ID NO:71)
```
atgaagaagcccgagctcaccgctaccagcgttgaaaaatttctcatcga gaagttcgacagtgtgagcgacctgatgcagttgtcggagggcgaagaga gccgagccttcagcttcgatgtcggcggacgcggctatgtactgcgggtg aatagctgcgctgatggcttctacaaagaccgctacgtgtaccgccactt cgccagcgctgcactacccatccccgaagtgttggacatcggcgagttca gcgagagcctgacatactgcatcagtagacgcgcccaaggcgttactctc caagacctccccgaaacagagctgcctgctgtgttacagcctgtcgccga agctatggatgctattgccgccgccgacctcagtcaaaccagcggcttcg gcccattcgggcccaaggcatcggccagtacacaacctggcgggatttc atttgcgccattgctgatccccatgtctaccactggcagaccgtgatgga cgacaccgtgtccgccagcgtagctcaagccctggacgaactgatgctgt gggccgaagactgtcccgaggtgcgccacctcgtccatgccgacttcggc agcaacaacgtcctgaccgacaacggccgcatcaccgccgtaatcgactg gtccgaagctatgttcggggacagtcagtacgaggtggccaacatcttct tctggcggccctggctggcttgcatggagcagcagactcgctacttcgag cgccggcatcccgagctggccggcagccctcgtctgcgagcctacatgct gcgcatcggcctggatcagctctaccagagcctcgtggacggcaacttcg acgatgctgcctgggctcaaggccgctgcgatgccatcgtccgcagcggg gccggcaccgtcggtcgcacacaaatcgctcgccggagcgcagccgtatg gaccgacggctgcgtcgaggtgctggccgacagcggcaaccgccggccca gtacacgaccgcgcgctaaggaaggcggtggaggtagtggtggcggaggt agctacgta;
``` hneo-4:
(SEQ ID NO:72)
```
GCTAGCGCCACCATGATCGAACAAGAGGGCCTCCATGCTGGCAGTCCCGC

AGCTTGGGTCGAACGCTTTGTTCGGGTACGACTGGGCCCAGCAGACCATC

GGATGTAGCGATGCGGCCGTGTTCCGTCTAAGCGCTCAAGGCCGGCCCGT
```

```
-continued
GCTGTTCGTGAAGACCGACCTGAGCGGCGCCCTGAACGAGCTTCAAGACG
AGGCTGCGCGCCTGAGCTGGCTGGCCACCACCGGTGTACCCTGCGCCGCT
GTGTTGGATGTTGTGACCGAAGCCGGCCGGGACTGGCTGCTGCTGGGCGA
GGTCCCTGGCCAGGATCTGCTGAGCAGCCACCTTTGCCCCCGCTGAGAAG
GTTTCCATCATGGCCGATGCAATGCGGCGCCTGCACACCCTGGACCCGGG
TACATGCCCCTTCGACCACCAGGCTAAGCATCGGATCGAGCGTGCTCGGA
CCCGCATGGAGGCCGGCCTGGTGGACCAGGACGACCTGGACGAGGAGCAT
CAGGGCCTGGCCCCCGCTGAACTGTTCGCCCGCCTGAAAGCCCGCATGCC
GGACGGTGAGGACCTGGTTGTGACACATGGTGATGCCTGCGTCCCTAACA
TCATGGTCGAGAATGGCCGCTTTCTCCGGCTTCATCGACTGCGGTCGCCT
AGGAGTTGCCGACCGCTAGCAGGACATCGCGCTGGCCACCCGCGACATCG
CTGAGGAGCTTTGGCGGCGAGTGGGCCGACCGCTTCTTAGTCTTGTACGG
CATCGCAGCTCCCGACAGCCAGCGCATCGCCTTCTACCGCCTGCTGGACG
AGTTCTTTTAATCTAGA;
``` and

```
hneo-5:
                                        (SEQ ID NO: 73)
GCTAGCGCCACCATGATCGAACAAGACGGCCTCCATGCTGGCAGTCCCGC
AGCTTGGGTCGAACGCTTGTTCGGGTACGACTGGGCCCAGCAGACCATGG
GATGTAGCGATGGGGCCGTGTTTCCGTCTAAGCGCTCAAGGCGGGCCCGT
GCTGTTCGTGAAGAGCGACCTGAGCGGCGCCCTGAACGAGCTTCAAGACG
AGGCTGCCCGCCTGAGCTGGCTGGCCACCACGGGCGTACCCTGCGCCGCT
GTGTTTGGATGTTGTGACCGAAGCCGGCCGGGACTGGCTGCTGCTGGGCG
AGGTGCCTGGCCAGGATCTGCTGAGCAGCCACCTTTGCCCCCGCTGAGAA
GGTTCTATCATGGCCGATGCAATGCGGCGCCTGCACACCCTGGACCCCGC
TACCTGCGCCTTCGACCACCAGGCTAAGCATCGGATCGAGCGTGCTCGGA
CCCGCATGGAGGCCGGCCTGGTGGACGAGGACGACGTGGACGAGGAGCAT
CAGGGGCTGGCCGCCCCTGAACTGTTCGCCCGACTGAAAGCCCGCATGCC
GGAGGGTGAGGACCTGGTTGTCACACACGGAGATGCCTGCCTCCCTAACA
TCATGGTCGAGAATGGCCGCTTGTCCGGCTTCATCGAGTGCGGTCGCCTA
GGAGTTGCCGACCGCTACCAGGACATCGCCCTGGCCACCCGCGACATCGC
TGAGGAGCTTGGCGGCGAGTGGGCCGACCGCTTCTTAGTCTTGTACGGCA
TCGCAGCTCCCGACAGCCAGCGCATCGCCTTCTACCGCTGCTCGACGAGT
TCTTTTTTAATGATCTAGA.
```

The synthetic nucleotide sequence of the invention may be employed in fusion constructs. For instance, a synthetic sequence for a selectable polypeptide may be fused to a wild-type sequence or to another synthetic sequence which encodes a different polypeptide. For instance, the neo sequence in the following examples of a synthetic *Renilla* luciferase-neo sequence may be replaced with a synthetic neo sequence of the invention:

```
                                        SEQ ID NO: 12)
atggcttccaaggtgtacgacccgagcaacgcaaacgcatgatcactgg
gcctcagtggtgggctcgctgcaagcaaatgaacgtgctggactccttca
tcaactactatgattccgagaagcacgccgagaacgccgtgattttctg
catggtaacgctgcctccagctacctgtggaggcacgtcgtgcctcacat
cgagcccgtggctagatgcatcatccctgatctgatcggaatgggtaagt
ccggcaagagcgggaatggctcatatcgcctcctggatcactacaagtac
ctcaccgcttggttcgagctgctgaaccttccaaagaaaatcatctttgt
gggccacgactgggggcttgtctggccttttcactactcctacgagcacc
aagacaagatcaaggccatcgtccatgctgagagtgtcgtggacgtgatc
gagtcctgggacgagtggcctgacatcgaggaggatatcgccctgatcaa
gagcgaagagggcgagaaaatggtgcttgagaataacttcttcgtcgaga
ccatgctcccaagcaagatcatgcggaaactggagcctgaggagttcgct
gcctacctggagccattcaaggagaagggcgaggttagacggcctaccct
ctcctggcctcgcgagatccctctcgttaagggaggcaagcccgacgtcg
tccagattgtccgcaactacaacgcctaccttcgggccagcgacgatctg
cctaagatgttcatcgagtccgacccctggttctttttccaacgctattgt
cgagggagctaagaagttccctaacaccgagttcgtgaaggtgaagggcc
tccacttcagccaggaggacgctccagatgaaatgggtaagtacatcaag
agcttcgtggagcgcgtgctgaagaacgagcagaccggtggtgggagcgg
aggtggcggatcaggtggcggaggctccggagggattgaacaagatggat
tgcacgcaggttctccggccgcttgggtggagaggctattcggctatgac
tgggcacaacagacaatcggctgctctgatgccgccgtgttccggctgtc
agcgcaggggcgcccggttctttttgtcaagaccgacctgtccggtgccc
tgaatgaactgcaggacgaggcagcgcggctatcgtggctggccacgacg
ggcgttccttgcgcagctgtgctcgacgttgtcactgaagcgggaaggga
ctggctgctattgggcgaagtgccggggcaggatctcctgtcatctcacc
ttgctcctgccgagaaagtatccatcatggctgatgcaatgcggcggctg
catacgcttgatccggctacctgcccattcgaccaccaagcgaaacatcg
catcgagcgagcacgtactcggatggaagccggtcttgtcgatcaggatg
atctggacgaagagcatcaggggctcgcgccagccgaactgttcgccagg
ctcaaggcgcgcatgcccgacggcgaggatctcgtcgtgacccatggcga
tgcctgcttgccgaatatcatggtggaaaatggccgcttttctggattca
tcgactgtggccgctgggtgtggcggaccgctatcaggacatagcgttg
gctaccgtgatattgctgaagagcttggcggcgaatgggctgaccgctt
cctcgtgctttacggtatcgccgctcccgattcgcagcgcatcgccttct
atgccttcttgacgagttcttctaa
(hrl-neo fusion;
``` and (SEQ ID NO:13)
atgattgaacaagatggattgcacgcaggttctccggccgcttgggtgga gaggctattcggctatgactgggcacaacagacaatcggctgctctgatg ccgccgtgttccggctgtcagcgcaggggcgcccggttcttttttgtcaag accgacctgtccggtgccctgaatgaactgcaggacgaggcagcgcggct atcgtggctggccacgacgggcgttccttgcgcagctgtgctcgacgttg tcactgaagcgggaagggactggctgctattgggcgaagtgccggggcag gatctcctgtcatctccaccttgctcctgccgagaaagtatccatcatggc tgatgcaatgcggcggctgcatacgcttgatccggctacctgcccattcg accaccaagcgaaacatcgcatcgagcgagcacgtactcggatggaagcc ggtcttgtcgatcaggatgatctggacgaagagcatcaggggctcgcgcc agccgaactgttcgccaggctcaaggcgcgcatgcccgacggcgaggatc tcgtcgtgacccatggcgatgcctgcttgccgaatatcatggtggaaaat ggccgcttttctggattcatcgactgtggccggctgggtgtggcggaccg ctatcaggacatagcgttggctacccgtgatattgctgaagagcttggcg gcgaatgggctgaccgcttcctcgtgctttacggtatcgccgctcccgat tcgcagcgcatcgccttctatcgccttcttgacgagttcttcaccggtgg tgggagcggaggtggcggatcaggtggcggaggctccggaggggcttcca aggtgtacgaccccgagcaacgcaaacgcatgatcactgggcctcagtgg tgggctcgctgcaagcaaatgaacgtgctggactccttcatcaactacta tgattccgagaagcacgccgagaacgccgtgattttctgcatggtaacg ctgcctccagctacctgtggaggcacgtcgtgcctcacatcgagcccgtg gctagatgcatcatccctgatctgatcggaatgggtaagtccggcaagag cgggaatggctcatatcgcctcctggatcactacaagtacctcaccgctt ggttcgagctgctgaaccttccaaagaaaatcatctttgtgggccacgac tgggggggcttgtctggcctttcactactcctacgagcaccaagacaagat caaggccatcgtccatgctgagagtgtcgtggacgtgatcgagtcctggg acgagtggcctgacatcgaggaggatatcgccctgatcaagagcgaagag -continued ggcgagaaaatggtgcttgagaataacttcttcgtcgagaccatgctccc aagcaagatcatgcggaaactggagcctgaggagttcgctgcctacctgg agccattcaaggagaagggcgaggttagacggcctaccctctcctggcct cgcgagatccctctcgttaagggaggcaagcccgacgtcgtccagattgt ccgcaactacaacgcctaccttcgggccagcgacgatctgcctaagatgt tcatcgagtccgaccctgggttcttttccaacgctattgtcgagggagct aagaagttccctaacaccgagttcgtgaaggtgaagggcctccacttcag ccaggaggacgctccagatgaaatgggtaagtacatcaagagcttcgtgg agcgcgtgctgaagaacgagcagtaa
(neo-hrl-fusion;.

EXAMPLE 5

Transcription Factor Binding Sites Used to Identify Sites in Selected Synthetic Sequences TF Binding Site Libraries The TF binding site library ("Matrix Family Library") is part of the GEMS Launcher package. Table 16 shows the version of the Matrix Family Library which was used in the design of a particular sequence and Table 17 shows a list of all vertebrate TF binding sites ("matrices") in Matrix Family Library Version 2.4, as well as all changes made to vertebrate matrices in later versions up to 4.1 (section "GENOMATIX MATRIX FAMILY LIBRARY INFORMATION Versions 2.4 to 4.1"). (Genomatix has a copyright to all Matrix Library Family information).

TABLE 16

| Synthetic DNA sequence | Genomatix Matrix Family Library |
|---|---|
| pGL4B-NN3* | Version 2.4 May 2002 |
| luc2A8 and luc2B10 | Version 3.0 November 2002 |
|  | Version 3.1.1 April 2003 |
| hhyg3 | Version 3.1.2 June 2003 |
| hneo3 |  |
| hhyg4 | Version 3.3 August 2003 |
| SpeI-NcoI-Ver2** | Version 4.0 November 2003 |
| hneo5 | Version 4.1 February 2004 |
| hpuro2 |  |

*NotI-NcoI fragment in pGL4 including amp gene (pGL4B-NN3)
**SpeI-NcoI-Ver2 (replacement for SpeI-NcoI fragment in pGL4B-NN3

TABLE 17

GENOMATIX MATRIX FAMILY LIBRARY INFORMATION
Versions 2.4 to 4.1

| Family | Family Information | Matrix Name | Information |
|---|---|---|---|
| V$AHRR | AHR-arnt heterodimers and AHR-related factors | V$AHRARNT.01 | aryl hydrocarbon receptor/Arnt heterodimers |
|  |  | V$AHR.01 | aryl hydrocarbon/dioxin receptor |
|  |  | V$AHRARNT.02 | aryl hydrocarbon/Arnt heterodimers, fixed core |
| V$AP1F | AP1 and related factors | V$AP1.01 | AP1 binding site |
|  |  | V$AP1.02 | activator protein 1 |
|  |  | V$AP1.03 | activator protein 1 |
|  |  | V$AP1FJ.01 | activator protein 1 |
|  |  | V$NFE2.01 | NF-E2 p45 |
|  |  | V$VMAF.01 | v-Maf |

TABLE 17-continued

GENOMATIX MATRIX FAMILY LIBRARY INFORMATION
Versions 2.4 to 4.1

| Family | Family Information | Matrix Name | Information |
|---|---|---|---|
| | | V$TCF11MAFG.01 | TCF11/MafG heterodimers, binding to subclass of AP1 sites |
| | | V$BEL1.01 | Bel-1 similar region |
| V$AP2F | Activator Protein 2 | V$AP2.01 | activator protein 2 |
| V$AP4R | AP4 and Related proteins | V$AP4.01 | activator protein 4 |
| | | V$AP4.02 | activator protein 4 |
| | | V$TH1E47.01 | Thing1/E47 heterodimer TH1 bHLH member specific expression in a variety of embryonic tissues |
| | | V$TAL1ALPHAE47.01 | Tal-1alpha/E47 heterodimer |
| | | V$TAL1BETAE47.01 | Tal-1beta/E47 heterodimer |
| | | V$TAL1BETAITF2.01 | Tal-1beta/ITF-2 heterodimer |
| | | V$AP4.03 | activator protein 4 |
| V$AREB | Atp1a1 regulatory element binding | V$AREB6.04 | AREB6(Atp1a1 regulatory element binding factor 6) |
| | | V$AREB6.02 | AREB6 (Atp1a1 regulatory element binding factor 6) |
| | | V$AREB6.03 | AREB6 (Atp1a1 regulatory element binding factor 6) |
| | | V$AREB6.01 | AREB6 (Atp1a1 regulatory element binding factor 6) |
| V$ARP1 | Apolipoprotein aI and cIII gene Repressor Protein | V$ARP1.01 | apolipoprotein AI regulatory protein 1 |
| V$BARB | BARbiturate-Inducible El. box from Pro+eukaryot. genes | V$BARBIE.01 | barbiturate-inducible element |
| V$BCL6 | POZ domain zinc finger expressed in B-Cells | V$BCL6.01 | POZ/zinc finger protein, transcriptional repressor, translocations observed in diffuse large cell lymphoma |
| | | V$BCL6.02 | POZ/zinc finger protein, transcriptional repressor, translocations observed in diffuse large cell lymphoma |
| V$BRAC | Brachyury gene, mesoderm developmental factor | V$TBX5.01 | T-Box factor 5 site (TBX5), mutations related to Holt-Oram syndrome |
| | | V$BRACH.01 | Brachyury |
| V$BRNF | Brn POU domain factors | V$BRN3.01 | POU transcription factor |
| | | V$BRN2.01 | POU factor Brn-3 (N-Oct 3) |
| V$CABL | C-abl DNA binding sites | V$CABL.01 | Multifunctional c-Abl src type tyrosine kinase |
| V$CART | Cart-1 (cartilage homeoprotein 1) | V$XVENT2.01 | Xenopus homeodomain factor Xvent-2; early BMP signaling response |
| | | V$CART1.01 | Cart 1 (cartilage homeoprotein 1) |
| V$CDXF | Vertebrate caudal related homeodomain protein | V$CDX2.01 | Cdx 2 mammalian caudal related intestinal transcr. factor |
| V$CEBP | Ccaat/Enhancer Binding Protein | V$CEBPB.01 | CCAAT/enhancer binding protein beta |
| | | V$CEBP.02 | C/EBP binding site |
| V$CHOP | CHOP binding protein | V$CHOP.01 | heterodimers of CHOP and C/EBPalpha |
| V$CLOX | CLOX and CLOX homology (CDP) factors | V$CDPCR3HD.01 | cut-like homeodomain protein |
| | | V$CDP.01 | cut-like homeodomain protein |

TABLE 17-continued

GENOMATIX MATRIX FAMILY LIBRARY INFORMATION
Versions 2.4 to 4.1

| Family | Family Information | Matrix Name | Information |
|---|---|---|---|
| | | V$CDP.02 | transcriptional repressor CDP |
| | | V$CDPCR3.01 | cut-like homeodomain protein |
| | | V$CLOX.01 | Clox |
| V$CMYB | C-MYB, cellular transcriptional activator | V$CMYB.01 | c-Myb important in hematopoesis, cellular equivalent to avian myoblastosis virus oncogene v-myb |
| V$COMP | factors which COoperate with Myogenic Proteins | V$COMP1.01 | COMP 1, cooperates with myogenic proteins in multicomponent complex |
| V$COUP | Repr. of RXR-mediated activ. & retinoic acid responses | V$COUP.01 | COUP antagonizes HNF-4 by binding site competition or synergizes by direct protein-protein interaction with HNF-4 |
| V$CP2F | CP2-erythrocyte Factor related to drosophila Elf1 | V$CP2.01 | CP2 |
| V$CREB | Camp-Responsive Element Binding proteins | V$CREBP1.01 | cAMP-responsive element binding protein 1 |
| | | V$CREBP1CJUN.01 | CRE-binding protein 1/c-Jun heterodimer |
| | | V$CREB.01 | cAMP responsive element binding protein |
| | | V$HLF.01 | hepatic leukemia factor |
| | | V$E4BP4.01 | E4BP4 bZIP domain, transcriptional repressor |
| | | V$CREB.02 | cAMP responsive element binding protein |
| | | V$CREB.03 | cAMP response element-binding protein |
| | | V$CREB.04 | cAMP response element binding protein |
| | | V$CREBP.1.02 | CRE-binding protein 1 |
| | | V$ATF.02 | ATF binding site |
| | | V$ATF.01 | activating transcription factor |
| | | V$TAXCREB.01 | Tax/CREB complex |
| | | V$TAXCREB.02 | Tax/CREB complex |
| | | V$VJUN.01 | v-Jun |
| V$E2FF | E2F-myc activator/cell cycle regulator | V$E2F.02 | E2F, involved in cell cycle regulation, interacts with Rb p107 protein |
| | | V$E2F.03 | E2F, involved in cell cycle regulation, interacts with Rb p107 protein |
| | | V$E2F.01 | E2F involved in cell cycle regulation, interacts with Rb p107 protein |
| V$E2TF | papillioma virus E2 Transcriptional activator | V$E2.01 | BPV bovine papilloma virus regulator E2 |
| | | V$E2.02 | papilloma virus regulator E2 |
| V$EBOR | E-BOx Related factors | V$DELTAEF1.01 | deltaEF1 |
| | | V$XBP1.01 | X-box-binding protein 1 |
| V$EBOX | E-BOX binding factors | V$USF.02 | upstream stimulating factor |
| | | V$USF.03 | upstream stimulating factor |
| | | V$MYCMAX.03 | MYC-MAX binding sites |
| | | V$SREBP.03 | Sterol regulatory element binding protein |
| | | V$SREBP.02 | Sterol regulatory element binding protein |
| | | V$MYCMAX.02 | c-Myc/Max heterodimer |
| | | V$NMYC.01 | N-Myc |
| | | V$ATF6.01 | Member of b-zip family, induced by ER damage/stress |

TABLE 17-continued

GENOMATIX MATRIX FAMILY LIBRARY INFORMATION
Versions 2.4 to 4.1

| Family | Family Information | Matrix Name | Information |
|---|---|---|---|
| | | V$USF.01 | upstream stimulating factor |
| | | V$MYCMAX.01 | c-Myc/Max |
| | | V$MAX.01 | Max |
| | | V$ARNT.01 | AhR nuclear translocator homodimers |
| | | V$SREBP.01 | Sterol regulatory element binding protein 1 and 2 |
| V$ECAT | Enhancer-CcAaT binding factors | V$NFY.02 | nuclear factor Y (Y-box binding factor) |
| | | V$NFY.03 | nuclear factor Y (Y-box binding factor) |
| | | V$NFY.01 | nuclear factor Y (Y-box binding factor) |
| V$EGRF | EGR/nerve growth Factor Induced protein C & rel. fact. | V$EGR1.01 | Egr-1/Krox-24/NGFI-A immediate-early gene product |
| | | V$EGR2.01 | Egr-2/Krox-20 early growth response gene product |
| | | V$EGR3.01 | early growth response gene 3 product |
| | | V$NGFIC.01 | nerve growth factor suppresor induced protein C |
| | | V$WT1.01 | Wilms Tumor |
| V$EKLF | Erythroid krueppel like factor | V$EKLF.01 | Erythroid krueppel like factor (EKLF) |
| V$ETSF | Human and murine ETS 1 Factors | V$CETS1P54.01 | c-Ets-1(p54) |
| | | V$NRF2.01 | nuclear respiratory factor 2 |
| | | V$GABP.01 | GABP: GA binding protein |
| | | V$ELK1.02 | Elk-1 |
| | | V$FLI.01 | ETS family member FLI |
| | | V$ETS2.01 | c-Ets-2 binding site |
| | | V$ETS1.01 | c-Ets-1 binding site |
| | | V$ELK1.01 | Elk-1 |
| | | V$PU1.01 | Pu.1 (Pu120) Ets-like transcription factor identified in lymphoid B-cells |
| V$EVI1 | EVI1-myleoid transforming protein | V$EVI1.06 | Ecotropic viral integration site 1 encoded factor |
| | | V$EVI1.02 | Ecotropic viral integration site 1 encoded factor |
| | | V$EVI1.03 | Ecotropic viral integration site 1 encoded factor |
| | | V$EVI1.05 | Ecotropic viral integration site 1 encoded factor |
| | | V$EVI1.04 | Ecotropic viral integration site 1 encoded factor |
| | | V$EVI1.01 | Ecotropic viral integration site I encoded factor |
| V$FKHD | Fork Head Domain factors | V$HFH1.01 | HNF-3/Fkh Homolog 1 |
| | | V$HFH2.01 | HNF-3/Fkh Homolog 2 |
| | | V$HFH3.01 | HNF-3/Fkh Homolog 3 (=Freac-6) |
| | | V$HFH8.01 | HNF-3/Fkh Homolog-8 |
| | | V$XFD1.01 | Xenopus fork head domain factor 1 |
| | | V$XFD2.01 | Xenopus fork head domain factor 2 |
| | | V$XFD3.01 | Xenopus fork head domain factor 3 |
| | | V$HNF3B.01 | Hepatocyte Nuclear Factor 3beta |

TABLE 17-continued

GENOMATIX MATRIX FAMILY LIBRARY INFORMATION
Versions 2.4 to 4.1

| Family | Family Information | Matrix Name | Information |
|---|---|---|---|
| | | V$FREAC2.01 | Fork head RElated ACtivator-2 |
| | | V$FREAC3.01 | Fork head RElated ACtivator-3 |
| | | V$FREAC4.01 | Fork head RElated ACtivator-4 |
| | | V$FREAC7.01 | Fork head RElated ACtivator-7 |
| | | V$LMO2COM.02 | complex of Lmo2 bound to Tal-1, E2A proteins, and GATA-1, half-site 2 |
| | | V$GATA1.04 | GATA-binding factor 1 |
| | | V$GATA1.05 | GATA-binding factor 1 |
| | | V$GATA2.01 | GATA-binding factor 2 |
| | | V$GATA2.02 | GATA-binding factor 2 |
| V$GATA | GATA binding factors | V$GATA3.01 | GATA-binding factor 3 |
| | | V$GATA3.02 | GATA-binding factor 3 |
| | | V$GATA.01 | GATA binding site (consensus) |
| | | V$GATA1.03 | GATA-binding factor 1 |
| | | V$GATA1.01 | GATA-binding factor 1 |
| | | V$GATA1.02 | GATA-binding factor 1 |
| VSGFI1 | Growth Factor Independence-transcriptional repressor | V$GFI1.01 | growth factor independence I zinc finger protein acts as transcriptional repressor |
| V$GKLF | Gut-enriched Krueppel Like binding Factor | V$GKLF.01 | gut-enriched Krueppel like factor |
| V$GREF | Glucocorticoid responsive and related elements | V$GRE.01 | Glucocorticoid receptor, C2C2 zinc finger protein binds glucocorticoid dependent to GREs |
| | | V$ARE.01 | Androgene receptor |
| | | V$PRE.01 | Progesterone receptor binding site |
| V$HAML | Human Acute Myelogenous Leukemia factors | V$AML1.01 | runt-factor AML-1 |
| V$HEAT | HEATshock factors | V$HSF1.01 | heat shock factor 1 |
| V$HEN1 | E-box binding factor without transcript. activation | V$HEN1.01 | HEN1 |
| | | V$HEN1.02 | HEN1 |
| V$HMTB | Human muscle-specific Mt binding site | V$MTBF.01 | muscle specific Mt binding site |
| V$HNF1 | Hepatic Nuclear Factor 1 | V$HNF1.01 | hepatic nuclear factor 1 |
| | | V$HNF1.02 | Hepatic nuclear factor 1 |
| V$HNF4 | Hepatic Nuclear Factor 4 | V$HNF4.01 | Hepatic nuclear factor 4 |
| | | V$HNF4.02 | Hepatic nuclear factor 4 |
| V$HOMS | Homeodomain subfamily S8 | V$S8.01 | Binding site for S8 type homeodmains |
| V$HOXF | Factors with moderate activity to homeo domain consensus sequence | V$HOXA9.01 | Member of the vertebrate. HOX - cluster of homeobox factors |
| | | V$HOX1-3.01 | Hox-1.3, vertebrate homeobox protein |
| V$LKRS | Ikaros zinc finger family | V$LYF1.01 | LyF-I (Ikaros 1), enriched in B and T lymphocytes |
| | | V$IK2.01 | Ikaros 2, potential regulator of lymphocyte differentiation |
| | | V$IK1.01 | Ikaros 1, potential regulator of lymphocyte differentiation |
| | | V$IK3.01 | Ikaros 3, potential regulator of lymphocyte differentiation |
| V$IRFF | Interferon Regulatory Factors | V$IRF1.01 | interferon regulatory factor 1 |
| | | V$IRF2.01 | interferon regulatory factor 2 |
| | | V$ISRE.01 | interferon-stimulated response element |

TABLE 17-continued

GENOMATIX MATRIX FAMILY LIBRARY INFORMATION
Versions 2.4 to 4.1

| Family | Family Information | Matrix Name | Information |
|---|---|---|---|
| V$LEFF | LEF1/TCF | V$LEF1.01 | TCF/LEF-1, involved in the Wnt signal transduction pathway |
| V$LTUP | Lentiviral Tata UPstream element | V$TAACC.01 | Lentiviral TATA upstream element |
| V$MEF2 | MEF2-myocyte-specific enhancer-binding factor | V$MEF2.05 | MEF2 |
| | | V$MEF2.01 | myogenic enhancer factor 2 |
| | | V$HMEF2.01 | myocyte enhancer factor |
| | | V$MMEF2.01 | myocyte enhancer f |
| | | V$RSRFC4.01 | related to serum response factor, C4 |
| | | V$RSRFC4.02 | related to serum response factor, C4 |
| | | V$AMEF2.01 | myocyte enhancer factor |
| | | V$MEF2.02 | myogenic MADS factor MEF-2 |
| | | V$MEF2.03 | myogenic MADS factor MEF-2 |
| | | V$MEF2.04 | myogenic MADS factor MEF-2 |
| V$MEF3 | MEF3 BINDING SITES | V$MEF3.01 | MEF3 binding site present in skeletal muscle-specific transcriptional enhancers |
| VSMEIS | Homeodomain factor aberrantly expressed in myeloid leukemia | V$MEIS1.01 | Homeobox protein MEIS1 binding site |
| V$MINI | Muscle INItiator | V$MUSCLE INI.01 | Muscle Initiator Sequence |
| | | V$MUSCLE INI.02 | Muscle Initiator Sequence |
| | | V$MUSCLE INI.03 | Muscle Initiator Sequence |
| V$MOKF | Mouse Krueppel like factor | V$MOK2.01 | Ribonucleoprotein associated zinc finger protein MOK-2 |
| V$MTF1 | Metal induced transcription factor | V$MTF-1.01 | Metal transcription factor 1, MRE |
| V$MYOD | MYOblast Determining factor | V$MYOD.02 | myoblast determining factor |
| | | V$MYF5.01 | Myf5 myogenic bHLH protein |
| | | V$MYOD.01 | myoblast determination gene product |
| | | V$LMO2COM.01 | complex of Lmo2 bound to Tal-1, E2A proteins, and GATA-1, half-site 1 |
| | | V$E47.01 | MyoD/E47 and MyoD/E12 dimers |
| | | V$E47.02 | TAL1/E47 dimers |
| V$MYOF | MYOgenic Factors | V$NF1.01 | nuclear factor 1 |
| | | Y$MYOGNF1.01 | myogenin/nuclear factor 1 or related factors |
| V$MYT1 | Xenopus MYT1 C2HC zinc finger protein | V$MYT1.02 | MyT1 zinc finger transcription factor involved in primary neurogenesis |
| | | V$MYT1.01 | MyTi zinc finger transcription factor involved in primary neurogenesis |
| V$MZF1 | Myeliod Zinc Finger 1 factors | V$MZF1.01 | MZF1 |
| V$NFAT | Nuclear Factor of Activated T-cells | V$NFAT.01 | Nuclear factor of activated T-cells |
| V$NFKB | Nuclear Factor Kappa B/c-rel | V$CREL.01 | c-Rel |
| | | V$NFKAPPAB.01 | NF-kappaB |
| | | V$NFKAPPAB65.01 | NF-kappaB (p65) |
| | | V$NFKAPPAB50.01 | NF-kappaB (p50) |
| | | V$NFKAPPAB.02 | NF-kappaB |
| | | V$NFKAPPAB.03 | NF-kappaB |

TABLE 17-continued

GENOMATIX MATRIX FAMILY LIBRARY INFORMATION
Versions 2.4 to 4.1

| Family | Family Information | Matrix Name | Information |
|---|---|---|---|
| V$NKXH | NKX - Homeodomain | V$NKX25.01 | homeo domain factor Nkx-2.5/Csx, tinman homolog, high affinity sites |
| | | V$NKX25.02 | homeo domain factor Nkx-2.5/Csx, tinman homolog low affinity sites |
| | | V$NKX31.01 | prostate-specific homeodomain protein NKX3.1 |
| V$NOLF | Neuron-specific-OLFactory factor | V$OLF.101 | olfactory neuron-specific factor |
| V$NRSF | Neuron-restrictive Silencer Factor | V$NRSF.01 | neuron-Restrictive silencer factor |
| | | V$NRSE.01 | neural-restrictive-silencer-element |
| V$OAZF | Olfactory associated zinc finger protein | V$ROAZ.01 | Rat C2H2 Zn finger protein involved in olfactory neuronal differentiation |
| V$OCT1 | OCTamer binding protein | V$OCT1.02 | octamer-binding factor 1 |
| | | V$OCT1.06 | octamer-binding factor 1 |
| | | V$OCT.01 | Octamer binding site OCT1/OCT2 consensus) |
| | | V$OCT1.05 | octamer-binding factor 1 |
| | | V$OCT1.04 | octamer-binding factor 1 |
| | | V$OCT1.03 | octamer-binding factor 1 |
| | | V$OCT1.01 | octamer-binding factor 1 |
| V$OCTB | OCT6 Binding factors_astrocytes + glioblastoma cells | V$TST1.01 | POU-factor Tst-1/Oct-6 |
| V$OCTP | OCT1 binding factor (POU-specific domain) | V$OCT1P.01 | octamer-binding factor 1, POU-specific domain |
| V$P53F | p53 tumor suppr.-neg. regulat. of the tumor suppr. Rb | V$P53.01 | tumor suppressor p53 |
| V$PAX1 | PAX-1 binding site | V$PAX1.01 | Pax-1 paired domain protein expressed in the developing vertebral column of mouse embryos |
| V$PAX3 | PAX-3 binding sites | V$PAX3.01 | Pax-3 paired domain protein expressed in embryo genesis, mutations correlate to Waardenburg Syndrome |
| V$PAX4 | Heterogeneous PAX-4 binding sites | V$PAX4.01 | PAX-4 paired domain protein, together with PAX-6 involved in pancreatic development |
| V$PAX5 | PAX-5/PAX-9 B-cell-specific activating protein | V$PAX9.01 | zebrafish PAX9 binding sites |
| | | V$PAX5.01 | B cell specific activating protein |
| | | V$PAX5.02 | B cell specific activating protein |
| V$PAX6 | Activ. involved in Iris development in the mouse eye | V$PAX6.01 | Pax 6 paired domain protein |
| V$PAX8 | PAX-2/5/8 binding sites | V$PAX8.01 | PAX 2/5/8 binding site |
| V$PBXF | Homeo domain factor PBX-1 | V$PBX1.01 | homeo domain factor Pbx-1 |
| V$PCAT | Promoter-CcAaT binding factors | V$ACAAT.01 | Avian C-type LTR CCAAT box |
| | | V$CAAT.01 | cellular and viral CCAAT box |
| | | V$CLTR_CAAT.01 | Mammalian C-type LTR CCAAT box |

TABLE 17-continued

GENOMATIX MATRIX FAMILY LIBRARY INFORMATION
Versions 2.4 to 4.1

| Family | Family Information | Matrix Name | Information |
|---|---|---|---|
| V$PDX1 | Pancreatic and intestinal homeodomain transcr. factor | V$PDX1.01 | Pdxl (IDX1/IPF1) pancreatic and intestinal homeodomain TF |
|  |  | V$ISL1.01 | Pancreatic and intestinal lim-homeodomain factor |
| V$PERO | PEROxisome proliferator-activated receptor | V$PPARA.01 | PPAR/RXR heterodimers |
| V$PIT1 | GHF-1 pituitary specific pou domain transcription factor | V$PIT1.01 | Pit1, GHF-1 pituitary specific pou domain transcription factor |
| V$RARF | Nuclear receptor for retenoic acid | V$RAR.01 | Retinoic acid receptor, member of nuclear receptors |
|  |  | V$RTR.01 | Retinoid receptor-related testis-associated receptor (GCNF/RTR) |
| V$RBIT | Regulator of B-Cell IgH transcription | V$BRIGHT.01 | Bright, B cell regulator of IgH transcnption |
| V$RBPF | RBPJ - kappa | V$RBPJK.01 | Mammalian transcriptional repressor RBP-Jkappa/CBF1 |
| V$REBV | Epstein-Barr virus transcription factor R | V$EBVR.01 | Epstein-Barr virus transcription factor R |
| V$RORA | Estrogen receptor and rar-Rel. Orphan Receptor Alpha | V$RORA1.01 | RAR-related orphan receptor alpha1 |
|  |  | V$RORA2.01 | RAR-related orphan receptor alpha2 |
|  |  | V$ER.01 | estrogen receptor |
| V$RREB | Ras-REsponsive element Binding protein | V$RREB1.01 | Ras-responsive element binding protein 1 |
| V$RXRF | RXR heterodimer binding sites | V$FXRE.01 | Famesoid X - activated receptor (RXR/FXR dimer) |
|  |  | V$VDR_RXR.01 | VDR/RXR Vitamin D receptor RXR heterodimer site |
|  |  | V$VDR_RXR.02 | VDRlRXR Vitamin D receptor RXR heterodimer site |
|  |  | V$LXRE.01 | Nuclear receptor involved in the regulation lipid homeostasis |
| V$SATB | Special AT-rich sequence binding protein | V$SATB1.01 | Special AT-rich sequence-binding protein 1, predominantly expressed in thymocytes, binds to matrix attachment regions (MARs) |
| V$SEF1 | SEF1 protein in mouse Retrovirus SL3-3 | V$SEF1.01 | SEF1 binding site |
| V$SF1F | Vertebrate steroidogenic factor | V$SF1.01 | SF1 steroidogenic factor 1 |
| V$SMAD | Vertebrate SMAD family of transcription factors | V$SMAD3.01 | Smad3 transcription factor involved in TGF-beta signaling |
|  |  | V$SMAD4.01 | Smad4 transcription factor involved in TGF-beta signaling |
|  |  | V$FAST1.01 | FAST-1 SMAD interacting protein |
| V$SORY | SOx/sRY-sex/testis determinig and related HMG Box factors | V$SOX5.01 | Sox 5 |
|  |  | V$SRY.01 | sex determining region Y gene product |
|  |  | V$HMGIY.01 | HMGI(Y) high-mobility-group protein I (Y), architectural transcription factor organizing the framework of a nuclear protein-DNA transcriptional complex |

TABLE 17-continued

GENOMATIX MATRIX FAMILY LIBRARY INFORMATION
Versions 2.4 to 4.1

| Family | Family Information | Matrix Name | Information |
|---|---|---|---|
| | | V$SOX9.01 | SOX (SRY-related HMG box) |
| V$SP1F | GC-Box factors_SP1/GC | V$SP1.01 | stimulating protein 1 SP1, ubiquitous zinc finger transcription factor |
| | | V$GC.01 | GC box elements |
| V$SRFF | Serum Response element binding Factor | V$SRF.02 | serum response factor |
| | | V$SRF.03 | serum responsive factor |
| | | V$SRF.01 | serum response factor |
| V$STAT | Signal Transducer and Activator of Transcript. factors | V$STAT.01 | signal transducers and activators of transcription |
| | | V$STAT5.01 | STAT5: signal transducer and activator of transcription 5 |
| | | V$STAT6.01 | STAT6: signal transducer and activator of transcription 6 |
| | | V$STAT1.01 | signal transducer and activator of transcription 1 |
| | | V$STAT3.01 | signal transducer and activator of transcription 3 |
| V$T3RH | Viral homolog of thyroid hormon receptor alpha1 (AEV vErbA) | V$T3R.01 thyroid hormone receptor | vErbA, viral homolog of thyroid hormone receptor alpha1 |
| VTBPF | Tata-Binding Protein Factor | V$TATA.02 | Mammalian C-type LTR TATA box |
| | | V$ATATA.01 | Avian C-type LTR TATA box |
| | | V$TATA.01 | cellular and viral TATA TATA box |
| | | V$MTATA.01 | Muscle TATA box |
| V$TCFF | TCF11 transcription Factor | V$TCF11.01 | TCF11/KCR-F1/Nrfl homodimers |
| V$TEAF | TEA/ATTS DNA binding domain factors | V$TEF1.01 | TEF-1 related muscle factor |
| V$TTFF | Thyroid transcription factor-1 | V$TTF1.01 | Thyroid transcription factor 1 (TTF1) binding site |
| V$VBPF | chicken Vitellogenin gene Binding Protein factor | V$VBP.01 | PAR-type chicken vitellogenin promoter-binding protein |
| V$VMYB | AMV-viral myb oncogene | V$VMYB.02 | v-Myb |
| | | V$VMYB.01 | v-Myb |
| V$WHZF | Winged Helix and ZF5 binding sites | V$WHN.01 | winged helix protein, involved in hair keratinization and thymus epithelium differentiation |
| V$XBBF | X-box binding Factors | V$RFX1.01 | X-box binding protein RFX1 |
| | | V$RFX1.02 | X-box binding protein RFX1 |
| | | V$MIF1.01 | MIBP-1/RFX1 complex |
| V$XSEC | Xenopus SEleno Cystein t-RNA activiating factor | V$STAF.02 | Se-Cys tRNA gene transcription activating factor |
| | | V$STAF.01 | Se-Cys tRNA gene transcription activating factor |
| V$YY1F | activator/repressor binding to transcr. init. site | V$YY1.01 | Yin and Yang 1 |
| V$ZBPF | Zinc binding protein factor | V$ZBP89.01 | Zinc finger transcription factor ZBP-89 |
| V$ZFIA | ZincFinger with InterAction domain factors | V$ZID.01 | zinc finger with interaction domain |

© Genomatix Software GmbH 1998–2002 - All rights reserved.

B. Chances from Family Library Version 2.4 to Version 3.0

Matrix Family Library Version 3.0 (November 2002) contains 452 weight matrices in 216 families (Vertebrates: 314 matrices in 128 families)

New Weight Matrices—Vertebrates

| Name | Family Information | Matrix Name | Matrix information |
|---|---|---|---|
| V$AP1F | AP1 and related factors | V$BACH1.01 | BTB/POZ-bZIP transcription factor BACH1 forms heterodimers with the small Maf protein family |
| V$CIZF | CAS interating zinc finger protei | V$NMP4.01 | NMP4 (nuclear matrix protein 4)/CIZ (Cas-interacting zinc finger protein) |
| V$CREB | Camp-Responsive Element Binding proteins | V$ATF6.02 | Activating transcription factor 6, member of b-zip family, induced by ER stress |
| V$E4FF | Ubiquitous GLI-Krueppel like zinc finger involved in cell cycle regulation | V$E4F.01 | GLI-Krueppel-related transcription factor, regulator of adenovirus E4 promoter |
| V$GFI1 | Growth Factor Independence-transcriptional repressor | V$GfI1B.01 | Growth factor independence 1 zinc finger protein Gfi-1B |
| V$GLIF | GLI zinc finger family | V$GLI1.01 | Zinc finger transcription factor GLI1 |
| V$HAML | Human Acute Myelogenous Leukemia factors | V$AML3.01 | Runt-related transcription factor 2/CBFA1 (core-binding factor, runt domain, alpha subunit 1) |
| V$HESF | Vertebrate homologues of enhancer of split complex | V&HES1.01 | Drosophila hairy and enhancer of split homologue 1 (HES-1) |
| V$HIFF | Hypoxia inducible factor, bHLH/PAS protein family | V$HIF1.01 | Hypoxia induced factor-1 (HIF-1) |
| | | V$HIF1.02 | Hypoxia inducible factor, bHLH/PAS protein family |
| V$HNF6 | Onecut Homeodomain factor HNF6 | V$HNF6.01 | Liver enriched Cut - Homeodomain transcription factor HNF6 (ONECUT) |
| V$HOXF | Factors with moderate activity to homeo domain consensus sequence | V$CRX.01 | Cone-rod homeobox-containing transcription factor/otx-like homeobox gene |
| | | V$EN1.01 | Homeobox protein engrailed (en-1) |
| | | V$PTX1.01 | Pituitary Homeobox 1 (Ptx1) |
| V$IRFF | Interferon Regulatory Factors | V$IRF3.01 | Interferon regulatory factor 3 (LRF-3) |
| | | V$LRF7.01 | Interferon regulatory factor 7(IRF-7) |
| V$MAZF | Myc associated zinc fingers | V$MAZ.01 | Myc associated zinc finger protein (MAZ) |
| | | V$MAZR.01 | MYC-associated zinc finger protein related transcription factor |
| V$MEIS | Homeodomain factor aberrantly expressed in myeloid leukemia | V$MEIS1.01 | Binding site for monomeric Meis 1 homeodomain protein |
| V$MITF | Microphthalmia transcription factor | V$MIT.01 | MIT (microphthalmia transcription factor) and TFE3 |

-continued

| Name | Family Information | Matrix Name | Matrix information |
|---|---|---|---|
| V$MOKF | Mouse Krueppel like factor | V$MOK2.02 | Ribonucleoprotein associated zinc finger protein MOK-2 (human) |
| V$NEUR | NeuroD, Beta2, HLH domain | V$NEUROD1.01 | DNA binding site for NEUROD1 (BETA-2/E47 dimer) |
| V$NF1F | Nuclear Factor 1 | V$NF1.02 | Nuclear factor 1 (CTF1) |
| V$NXXH | NKX/DLX Homeodomain sites | V$DLX1.01 | DLX-1, -2, and -5 binding sites |
| | | V$DLX3.01 | Distal-less 3 homeodomain transcription facto |
| | | V$HMX3.01 | H6 homeodornain HMX3/Nkx5.1 transcription factor |
| | | V$MSX.01 | Homeodoinain proteins MSX-1 and MSX-2 |
| | | V$MSX2.01 | Muscle segment homeo box 2, homologue of Drosophila (HOX 8) |
| V$NRLF | Neural retina leucine zipper | V$NRL.01 | Neural retinal basic leucine zipper factor (bZIP) |
| V$PARF | PAR/bZIP family | V$DBP.01 | Albumin D-box binding |
| V$PBXC | PBX1 - MEIS1 complexes | V$PBX1_MEIS1.01 | Binding site for a Pbx1/Meis1 heterodimer |
| | | V$PBX1_MEIS1.02 | Binding site for a Pbx1/Meis1 heterodimer |
| | | V$PBX1_MEIS1.03 | Binding site for a Pbx1/Meis1 heterodimer |
| V$PLZF | C2H2 zinc finger protein PLZF | V$PLZF.01 | Promyelocytic leukemia zink finger (TF with nine Krueppel-like zink fingers) |
| V$PXRF | Pregnane X receptor | V$PXRCAR.01 | Halfsite of PXR (pregnane X receptor)/RXR resp. CAR (constitutive androstane receptor)/RXR heterodimer binding site |
| V$RQRA | v-ERB and rar-related Orphan Receptor Alpha | V$NBRE.01 | Monomers of the nur subfamily of nuclear receptors (nur77, nurr1, nor-1) |
| V$SF1F | Vertebrate steroidogenic factor | V$FTF.01 | Alpha (1)-fetoprotein transcription factor (FTF), liver receptor homologue-1 (LHR-1) |
| V$SIXF | Sine oculis (SIX) homeodomain factors | V$SIX3.01 | SIX3/SIXdomain (SD) and Homeodomain (HD) transcription factor |
| V$TALE | TALE Homeodomain class recognizing TG motives | V$TGIF.01 | TG-interacting factor belonging to TALE class of homeodomam factors |
| V$ZF5F | ZF5 POZ domain zinc finger | V$ZF5.01 | Zinc finger/POZ domain transcription factor |

Weight Matrices Renamed

V$MEIS 1.01 renamed to V$MEIS1_HOXA9.01

Weight Matrices Moved to Other Families

V$BEL1.01 moved from V$AP1F to V$BEL1
V$NF 1.01 moved from V$MYOF to V$NF1
V$ER.01 moved from V$RORA to V$EREF
V$T3R.01 moved from V$T3RH to V$RORA
V$CLTR_CAAT.01 moved from V$PCAT to V$RCAT
V$FAST1.01 moved from V$SMAD to V$FAST

Weight Matrices Removed

V$MUSCLE_INI.03

C. Changes from Family Library Version 3.0 to Version 3.1

Matrix Family Library Version 3.1 contains 456 weight matrices in 216 families (Vertebrates: 318 matrices in 128 families)

New Weight Matrices—Vertebrates

| Family | Family Information | Matrix Name | Matrix Information |
|---|---|---|---|
| V$LEFF | LEF1/TCF | V$LEF1.02 | TCF/LEF-1, involved in the Wnt signal transduction pathway |

| Family | Family Information | Matrix Name | Matrix Information |
|---|---|---|---|
| V$PAX2 | PAX-2 binding sites | V$PAX2.01 | Zebrafish PAX2 paired domain protein |
| V$PAX5 | PAX-5/PAX-9 B-cell-specific activating protein | V$PAX5.03 | PAX5 paired domain protein |
| V$PAX6 | PAX-4/PAX-6 paired domain binding sites | V$PAX4_PD.01 | PAX4 paired domain binding site |
| | | V$PAX6.02 | PAX6 paired domain and homeodomain are required for binding to this site |
| V$ZBPF | Zinc binding protein factor | V$ZF9.01 | Core promoter-binding protein (CPBP) with 3 Krueppel-type zinc fingers |

Weight Matrices Modified
 V$AML1.01
 V$AML3.01

Weight Matrices Moved to Other Families
 V$ARNT.01 moved from V$EBOX to V$HIFF (ARNT is a synonym for HIF1 B)

Weight Matrices Removed
 V$SEF1.01
 V$OCT1.03

Version 3.1.1 (April 2003)
 Matrices V$IRF3.01 and V$IRF7.01 corrected.

Version 3.1.2 (June 2003)
 Matrix V$GfIIB.01 corrected.

D. Changes from Family Library Version 3.1 to Version 3.3

Matrix Family Library Version 3.3 (August 2003) contains 485 weight matrices in 233 families (Vertebrates: 326 matrices in 130 families)

New Weight Matrices—Vertebrates

| Family | Family Information | Matrix Name | Matrix Information |
|---|---|---|---|
| V$EREF | Estrogen Response Elements | V$ER.02 | Canonical palindromic estrogen response element (ERE) |
| V$SP1F | GC-Box factors_SP1/GC | V$BTEB3.01 | Basic transcription element (BTE) binding protein, BTEB3, FKLF-2 |
| V$CDEF | Cell cycle regulators: Cell cycle dependent element | V$CDE.01 | Cell cycle-dependent element, CDF-1 binding site (CDE/CHR tandem elements regulate cell cycle dependent repression) |
| V$CHRF | Cell cycle regulators: Cell cycle homology element | V$CHR.01 | Cell cycle gene homology region (CDE/CHR tandem elements regulate cell cycle dependent repression) |
| V$HIFF | Hypoxia inducible factor, bHLH/PAS protein family | V$CLOCK_BMAL1.01 | Binding site of ClockIBMAL1 heterodimer, NPAS2/BMAL1 heterodimer |
| V$FKHD | Fork Head Domain factors | V$FKHRL1.01 | Fkh-domain factor FKHRL1 (FOXO) |
| V$P53F | p53 tumor suppr.-neg. regulat. of the tumor suppr. Rb | V$P53.02 | Tumor suppressor p53 (5' half site) |
| | | V$P53.03 | Tumor suppressor p53 (3' half site) |

Weight Matrices Modified
 V$GFI1.01

E. Changes from Family Library Version 3.3 to Version 4.0

Matrix Family Library Version 4.0 (November 2003) contains 535 weight matrices in 253 families (Vertebrates: 339 matrices in 136 families)

New Weight Matrices—Vertebrates

| Family | Family Information | Matrix Name | Matrix Information |
|---|---|---|---|
| V$AARF | AARE binding factors | V$AARE.01 | Amino acid response element, ATF4 binding site |
| V$AP1R | MAF and AP1 related factors | V$BACH2.01 | Bach2 bound TRE |
| | | V$NFE2L2.01 | Nuclear factor (erythroid-derived 2)-like 2, NRF2 |
| V$CDXF | Vertebrate caudal related homeodomain protein | V$CDX1.01 | Intestine specific homeodomain factor CDX-1 |
| V$DEAF | Homolog to deformed epidennal autoregulatory factor-1 from D. melanogaster | V$NUDR.01 | NUDR (nuclear DEAF-1 related transcriptional regulator protein |
| V$ETSF | Human and murine factors | V$ELF2.01 | ETS - family member ELF-2 (NERF1a) |
| V$GABF | GA-boxes | V$GAGA.01 | GAGA-Box |
| V$HNF1 | Hepatic Nuclear Factor 1 | V$HNF1.03 | Hepatic nuclear factor 1 |

-continued

| Family | Family Information | Matrix Name | Matrix Information |
|---|---|---|---|
| V$HOXF | Factors with moderate activity to homeo domain consensus sequence | V$GSC.01 | Vertebrate bicoid-type homeodomain protein Goosecoid |
| V$LHXF | Lim homeodomain factors | V$LHX3.01 | Homeodomain binding site in LIM/Homeodomain factor LHX3 |
| V$NKXH | NKX/DLX - homeodomain sites | V$NKX32.01 | Homeodomain protein NKX3.2 (BAPX1, NKX3B, Bagpipe homolog) |
| V$RBPF | RBPJ - kappa | V$RBPJK.02 | Mammalian transcriptional repressor RBP-Jkappa/CBF1 |
| V$RP58 | RP58 (ZFP238) zinc finger protein | V$RP58.01 | Zinc finger protein RP58 (ZNF238), associated preferentially with heterochromatin |

Weight Matrices Modified
V$GRE.01
V$NFY.03

Weight Matrices Moved to Other Families
V$BACHI1.01 moved from V$AP1F to V$AP1R
V$NFE2.01 moved from V$AP1F to V$AP1R
V$TCF11MAFG.01 moved from V$AP1F to V$AP1R
V$VMAF.01 moved from V$AP1F to V$AP1R F. Chances from Family Library Version 4.0 to Version 4.1

Matrix Family Library Version 4.1 (February 2004) contains 564 weight matrices in 262 families (Vertebrates: 356 matrices in 138 families)

New Weight Matrices—Vertebrates

| Family | Family Information | Matrix Name | Matrix Information |
|---|---|---|---|
| V$BNCF | Basonuclein rDNA transcription factor (PolI) | V$BNC.01 | Basonuclin, cooperates with USF1 in rDNA PolI transcription) |
| V$CMYB | C-myb, cellular transcriptional activator | V$CMYB.02 | c-Myb, important in hematopoesis, cellular equivalent to avian myoblastosis virus oncogene v-myb |
| V$CP2F | CP2-erythrocyte Factor related to drosophila Elf1 | V$CP2.02 | LBP-1c (leader-binding protein-1c), LSF (late SV40 factor), CP2, SEF (SAA3 enhancer factor) |
| V$EKLF | Basic and erythroid Krueppel like factors | V$BKLF.01 | Basic krueppel-like factor (KLF3) |
| V$HAND | bHLH transcription factor dimer of HAND2 and E12 | V$HAND2_E12.01 | Heterodimers of the bHLH transcription factors HAND2 (Thing2) and E12 |

-continued

| Family | Family Information | Matrix Name | Matrix Information |
|---|---|---|---|
| V$HIFF | Hypoxia inducible factor, bHLH/PAS protein family | V$DEC1.01 | Basic helix-loop-helix protein known as Dec1, Stra13 or Sharp2 |
| V$HNF6 | Onecut Homeodomain factor HNF6 | V$OC2.01 | CUT-homeodomain transcription factor Onecut-2 |
| V$HOXF | Factors with moderate activity to homeo domain consensus sequence | V$OTX2.01 | Homeodomain transcription factor Otx2 (homolog of Drosophila orthodenticle) |
| | | V$GSH1.01 | Homeobox transcription factor Gsh-1 |
| V$IRFF | Interferon Regulatory Factors | V$IRF4.01 | Interferon regulatory factor (IRF)-related protein (NF-EM5, PIP, LSIRF, ICSAT) |
| V$LHXF | Lim homeodomain factors | V$LMX1B.01 | LIM-homeodomain transcription factor |
| V$MYT1 | MYT1 C2HC zinc finger protein | V$MYT1L.01 | Myelin transcription factor 1-like, neuronal C2HC zinc finger factor 1 |
| V$NEUR | NeuroD, Beta2, HLH domain | V$NEUROG.01 | Neurogenin 1 and 3 (ngn1/3) binding sites |
| V$VMYB | AMV-viral myb oncogene | V$VMYB.03 | v-Myb, viral myb variant from transformed BM2 cells |
| | | V$VMYB.04 | v-Myb, AMV v-myb |
| | | V$VMYB.05 | v-Myb, variant of AMV v-myb |
| V$ZBPF | Zinc binding protein factor | V$ZNF202.01 | Transcriptional repressor, binds to elements found predominantly in genes that participate in lipid metabolism |

Weight Matrices Modified
V$CMYB.01
V$PTX1.01

Copyright © Genomatix Software GmbH 1998-2004—All rights reserved

EXAMPLE 6

Summary of Design for Particular Selectable Genes

TF Binding Sites and Search Parameters

Each TF binding site ("matrix") belongs to a matrix family that groups functionally similar matrices together, eliminating redundant matches by MatInspector professional (the search program). Searches were limited to vertebrate TF binding sites. Searches were performed by matrix family, i.e., the results show only the best match from a family for each site. MatInspector default parameters were used for the core and matrix similarity values (core similarity=0.75, matrix similarity=optimized).

TABLE 18

Gene Designations

| Sequence | Description | Matrix Library |
|---|---|---|
| A. Synthetic hygromycin gene | | |
| hyg | from pcDNA3.1/Hygro | Not applicable |
| hhyg | humanized ORF | Not applicable |
| hhyg-1 | First removal of undesired sequence matches | Ver 3.1.2 June 2003 |
| hhyg-2 | Second removal of undesired sequence matches | Ver 3.1.2 June 2003 |
| hhyg-3 | Third removal of undesired sequence matches | Ver 3.1.2 June 2003 |
| hHygro | Changes to ORF and add linker | Ver 3.3 August 2003 |
| hhyg-4 | Fourth removal of undesired sequence matches | Ver 3.3 August 2003 |
| B. Synthetic neomycin gene | | |
| neo | from pCI-neo or psiSTRIKE neo | Not applicable |
| hneo | humanized ORF | Not applicable |
| hneo-1 | First removal of undesired sequence matches | Ver 3.1.2 June 2003 |
| hneo-2 | Second removal of undesired sequence matches | Ver 3.1.2 June 2003 |
| hneo-3 | Third removal of undesired sequence matches | Ver 3.1.2 June 2003 |
| hneo-4 | Changed 5' and 3' flanking regions/cloning sites | Ver 4.1 February 2004 |
| hneo-5 | Fourth removal of undesired sequence matches | Ver 4.1 February 2004 |
| C. Synthetic puromycin gene | | |
| puro | from psiSTRIKE puromycin | Not applicable |
| hpuro | humanized ORF | Not applicable |
| hpuro-1 | First removal of undesired sequence matches | Ver 4.1 February 2004 |
| hpuro-2 | Second removal of undesired sequence matches | Ver 4.1 February 2004 |

Note: the above sequence names designate the ORF only (except for Hhygro which includes flanking sequences). Addition of "F" to the sequence name indicates the presence of up- and down-stream flanking sequences. Additional letters (e.g., "B") indicate changes were made only to the flanking regions

TABLE 19

Sequences in Synthetic Hygromycin Genes
TFBS in hhyg
Before removal of TFBS from hhyg (94 matches)

| Family/matrix** | Further Information |
|---|---|
| V$PCAT/CAAT.01 | cellular and viral CCAAT box |
| V$MINI/MUSCLE_INI.02 | Muscle Initiator Sequence |
| V$MINI/MUSCLE_INI.01 | Muscle Initiator Sequence |
| V$ETSF/PU1.01 | Pu.1 (Pu120) Ets-like transcription factor identified in lymphoid B-cells |
| V$AHRR/AHRARNT.02 | Aryl hydrocarbon/Arnt heterodimers, fixed core |
| V$EGRF/EGR3.01 | early growth response gene 3 product |
| V$AP4R/AP4.01 | Activator protein 4 |
| V$EGRF/NGFIC.01 | Nerve growth factor-induced protein C |
| V$MAZF/MAZ.01 | Myc associated zinc finger protein (MAZ) |
| V$ZBPF/ZF9.01 | Core promoter-binding protein (CPBP) with 3 Krueppel-type zinc fingers |
| V$CREB/ATF6.02 | Activating transcription factor 6, member of b-zip family, induced by ER stress |
| V$EGRF/EGR3.01 | early growth response gene 3 product |
| V$ZBPF/ZF9.01 | Core promoter-binding protein (CPBP) with 3 Krueppel-type zinc fingers |
| V$HIFF/HIF1.02 | Hypoxia inducible factor, bHLH/PAS protein family |
| V$E2FF/E2F.01 | E2F, involved in cell cycle regulation, interacts with Rb p107 protein |
| V$AP4R/AP4.01 | Activator protein 4 |
| V$HEN1/HEN1.02 | HEN1 |
| V$MYOD/E47.01 | MyoD/E47 and MyoD/E12 dimers |
| V$EGRF/EGR3.01 | early growth response gene 3 product |
| V$MOKF/MOK2.02 | Ribonucleoprotein associated zinc finger protein MOK-2 (human) |
| V$SP1F/GC.01 | GC box elements |
| V$NRSF/NRSE.01 | Neural-restrictive-silencer-element |
| V$RORA/RORA2.01 | RAR-related orphan receptor alpha2 |
| V$ZBPF/ZF9.01 | Core promoter-binding protein (CPBP) with 3 Krueppel-type zinc fingers |
| V$ZF5F/ZF5.01 | Zinc finger/POZ domain transcription factor |
| V$AHRR/AHRANT.02 | Aryl hydrocarbon/Arnt heterodimers, fixed core |
| V$AP1F/TCF11MAFG.01 | TCF11/MafG heterodimers, binding to subclass of AP1 sites |
| V$EKLF/EKLF.01 | Erythroid krueppel like factor (EKLF) |
| V$NRSF/NRSF.01 | Neuron-restrictive silencer factor |
| V$NRSF/NRSE.01 | Neural-restrictive-silencer-element |
| V$EBOX/MYCMAX.03 | MYC-MAX binding sites |
| V$RXRF/FXRE.01 | Farnesoid X - activated receptor (RXR/FXR dimer) |
| V$AHRR/AHRARNT.02 | Aryl hydrocarbon/Arnt heterodimers, fixed core |
| V$WHZF/WHN.01 | Winged helix protein, involved in hair keratinization and thymus epithelium differentiation |
| V$EGRF/EGR1.01 | Egr-1/Krox-24/NGFI-A immediate-early gene product |
| V$SMAD/SMAD3.01 | Smad3 transcription factor involved in TGF-beta signaling |
| V$MOKF/MOK2.01 | Ribonucleoprotein associated zinc finger protein MOK-2 (mouse) |
| V$MYOD/MYOD.02 | Myoblast determining factor |
| V$E4FF/E4F.01 | GLI-Krueppel-related transcription factor, regulator of adenovirus E4 promoter |
| V$MOKF/MOK2.01 | Ribonucleoprotein associated zinc finger protein MOK-2 (mouse) |
| V$EGRF/EGR2.01 | Egr-2/Krox-20 early growth response gene product |
| V$EGRF/EGR3.01 | early growth response gene 3 product |
| Y$HIFF/HIF1.02 | Hypoxia inducible factor, bHLH/PAS protein family |
| V$EBOX/USF.02 | Upstream stimulating factor |
| V$HIFF/ARNT.01 | AhR nuclear translocator homodimers |
| V$ZF5F/ZF5.01 | Zinc finger/POZ domain transcription factor |
| V$EBOX/ATF6.01 | Member of b-zip family, induced by ER damage/stress, binds to the ERSE in association with NF-Y |
| V$BEL1/BEL1.01 | Bel-1 similar region (defined in Lentiviral LTRs) |
| V$NRSF/NRSE.01 | Neural-restrictive-silencer-element |
| V$MYOD/MYOD.01 | Myoblast determination gene product |
| V$NEUR/NEUROD1.01 | DNA binding site for NEUROD1 (BETA-2/E47 dimer) |
| V$AHRR/AHRARNT.01 | Aryl hydrocarbon receptor/Arnt heterodimers |

TABLE 19-continued

Sequences in Synthetic Hygromycin Genes
TFBS in hhyg
Before removal of TFBS from hhyg (94 matches)

| Family/matrix** | Further Information |
|---|---|
| V$SHIFF/ARNT.01 | AhR nuclear translocator homodimers |
| V$VMYB/VMYB.02 | v-Myb |
| V$MOKF/MOK2.01 | Ribonucleoprotein associated zinc finger protein MOK-2 (mouse) |
| V$PAX5/PAX5.01 | B-cell-specific activating protein |
| V$PBXC/PBX1_MEIS1.02 | Binding site for a Pbx1/Meis1 heterodimer |
| V$MYOF/MYOGNF1.01 | Myogenin/nuclear factor 1 or related factors |
| V$SRFF/SRF.03 | Serum responsive factor |
| V$CP2F/CP2.01 | CP2 |
| V$OAZF/ROAZ.01 | Rat C2H2 Zn finger protein involved in olfactor neuronal differentiation |
| V$AHRR/AHR.01 | Aryl hydrocarbon/dioxin receptor |
| V$MINI/MUSCLE_INI.01 | Muscle Initiator Sequence |
| V$PAX5/PAX5.02 | B-cell-specific activating protein |
| V$ZBPF/ZF9.01 | Core promoter-binding protein (CPBP) with 3 Krueppel-type zinc fingers |
| V$EBOX/ATF6.01 | Member of b-zip family, induced by ER damage/stress, binds to the ERSE in association with NF-Y |
| V$SEGRF/NGFIC.01 | Nerve growth factor-induced protein C |
| V$ZF5F/ZF5.01 | Zinc finger/POZ domain transcription factor |
| V$AP4R/AP4.02 | Activator protein 4 |
| V$XBBF/MIF1.01 | MIBP-1/RFX1 complex |
| V$EGRF/EGR3.01 | early growth response gene 3 product |
| V$WHZF/WHN.01 | Winged helix protein, involved in hair keratinization and thymus epithelium differentiation |
| V$PAX5/PAX5.01 | B-cell-specific activating protein |
| V$WHZF/WHN0.1 | Winged helix protein, involved in hair keratinization and thymus epithelium differentiation |
| V$PAX5/PAX5.01 | B-cell-specific activating protein |
| V$PAX5/PAX5.03 | PAX5 paired domain protein |
| V$PAX5/PAX5.03 | PAX5 paired domain protein |
| V$ZBPF/ZF9.01 | Core promoter-binding protein (CPBP) with 3 Krueppel-type zinc fingers |
| V$CP2F/CP2.01 | CP2 |
| V$MINI/MUSCLE_INI.02 | Muscle Initiator Sequence |
| V$AP2F/AP2.01 | Activator protein 2 |
| V$PAX5/PAX.01 | B cell-specific activating protein |
| V$AHRR/AHRARNT.02 | Aryl hydrocarbon/Arnt heterodimers, fixed core |
| V$MINI/MUSCLE_INI.02 | Muscle Initiator Sequence |
| V$EGRF/EGR3.01 | early growth response gene 3 product |
| V$SP1F/SP1.01 | stimulating protein 1 SP1, ubiquitous zinc finger transcription factor |
| V$ZBPF/ZF9.01 | Core promoter-binding protein (CPBP) with 3 Krueppel-type zinc fingers |
| V$EGRF/EGR1.01 | Egr-1/Krox-24/NGFI-A immediate-early gene product |
| V$EGRF/WT1.01 | Wilms Tumor Suppressor |
| V$SP1F/SP1.01 | stimulating protein 1 SP1, ubiquitous zinc finger transcription factor |
| V$RCAT/CLTR_CAAT.01 | Mammalian C-type LTR CCAAT box |
| V$ZBPF/ZF9.01 | Core promoter-binding protein (CPBP) with 3 Krueppel-type zinc fingers |
| V$EGRF/WT1.01 | Wilms Tumor Suppressor |
| V$EGRF/WT1.01 | Wilms Tumor Suppressor |
| V$NF1F/NF1.01 | Nuclear factor 1 |
| V$PDX1/PDX1.01 | Pdx1 (IDX1/IPF1) pancreatic and intestinal homeodomain TF |

**matches are listed in order of occurrence-in the corresponding sequence

TFBS in hhyg3
After removal of TFBS from hhyg2 (3 matches)

| Family/matrix** | Further Information |
|---|---|
| V$MINI/MUSCLE_INI.02 | Muscle Initiator Sequence |
| V$PAX5/PAX5.02 | B-cell-specific activating protein |
| V$VMYB/VMYB.02 | v-Myb |

**matches are listed in order of occurrence in the corresponding sequence

TFBS in hHygro
Before removal of TFBS from hHygro (5 matches, excluding linker)

| Family/matrix** | Further Information |
|---|---|
| V$MINI/MUSCLE_INI.02 | Muscle Initiator Sequence |
| V$PAX5/PAX5.02 | B-cell-specific activating protein |
| V$AREB/AREB6.04 | AREB6 (Atp1a1 regulatory element binding factor 6) |
| V$VMYB/VMYB.02 | v-Myb |
| V$CDEF/CDE.01 | Cell cycle-dependent element, CDF-1 binding site (CDE/CHR tandem elements regulate cell cycle dependent repression) |

**matches are listed in order of occurrence in the corresponding sequence

TFBS in hhyg4
After removal of TFBS from hHygro (4 matches)

| Family/matrix** | Further Information |
|---|---|
| V$MINI/MUSCLE_INI.02 | Muscle Initiator Sequence |
| V$PAX5/PAX5.02 | B-cell-specific activating protein |
| V$AREB/AREB6.04 | AREB6 (Atp1a1 regulatory element binding factor 6) |
| V$VMYB/VMYB.02 | v-Myb |

**matches are listed in order of occurrence in the corresponding sequence

TABLE 20

Sequences in Synthetic Neomycin Genes
TFBS in hneo
Before removal of TFBS from hneo (69 matches)

| Family/matrix** | Further Information |
|---|---|
| V$PCAT/CAAT.01 | cellular and viral CCAAT box |
| V$ZFIA/ZID.01 | Zinc finger with interaction domain |
| V$AP1F/TCF11MAFG.01 | TCF11/MafG heterodimers, binding to subclass of AP1 sites |
| V$MINI/MUSCLE_INI.01 | Muscle Initiator Sequence |
| V$AHRR/AHRARNT.01 | Aryl hydrocarbon receptor/Arnt heterodimers |
| V$HIFF/HIF1.02 | Hypoxia inducible factor, bHLH/PAS protein family |
| V$SP1F/GC.01 | GC box elements |
| V$MINI/MUSCLE_INI.02 | Muscle Initiator Sequence |
| V$CP2F/CP2.01 | CP2 |
| V$WHZF/WHN.01 | Winged helix protein, involved in hair keratinization and thymus epithelium differentiation |
| V$PAX5/PAX5.02 | B-cell-specific activating protein |
| V$ZF5F/ZF5.01 | Zinc finger/POZ domain transcription factor |
| V$ZBPF/ZF9.01 | Core promoter-binding protein (CPBP) with 3 Krueppel-type zinc fingers |
| V$ZBPF/ZF9.01 | Core promoter-binding protein (CPBP) with 3 Krueppel-type zinc fingers |

TABLE 20-continued

Sequences in Synthetic Neomycin Genes
TFBS in hneo
Before removal of TFBS from hneo (69 matches)

| Family/matrix** | Further Information |
|---|---|
| V$HIFF/HIF1.02 | Hypoxia inducible factor, bHLH/PAS protein family |
| V$AHRR/AHRARNT.01 | Aryl hydrocarbon receptor/Arnt heterodimers |
| V$NRSF/NRSE.01 | Neural-restrictive-silencer-element |
| V$HIFF/HIF1.02 | Hypoxia inducible factor, bHLH/PAS protein family |
| V$CREB/ATF6.02 | Activating transcription factor 6, member of b-zip family, induced by ER stress |
| V$RXRF/VDR_RXR.01 | VDR/RXR Vitamin D receptor RXR heterodimer site |
| V$PCAT/CAAT.01 | cellular and viral CCAAT box |
| V$NRSF/NRSE.01 | Neural-restrictive-silencer-element |
| V$P53F/P53.01 | Tumor suppressor p53 |
| V$NEUR/NEUROD1.01 | DNA binding site for NEUROD1 (BETA-2/E47 dimer) |
| V$EBOX/USF.03 | Upstream stimulating factor |
| V$MYOD/MYOD.02 | Myoblast determining factor |
| V$NRSF/NRSE.01 | Neural-restrictive-silencer-element |
| V$WHZF/WHN.01 | Winged helix protein, involved in hair keratinization and thymus epithelium differentiation |
| V$EBOX/MYCMAX.03 | MYC-MAX binding sites |
| V$HESF/HES1.01 | Drosophila hairy and enhancer of split homologue 1 (HES-1) |
| V$NEUR/NEUROD1.01 | DNA binding site for NEUROD1 (BETA-2/E47 dimer) |
| V$MYOD/MYOD.02 | Myoblast determining factor |
| V$REBV/EBVR.01 | Epstein-Barr virus transcription factor R |
| V$PAX5/PAX5.02 | B-cell-specific activating protein |
| V$ZF5F/ZF5.01 | Zinc finger/POZ domain transcription factor |
| V$ZF5F/ZF5.01 | Zinc finger/POZ domain transcription factor |
| V$EGRF/WT1.01 | Wilms Tumor Suppressor |
| V$EGRF/WT1.01 | Wilms Tumor Suppressor |
| V$ZBPF/ZF9.01 | Core promoter-binding protein (CPBP) with 3 Krueppel-type zinc fingers |
| V$MINI/MUSCLE_INI.01 | Muscle Initiator Sequence |
| V$NRSF/NRSF.01 | Neuron Initiator silencer factor |
| U$Pf1MI/Pf1MI | RE II-IP |
| V$NRSF/NRSE.01 | Neural-restrictive-silencer-element |
| V$MOKF/MOK2.02 | Ribonucleoprotein associated zinc finger protein MOK-2 (human) |
| V$AP2F/AP2.01 | Activator protein 2 |
| V$AP1F/AP1FJ.01 | Activator protein 1 |
| VPAX5/PAX5.03 | PAX5 paired domain protein |
| V$EGRF/EGR3.01 | early growth response gene 3 product |
| V$WHZF/WHN.01 | Winged helix protein, involved in hair keratinization and thymus epithelium differentiation |
| V$PAX6/PAX4_PD.01 | PAX4 paired domain binding site |
| V$VMYB/VMYB.02 | v-Myb |
| V$BEL1/BEL1.01 | Bel-1 similar region (defined in Lentivirus LTRs) |
| V$MOKF/MOK2.01 | Ribonucleoprotein associated zinc finger protein MOK-2 (mouse) |
| V$EGRF/EGR1.01 | Egr-1/Krox-24/NGFI-A immediate-early gene product |
| V$EBOX/ATF6.01 | Member of b-zip family, induced by ER damage/stress, binds to the ERSE in association with NF-Y |
| V$EGRF/EGR3.01 | early growth response gene 3 product |
| V$NRSF/NRSE.01 | Neural-restrictive-silencer-element |
| V$ETSF/ETS1.01 | c-Ets-1 binding site |
| V$NRSF/NRSF.01 | Neuron-restrictive silencer factor |
| V$SP1F/SP1.01 | stimulating protein 1 SP1, ubiquitous zinc finger transcription factor |
| V$ZBPF/ZBP89.01 | Zinc finger transcription factor ZBP-89 |
| V$PAX5/PAX5.03 | PAX5 paired domain protein |
| V$GREF/ARE.01 | Androgene receptor binding site |

TABLE 20-continued

Sequences in Synthetic Neomycin Genes
TFBS in hneo
Before removal of TFBS from hneo (69 matches)

| Family/matrix** | Further Information |
|---|---|
| V$BCL6/BCL6.02 | POZ/zinc finger protein, transcriptional repressor, translocations observed in diffuse large cell lymphoma |
| V$CLOX/CDP.01 | cut-like homeodomain protein |

**matches are listed in order of occurrence in the corresponding sequence

TFBS in hneo3
After removal of TFBS from hneo2=before removal of TFBS from hneo3 (0 matches)

TFBS in hneo4
After removal of TFBS from hneo3 = before removal of TFBS from hneo4 (7 matches)

| Family/matrix** | Further Information |
|---|---|
| V$PAX5/PAX9.01 | Zebrafish PAX9 binding sites |
| V$AARF/AARE.01 | Amino acid response element, ATF4 binding site |
| V$P53F/P53.02 | Tumor suppressor p53 (5' half site) |
| V$AP1R/BACH2.01 | Bach2 bound TRE |
| V$NEUR/NEUROG.01 | Neurogenin 1 and 3 (ngn1/3) binding sites |
| V$CMYB/CMYB.01 | c-Myb, important in hematopoesis, cellular equivalent to avian myoblastosis virus oncogene v-myb |
| V$HOXF/CRX.01 | Cone-rod homeobox-containing transcription factor/otx-like homeobox gene |

**matches are listed in order of occurrence in the corresponding sequence

TFBS in hneo5
After removal of TFBS from hneo4 (0 matches)

TABLE 21

Sequences in Synthetic Puromycin Genes
TFBS matches in hpuro
Before removal of TFBS from hpuro (68 matches)

| Family/matrix** | Further Information |
|---|---|
| V$CDEF/CDE.01 | Cell cycle-dependent element, CDF-1 binding site (CDE/CHR tandem elements regulate cell cycle dependent repression) |
| V$PAX3/PAX3.01 | Pax-3 paired domain protein, expressed in embryogenesis, mutations correlate to Waardenburg Syndrome |
| V$CREB/ATF6.02 | Activating transcription factor 6, member of b-zip family, induced by ER stress |
| V$EBOR/XBP1.01 | X-box-binding protein 1 |
| V$P53F/P53.03 | Tumor suppressor p53 (3' half site) |
| V$HESF/HES1.01 | Drosophila hairy and enhancer of split homologue 1 (HES-1) |
| V$MTF1/MTF-1.01 | Metal transcription factor 1, MRE |
| V$EKLF/EKLF.01 | Erythroid krueppel like factor (EKLF) |
| V$EGRF/EGR1.01 | Egr-1/Krox-24/NGFI-A immediate early gene product |
| V$EBOX/ATF6.01 | Member of b-zip family, induced by ER damage/stress, binds to the ERSE in association with NF-Y |
| V$EBOX/ATF6.01 | Member of b-zip family, induced by ER damage/stress, binds to the ERSE in association with NF-Y |

TABLE 21-continued

Sequences in Synthetic Puromycin Genes
TFBS matches in hpuro
Before removal of TFBS from hpuro (68 matches)

| Family/matrix** | Further Information |
|---|---|
| V$CMYB/CMYB.01 | c-Myb, important in hematopoesis, cellular equivalent to avian myoblastosis virus oncogene v-myb |
| V$AHRR/AHRARNT.01 | Aryl hydrocarbon receptor/Arnt heterodimers |
| V$EBOX/MYCMAX.03 | MYC-MAX binding sites |
| V$RORA/RORA2.01 | RAR-related orphan receptor alpha2 |
| V$EBOX/MYCMAX.03 | MYC-MAX binding sites |
| V$HIFF/HIF1.02 | Hypoxia inducible factor, bHLH/PAS protein family |
| V$EGRF/EGR3.01 | early growth response gene 3 product |
| V$EGRF/WT1.01 | Wilms Tumor Suppressor |
| V$HAML/AML3.01 | Runt-related transcription factor 2/CBFA1 (core-binding factor, runt domain, alpha subunit 1) |
| V$PAX5/PAX5.03 | PAX5 paired domain protein |
| V$EBOX/ATF6.01 | Member of b-zip family, induced by ER damage/stress, binds to the ERSE in association with NF-Y |
| V$HIFF/HIF1.02 | Hypoxia inducible factor, bHLH/PAS protein family |
| V$ZBPF/ZBP89.01 | Zinc finger transcription factor ZBP-89 |
| V$OAZF/ROAZ.01 | Rat C2H2 Zn finger protein involved in olfactory neuronal differentiation |
| V$GABF/GAGA.01 | GAGA-Box |
| V$EBOX/MYCMAX.03 | MYC-MAX binding sites |
| V$MYOD/MYF5.01 | Myf5 myogenic bHLH protein |
| V$AP4R/TAL1BETAE47.01 | Tal-1beta/E47 heterodimer |
| V$NEUR/NEUROG.01 | Neurogenin 1 and 3 (ngn1/3) binding sites |
| V$HAND/HAND2_E12.01 | Heterodimers of the bHLH transcription factors HAND2 (Thing2) and E12 |
| V$MAZF/MAZR.01 | MYC-associated zinc finger protein related transcription factor |
| Y$ZBPF/ZNF202.01 | Transcriptional repressor, binds to elements found predominantly in genes that participate in lipid metabolism |
| V$SP1F/SP1.01 | Stimulating protein 1 SP1, ubiquitous zinc finger transcription factor |
| V$AP2F/AP2.01 | Activator protein 2 |
| V$RREB/RREB1.01 | Ras-responsive element binding protein 1 |
| V$XBBF/MIF1.01 | MIBP-1/RFX1 complex |
| V$CREB/TAXCREB.01 | Tax/CREB complex |
| V$EGRF/EGR3.01 | early growth response gene 3 product |
| V$MOKF/MOK2.01 | Ribonucleoprotein associated zinc finger protein MOK-2 (mouse) |
| V$MOKF/MOK2.01 | Ribonucleoprotein associated zinc finger protein MOK-2 (mouse) |
| V$PAX5/PAX5.01 | B-cell-specific activating protein |
| V$NRSF/NRSE.01 | Neural-restrictive-silencer-element |
| V$MINI/MUSCLE_INI.02 | Muscle Initiator Sequence |
| V$EBOX/ATF6.01 | Member of b-zip family, induced by ER damage/stress, binds to the ERSE in association with NF-Y |
| V$DEAF/NUDR.01 | NUDR (nuclear DEAF-1 related transcriptional regulator protein) |
| V$AHRR/AHRARNT.01 | Aryl hydrocarbon receptor/Arnt heterodimers |
| V$ZF5F/ZF5.01 | Zinc finger/POZ domain transcription factor |
| V$EGRF/EGR1.01 | Egr-1/Krox-24/NGFI-A immediate-early gene product |
| V$HIFF/HIF1.02 | Hypoxia inducible factor, bHLH/PAS protein family |
| V$ETSF/ETS1.01 | c-Ets-1 binding site |
| V$STAT/STAT1.01 | Signal transducer and activator of transcription 1 |

TABLE 21-continued

Sequences in Synthetic Puromycin Genes
TFBS matches in hpuro
Before removal of TFBS from hpuro (68 matches)

| Family/matrix** | Further Information |
|---|---|
| V$BCL6/BCL6.01 | POZ/zinc finger protein, transcriptional repressor, translocations observed in diffuse large cell lymphoma |
| V$ZF5F/ZF5.01 | Zinc finger/POZ domain transcription factor |
| V$BCL6/BCL6.02 | POZ/zinc finger protein, transcriptional repressor, translocations observed in diffuse large cell lymphoma |
| V$EGRF/EGR3.01 | early growth response gene 3 product |
| V$CREB/ATF6.02 | Activating transcription factor 6, member of b-zip family, induced by ER stress |
| V$HIFF/HIF1.02 | Hypoxia inducible factor, bHLH/PAS protein family |
| V$EBOR/XBP1.01 | X-box-binding protein 1 |
| V$DEAF/NUDR.01 | NUDR (nuclear DEAF-1 related transcriptional regulator protein) |
| V$RXRF/VDR_RXR.01 | VDR/RXR Vitamin D receptor RXR heterodimer site |
| V$AP2F/AP2.01 | Activator protein 2 |
| V$REBV/EBVR.01 | Epstein-Barr virus transcription factor R |
| V$ZBPF/ZF9.01 | Core promoter-binding protein (CPBP) with 3 Krueppel-type zinc fingers |
| V$MYOD/LMO2COM.01 | Complex of Lmo2 bound to Tal-1, E2A proteins, and GATA-1, half-site 1 |
| V$AREB/AREB6.03 | AREB6 (Atp1a1 regulatory element binding factor 6) |
| V$RXRF/FXRE.01 | Farnesoid X - activated receptor (RXR/FXR dimer) |
| V$AHRR/AHR.01 | Aryl hydrocarbon/dioxin receptor |

**matches are listed in order of occurrence in the corresponding sequence

TFBS matches in hpuro1
After removal of TFBS from hpuro = before removal of TFBS from hpuro1 (4 matches)

| Family/matrix** | Further Information |
|---|---|
| V$NEUR/NEUROG.01 | Neurogenin 1 and 3 (ngn1/3) binding sites |
| V$PAX5/PAX5.02 | B-cell-specific activating protein |
| V$REBV/EBVR.01 | Epstein-Barr virus transcription factor R |
| V$AHRR/AHR.01 | Aryl hydrocarbon/dioxin receptor |

**matches are listed in order of occurrence in the corresponding sequence

TFBS matches in hpuro2
After removal of TFBS from hpuro1 (2 matches)

| Family/matrix** | Further Information |
|---|---|
| V$NEUR/NEUROG.01 | Neurogenin 1 and 3 (ngn1/3) binding sites |
| V$BCL6/BCL6.02 | POZ/zinc finger protein, transcriptional repressor, translocations observed in diffuse large cell lymphoma |

**matches are listed in order of occurrence in the corresponding sequence

EXAMPLE 7

Summary of Design of Synthetic Firefly Luciferase Genes

TF Binding Sites and Search Parameters

The TF binding sites are from the TF binding site library ("Matrix Family Library") that is part of the GEMS Launcher package. Each TF binding site ("matrix") belongs to a matrix family that groups functionally similar matrices together, eliminating redundant matches by MatInspector professional (the search program). Searches were limited to vertebrate TF binding sites. Searches were performed by matrix family, i.e. the results show only the best match from a family for each site. MatInspector default parameters were used for the core and matrix similarity values (core similarity=0.75, matrix similarity=optimized).

TABLE 22

Luc Gene Designations
Synthetic luc gene (versions A and B)

| Sequence* | Description | Matrix Library |
|---|---|---|
| Luc | wild-type gene | (not applicable) |
| luc+ | improved gene from Promega's pGL3 vectors | (not applicable) |
| hluc+ | Improved gene form Promega's pGL3 (R2.1)-Basic | (not applicable) |
| | Codon optimization strategy A | |
| hluc + ver2A1 | codon optimized luc+ (strategy A) | Ver 3.0 November 2002 |
| hluc + ver2A2 | First removal of undesired sequence matches | Ver 3.0 November 2002 |
| hluc + ver2A3 | Second removal of undesired sequence matches | Ver 3.0 November 2002 |
| hluc + ver2A4 | Third removal of undesired sequence matches | Ver 3.0 November 2002 |
| hluc + ver2A5 | Fourth removal of undesired sequence matches | Ver 3.0 November 2002 |
| hluc + ver2A6 | Fifth removal of undesired sequence matches | Ver 3.0 November 2002 |
| hluc + ver2A7 | Sixth removal of undesired sequence matches | Ver 3.1.1 April 2003 |
| hluc + ver2A8 | Removal of BglI (RE) site | Ver 3.1.1 April 2003 |
| | Codon optimization strategy B | |
| hluc + ver2B1 | codon optimized luc+ (strategy B) | Ver 3.0 November 2002 |
| hluc + ver2B2 | First removal of undesired sequence matches | Ver 3.0 November 2002 |
| hluc + ver2B3 | Second removal of undesired sequence matches | Ver 3.0 November 2002 |
| hluc + ver2B4 | Third removal of undesired sequence matches | Ver 3.0 November 2002 |
| hluc + ver2B5 | Fourth removal of undesired sequence matches | Ver 3.0 November 2002 |
| hluc + ver2B6 | Fifth removal of undesired sequence matches | Ver 3.0 November 2002 |
| hluc + ver2B7 | Sixth removal of undesired sequence matches | Ver 3.1.1 April 2003 |
| hluc + ver2B8 | Removal of SmaI (RE), Ptx 1 (TF) sites | Ver 3.1.1 April 2003 |
| hluc + ver2B9 | Removal of additional CpG sequences | Ver 3.1.1 April 2003 |
| hluc + ver2B10 | Removal of BglI (RE) site | Ver 3.1.1 April 2003 |

*the sequence names designate open reading frames; RE = restriction enzyme recognition sequence

TABLE 23

Sequences in Synthetic Luc Genes (version A)
TFBS in hluc + ver2A1
Before removal of TFBS from hluc + ver2A1 (110 matches)

| Family/matrix* | Further Information |
|---|---|
| V$MINI/MUSCLE_INI.02 | Muscle Initiator Sequence |
| V$WHZF/WHN.01 | winged helix protein, involved in hair keratinization and thymus epithelium differentiation |
| V$GREF/PRE.01 | Progesterone receptor binding site |
| V$MAZF/MAZR.01 | MYC-associated zinc finger protein related transcription factor |
| V$SP1F/SP1.01 | stimulating protein 1 SP1, ubiquitous zinc finger transcription factor |
| V$ZBPF/ZBP89.01 | Zinc finger transcription factor ZBP-89 |
| V$SF1F/SF1.01 | SF1 steroidogenic factor 1 |
| V$EGRF/NGFIC.01 | Nerve growth factor-induced protein C |
| V$MINI/MUSCLE_INI.01 | Muscle Initiator Sequence |
| V$EGRF/EGR2.01 | Egr-2/Krox-20 early growth response gene product |
| V$ZF5F/ZF5.01 | Zinc finger/POZ domain transcription factor |
| V$HESF/HES1.01 | Drosophila hairy and enhancer of split homologue 1 (HES-1) |
| V$NRSF/NRSE.01 | neural-restrictive-silencer-element |
| V$PAX5/PAX5.02 | B-cell-specific activating protein |
| V$HAML/AML3.01 | Runt-related transcription factor 2/CBFA1 (core-binding factor, runt domain, alpha subunit 1) |
| V$GREF/PRE.01 | Progesterone receptor binding site |
| V$P53F/P53.01 | tumor suppressor p53 |
| V$ZF5F/ZF5.01 | Zinc finger/POZ domain transcription factor |
| V$EBOX/ATF6.01 | Member of b-zip family, induced by ER damage/stress, binds to the ERSE in association with NF-Y |
| V$EGRF/EGR3.01 | (early growth response gene 3 product |
| V$NF1F/NF1.01 | Nuclear factor 1 |
| V$EGRF/EGR3.01 | early growth response gene 3 product |
| V$REBV/EBVR.01 | Epstein-Barr virus transcription factor R |
| V$MOKF/MOK2.01 | Ribonucleoprotein associated zinc finger protein MOK-2 (mouse) |
| V$PBXC/PBXI_MEIS1.01 | Binding site for a Pbx1/Meis1 heterodimer |
| V$XSEC/STAF.01 | Se-Cys tRNA gene transcription activating factor |
| V$COMP/COMP1.01 | COMP1, cooperates with myogenic proteins in multicomponent complex |
| V$MYOF/MYOGNF1.01 | Myogenin/nuclear factor 1 or related factors |
| V$NEUR/NEUROD1.01 | DNA binding site for NEUROD1 (BETA-2/E47 dimer) |
| V$MYOD/MYOD.02 | myoblast determining factor |
| V$AP2F/AP2.01 | Activator protein 2 |
| V$EVI1/EVI1.02 | Ecotropic viral integration site 1 encoded factor |
| V$SMAD/SMAD4.01 | Smad4 transcription factor involved in TGF-beta signaling |
| V$MYOD/MYF5.01 | Myf5 myogenic bHLH protein |
| V$HESF/HES1.01 | Drosophila hairy and enhancer of split homologue 1 (HES-1) |
| V$PAX5/PAX5.01 | B-cell-specific activating protein |
| V$EBOX/ATF6.01 | Member of b-zip family, induced by ER damage/stress, binds to the ERSE in association with NF-Y |
| V$SP1F/GC.01 | GC box elements |
| V$MAZF/MAZR.01 | MYC-associated zinc finger protein related transcription factor |
| V$RREB/RREB1.01 | Ras-responsive element binding protein 1 |
| V$AHRR/AHRARNT.01 | Aryl hydrocarbon receptor/Arnt heterodimers |
| V$HIFF/HIF1.02 | Hypoxia inducible factor, bHLH/PAS protein family |
| V$ZF5F/ZF5.01 | Zinc finger/POZ domain transcription factor |
| V$EBOX/ATF6.01 | Member of b-zip family, induced by ER damage/stress, binds to the ERSE in association with NF-Y |

TABLE 23-continued

Sequences in Synthetic Luc Genes (version A)
TFBS in hluc + ver2A1
Before removal of TFBS from hluc + ver2A1 (110 matches)

| Family/matrix* | Further Information |
|---|---|
| V$YY1F/YY1.01 | Yin and Yang 1 |
| V$ETSF/GABP.01 | GABP: GA binding protein |
| V$MOKF/MOK2.01 | Ribonucleoprotein associated zinc finger protein MOK-2 (mouse) |
| V$ETSF/ELK1.02 | Elk-1 |
| V$EBOX/MYCMAX.03 | MYC-MAX binding sites |
| V$E4FF/E4F.01 | GLI-Krueppel-related transcription factor, regulator of adenovirus E4 promoter |
| V$XBBF/RFX1.01 | X-box binding protein RFX1 |
| V$EVI1/EVI1.06 | Ecotropic viral integration site 1 encoded factor |
| V$MOKF/MOK2.01 | Ribonucleoprotein associated zinc finger protein MOK-2 (mouse) |
| V$NF1F/NF1.01 | Nuclear factor 1 |
| V$PBXC/PBX1_MEIS1.02 | Binding site for a Pbxl/Meis1 heterodimer |
| V$ZF5F/ZF5.01 | Zinc finger/POZ domain transcription factor |
| V$HESF/HES1.01 | Drosophila hairy and enhancer of split homologue 1 (HES-1) |
| V$PAX5/PAX5.01 | B-cell-specific activating protein |
| V$ETSF/GABP.01 | GABP: GA binding-protein |
| V$MYOD/MYOD.02 | myoblast determining factor |
| V$XSEC/STAF.01 | Se-Cys tRNA gene transcription activating factor |
| V$OAZF/ROAZ.01 | Rat C2H2 Zn finger protein involved in olfactory neuronal differentiation |
| V$AP2F/AP2.01 | Activator protein 2 |
| V$PAX3/PAX3.01 | Pax-3 paired domain protein, expressed in embryogenesis, mutations correlate to Waardenburg Syndrome |
| V$AP2F/AP2.01 | Activator protein 2 |
| V$MTF1/MTF-1.01 | Metal transcription factor 1, MRE |
| V$SF1F/FTF.01 | Alpha (1)-fetoprotein transcription factor (FTF), liver receptor homologue-1 (LHR-1) |
| V$SMAD/SMAD4.01 | Smad4 transcription factor involved in TGF-beta signaling |
| V$NFKB/NFKAPPAB.01 | NF-kappaB |
| V$EKLF/EKLF.01 | Erythroid krueppel like factor (EKLF) |
| V$CREB/TAXCREB.01 | Tax/CREB complex |
| V$E2FF/E2F.03 | E2F, involved in cell cycle regulation, interacts with Rb p107 protein |
| V$CP2F/CP2.01 | CP2 |
| V$AHRR/AHRARNT.01 | Aryl hydrocarbon receptor/Arnt heterodimers |
| V$EGRF/EGR2.01 | Egr-2/Krox-20 early growth response gene product |
| V$ZF5F/ZF5.01 | Zinc finger/POZ domain transcription factor |
| V$EBOR/XBP.01 | X-box-binding protein 1 |
| V$FKHD/XFD3.01 | Xenopus fork head domain factor 3 |
| V$AP2F/AP2.01 | Activator protein 2 |
| V$EGRF/NGFIC.01 | Nerve growth factor-induced protein C |
| V$PCAT/ACAAT.01 | Avian C-type LTR CCAAT box |
| V$PBXC/PBX1_MEIS1.02 | Binding site for a Pbx1/Meis1 heterodimer |
| V$AHRR/AHRARNT.02 | Aryl hydrocarbon/Arnt heterodimers, fixed core |
| V$MOKF/MOK2.01 | Ribonucleoprotein associated zinc finger protein MOK-2 (mouse) |
| V$GREF/GRE.01 | Glucocorticoid receptor, C2C2 zinc finger protein binds glucocorticoid dependent to GREs |
| V$NEUR/NEUROD1.01 | DNA binding site for NEUROD1 (BETA-2/E47 dimer) |
| V$NRSF/NRSE.01 | neural-restrictive-silencer-element |
| V$NRSF/NRSE.01 | neural-restrictive-siiencer-element |
| V$AHRR/AHRARNT.02 | Aryl hydrocarbon/Arnt heterodimers, fixed core |
| V$EBOX/ATF6.01 | Member of b-zip family, induced by ER damage/stress, binds to the ERSE in association with NF-Y |
| V$HIFF/HIF1.02 | Hypoxia inducible factor, bHLH/PAS protein family |
| V$EGRF/EGR3.01 | early growth response gene 3 product |
| V$EGRF/EGR3.01 | early growth response gene 3 product |
| V$WHZF/WHN.01 | winged helix protein, involved in hair keratinization and thymus epithelium differentiation |
| V$AP2F/AP2.01 | Activator protein 2 |
| V$HIFF/HIF1.02 | Hypoxia inducible factor, bHLH/PAS protein family |
| V$NRSF/NRSE.01 | neural-restrictive-silencer-element |
| V$ZFIA/ZID.01 | zinc finger with interaction domain |
| V$SMAD/SMAD4.01 | Smad4 transcription factor involved in TGF-beta signaling |
| V$AHRR/AHRARNT.02 | Aryl hydrocarbon/Arnt heterodimers, fixed core |
| V$EBOX/MYCMAX.01 | c-Myc/Max heterodimer |
| V$EBOX/USF.03 | upstream stimulating factor |
| V$EGRF/EGR1.01 | Egr-1/Krox-24/NGFI-A immediate-early gene product |
| V$MINI/MUSCLE_INI.01 | Muscle Initiator Sequence |
| V$MOKF/MOK2.01 | Ribonucleoprotein associated zinc finger protein MOK-2 (mouse) |
| V$NRSF/NRSE.01 | neural-restrictive-silencer-element |
| V$NF1F/NF1.01 | Nuclear factor 1 |
| V$SF1F/SF1.01 | SF1 steroidogenic factor 1 |

**matches are listed in order of occurrence in the corresponding sequence

TFBS in hluc + ver2A3
After removal of TFBS from hluc + ver2A2 = before removal of TFBS from hluc + ver2A3 (8 matches)

| Family/matrix** | Further Information |
|---|---|
| V$EGRF/EGR2.01 | Egr-2/Krox-20 early growth response gene product |
| V$HAML/AML3.01 | Runt-related transcription factor 2/CBFA1 (core-binding factor, runt domain, alpha subunit 1) |
| V$MYOF/MYOGNF1.01 | Myogenin/nuclear factor 1 or related factors |
| V$NF1F/NF1.01 | Nuclear factor 1 |
| V$ETSF/GABP.01 | GABP: GA binding protein |
| V$NFKB/NFKAPPAB.01 | NF-kappaB |
| V$EKLF/EKLF.01 | Erythroid krueppel like factor (EKLF) |
| V$FKHD/XFD3.01 | Xenopus fork head domain factor 3 |

**matches are listed in order of occurrence in the corresponding sequence

TFBS in hluc + ver2A6
After removal of TFBS from hluc + ver2A5 (2 matches)

| Family/matrix** | Further Information |
|---|---|
| V$HAML/AML3.01 | Runt-related transcription factor 2/CBFA1 (core-binding factor, runt domain, alpha subunit 1) |
| V$FKHD/XFD3.01 | Xenopus fork head domain factor 3 |

**matches are listed in order of occurrence in the corresponding sequence

TFBS in hluc + ver2A6
Before removal of TFBS from hluc + ver2A6 (4 matches)

| Family/matrix** | Further Information |
|---|---|
| V$PAX5/PAX5.03 | PAX5 paired domain protein |
| V$LEFF/LEF1.02 | TCF/LEF-1, involved in the Wnt signal transduction pathway |
| V$IRFF/IRF7.01 | Interferon regulatory factor 7 (IRF-7) |
| V$FKHD/XFD3.01 | Xenopus fork head domain factor 3 |

**matches are listed in order of occurrence in the corresponding sequence

TFBS in hluc + ver2A7
After removal of TFBS from hluc + ver2A6 = before removal of TFBS from hluc + ver2A7 (1 match)

| Family/matrix | Further Information |
|---|---|
| V$FKHD/XFD3.01 | Xenopus fork head factor 3 |

TFBS in hluc + ver2A8
After removal of TFBS from hluc + ver2A7 (1 match)

| Family/matrix | Further Information |
|---|---|
| V$FKHD/XFD3.01 | Xenopus fork head domain factor 3 |

TABLE 24

Sequences in Synthetic Luc Genes (version B)
TFBS in hluc + ver2B1
Before removal of TFBS from hluc + ver2B1 (187 matches)

| Family/matrix** | Further Information |
|---|---|
| V$HOXF/PTX1.01 | Pituitary Homeobox 1 (Ptx1) |
| V$OCT1/OCT1.04 | octamer-binding factor 1 |
| V$OCTP/OCT1P.01 | octamer-binding factor 1, POU-specific domain |
| V$NKXH/NKX25.02 | homeo domain factor Nkx-2.5/Csx, tinman homolog low affinity sites |
| V$BARB/BARBIE.01 | barbiturate-inducible element |
| V$TBPF/TATA.01 | cellular and viral TATA box elements |
| V$GATA/GATA.01 | GATA binding site (consensus) |
| V$AP4R/AP4.01 | Activator protein 4 |
| V$HEN1/HEN1.02 | HEN1 |
| V$SRFF/SRF.01 | serum response factor |
| V$PARF/DBP.01 | Albumin D-box binding protein |
| V$MOKF/MOK2.01 | Ribonucleoprotein associated zinc finger protein MOK-2 (mouse) |
| V$EV11/EVI1.04 | Ecotropic viral integration site 1 encoded factor |
| V$GFI1/GfI1B.01 | Growth factor independence 1 zinc finger protein Gfi-1B |
| V$RBPF/RBPJK.01 | Mammalian transcriptional repressor RBP-kappa/CBF1 |
| V$TBPF/TATA.02 | Mammalian C-type LTR TATA box |
| V$AP4R/TAL1ALPHAE47.01 | Tal-1alpha/E47 heterodimer |
| V$SRFF/SRF.01 | serum response factor |
| V$OCTP/OCT1P.01 | octamer-binding factor 1, POU-specific domain |
| V$BRNF/BRN2.01 | POU factor Brn-2 (N-Oct 3) |
| V$CREB/E4BP4.01 | E4BP4, bZIP domain, transcriptional repressor |
| V$VBPF/VBP.01 | PAR-type chicken vitellogenin promoter-binding protein |
| V$EVI1/EVI1.04 | Ecotropic viral integration site 1 encoded factor |

TABLE 24-continued

Sequences in Synthetic Luc Genes (version B)
TFBS in hluc + ver2B1
Before removal of TFBS from hluc + ver2B1 (187 matches)

| Family/matrix** | Further Information |
|---|---|
| V$CLOX/CDPCR3.01 | cut-like homeodomain protein |
| V$GFI1/GfI1B.01 | Growth factor independence 1 zinc finger protein Gfi-1B |
| V$GATA/LMO2COM.02 | complex of Lmo2 bound to Tal-1, E2A proteins, and GATA-1, half-site 2 |
| V$SRFF/SRF.01 | serum response factor |
| V$HOXT/MEIS1_HOXA9.01 | Homeobox protein MEIS1 binding site |
| V$OCT1/OCT1.03 | octamer-binding factor 1 |
| V$GFI1/GFI1.01 | Growth factor independence 1 zinc finger protein acts as transcriptional repressor |
| V$HNF6/HNF6.01 | Liver enriched Cut - Homeodomain transcription factor HNF6 (ONECUT) |
| V$HAML/AML1.01 | runt-factor AML-1 |
| V$GREF/PRE.01 | Progesterone receptor binding site |
| V$STAT/STAT5.01 | STAT5: signal transducer and activator of transcription 5 |
| V$TBPF/TATA.01 | cellular and viral TATA box elements |
| V$CLOX/CDP.01 | cut-like homeodomain protein |
| V$FKHD/HFH8.01 | HNF-3/Fkh Homolog-8 |
| V$FAST/FAST1.01 | FAST-1 SMAD interacting protein |
| V$GFI1/GfI1B.01 | Growth factor independence 1 zinc finger protein Gfi-1B |
| V$CART/CART1.01 | Cart-1 (cartilage homeoprotein 1) |
| V$HMTB/MTBF.01 | muscle-specific Mt binding site |
| V$TBPF/TATA.01 | cellular and viral TATA box elements |
| V$FKHD/XFD2.01 | Xenopus fork head domain factor 2 |
| V$BRNF/BRN2.01 | POU factor Brn-2 (N-Oct 3) |
| V$MEF2/AMEF2.01 | myocyte enhancer factor |
| V$BRNF/BRN2.01 | POU factor Brn-2 (N-Oct 3) |
| V$BEL1/BEL1.01 | Bel-1 similar region (defined in Lentivirus LTRs) |
| V$NOLF/OLF1.01 | olfactory neuron-specific factor |
| V$OCT1/OCT1.06 | octamer-binding factor 1 |
| V$NFKB/NFKAPPAB.02 | NF-kappaB |
| V$BCL6/BCL6.02 | POZ/zinc finger protein, transcriptional repressor, translocations observed in diffuse large cell lymphoma |
| V$MOKF/MOK2.01 | Ribonucleoprotein associated zinc finger protein MOK-2 (mouse) |
| V$HEAT/HSF1.01 | heat shock factor 1 |
| V$OCTP/OCT1P.01 | octamer-binding factor 1, POU-specific domain |
| V$PIT1/PIT1.01 | Pit1, GHF-1 pituitary specific pou domain transcription factor |
| V$HOXF/CRX.01 | Cone-rod homeobox-containing transcription factor/otx-like homeobox gene |
| V$HNF6/HNF6.01 | Liver enriched Cut - Homeodomain transcription factor HNF6 (ONECUT) |
| V$CLOX/CLOX.01 | Clox |
| V$BCL6/BCL6.02 | POZ/zinc finger protein, transcriptional repressor, translocations observed in diffuse large cell lymphoma |
| V$HOXF/PTX1.01 | Pituitary Homeobox 1 (Ptx1) |
| V$GATA/GATA1.02 | GATA-binding factor 1 |
| V$FKHD/FREAC4.01 | Fork head RElated ACtivator-4 |
| V$E4FF/E4F.01 | GLI-Krueppel-related transcription factor, regulator of adenovirus E4 promoter |
| V$PDX1/ISL1.01 | Pancreatic and intestinal lim-homeodomain factor |
| V$CART/CART1.01 | Cart-1 (cartilage homeoprotein 1) |
| V$GFI1/GFI1.01 | Growth factor independence 1 zinc finger protein acts as transcriptional repressor |
| V$IRFF/IRF3.01 | Interferon regulatory factor 3 (IRF-3) |
| V$BARB/BARBIE.01 | barbiturate-inducible element |
| V$PBXF/PBX1.01 | homeo domain factor Pbx-1 |
| V$EVI1/EVI1.02 | Ecotropic viral integration site 1 encoded factor |
| V$GATA/GATA2.01 | GATA-binding factor 2 |
| V$BRNF/BRN2.01 | POU factor Brn-2 (N-Oct 3) |

TABLE 24-continued

Sequences in Synthetic Luc Genes (version B)
TFBS in hluc + ver2B1
Before removal of TFBS from hluc + ver2B1 (187 matches)

| Family/matrix** | Further Information |
|---|---|
| V$PARF/DBP.01 | Albumin D-box binding protein |
| V$BRNF/BRN3.01 | POU transcription factor Brn-3 |
| V$ZBPF/ZBP89.01 | Zinc finger transcription factor ZBP-89 |
| V$CREB/TAXCREB.02 | Tax/CREB complex |
| V$GREF/PRE.01 | Progesterone receptor binding site |
| V$RBPF/RBPJK.01 | Mammalian transcriptional repressor RBP-Jkappa/CBF1 |
| V$GATA/GATA3.02 | GATA-binding factor 3 |
| V$STAT/STAT.01 | signal transducers and activators of transcription |
| V$IKRS/IK2.01 | Ikaros 2, potential regulator of lymphocyte differentiation |
| V$SRFF/SRF.01 | serum response factor |
| V$SEF1/SEF1.01 | SEF1 binding site |
| V$HAML/AML1.01 | runt-factor AML-1 |
| V$MOKF/MOK2.02 | Ribonucleoprotein associated zinc finger protein MOK-2 (human) |
| V$FKHD/FREAC2.01 | Fork head RElated ACtivator-2 |
| V$HMTB/MTBF.01 | muscle-specific Mt binding site |
| V$GFI1/GFI1.01 | Growth factor independence 1 zinc finger protein acts as transcriptional repressor |
| V$ECAT/NFY.03 | nuclear factor Y (Y-box binding factor) |
| V$HOXT/MEIS1_HOXA9.01 | Homeobox protein MEIS 1 binding site |
| V$PCAT/ACAAT.01 | Avian C-type LTR CCAAT box |
| V$HNF6/HNF6.01 | Liver enriched Cut - Homeodomain transcription factor HNF6 (ONECUT) |
| V$CLOX/CLOX.01 | Clox |
| V$GATA/GATA3.02 | GATA-binding factor 3 |
| V$AREB/AREB6.04 | AREB6 (Atp1al regulatory element binding factor 6) |
| V$GATA/GATA3.02 | GATA-binding factor 3 |
| V$FKHD/HNF3B.01 | Hepatocyte Nuclear Factor 3beta |
| V$IRFF/IRF1.01 | interferon regulatory factor 1 |
| V$NKXH/NKX31.01 | prostate-specific homeodomain protein NKX3.1 |
| V$PBXF/PBX1.01 | homeo domain factor Pbx-1 |
| V$ECAT/NFY.03 | nuclear factor Y (Y-box binding factor) |
| V$PBXC/PBX1_MEIS1.02 | Binding site for a Pbx1/Meis1 heterodimer |
| V$CLOX/GDP.02 | transcriptional repressor CDP |
| V$HOXT/MEIS1_HOXA9.01 | Homeobox protein MEIS1 binding site |
| V$HOXF/HOXA9.01 | Member of the vertebrate HOX - cluster of homeobox factors |
| V$GATA/GATA.01 | GATA binding site (consensus) |
| V$NKXH/NKX31.01 | prostate-specific homeodomain protein NKX3.1 |
| V$GATA/GATA3.02 | GATA-binding factor 3 |
| V$HOXF/CRX.01 | Cone-rod homeobox-containing transcription factor/otx-like homeobox gene |
| V$CART/CART1.01 | Cart-1 (cartilage homeoprotein 1) |
| V$OCT1/OCT1.02 | octamer-binding factor 1 |
| V$MAZF/MAZR.01 | MYC-associated zinc finger protein related transcription factor |
| V$ZBPF/ZBP89.01 | Zinc finger transcription factor ZBP-89 |
| V$GATA/GATA3.02 | GATA-binding factor 3 |
| V$HOXF/CRX.01 | Cone-rod homeobox-containing transcription factor/otx-like homeobox gene |
| V$CLOX/CDPCR3.01 | cut-like homeodomain protein |
| V$AP1F/VMAF.01 | v-Maf |
| V$AP4R/TAL1ALPHAE47.01 | Tal-1alpha/E47 heterodimer |
| V$PAX8/PAX8.01 | PAX 2/5/8 binding site |
| V$BRAC/BRACH.01 | Brachyury |
| V$GATA/GATA1.02 | GATA-binding factor 1 |
| V$RREB/RREB1.01 | Ras-responsive element binding protein 1 |
| V$MZF1/MZF1.01 | MZF1 |
| V$MOKF/MOK2.02 | Ribonucleoprotein associated zinc finger protein MOK-2 (human) |
| V$HOXF/PTX1.01 | Pituitary Homeobox 1 (Ptx1) |
| V$LTUP/TAACC.01 | Lentiviral TATA upstream element |
| V$AP4R/TH1E47.01 | Thing1/E47 heterodimer, TH1 bHLH member specific expression in a variety of embryonic tissues |
| V$XSEC/STAF.01 | Se-Cys tRNA gene transcription activating factor |
| V$IKRS/IK3.01 | Ikaros 3, potential regulator of lymphocyte differentiation |
| V$AP1F/AP1.01 | AP1 binding site |
| V$MAZF/MAZ.01 | Myc associated zinc finger protein (MAZ) |
| V$MZF1/MZF1.01 | MZF1 |
| V$CLOX/CDPCR3.01 | cut-like homeodomain protein |
| V$P53F/P53.01 | tumor suppressor p53 |
| V$SMAD/SMAD3.01 | Smad3 transcription factor involved in TGF-beta signaling |
| V$HMTB/MTBF.01 | muscle-specific Mt binding site |
| V$OCT1/OCT1.03 | octamer-binding factor 1 |
| V$FKHD/XFD3.01 | Xenopus fork head domain factor 3 |
| V$PIT1/PIT1.01 | Pit1, GHF-1 pituitary specific pou domain transcription factor |
| V$OCTP/OCT1P.01 | octamer-binding factor 1, POU-specific domain |
| V$HOXF/HOX1-3.01 | Hox-1.3, vertebrate homeobox protein |
| V$PBXF/PBX1.01 | homeo domain factor Pbx-1 |
| V$ECAT/NFY.03 | nuclear factor Y (Y-box binding factor) |
| V$PBXC/PBX1_MEIS1.02 | Binding site for a Pbx1/Meis1 heterodimer |
| V$CLOX/CDP.02 | transcriptional repressor CDP |
| V$HOXT/MEIS1_HOXA9.01 | Homeobox protein MEIS1 binding site |
| V$HOXF/HOXA9.01 | Member of the vertebrate HOX - cluster of homeobox factors |
| V$GATA/GATA1.02 | GATA-binding factor 1 |
| V$PCAT/ACAAT.01 | Avian C-type LTR CCAAT box |
| V$XSEC/STAF.01 | Se-Cys tRNA gene transcription activating factor |
| V$OCTP/OCT1P.01 | octamer-binding factor 1, POU-specific domain |
| V$CLOX/CDP.01 | cut-like homeodomain protein |
| V$FAST/FAST1.01 | FAST-1 SMAD interacting protein |
| V$ECAT/NFY.01 | nuclear factor Y (Y-box binding factor) |
| V$MEF2/MMEF2.01 | myocyte enhancer factor |
| V$TBPF/TATA.02 | Mammalian C-type LTR TATA box |
| V$FAST/FAST1.01 | FAST-1 SMAD interacting protein |
| V$LTUP/TAACC.01 | Lentiviral TATA upstream element |
| V$MOKF/MOK2.01 | Ribonucleoprotein associated zinc finger protein MOK-2 (mouse) |
| V$BRNF/BRN2.01 | POU factor Brn-2 (N-Oct 3) |
| V$HOXF/CRX.01 | Cone-rod homeobox-containing transcription factor/otx-like homeobox gene |
| V$NKXH/NKX31.01 | prostate-specific homeodomain protein NKX3.1 |
| V$HEN1/HEN1.01 | HEN1 |
| V$BEL1/BEL1.01 | Bel-1 similar region (defined in Lentivirus LTRs) |
| V$HOXF/PTX1.01 | Pituitary Homeobox 1 (Ptx1) |
| V$BRNF/BRN2.01 | POU factor Brn-2 (N-Oct 3) |
| V$NFKB/NFKAPPAB.01 | NF-kappaB |
| V$HAML/AML1.01 | runt-factor AML-1 |
| V$ZFIA/ZID.01 | zinc finger with interaction domain |
| V$XSEC/STAF.02 | Se-Cys tRNA gene transcription activating factor |
| V$IKRS/IK1.01 | Ikaros 1, potential regulator of lymphocyte differentiation |
| V$FAST/FAST1.01 | FAST-1 SMAD interacting protein |
| V$MOKF/MOK2.01 | Ribonucleoprotein associated zinc finger protein MOK-2 (mouse) |
| V$BEL1/BEL1.01 | Bel-1 similar region (defined in Lentivirus LTRs) |
| V$EGRF/WT1.01 | Wilms Tumor Suppressor |
| V$MAZF/MAZR.01 | MYC-associated zinc finger protein related transcription factor |
| V$ZBPF/ZBP89.01 | Zinc finger transcription factor ZBP-89 |

Sequences in Synthetic Luc Genes (version B)
TFBS in hluc + ver2B1
Before removal of TFBS from hluc + ver2B1 (187 matches)

| Family/matrix** | Further Information |
|---|---|
| V$ZBPF/ZBP89.01 | Zinc finger transcription factor ZBP-89 |
| V$SP1F/GC.01 | GC box elements |
| V$RREB/RREB1.01 | Ras-responsive element binding protein 1 |
| V$MOKF/MOK2.01 | Ribonucleoprotein associated zinc finger protein MOK-2 (mouse) |
| V$MEIS/MEIS1.01 | Binding site for monomeric Meis1 homeodomain protein |
| V$BCL6/BCL6.02 | POZ/zinc finger protein, transcriptional repressor, translocations observed in diffuse large cell lymphoma |
| V$GATA/GATA3.02 | GATA-binding factor 3 |
| V$HOXF/CRX.01 | Cone-rod homeobox-containing transcription factor/otx-like homeobox gene |
| V$HOX/CRX.01 | Cone-rod homeobox-containing transcription factor/otx-like homeobox gene |
| V$MAZF/MAZR.01 | MYC-associated zinc finger protein related transcription factor |
| V$MZF1/MZF.01 | MZF1 |
| V$PDX1/PDX1.01 | Pdx1 (IDX1/IPF1) pancreatic and intestinal homeodomain TF |

**matches are listed in order of occurrence in the corresponding sequence

TFBS in hluc + ver2B3
After removal of TFBS from hluc + ver2B2 = before removal of TFBS from hluc + ver2B3 (35 matches)

| Family/matrix** | Further Information |
|---|---|
| V$OCT1/OCT1.04 | octamer-binding factor 1 |
| V$BARB/BARBIE.01 | barbiturate-inducible element |
| V$NFKB/NFKAPPAB.02 | NF-kappaB |
| V$OCTP/OCT1P.01 | octamer-binding factor 1, POU-specific domain |
| V$PIT1/PIT1.01 | Pit1, GHF-1 pituitary specific pou domain transcription factor |
| V$HOXF/PTX1.01 | Pituitary Homeobox 1 (Ptx1) |
| V$FKHD/FREAC4.01 | Fork head RElated ACtivator-4 |
| V$E4FF/E4F.01 | GLI-Krueppel-related transcription factor, regulator of adenovirus E4 promoter |
| V$EVI1/EVI1.02 | Ecotropic viral integration site 1 encoded factor |
| V$GATA/GATA2.01 | GATA-binding factor 2 |
| V$GREF/PRE.01 | Progesterone receptor binding site |
| V$RBPF/RBPJK.01 | Mammalian transcriptional repressor Jkappa/CBF1 |
| V$STAT/STAT.01 | signal transducers and activators of transcription |
| V$IKRS/IK2.01 | Ikaros 2, potential regulator of lymphocyte differentiation |
| V$FKHD/FREAC2.01 | Fork head RElated ACtivator-2 |
| V$SRFF/SRF.01 | serum response factor |
| V$GREF/PRE.01 | Progesterone receptor binding site |
| V$CLOX/CDPCR3.01 | cut-like homeodomain protein |
| V$AP4R/TAL1ALPHAE47.01 | Tal-1alpha/E47 heterodimer |
| V$GATA/GATA1.02 | GATA-binding factor 1 |
| V$FKHD/XFD3.01 | Xenopus fork head domain factor 3 |
| V$PBXF/PBX1.01 | homeo domain factor Pbx-1 |
| V$ECAT/NFY.03 | nuclear factor Y (Y-box binding factor) |
| V$PBXC/PBX1_MEIS1.02 | Binding site for a Pbx1/Meis1 heterodimer |
| V$CLOX/CDP.02 | transcriptional repressor CDP |
| V$HOXT/MEIS1_HOXA9.01 | Homeobox protein MEIS1 binding site |
| V$HOXF/HOXA9.01 | Member of the vertebrate HOX - cluster of homeobox factors |

TFBS in hluc + ver2B3
After removal of TFBS from hluc + ver2B2 = before removal of TFBS from hluc + ver2B3 (35 matches)

| Family/matrix** | Further Information |
|---|---|
| V$GATA/GATA1.02 | GATA-binding factor 1 |
| V$MINI/MUSCLE_INI.01 | Muscle Initiator Sequence |
| V$CLOX/CDP.01 | cut-like homeodomain protein |
| V$BRNF/BRN2.01 | POU factor Brn-2 (N-Oct 3) |
| V$NFKB/NFKAPPAB.01 | NF-kappaB |
| V$ZFIA/ZID.01 | zinc finger with interaction domain |
| V$BCL6/BCL6.02 | POZ/zinc finger protein, transcriptional repressor, translocations observed in diffuse large cell lymphoma |
| V$HOXF/CRX.01 | Cone-rod homeobox-containing transcription factor/otx-like homeobox gene |

**matches are listed in order of occurrence in the corresponding sequence

TFBS in hluc + ver2B6
After removal of TFBS from hluc + ver2B5 (2 matches)

| Family/matrix** | Further Information |
|---|---|
| V$HOXF/PTX1.01 | Pituitary Homeobox 1 (Ptx1) |
| V$FKHD/XFD3.01 | Xenopus fork head domain factor 3 |

**matches are listed in order of occurrence in the corresponding sequence

TFBS in hluc + ver2B6
Before removal of TFBS from hluc + ver2B6 (6 matches)

| Family/matrix** | Further Information |
|---|---|
| V$PAX6/PAX4_PD.01 | PAX4 paired domain binding site |
| V$HOXF/PTX1.01 | Pituitary Homeobox 1 (Ptx1) |
| V$FKHD/XFD3.01 | Xenopus fork head domain factor 3 |
| V$PAX6/PAX6.02 | PAX6 paired domain and homeodomain are required for binding to this site |
| V$PAX5/PAX5.03 | PAX5 paired domain protein |
| V$IRFF/IRF3.01 | Interferon regulatory factor 3 (IRF-3) |

**matches are listed in order of occurrence in the corresponding sequence

TFBS in hluc + ver2B7
After removal of TFBS from hluc + ver2B6 = before removal of TFBS from hluc + ver2B7 (2 matches)

| Family/matrix** | Further Information |
|---|---|
| V$HOXF/PTX1.01 | Pituitary Homeobox 1 (Ptx1) |
| V$FKHD/XFD3.01 | Xenopus fork head domain factor 3 |

**matches are listed in order of occurrence in the corresponding sequence

TFBS in hluc + ver2B8
After removal of TFBS from hluc + ver2B7 = before removal of TFBS from hluc + ver2B8 (1 match)

| Family/matrix | Further Information |
|---|---|
| V$FKHD/XFD3.01 | Xenopus fork head domain factor 3 |

TFBS in hluc + ver2B9
After removal of TFBS from hluc + ver2B8 = before removal of TFBS
from hluc + ver2B9 (1 match)

| Family/matrix | Further Information |
|---|---|
| V$FKHD/XFD3.01 | Xenopus fork head domain factor 3 |

TFBS in hluc + ver2B10
After removal of TFBS from hluc + ver2B9 (1 match)

| Family/matrix | Further Information |
|---|---|
| V$FKHD/XFD3.01 | Xenopus fork head domain factor 3 |

EXAMPLE 8

Summary of Design for pGL4 Sequences

FIG. 2 depicts the design scheme for the pGL4 vector. A portion of the vector backbone in pGL3 which includes an bla gene and a sequence between bla and a multiple cloning region, but not a second open reading frame, was modified to yield pGL4. pGL4 includes an ampicillin resistance gene between a NotI and a SpeI site, the sequence of which was modified to remove regulatory sequences but not to optimize codons for mammalian expression (bla-1-bla-5), and a SpeI-NcoI fragment that includes a multiple cloning region and a translation trap. The translation trap includes about 60 nucleotides having at least two stop codons in each reading frame. The SpeI-NcoI fragment from a parent vector, pGL4-basics-5F2G-2, was modified to decrease undesired regulatory sequences (MCS-1 to MCS-4; SEQ ID Nos. 76-79). One of the resulting sequences, MCS-4, was combined with a modified ampicillin resistance gene, bla-5 (SEQ ID NO:84), to yield pGL4B-4NN (SEQ ID NO:95). pGL4B-4NN was further modified (pGL4-NN1-3; SEQ ID Nos. 96-98). To determine if additional polyA sequences in the SpeI-NcoI fragment further reduced expression from the vector backbone, various polyA sequences were inserted therein. For instance, pGL4NN-Blue Heron included a c-mos polyA sequence in the SpeI-NcoI fragment. However, removal of regulatory sequences in polyA sequences may alter the secondary structure and thus the function of those sequences.

In one vector, the SpeI-NcoI fragment from pGL3 (SpeI-NcoI start ver 2; SEQ ID NO:48) was modified to remove one transcription factor binding site and one restriction enzyme recognition site, and after the multiple cloning region, yielding SpeI-NcoI ver2 (SEQ ID NO:49).

TF Binding Sites and Search Parameters

Each TF binding site ("matrix") belongs to a matrix family that groups functionally similar matrices together, eliminating redundant matches by MatInspector professional (the search program). Searches were limited to vertebrate TF binding sites. Searches were performed by matrix family, i.e., the results show only the best match from a family for each site. MatInspector default parameters were used for the core and matrix similarity values (core similarity=0.75, matrix similarity=optimized), except for sequence MCS-1 (core similarity=1.00, matrix similarity=optimized).

TABLE 25

Description of Designed Sequences
pGL4 sequences

| Sequence | Description | Matrix Library |
|---|---|---|
| | SpeI-NcoI fragment with MCS, translation trap | |
| MCS-1 | SpeI-NcoI from pGL4-basics-5F2G-2 | Ver 2.2 September 2001 |
| MCS-2 | First removal of undesired sequence matches | Ver 2.2 September 2001 |
| MCS-3 | Second removal of undesired sequence matches | Ver 2.2 September 2001 |
| MCS-4 | Third removal of undesired sequence matches | Ver 2.3 February 2001 |
| | NotI-SpeI fragment with bla gene | |
| Bla bla-1* | Beta-lactamase gene from pGL3 vectors SacII (RE) added, BsmAI (RE) site removed (*) | Ver 2.2 September 2001 |
| bla-2* | First removal of undesired sequence matches | Ver 2.3 February 2001 |
| bla-3* | Second removal of undesired sequence matches | Ver 2.3 February 2001 |
| bla-4* | Third removal of undesired sequence matches | Ver 2.3 February 2001 |
| bla-5* | Fourth removal of undesired sequence matches | Ver 2.3 February 2001 |
| | NotI-NcoI fragment with bla, translation trap, MCS | |
| pGL4B-4NN | Combination of bla-5 and MCS-4 sections | Ver 2.4 May 2002 |
| pGL4B-4NN1 | First removal of undesired sequence matches | Ver 2.4 May 2002 |
| pGL4B-4NN2 | Second removal of undesired sequence matches | Ver 2.4 May 2002 |
| pGL4B-4NN3 | Third version after removal of CEBP (TF) site | Ver 2.4 May 2002 |
| | SpeI-NcoI fragment with translation trap, polyA, MCS | |
| SpeI-NcoI-Ver2-start | Existing MCS replaced with new MCS | Ver 4.0 November 2003 |
| SpeI-NcoI-Ver2 | First removal of undesired sequence matches | Ver 4.0 November 2003 |

(*) Bla codon usage was not optimized for expression in mammalian cells. Low usage *E. coli* codons were avoided when changes were introduced to remove undesired sequence elements.

TABLE 26

Sequences in Synthetic SpeI-NcoI fragment of pGL4
TFBS in MCS-1
Before removal of TFBS from MCS-1 (14 matches)

| Name of Family/matrix** | Further Information |
|---|---|
| V$PAX3/PAX3.01 | Pax-3 paired domain protein, expressed in embryogenesis, mutations correlate to Waardenburg Syndrome |
| V$GATA/GATA.01 | GATA binding site (consensus) |

TABLE 26-continued

Sequences in Synthetic SpeI-NcoI fragment of pGL4
TFBS in MCS-1
Before removal of TFBS from MCS-1 (14 matches)

| Name of Family/matrix** | Further Information |
|---|---|
| V$NKXH/NKX31.01 | prostate-specific homeodomain protein NKX3.1 |
| V$CREB/E4BP4.01 | E4BP4, bZIP domain, transcriptional repressor |
| V$BRN2/BRN2.01 | POU factor Brn-2 (N-Oct 3) |
| V$CREB/E4BP4.01 | E4BP4, bZIP domain, transcriptional repressor |
| V$NKXH/NKX31.01 | prostate-specific homeodomain protein NKX3.1 |
| V$ZFIA/ZID.01 | zinc finger with interaction domain |
| V$CP2F/CP2.01 | CP2 |
| V$BRAC/BRACH.01 | Brachyury |
| V$PAX6/PAX6.01 | Pax-6 paired domain protein |
| V$NKXH/NKX31.01 | prostate-specific homeodomain protein NKX3.1 |
| V$TEAF/TEF1.01 | TEF-1 related muscle factor |
| V$ETSF/ELK1.02 | Elk-1 |

**matches are listed in order of occurrence in the corresponding sequence

TFBS in MCS-2
After removal of TFBS from MCS-1 = before removal of TFBS from MCS-2 (12 matches)

| Name of family/matrix** | Further Information |
|---|---|
| V$GATA/GATA.01 | GATA binding site (consensus) |
| V$NKXH/NKX31.01 | prostate-specific homeodomain protein NKX3.1 |
| V$TBPF/ATATA.01 | Avian C-type LTR TATA box |
| V$CART/CART1.01 | Cart-1 (cartilage homeoprotein 1) |
| V$CREB/E4BP4.01 | E4BP4, bZIP domain, transcriptional repressor |
| V$BRN2/BRN2.01 | POU factor Brn-2 (N-Oct 3) |
| V$CREB/E4BP4.01 | E4BP4, bZIP domain, transcriptional repressor |
| V$TBPF/ATATA.01 | Avian C-type LTR TATA box |
| V$NKXH/NKX31.01 | prostate-specific homeodomain protein NKX3.1 |
| V$PAX6/PAX6.01 | Pax-6 paired domain protein |
| V$PAX8/PAX8.01 | PAX 2/5/8 binding site |
| V$PAX1/PAX1.01 | Pax1 paired domain protein, expressed in the developing vertebral column of mouse embryos |

**matches are listed in order of occurrence in the corresponding sequence

TFBS in MCS-3
After removal of TFBS from MCS-2=before removal of TFBS from MCS-4 (0 matches)

TFBS in MCS-4
After removal of TFBS from MCS-3 (0 matches)

TABLE 27

Sequences in Synthetic NotI-SpeI Fragment of pGL4
TFBS in bla-1
Before removal of TFBS from bla-1 (94 matches)

| Name of family/matrix** | Further Information |
|---|---|
| V$GATA/GATA1.02 | GATA-binding factor 1 |
| V$HOXF/HOX1-3.01 | Hox-1.3, vertebrate homeobox protein |
| V$TBPF/ATATA.01 | Avian C-type LTR TATA box |
| V$ETSF/NRF2.01 | nuclear respiratory factor 2 |
| V$OCTP/OCT1P.01 | octamer-binding factor 1, POU-specific domain |
| V$ETSF/ELK1.02 | Elk-1 |
| V$GKLF/GKLF.01 | gut-enriched Krueppel-like factor |
| V$E2FF/E2F.02 | E2F, involved in cell cycle regulation, interacts with Rb p107 protein |
| V$ETSF/NRF2.01 | nuclear respiratory factor 2 |
| V$AP1F/VMAF.01 | v-Maf |
| V$XBBF/RFX1.01 | X-box binding protein RFX1 |
| V$AREB/AREB6.04 | AREB6 (Atp1a1 regulatory element binding factor 6) |
| V$CMYB/CMYB.01 | c-Myb, important in hematopoesis, cellular equivalent to avian myoblastosis virus oncogene v-myb |
| V$VMYB/VMYB.02 | v-Myb |
| V$EBOX/NMYC.01 | N-Myc |
| V$VBPF/VBP.01 | PAR-type chicken vitellogenin promoter-binding protein |
| V$CMYB/CMYB.01 | c-Myb, important in hematopoesis, cellular equivalent to avian myoblastosis virus oncogene v-myb |
| V$GATA/GATA3.02 | GATA-binding factor 3 |
| V$PAX8/PAX8.01 | PAX 2/5/8 binding site |
| V$HNF4/HNF4.02 | Hepatic nuclear factor 4 |
| V$E2FF/E2F.01 | E2F, involved in cell cycle regulation, interacts with Rb p107 protein |
| V$NFAT/NFAT.01 | Nuclear factor of activated T-cells |
| V$ECAT/NFY.02 | nuclear factor Y (Y-box binding factor) |
| V$TBPF/TATA.02 | Mammalian C-type LTR TATA box |
| V$MYT1/MYT1.02 | MyT1 zinc finger transcription factor involved in primary neurogenesis |
| V$GATA/GATA3.01 | GATA-binding factor 3 |
| V$CREB/CREB.02 | cAMP-responsive element binding protein |
| V$WHZF/WHN.01 | winged helix protein, involved in hair keratinization and thymus epithelium differentiation |
| V$IRFF/ISRE.01 | interferon-stimulated response element |
| V$NRSF/NRSE.01 | neural-restrictive-silencer-element |
| V$TCFF/TCF11.01 | TCF11/KCR-F1/Nrf1 homodimers |
| V$STAT/STAT.01 | signal transducers and activators of transcription |
| V$ECAT/NFY.03 | nuclear factor Y (Y-box binding factor) |
| V$OCT1/OCT1.05 | octamer-binding factor 1 |
| V$OCTP/OCT1P.01 | octamer-binding factor 1, POU-specific domain |
| V$NKXH/NKX25.02 | homeo domain factor Nkx-2.5/Csx, tinman homolog low affinity sites |
| V$PIT1/PIT1.01 | Pit1, GHF-1 pituitary specific pou domain transcription factor |
| V$CLOX/CDPCR3.01 | cut-like homeodomain protein |
| V$GREF/ARE.01 | Androgene receptor binding site |
| V$GATA/GATA1.04 | GATA-binding factor 1 |
| V$E2TF/E2.02 | papilloma virus regulator E2 |
| V$RPOA/POLYA.01 | Mammalian C-type LTR Poly A signal |
| V$VMYB/VMYB.02 | v-Myb |
| V$CEBP/CEBPB.01 | CCAAT/enhancer binding protein beta |
| V$VBPF/VBP.01 | PAR-type chicken vitellogenin promoter-binding protein |
| V$CREB/HLF.01 | hepatic leukemia factor |
| V$SF1F/SF1.01 | SF1 steroidogenic factor 1 |
| V$XBBF/MIF1.01 | MIBP-1/RFX1 complex |
| V$IKRS/IK2.01 | Ikaros 2, potential regulator of lymphocyte differentiation |
| V$MINI/MUSCLE_INI.02 | Muscle Initiator Sequence |
| V$PCAT/CLTR_CAAT.01 | Mammalian C-type LTR CCAAT box |
| V$PAX5/PAX5.01 | B-cell-specific activating protein |
| V$RPAD/PADS.01 | Mammalian C-type LTR Poly A downstream element |
| V$XBBF/RFX1.02 | X-box binding protein RFX1 |
| V$CEBP/CEBPB.01 | CCAAT/enhancer binding protein beta |
| V$CREB/HLF.01 | hepatic leukemia factor |
| V$HNF1/HNF1.01 | hepatic nuclear factor 1 |
| V$VMYB/VMYB.01 | v-Myb |

TABLE 27-continued

Sequences in Synthetic NotI-SpeI Fragment of pGL4
TFBS in bla-1
Before removal of TFBS from bla-1 (94 matches)

| Name of family/matrix** | Further Information |
|---|---|
| V$NKXH/NKX31.01 | prostate-specific homeodomain protein NKX3.1 |
| V$XBBF/RFX1.01 | X-box binding protein RFX1 |
| V$STAT/STAT.01 | signal transducers and activators of transcription |
| V$HNF1/HNF1.01 | hepatic nuclear factor 1 |
| V$HMYO/S8.01 | S8 |
| V$SORY/SOX5.01 | Sox-5 |
| V$RBIT/BRIGHT.01 | Bright, B cell regulator of IgH transcription |
| V$NKXH/NKX25.02 | homeo domain factor Nkx-2.5/Csx, tinman homolog low affinity sites |
| V$GATA/GATA1.02 | GATA-binding factor 1 |
| V$BARB/BARBIE.01 | barbiturate-inducible element |
| V$MTF1/MTF-1.01 | Metal transcription factor 1, MRE |
| V$NFKB/CREL.01 | c-Rel |
| V$ETSF/ELK1.02 | Elk-1 |
| V$CLOX/CDP.01 | cut-like homeodomain protein |
| V$RPOA/LPOLYA.01 | Lentiviral Poly A signal |
| V$GATA/GATA1.03 | GATA-binding factor 1 |
| V$ZFIA/ZID.01 | zinc finger with interaction domain |
| V$WHZF/WHN.01 | winged helix protein, involved in hair keratinization and thymus epithelium differentiation |
| V$PAX1/PAX1.01 | Pax1 paired domain protein, expressed in the developing vertebral column of mouse embryos |
| V$GATA/LMO2COM.02 | complex of Lmo2 bound to Tal-1, E2A proteins, and GATA-1, half-site 2 |
| V$NRSF/NRSF.01 | neuron-restrictive silencer factor |
| V$AP4R/TAL1BETAE47.01 | Tal-1beta/E47 heterodimer |
| V$GATA/LMO2COM.02 | complex of Lmo2 bound to Tal-1, E2A proteins, and GATA-1, half-site 2 |
| V$GATA/GATA1.02 | GATA-binding factor 1 |
| V$XBBF/RFX1.01 | X-box binding protein RFX1 |
| V$AHRR/AHRARNT.02 | aryl hydrocarbon/Arnt heterodimers, fixed core |
| V$PAX5/PAX9.01 | zebrafish PAX9 binding sites |
| V$CLOX/CDP.02 | transcriptional repressor CDP |
| V$GATA/GATA1.01 | GATA-binding factor 1 |
| V$AP1F/TCF11MAFG.01 | TCF11/MafG heterodimers, binding to subclass of AP1 sites |
| V$BRN2/BRN2.01 | POU factor Brn-2 (N-Oct 3) |
| V$NKXH/NKX25.02 | homeo domain factor Nkx-2.5/Csx, tinman homolog low affinity sites |
| V$ECAT/NFY.02 | nuclear factor Y (Y-box binding factor) |
| V$FKHD/FREAC4.01 | Fork head RElated ACtivator-4 |
| V$NFAT/NFAT.01 | Nuclear factor of activated T-cells |
| V$IRFF/IRF1.01 | interferon regulatory factor 1 |
| V$E2FF/E2F.02 | E2F, involved in cell cycle regulation, interacts with Rb p107 protein |

**matches are listed in order of occurrence in the corresponding sequence

TFBS in bla-2
After removal of TFBS from bla-1 = before removal of TFBS from bla-2 = (51 matches)

| Name of family/matrix** | Further Information |
|---|---|
| V$GATA/GATA1.02 | GATA-binding factor 1 |
| V$ETSF/NRF2.01 | nuclear respiratory factor 2 |
| V$OCTP/OCT1P.01 | octamer-binding factor 1, POU-specific domain |
| V$ETSF/ELK1.02 | Elk-1 |
| V$EBOX/NMYC.01 | N-MYc |
| V$GATA/GATA3.02 | GATA-binding factor 3 |
| V$PAX8/PAX8.01 | PAX 2/5/8 binding site |
| V$HNF4/HNF4.02 | Hepatic nuclear factor 4 |
| V$E2FF/E2F.01 | E2F, involved in cell cycle regulation, interacts with Rb p107 protein |
| V$NFAT/NFAT.01 | Nuclear factor of activated T-cells |
| V$ECAT/NFY.02 | nuclear factor Y (Y-box binding factor) |
| V$TBPF/TATA.02 | Mammalian C-type LTR TATA box |
| V$MYT1/MYT1.02 | MyT1 zinc finger transcription factor involved in primary neurogenesis |
| V$GATA/GATA3.01 | GATA-binding factor 3 |
| V$CREB/CREB.02 | cAMP-responsive element binding protein |
| V$WHZF/WHN.01 | winged helix protein, involved in hair keratinization and thymus epithelium differentiation |
| V$NRSF/NRSE.01 | neural-restrictive-silencer-element |
| V$OCT1/OCT1.05 | octamer-binding factor 1 |
| V$CLOX/CDPCR3.01 | cut-like homeodomain protein |
| V$GREF/ARE.01 | Androgene receptor binding site |
| V$GATA/GATA1.04 | GATA-binding factor 1 |
| V$CEBP/CEBPB.01 | CCAAT/enhancer binding protein beta |
| V$CREB/HLF.01 | hepatic leukemia factor |
| V$VBPF/VBP.01 | PAR-type chicken vitellogenin promoter-binding protein |
| V$XBBF/MIF1.01 | MIBP-1/RFX1 complex |
| V$IKRS/IK2.01 | Ikaros 2, potential regulator of lymphocyte differentiation |
| V$PAX5/PAX5.01 | B-cell-specific activating protein |
| V$XBBF/RFX1.02 | X-box binding protein RFX1 |
| V$CEBP/CEBPB.01 | CCAAT/enhancer binding protein beta |
| V$CREB/HLF.01 | hepatic leukemia factor |
| V$XBBF/RFX1.02 | X-box binding protein RFX1 |
| V$GATA/GATA1.02 | GATA-binding factor 1 |
| V$BARB/BARBIE.01 | barbiturate-inducible element |
| V$MTF1/MTF-1.01 | Metal transcription factor 1, MRE |
| V$NFKB/CREL.01 | c-Rel |
| V$ETSF/ELK1.02 | Elk-1 |
| V$TBPF/TATA.01 | cellular and viral TATA box elements |
| V$MEIS/MEIS1.01 | Homeobox protein MEIS1 binding site |
| V$HOXF/HOXA9.01 | Member of the vertebrate HOX - cluster of homeobox factors |
| V$GATA/GATA1.03 | GATA-binding factor 1 |
| V$MEIS/MEIS1.01 | Homeobox protein MEIS1 binding site |
| V$NOLF/OLF1.01 | olfactory neuron-specific factor |
| V$AP4R/TAL1BETAE47.01 | Tal-1 beta/E47 heterodimer |
| V$GATA/GATA1.02 | GATA-binding factor 1 |
| V$XBBF/RFX1.01 | X-box binding protein RFX1 |
| V$AHRR/AHRARNT.02 | aryl hydrocarbon/Arnt heterodimers, fixed core |
| V$PAX5/PAX9.01 | zebrafish PAX9 binding sites |
| V$CLOX/CDP.02 | transcriptional repressor CDP |
| V$GATA/GATA1.01 | GATA-binding factor 1 |
| V$IRFF/IRF1.01 | interferon regulatory factor 1 |
| V$E2FF/E2F.02 | E2F, involved in cell cycle regulation, interacts with Rb p107 protein |

**matches are listed in order of occurrence in the corresponding sequence

TFBS in bla-3
After removal of TFBS from bla-2 = before removal of TFBS from bla-3 = (16 matches)

| Name of family/matrix** | Further Information |
|---|---|
| V$ETSF/NRF2.01 | nuclear respiratory factor 2 |
| V$E2FF/E2F.02 | E2F, involved in cell cycle regulation, interacts with Rb p107 protein |
| V$NFAT/NFAT.01 | Nuclear factor of activated T-cells |
| V$TBPF/TATA.02 | Mammalian C-type LTR TATA box |

-continued

TFBS in bla-3
After removal of TFBS from bla-2 = before removal of TFBS from
bla-3 = (16 matches)

| Name of family/matrix** | Further Information |
|---|---|
| V$MYT1/MYT1.02 | MyT1 zinc finger transcription factor involved in primary neurogenesis |
| V$WHZF/WHN.01 | winged helix protein, involved in hair keratinization and thymus epithelium differentiation |
| V$SORY/SOX5.01 | Sox-5 |
| V$CEBP/CEBPB.01 | CCAAT/enhancer binding protein beta |
| V$CREB/HLF.01 | hepatic leukemia factor |
| V$VBPF/VBP.01 | PAR-type chicken vitellogenin promoter-binding protein |
| V$PAX5/PAX5.01 | B-cell-specific activating protein |
| V$XBBF/RFX1.02 | X-box binding protein RFX1 |
| V$CREB/HLF.01 | hepatic leukemia factor |
| V$GATA/GATA1.03 | GATA-binding factor 1 |
| V$MEIS/MEIS.01 | Homeobox protein MEIS1 binding site |
| V$NOLF/OLF1.01 | olfactory neuron-specific factor |

**matches are listed in order of occurrence in the corresponding sequence

TFBS in bla-4
After removal of TFBS from bla-3 = before removal of TFBS from
bla-4 = (14 matches)

| Name of family/matrix** | Further Information |
|---|---|
| V$ETSF/NRF2.01 | nuclear respiratory factor 2 |
| V$NFAT/NFAT.01 | Nuclear factor of activated T-cells |
| V$WHZF/WHN.01 | winged helix protein, involved in hair keratinization and thymus epithelium differentiation |
| V$GATA/GATA3.01 | GATA-binding factor 3 |
| V$CEBP/CEBPB.01 | CCAAT/enhancer binding protein beta |
| V$EBOX/USF.02 | upstream stimulating factor |
| V$PAX5/PAX5.01 | B-cell-specific activating protein |
| V$XBBF/RFX1.02 | X-box binding protein RFX1 |
| V$GATA/GATA1.03 | GATA-binding factor 1 |
| V$MEIS/MEIS.01 | Homeobox protein MEIS1 binding site |
| V$ZFIA/ZID.01 | zinc finger with interaction domain |
| V$WHZF/WHN.01 | winged helix protein, involved in hair keratinization and thymus epithelium differentiation |
| V$PAX1/PAX1.01 | Pax1 paired domain protein, expressed in the developing vertebral column of mouse embryos |
| V$GATA/LMO2COM.02 | complex of Lmo2 bound to Tal-1, E2A proteins, and GATA-1, half-site 2 |

**matches are listed in order of occurrence in the corresponding sequence

TFBS in bla-5
After removal of TFBS from bla-4 (5 matches)

| Name of family/matrix** | Further Information |
|---|---|
| V$ETSF/NRF2.01 | nuclear respiratory factor 2 |
| V$WHZF/WHN.01 | winged helix protein, involved in hair keratinization and thymus epithelium differentiation |
| V$GATA/GATA3.01 | GATA-binding factor 3 |
| V$CEBP/CEBPB.01 | CCAAT/enhancer binding protein beta |
| V$EBOX/USF.02 | upstream stimulating factor |

**matches are listed in order of occurrence in the corresponding sequence

TABLE 28

Sequences in Synthetic NotI-NcoI Fragment of pGL4
TFBS in pGL4B-4NN
Before removal of TFBS from pGL4B-4NN = (11 matches)

| Name of family/matrix** | Further Information |
|---|---|
| V$SMAD/FAST1.01 | FAST-1 SMAD interacting protein |
| V$SMAD/FAST1.01 | FAST-1 SMAD interacting protein |
| V$ETSF/FLI.01 | ETS family member FLI |
| V$RBPF/RBPJK.01 | Mammalian transcriptional repressor RBP-Jkappa/CBF1 |
| V$ETSF/FLI.01 | ETS family member FLI |
| V$EBOX/USF.02 | upstream stimulating factor |
| V$CEBP/CEBPB.01 | CCAAT/enhancer binding protein beta |
| V$GATA/GATA3.01 | GATA-binding factor 3 |
| V$WHZF/WHN.01 | winged helix protein, involved in hair keratinization and thymus epithelium differentiation |
| V$ETSF/NRF2.01 | nuclear respiratory factor 2 |
| V$TBPF/ATATA.01 | Avian C-type LTR TATA box |

**matches are listed in order of occurrence in the corresponding sequence

TFBS in pGL4B-4NN1
After removal of TFBS from pGL4B-4NN = before removal of TFBS
from pGL4B-4NN1 (7 matches)

| Name of family/matrix** | Further Information |
|---|---|
| V$ETSF/NRF2.01 | nuclear respiratory factor 2 |
| V$WHZF/WHN.01 | winged helix protein, involved in hair keratinization and thymus epithelium differentiation |
| V$CEBP/CEBPB.01 | CCAAT/enhancer binding protein beta |
| V$EBOX/USF.02 | upstream stimulating factor |
| V$ETSF/FLI.01 | ETS family member FLI |
| V$SMAD/FAST1.01 | FAST-1 SMAD interacting protein |
| V$SMAD/FAST1.01 | FAST-1 SMAD interacting protein |

**matches are listed in order of occurrence in the corresponding sequence

TFBS in pGL4B-4NN2
After removal of TFBS from pGL4B-4NN1 = before removal of TFBS
from pGL4B-4NN2 (4 matches)

| Name of family/matrix** | Further Information |
|---|---|
| V$ETSF/NRF2.01 | nuclear respiratory factor 2 |
| V$WHZF/WHN.01 | winged helix protein, involved in hair keratinization and thymus epithelium differentiation |
| V$CEBP/CEBPB.01 | CCAAT/enhancer binding protein beta |
| V$EBOX/USF.02 | upstream stimulating factor |

**matches are listed in order of occurrence in the corresponding sequence

TFBS in pGL4B-4NN3
After removal of TFBS from pGL4B-4NN2 (3 matches)

| Name of family/matrix** | Further Information |
|---|---|
| V$EBOX/USF.02 | upstream stimulating factor |
| V$WHZF/WHN.01 | winged helix protein, involved in hair keratinization and thymus epithelium differentiation |
| V$ETSF/NRF2.01 | nuclear respiratory factor 2 |

**matches are listed in order of occurrence in the corresponding sequence

TABLE 29

Sequences in Synthetic SpeI-NcoI section of pGL4
TFBS in SpeI-NcoI-Ver2-start
Before removal of TFBS from SpeI-NcoI-Ver2-start (34 matches)

| Family/matrix** | Further Information |
|---|---|
| V$PAX8/PAX8.01 | PAX 2/5/8 binding site |
| V$GATA/GATA1.02 | GATA-binding factor 1 |
| V$CREB/E4BP4.01 | E4BP4, bZIP domain, transcriptional repressor |
| V$NKXH/NKX31.01 | Prostate-specific homeodomain protein NKX3.1 |
| V$TBPF/ATATA.01 | Avian C-type LTR TATA box |
| V$CREB/E4BP4.01 | E4BP4, bZIP domain, transcriptional repressor |
| V$NKXH/NKX31.01 | Prostate-specific homeodomain protein NKX3.1 |
| V$CART/CART1.01 | Cart-1 (cartilage homeoprotein 1) |
| V$NKXH/NKX25.02 | Homeo domain factor Nkx-2.5/Csx, tinman homolog low affinity sites |
| V$ETSF/ELK1.01 | Elk-1 |
| V$CDXF/CDX2.01 | Cdx-2 mammalian caudal related intestinal transcr. factor |
| V$BRNF/BRN3.01 | POU transcription factor Brn-3 |
| V$TBPF/TATA.02 | Mammalian C-type LTR TATA box |
| V$FKHD/FREAC3.01 | Fork head related activator-3 (FOXC1) |
| V$OCT1/OCT1.02 | Octamer-binding factor 1 |
| V$CART/CART1.01 | Cart-1 (cartilage homeoprotein 1) |
| V$PDX1/PDX1.01 | Pdx1 (IDX1/IPF1) pancreatic and intestinal homeodomain TF |
| V$PARF/DBP.01 | Albumin D-box binding protein |
| V$GATA/GATA3.02 | GATA-binding factor 3 |
| V$VBPF/VBP.01 | PAR-type chicken vitellogenin promoter-binding protein |
| V$AP4R/TAL1ALPHAE47.01 | Tal-1 alpha/E47 heterodimer |
| V$RP58/RP58.01 | Zinc finger protein RP58 (ZNF238), associated preferentially with heterochromatin |
| V$COMP/COMP1.01 | COMP1, cooperates with myogenic proteins in multicomponent complex |
| V$CLOX/CLOX.01 | Clox |
| V$TBPF/ATATA.01 | Avian C-type LTR TATA box |
| V$PBXC/PBX1_MEIS1.02 | Binding site for a Pbx1/Meis1 heterodimer |
| V$PBXF/PBX1.01 | Homeo domain factor Pbx-1 |
| V$IRFF/IRF1.01 | Interferon regulatory factor 1 |
| V$TEAF/TEF1.01 | TEF-1 related muscle factor |
| V$EBOX/ATF6.01 | Member of b-zip family, induced by ER damage/stress, binds to the ERSE in association with NF-Y |
| V$NKXH/NKX32.01 | Homeodomain protein NKX3.2 (BAPX1, NKX3B, Bagpipe homolog) |
| V$E2TF/E2.02 | Papilloma virus regulator E2 |
| V$EVI1/EVI1.05 | Ecotropic viral integration site 1 encoded factor |
| V$GATA/GATA3.02 | GATA-binding factor 3 |

**matches are listed in order of occurrence in the corresponding sequence

TFBS in SpeI-NcoI-Ver2
After removal of TFBS from SpeI-NcoI-Ver2-start (28 matches)

| Family/matrix** | Further Information |
|---|---|
| V$PAX8/PAX8.01 | PAX 2/5/8 binding site |
| V$GATA/GATA1.02 | GATA-binding factor 1 |
| V$CREB/E4BP4.01 | E4BP4, bZIP domain, transcriptional repressor |
| V$NKXH/NKX31.01 | Prostate-specific homeodomain protein NKX3.1 |
| V$TBPF/ATATA.01 | Avian C-type LTR TATA box |
| V$CREB/E4BP4.01 | E4BP4, bZIP domain, transcriptional repressor |
| V$NKXH/NKX31.01 | Prostate-specific homeodomain protein NKX3.1 |
| V$CART/CART1.01 | Cart-1 (cartilage homeoprotein 1) |
| V$NKXH/NKX25.02 | Homeo domain factor Nkx-2.5/Csx, tinman homolog low affinity sites |
| V$CDXF/CDX2.01 | Cdx-2 mammalian caudal related intestinal transcr. factor |
| V$BRNF/BRN3.01 | POU transcription factor Brn-3 |
| V$TBPF/TATA.02 | Mammalian C-type LTR TATA box |
| V$FKHD/FREAC3.01 | Fork head related activator-3 (FOXC1) |
| V$OCT1/OCT1.02 | Octamer-binding factor 1 |
| V$CART/CART1.01 | Cart-1 (cartilage homeoprotein 1) |
| V$PDX1/PDX1.01 | Pdx1 (IDX1/IPF1) pancreatic and intestinal homeodomain TF |
| V$PARF/DBP.01 | Albumin D-box binding protein |
| V$GATA/GATA3.02 | GATA-binding factor 3 |
| V$VBPF/VBP.01 | PAR-type chicken vitellogenin promoter-binding protein |
| V$AP4R/TAL1ALPHAE47.01 | Tal-1alpha/E47 heterodimer |
| V$RP58/RP58.01 | Zinc finger protein RP58 (ZNF238), associated preferentially with heterochromatin |
| V$COMP/COMP1.01 | COMP1, cooperates with myogenic proteins in multicomponent complex |
| V$CLOX/CLOX.01 | Clox |
| V$TBPF/ATATA.01 | Avian C-type LTR TATA box |
| V$PBXC/PBX1_MEIS1.02 | Binding site for a Pbx1/Meis1 heterodimer |
| V$PBXF/PBX1.01 | Homeo domain factor Pbx-1 |
| V$IRFF/IRF1.01 | Interferon regulatory factor 1 |
| V$TEAF/TEF1.01 | TEF-1 related muscle factor |

**matches are listed in order of occurrence in the corresponding sequence

The number of consensus transcription factor binding sites present in the vector backbone (including the ampicillin resistance gene) was reduced from 224 in pGL3 to 40 in pGL4, and the number of promoter modules was reduced from 10 in pGL3 to 4 for pGL4, using databases, search programs and the like as described herein. Other modifications in pGL4 relative to pGL3 include the removal of the f1 origin of replication and the redesign of the multiple cloning region.

MCS-1 to MCS-4 have the following sequences (SEQ ID Nos:76-79)

MCS-1
ACTAGTCGTCTCTCTTGAGAGACCGCGATCGCCACCATGATAAGTAA

GTAATATTTAAATAAGTAAGGCCTGAGTGGCCCTCGAGCCAGCCTTGA

GTTGGTTGAGTCCAAGTCACGTCTGGAGATCTGGTACCTACGCGTGA

GCTCTACGTAGCTAGCGGCCTCGGCGGCCGAATTCTTGCGATCTAAG

TAAGCTTGGCATTCCGGTACTGTTGGTAAAGCCACCATGG

MCS-2
ACTAGTACGTCTCTCTTGAGAGACCGCGATCGCCACCATGATAAGTA

AGTAATATTTAAATAAGTAAGGCCTGAGTGGCCCTCGAGTCCAGCCTT

GAGTTGGTTGAGTCCAAGTCACGTGTGGAGATCTGGTACCTTACGCGT

AGAGCTCTACGTAGCTAGCGGCCTGGGCGGCCGAATTCTTGCGATCT

AAGCTTGGCAATCCGGTACTGTTGGTAAAGCCACCATGG

MCS-3
ACTAGTACGTCTCTCTTGAGAGACCGCGATCGCATGCCTAGGTAGGT

AGTATTAGAGCATAGGTAGAGGCCTAAGTGGCCCTCGAGTCCAGGCT

-continued
TGAGTTGGTTGAGTCCAAGTCACGTCTGGAGATCTGGTACCTTACGCG
TATGAGCTCTACGTAGCTAGCGGCCTCGGCGGCCGAATTCTTGCGAT
GTAAGCTTGGCAATCCGGTACTGTTGGTAAAGCCACCATGG MCS-4
ACTAGTACGTCTCTCTTGAGAGACCGCGATCGCCACCATGTCTAGGT
AGGTAGTAAACGAAAGGGCTTAAAGGCCTAAGTGGCCCTCGAGTCCA
GCCTTGAGTGGTTGAGTCCAAGTCACGTTTGGAGATCTGGTACGTTA
CGCGTATGAGCTCTACGTAGCTAGCGGCCTCGGCGGCCGAATTCTTG
CGATCTAAGCTTGGCAATCCGGTACTGTTGGTAAAGCCACCATGG bla has the following sequence:

(SEQ ID NO:41)
ATGAGTATTCAAGATTTCCGTGTCGCCCTTATTCCCTTTTTTGCGGCAT
TTTGCCTTCCTGTTTTTGCTCACCCAGAAACGCTGGTGAAAGTAAAAGAT
GCTGAAGATCAGTTGGGTGCACGAGTGGGTTACATCGAACTGGATCTCAA
CAGCGGTAAGATCCTTTGAGAGTTTTTCGCCCCGAAGAACGTTTTCCAAT
GATGAGCACTTTTAAAGTTTCTGCTATGTGGCGCGGTATTATCCCGTATT
GACGCCGGGCAAGAGCAACTCGGTCGCCGCATACACTATTCTCAGAATGA
CTTTGGTTTGAGTACTCACCAGTCACAGAAAAGCATCTTACGGATGGCAT
GACAGTAAGAGAATTATGCAGTGCTGCCATAACCATGAGTGATAACACTG
CGGCGAACTTTACTTCTGACAACGATCGGAGGACCGAAGGAGCTAACCGC
TTTTTTGCACAACATGGGGGATCATGTAACTCGCCTTGATCGTTTGGGAA
CCGGAGCTGAATGAAGCCATACCAAACGACGAGCGTGACACCACGATGCC
TGTAGCAATGGCAACAACGTTGCGCAAACTATTAACTGGCGAACTACTTA
CTCTAGCTTTCCCGGCAACAATAATAGACTGGATGGAGGCGGATAAAGTT
GCAGGACCACTTCTGCGCTCGGCCGTTCCGGCTGGCTGGTTTATTGGTGA
TAAATCTGGAGCCGGTGAGCGTGGGTCTCGCGGTATCATTGCAGCACTGG
GGCCAGATGGTAAGCCCTCCCGTATCGTAGTTTTATCTACACGACGGGGA
GTCAGGCAACTATGGATGAACGAAATAGACAGATCGCTGAGATAGGTGCC
TCACTGATATGCATTGGTAA.

bla-1 to bla-5 have the following sequences (SEQ ID Nos:80-84):

bla-1
ACTAGTAACCCTGATAAATGCTTCAATAATATTGAAAAAGGAAGAGTATG
AGTATTCAACATTCCGTGTCGCCCTTATTCCCTTTTTGCGGCATTTTGCC
TTCCTGTTTTTGCTCACCCAGAAACGCTGGTGALAGTAAAAGATGCTGAA
GATCAGTTGGGTGCACGAGTGGGTTACATCGAACTGGATCTCAACAGCGG
TAAGATCCTTGAGAGTTTTCGCCCCGAAGAACGTTTTCCAATGATGAGCA
CTTTTTAAAGTTTCTGCTATGTGGCGCGGTATTATCCCGTATTTGACGCC
GGGCAAGAGCAACTCGGTCGCCGCATACACTATTCTCAGAATGACTTGGT
TGAGTACTCACCAGTCACAGAAAAGCATCTTACGGATGGCATGACAGTAA GAGAATTTATGCAGTGCTGCCATAACCATGAGTGATAACACCGCGGCGAA
CTTACTTTGTGACAACGATCGGAGGACCGAAGGAGCTAACCGCTTTTTGC
ACAACATGGGGGATCATGTAACTCGCCTTGATCGTTGGGAACCGGAGCTG
AATGAAGCCATACCAAACGACGAGCGTGACACCACGATGCCTGTAGCAAT
GGCAACAAGGTTGCGCAAACTATTAACTGGCGAACTACTTACTCTAGCTT
CCCGGCAACAATTAATAGACTGGATGGAGGCGGATAAAGTTGCAGGACCA
CTTCTGCGCTCGGCCCTTCCGGCTGGCTGGTTTATTGCTGATAAATCTGG
AGCCGGTGAGCGTGGCTCTCGCGGTATCATTGCAGCACTGGGGCCAGATG
GTAAGCGCTCCCGTATCGTAGTITATCTACACGACGGGGAGTCAGGCAAC
TATGGATGAACGAAATAGACAGATCGCTGAGATAGGTGCCTCAGTGATTA
AGCATTTGGTAACCACTGCAGTGGTTTTCCTTTTGCGGCGGC bla-2
ACTAGTAACCCTGATAAATGCTGCAAACATATTGAAAAAGGAAGAGTATG
AGTATTCAACATTTCCGTGTCGCACTCATTCCCTTCTTTTGCGGCATTTT
TGCTTGCCTGTTTTTGCACACCCCGAAACGCTGGTGAAAGTAAAAGATGC
TGAAGATCAAGTGGGTGCACGAGTGGGCTATATGGAACTGGATCTCAATA
GGGGTAAGATCCTTGAGAGTTTTCGCCCCGAAGAACGTTTCCAATGATGA
GCACTTTAAAGTTCTGCTATGTGGCGCGGTATTTATCCCGTATTTGACGC
CGGGCAAGAGCAGCTCGGTCGCCGCATACACTACTCACAGAACGACTTGG
TTGAGTACTCGCCGGTCACGGAAAAGCATCTTACGGATGGCATGACAGTA
AGAGAATTTGTGTAGTGCTGCCATAACCATGAGTGATAACACCGCGGCCA
ACTTACTTCTGACAACGATCGGAGGCCCTAAGGAGCTGACCGCATTTTGC
ACAACATGGGGGATCATGTAACCCGGCTTGATCGTTGGGAACCGGAGCTG
AACGAAGCCATACCGAACGACGAGCGTGACACCACGATGCCTGTAGCAAT
GGCAACAACGTTGCGCAAACTACTCACTGGCGAACTTCTCACTCTAGCAT
CACGACAGCAACTCATAGACTGGATGGAGGCGGATAAAGTTGCAGGACCA
CTTCTGCGCTCGGCCCTTCCGGCTGGCTGGTTTTAACTGATAAATCCGGT
GCCGGTGAACGCGGCTCTCGCGGGATCATTGCTGCGCTGGGGCCAGATGG
TAAGCCCTCACGAATCGTAGTTATCTACACGACGGGGAGTCAGGCAACTA
TGGATGAACGAAATAGACAGATCGCTGAGATAGGTGCCTCACTGATCAAG
CACTGGTAGCCAGTGCAGTGGATAGCTTTTGCGGCCGC bla-3
ACTAGTAACCCTGACAAATGCTGCAAACATATTTGAAAAAGGAAGAGTAT
GAGCATCCAACATTTCGTGTCGCACTCATTTCCCTTCTTTGCGGCATTTT
TGCTTGCCTGTTTTGCACACCCCGAAACGCTGGTGAAAGTAAAAGATGCT
GAAGATCAACTGGGTGCAAGAGTGGGCTATATCGAACTGGATCTCAATAG
CGGCAAGATCCTTGAGTCTTTTCGCCCCGAAGAACGTTTTCCGATGATGA
GCACTTTAAAGGCTGCTATGTGGCGCGGTGTTTGTCCCGTATAGACGCCG
GGCAAGAGCAGCTTGGTCGCCGTATACACTACTCACAAAACGACTTGGTT
GAGTACTCGCCGGTCACGGAAAAGCATCTTACGGATGGCATGACGGTAAG
AGAATTTGTGTAGTGCTGCCATTACCATGAGCGACAATACCGCGGCCAAC -continued
TTACTTCTGACAACGATCGGAGGCCCTAAGGAGCTGACCGCATTTTGCA

CAACATGGGGGATCATGTAACCCGGCTTGACCGCTGGGAACCGGAGCTGA

ACGAAGCCATACCGAACGACGAGCGTGACACCACGATGCCTGTAGCAATG

GCAACAACGTTGCGGAAACTACTCACTGGCGAACTTCTCACTCTAGCATC

ACGACAGCAGCTCATAGACTGGATGGAGGCGGACAAAGTAGCAGGACCAC

TTCTTCGCTCGGCCCTCCCTGCTGGCTGGTTCATTTGCTGATAAATCCGG

TGCCGGTGAACGCGGCTCTCGGGGATCATTGCTGCGCTGGGGCCTGATG

GTAAGCCCTCACGAATCGTAGTAATCTACACGACGGGGAGTCAGGCCACT

ATGGACGAACGAAATAGACAGATCGCTGAGATCGGTGCCTCACTGATCAA

GCACTGGTAACCACTGCAGTGGTITAGGATTTGCGGCCGC bla-4
ACTAGTAACCCTGACAAATGCTGCAAACATATTGAAAAAGGAAGAGTATG

AGCATGCAACATTTTTCGTGTCGCACTCATTCCCTTCTTTGCGGCATTTT

GCTTGCCTGTTTTTTGCACACCCCGAAACGCTGGTGAAAGTAAAAGATGC

TGAAGATCAACTGGGTGCAAGAGTGGGCTATATCGAACTGGATCTCAATA

GCGGCAAGATCCTTGAGTCTTTTCCGCCCCGAAGAACGTTTTTCCGATGA

TGAGCACTTTCAAAGTACTGCTATGTGGCGCGGTGTTGTCCCGTATAGAC

GCCGGGCAAGAGCAGCTTGGTCGCCGTATACAGTACTCACAAAACGACTT

GGTTGAGTACTCGCCGGTCACGGAAAAGCATCTTACGGATGGCATGACGG

TAAGAGAATTITGTGTAGTGCTGCCATTACCATGAGCGATAATACCGCGG

CCAACTTTACTTTTCTGAGAACGATCGGAGGCGCTAAGGAGCTGACCGCA

TTTTGCACAACATGGGTGATCATGTGACCCGGCTTGACCGCTGGGAACCG

GAGCTGAACGAAGCCATACCGAACGACGAGCGTGACACCACGATGGCTGT

AGCAATGGCAACAACTCTTCGGAAACTACTCACTGGCGAACTTTCTCACT

CTAGCATCACGACAGCAGCTCATAGACTGGATGGAGGCGGACAAAGTAGC

AGGACCACTTCTTCGCTCGGCCCTCCCTGCTGGCTGGTTCATTGCTGATA

AATCTGGAGCCGGTGAGCGTGGCTCTCGCGGTATCATTGCTGCGCTGGGG

CCTGATGGTAAGCCCTCACGAATCGTAGTAATCTACACGACGGGGAGTCA

GGCCACTATGGACGAACGAAATAGACAGATCGCTGAGATCGGTGCCTCAC

TGATCAAGCACTGGTAACCACTGCAGTGGTTTAGCATTTTGCGGCCGC bla-5
ACTAGTAACCCTGACAAATGCTGCAAACATATTGAAAAAGGAAGAGTATG AGCATCCAACATTTfTCGTGTCGCACTCATTTCCCTTCTTGCGGCATTTT

GCTTGCCTGTTTTTGCACACCCCGAAACGCTGGTGAAAGTAAAAGATGCT

GAAGATCAACTGGGTGCAAGAGTGGGCTATATCGAACTGGATCTCAATAG

CGGCAAGATCCTTGAGTCTTTCCGCCCCGAAGAACGATTCCCGATGATGA

GCACTTTCAAAGTACTGCTATGTGGCGCGGTGTTTGTCCCGTATAGACGC

CGGGCAAGAGCAGCTTGGTCGCCGTATACACTACTCACAAAACGACTTGG

TTGAGTACTCGCCGGTCACGGAAAAGCATCTTACGGATGGCATGACGGTA

AGAGAATTGTGTAGTGCTGCCATTACCATGAGCGATAATACCGCGGCCAA

CTTACTTfCTGACAACGATCGGAGGCCCTAAGGAGCTGACCGCATTTTTG

-continued
CACAACATGGGTGATCATGTGACCCGGCTTGACCGCTGGGAACCGGAGCT

GAACGAAGCCATACCGAACGACGAGCGTGATACCACGATGCCAGTAGCAA

TGGCCACAACTCTTTCGGAAACTACTCACTGGCGAACTTCTCACTCTAGC

ATCACGACAGCAGCTCATAGACTGGATGGAGGCGGACAAAGTAGCAGGAC

CACTTCTTCGCTCGGCCCTCCCTGCTGGCTGGTTCATTGCTGACAAATCC

GGTGCCGGTGAAGGCGGCTCTCGCGGCATCATTGGCTGCGCTGGGGCCTG

ATGGTAAGCCCTCACGAATCGTAGTAATCTACACGACGGGGAGTCAGGCC

ACTATGGACGAACGAAATAGACAGATCGCTGAGATCGGTGCCTCACTGAT

CAAGCACTGGTAACCACTGCAGTGGTTTAGCATTTGCGGCCGCNNN.

TABLE 30

Pairwise identity of different bla gene versions

| | bla | bla-1 | bla-2 | bla-3 | bla-4 | bla-5 | bla in pGL4 (SEQ ID NO: 74) |
|---|---|---|---|---|---|---|---|
| bla | — | 99 | 93 | 90 | 89 | 88 | 87 |
| bla-1 | | — | 94 | 90 | 90 | 89 | 88 |
| bla-2 | | | — | 96 | 94 | 94 | 93 |
| bla-3 | | | | — | 98 | 98 | 97 |
| bla-4 | | | | | — | 99 | 97 |
| bla-5 | | | | | | — | 98 | note:
sequence "bla" is bla gene from pGL3-Basic; ClustalW (Slow/Accurate, IUB); sequence comparisons were of ORF only SpeI-NcoI ver2 start has the following sequence:

(SEQ ID NO:48)
ACTAGTACGTCTCTCAAGGATAAGTAAGTAATATTAAGGTACGGGAGGTA

CTTTTGGAGCGGCCGCAATAAAATATCTTTATTTTCATTACATCTGTGTG

TTGGTTTTTTGTGTGAATCGATAGTACTAACATACGCTCTCCATCAAAAC

AAAACGAAACAAAACAAACTAGCAAAATAGGCTGTCCCCAGTGCAAGTGC

AGGTGCCAGAACATTCTCTGGCCTAAGTGGCCGGTACCGAGCTCGCTAGC

CTCGAGGATATCAGATCTGGCCTCGGCGGCCAAGGTTTGGCAATCCGGTA

CTGTTTTGGTAAAGCCACCATGG;

and

SpeI-NcoI-Ver2 has the following sequence:

(SEQ ID NO:49)
ACTAGTACGTCTCTCAAGGATAAGTAAGTAATATTAAGGTACGGGAGGTA

TTTGGACAGGCCGCAATAAAATATCTTTATTTTTCATTACATCTGTGTGT

TGGTTTTTTGTGTGAATCGATAGTACTAACATACGCTCTCCATCAAAACA

AAACGAAACAAAACAAACTAGCAAAATAGGCTGTCCCCAGTGCAAGTGCA

GGTGCCAGAACATTTTCTCTGGCCTAACTGGCCGGTACCTGAGCTCGCTA

GCCTCGAGGATATCAGATCTGGCCTCGGCGGCCAAGCTTGGCAATCCGG

TACTGTTTGGTAAAGCCACCATGG pGL4 related sequences include (SEQ ID Nos.95-97):

pGL4B-4NN
GCGGCCGCAAATGCTAAACCACTGCAGTGGTTTACGAGTGCTTGATCAGT
GAGGCACCGATCTCAGCGATCTGTCTATTTTCGTTCGTCCATAGTGGCCT
GACTCCCCGTCGTGTAGATTACTACGATTCGTGAGGGCTTACCATGAGGC
CCCAGCGCAGCAATGATGCCGCGAGAGCCGCGTTCACCGGCACCGGATTT
GTCAGCAATGAACCAGCCAGCAGGGAGGGCCGAGCGAAGAAGTGGTCCTG
CTACTTTGTCCGCCTCCATCCAGTCTATGAGCTGCTGTCGTGATGCTAGA
GTGAGAAGTTCGCCAGTGAGTAGTTTTCCGAAGAGTTGTGGCCATTGCTA
CTGGCATCGTGGTATCACGGTCGTCGTTCGGTATGGCTTCGTTGAGCTCC
GGTTCCCAGCGGTCAAGCCGGGTCACATGATCACCCATGTTGTGCAAAAA
TGCGGTCAGCTCCTTAGGGCCTCCGATCGTTGTCAGAAGTAAGTTGGCCG
CGGTATTATCGCTCATGGTAATGGCAGCACTACACAATTCTCTTACCGTC
ATGCCATCCGTAAGATGCTTTTCCGTGACCGGCGAGTACTCAACCAAGTC
GTTTTGTGAGTAGTGTATACGGCGACCAAGCTGCTCTTGCCCGGCGTCTA
TACGGGACAACACCGCGCCACATAGCAGTACTTTTGAAAGTGCTCATGAT
CGGGAATCGTTTGTCGGGGCGGAAAGACTCAAGGATGTTGCCGCTATTTG
AGATCGAGTTCGATATAGCCCACTCTTGCACCCAGTTGATCTTCAGCATC
TTTTACTTTCACCAGCGTTTCGGGGTGTGCAAAAACAGGCAAGCAAAATG
CCGCAAAGAAGGGAATGAGTGCGAGACGAAAATGTTGGATGCTCATACTC
TTCCTTTTTCAATATGTTGCAGCATTGTCAGGGTTACTAGTACGTCTCTC
TTTGAGAGACCGCGATCGCCACCATGTCTAGGTAGGTAGTAAACGAAAGG
GCTTAAAGGCGTAAGTGGCCCTCGAGTCCAGCCTTGAGTTGGTTTGAGTC
CAAGTCACGTTGGAGATGTGGTACCTTACGCGTATGAGCTCTACGTAGCT
AGCGGCCTCGGCGGCCGAATTCTTTGCGATCTAAGCTTTGGCAATCCGGT
ACTGTTGGTAAAGCCACCATGG pGL4B-4NN1
gcggccgcaaatgctaaaccactgcagtggttaccagtgcttgatcagtg
aggcaccgatctcagcgatctgtctatttcgttcgtccatagtggcctga
ctccccgtcgtgtagattactacgattcgtgaggcttaccatcaggcccc
agcgcagcaatgatgccgcgagagccgcgttcaccggccccgatttgtc
agcaatgaaccagccagcagggagggccgagcgaagaagtggtcctgcta
ctttgtccgcctccatccagtctatgagctgctgtcgtgatgctagagta
agaagttcgccagtgagtagtttccgaagagttgtggccattgctactgg
catcgtggtatcacgctcgtcgttcggtatggcttcgttcaactccggtt
cccagcggtcaagccgggtcacatgatcacccatgttgtgcaaaaatgcg
gtcagctccttagggcctccgatcgttgtcagaagtaagttggccgcggt
gttgtcgctcatggtaatggcagcactacacaattctcttaccgtcatgc
catccgtaagatgcttttccgtgaccggcgagtactcaaccaagtcgttt tgtgagtagtgtatacggcgaccaagctgctcttgcccggcgtctatacg
ggacaacaccgcgccacatagcagtactttgaaagtgctcatcatcggga
atcgttcttcggggcggaaagactcaaggatcttgccgctattgagatcc
agttcgatatagcccactcttgcacccagttgatcttcagcatctttttac
tttcaccagcgtttcggggtgtgcaaaaacaggcaagcaaaatgccgcaa
agaagggaatgagtgcgacacgaaaatgttggatgctcatactcttcctt
tttcaatatgtttgcagcatttgtcagggttactagtacgtctctcttga
gagaccgcgatcgccaccatgtctaggtaggtagtaaacgaaagggctta
aaggcctaagtggccctcgagtccagccttgagttggttgagtccaagtc
acgtttggagatctggtaccttacgcgtatgagctctacgtagctagcgg
cctcggcggccgaattcttgcgttcgaagcttggcaatccggtactgttg
gtaaagccaccatgg;

and pGL4B-4NN2
GCGGCCGCAAATGCTAAACCACTGCAGTGGTTACCAGTGCTTGATCAGTG
AGGCACCGATCTCAGCGATCTGCCTATTTCGTTCGTCCATAGTGGCCTGA
CTCCCCGTCGTGTAGATCACTACGATTTCGTGAGGGCTTACGATCAGGCC
CCAGCGCAGCAATGATGCCGCGAGAGCCGCGTTCACCGGCCCCCGATTTG
TCAGCAATGAACCAGCCAGCAGGGAGGGCCGAGCGAAGAAGTGGTCCTGC
TACTTTGTCCGCCTCCATCCAGTCTATGAGCTGCTGTCGTGATGCTAGAG
TAAGAAGTTCGCCAGTGAGTAGTTTCCGAAGAGTTTGTGGCCATTGCTAC
TGGCATCGTGGTATCACGCTCGTCGTTCGGTATGGCTTCGTTCAACTCTG
GTTTGCCAGCGGTCAAGCCGGGTCACATGATCACCCATGTTGTGCAAAAA
TGCGGTCAGCTCCTTAGGGCCTCCGATCGTTGTCAGAAGTAAGTTGGCCG
CGGTGTTGTCGCTCATGGTAATGGCAGCACTACACAATTCTCTTACCGTG
ATGCCATCCGTAAGATGCTTTTCCGTGACCGGCGAGTACTCAACCAAGTC
GTTTTGTGAGTAGTGTATACGGCGACCAAGCTGGTCTTGCCCGGCGTCTA
TACGGGAGAACACCGCGCCACATAGCAGTACTTTGAAAGTGCTCATCATC
GGGAATCGTTCTTCGGGGCGGAAAGACTCAAGGATCTTTGCCGCTATGAG
ATCCAGTTCGATATAGCCCACTCTTGCACCCAGTTGATCTTCAGCATCTT
TTACTTTGACCAGCGTTTCGGGGTGTGCAAAAACAGGCAAGCAAAATGCC
GCAAAGAAGGGAATGAGTGCGACACGAAAATGTTGGATGCTCATACTCTT
CCTTTTCAATATGTTGCAGCATTTGTCAGGGTTACTAGTACGTCTCTCTT
GAGAGACCGCGATCGCCACCATGTCTAGGTAGGTAGTAAACGAAAGGGCT
TAAAGGCCTAAGTGGCCCTCGAGTCCAGCCTTGAGTTGGTTGAGTGCAAG
TCAGGTTGGAGATCTGGTACCTTACGCGTATGAGCTCTACGTAGCTAGGG
GCCTCGGCGGGCGAATTTCTTGCGTTTGGAAGCTTGGCAATGCGGTACTG
TTGGTAAAGCCACCATGG, as well as pGL4B-4NN3:

(SEQ ID NO:45)
GCGGCCGCAAATGCTAAACCACTGCAGTGGTTACCAGTGCTTGATCAGTG
AGGCACCGATCTCAGCGATCTGCCTATTTCGTTCGTCCATAGTGGGGTGA
CTCCCCGTCGTGTAGATCACTACGATTCGTGAGGGCTTACCATCAGGCCC
CAGCGCAGCAATGATGCCGCGAGAGCCGCGTTTCACCGGCCCCCGATTTG
TCAGCAATGAACCAGCCAGCAGGGAGOGCCGAGCGAAGAAGTGGTCCTGC
TAGTTTGTCCGCCTCCATCCAGTCTATGAGCTGCTGTCGTGATGCTAGAG
TAAGAAGTTCGCCAGTGAGTAGTTCGGAAGAGTGTGGCCATTGCTACTGG
CATCGTGGTATCACGCTCGTCGTTTCGGTATGGCTTTCGTTCAACTCTGG
TTCCCAGCGGTCAAGCCGGGTCACATGATCACCCATATTATGAAGAAATG
CAGTCAGCTCCTTTAGGGCCTCCGATCGTTGTCAGAAGTAAGTTGGCCGC
GGTGTTGTCGCTCATGGTAATGGCAGCACTACACAATTCTCTTTACCGTC
ATGCCATCCGTAAGATGCTTTTCCGTGACCGGCGAGTACTCAACCAAGTC
GTTTTGTGAGTAGTGTATACGGCGACCAAGCTGCTCTTGCCCGGCGTCTA
TACGGGAGAACACCGCGCCACATAGCAGTACTTTGAAAGTGCTCATCATC
GGGAATCGTTCTCGGGGCGGAAAGACTCAAGGATCTTGCCGCTATTTGAG
ATCCAGTTCGATATAGCCCACTCTTGCACCCAGTTGATCTTCAGCATCTT
TTACTTTCACCAGCGTTTCGGGGTGTGCAAAAACAGGCAAGCAAAATGCC
GCAAAGAAGGGAATGAGTGCGACACGAAAATGTTGGATGCTCATACTCTT
CCTTTTTCAATATGTTTGCAGCATTTGTCAGGGTTACTAGTAGGTCTCTC
TTTGAGAGACCGCGATCGCCACCATGTCTAGGTAGGTAGTAAACGAAAGG
GCTTAAAGGCCTAAGTGGCCCTCGAGTCGAGCCTTGAGTTGGTTGAGTCC
AAGTCACGTTTGGAGATCTGGTACCTTACGCGTATGAGGGTTGAGTCCAA
GTCACGTTTTGGAGATCTGGTACCTTACGGGTATGAGCTCTACGTAGCTA
GCGGCGTCGGCGGCCGAATTCTTGCGTTCGAAGCTTTGGCAATCCGGTAC
TGTTGGTAAAGCCACCATGG pGL4NN from Blue Heron:

(SEQ ID NO:46)
GCGGCCGCAAATGCTAAACCACTGCAGTGGTTACCAGTGCTTGATCAGTG
AGGCACCGATCTCAGCGATCTGCCTATTTTCGTTCGTCCATAGTGGCCTG
ACTCCCCGTCGTGTAGATCACTACGATTCGTGAGGGCTTACCATCAGGCC
CCAGCGCAGCAATGATGCCGCGAGAGCCGCGTTCACCGGCCCCCGATTTG
TCAGCAATGAACCAGCCAGCAGGGAGGGCCGAGGGAAGAAGTGGTGGTGC
TACTTTTGTCCGCCTCGATCCAGTCTATGAGCTGCTGTCGTGATGCTAGA
GTAAGAAGTTGGGCAGTGAGTAGTTTCCGAAGAGTTGTGGCCATTGCTAC
TGGCATCGTGGTATGACGCTCGTCGTTCGGTATGGCTTCGTTCAACTCTG
GTTCCCAGCGGTCAAGCCGGGTCACATGATCACCCATATTATGAAGAAAT
GCAGTCAGCTCCTTTAGGGCCTCCGATGGTTGTCAGAAGTAAGTTGGCCGC
GGTGTTGTCGCTCATGGTAATGGCAGCACTACACAATTCTCTTACCGTCA
TGCCATCCGTAAGATGCTTTTCCGTGACCGGCGAGTACTCAACCAAGTCG
TTTTGTGAGTAGTGTATACGGCGACCAAGCTGCTCTTGCCCGGCGTCTAT
ACGGGACAACACCGCGCCACATAGCAGTACTTTGAAAGTGCTCATCATCG
GGAATCGTTCTCGGGCGGAAAGACTCAAGGATCTTGCCGCTATTGAGAT
CCAGTTCGATATAGCCCACTCTTGCACCCAGTTGATCTTCAGGATCTTTT
ACTTTTGACCAGCGTTCGGGGTGTGCAAAAACAGGCAAGCAAAATGCCGC
AAAGAAGGGAATGAGTGGGACACGAAAATGTTGGATGCTCATACTCTTCC
TTTTCAATATGThTGCAGCATTLTGTCAGGGTTAGTAGTACGTCTCTCAA
GAGATTGTGCATACACAGTGACTCATACTTTCACGAATACTTGCATTGGA
TAAATACTAGACAACTTAGAAGTGAATATTTATGAGGTTGTCTTAAAATT
AAAAATTACAAAGTAATAAATCACATTGTAATGTATTTTGTGTGATACCC
AGAGGTTAAGGCAACCTATTTACTCTTATGCTCCTGAAGTCCACAATTCA
CAGTCCTGAACTATAATCTTATCTTTGTGATTGCTGAGCAAATTTGCAGT
ATAATTTTCAGTGCTTTAAATATGTCCTGCTTTACTATTCCTTTTTATTG
GGTTGATATGCGTGCACAGAATGGGGCTTCTATTAAAATATTCTTGAGAG
ACCGCGATCGCCACCATGTCTAGGTAGGTAGTAAACGAAAGGGCTTAAAG
GCCTAAGTGGCCCTCGAGTCCAGCCTTTGAGTTTGGTTGAGTCCAAGTCA
CGTTTTGGAGAATGGTACCTTACGCGTATGAGCTCTACGTAGCTAGCGGC
CTCGGCGGCCGAATTCTTGCGTTTCGAAGCTTGGCAATCCGGTACTGTTG
GTAAAGCCACCATGG, pGL4 with promoter changes:

(SEQ ID NO:47)
GCGGCCGCAAATGCTAAACCACTGCAGTGGTTACCAGTGCTTGATCAGTG
AGGCACCGATCTCAGCGATCTGCCTATTTCGTTTCGTCCATAGTGGGCTG
ACTCCCCGTCGTGTAGATCACTACGATTGGTGAGGGCTTACCATCAGGCC
CCAGCGCAGCAATGATGCCGCGAGAGCCGCGTTGCACCGGCCCCCGATTT
GTCAGCAATGAACCAGCCAGCAGGGAGGGCCGAGCGAAGAAGTGGTCCTG
CTAGTTTGTCCGCCTCCATCCAGTCTATGAGCTGCTGTCGTGATGCTAGA
GTAAGAAGTTCGCCAGTGAGTAGTTCCGAAGAGTTGTGGCCATTGCTACT
GGCATCGTGGTATCACGCTCGTCGTTCGGTATGGCTTCGTTCAACTCTGG
TTCCCAGCGGTCAAGCCGGGTCACATGATCACCCATATTATGAAGAAATG
CAGTCAGCTCCTTAGGGCCTCCGATCGTTGTCAGAAGTAAGTTGGGCGCG
GTGTTTGTCGCTCATGGTAATGGCAGCACTACACAATTCTCTTACCGTCA
TGCCATCCGTAAGATGCTTTTCCGTGACCGGCGAGTACTCAACCAAGTCG
TTTTGTGAGTAGTGTATACGGCGACCAAGCTGCTCTTGCCCGGCGTCTAT
ACGGGACAACACCGCGCCACATAGCAGTACTTTGAAAGTGCTCATCATCG
GGAATCGTTCTCGGGGCGGAAAGACTCAAGGATCTTTGCCGCTATTTGA
GATCCAGTTCGATATAGCCCACTCTGCACCCAGTTGATCTTCAGCATCTT

-continued
```
TTACTTTCACCAGCGTTTCGGGGTGTGCAAAAACAGGCAAGCAAAATGCC
GCAAAGAAGGGAATGAGTGCGACACGAAAATGTTGGATGCTCATACTGGT
CCTTTTTCAATATTATTGAAGCATTTATGAGGGTTACTAGTACGTCTCTC
AAGAGATTTGTGCATACACAGTGACTGATACTTTCACCAATACTTTTGCA
TTTTTGGATAAATACTAGACAACTTTAGAAGTGAATTATTTATGAGGTTG
TCTTAAAATTAAAAATTACAAAGTAATAAATCACATTGTAATGTATTTTT
GTGTGATACCCAGAGGTTTAAGGCAACCTATTACTCTTAT,
```

A hygromycin gene in a pGL4 vector:

(SEQ ID NO:88)
```
Atgaagaagcccgaactcaccgctaccagcgttgaaaaatttctcatcga
gaagttcgacagtgtgagcgacctgatgcagttgtcggagggcgaagaga
gccgagccttcagcttcgatgtcggcggacgcggctatgtactgcgggtg
aatagctgcgctgatggcttctacaaagaccgctacgtgtaccgccactt
cgccaccgctacagtccccgaagtgttggacatcggcgagttcagcgaga
gcctgacatactgcatcagtagacgcgcccaaggcgttactctccaagac
ctccccgaaacagagctgcctgctgtgttacagcctgtcgccgaagctat
ggatgctattgccgccgccgacctcagtcaaaccagcggcttcggcccat
tcgggcccaaggcatcggccagtacacaacctggcgggatttcatttgc
gccattgctgatccccatgtctaccactggcagaccgtgatggacgacac
cgtgtccgccagcgtagctcaagccctggacgaactgatgctgtgggccg
aagactgtcccgaggtgcgccacctcgtcatgccgacttcggcagcaac
aacgtcctgaccgacaacggccgcatcaccgccgtaatcgactggtccga
agctatgttcggggacagtcagtacgaggtggccaacatcttcttctggc
ggccctggctggcttgcatggagcagcagactcgctacttcgagcgccgg
catcccgagctggccggcagccctcgtctgcgagcctacatgctgcgcat
cggcctggatcagctctaccagagcctcgtggacggcaacttcgacatg
ctgcctgggctcaaggccgctgcgatgccatcgtccgcagcggggccggc
accgtcggtcgcacacaaatcgctcgccggagcgcagccgtatggaccga
cggctgcgtcgaggtgctggccgacagcggcaaccgccggcccagtacac
gaccgcgcgctaaggaggtaggtcgagtttaa,
```
pGL4.10

(SEQ ID NO:89)
```
ggcctaactggccggtacctgagctcgctagcctcgaggatatcaagatc
tggcctcggcggccaagcttggcaatccggtactgttggtaaagccacca
tggaagatgccaaaaacattaagaagggcccagcgccattctacccactc
gaagacgggaccgccggcgagcagctgcacaaagccatgaagcgctacgc
cctggtgcccggcaccatcgcctttaccgacgcacatatcgaggtggaca
ttacctacgccgagtacttcgagatgagcgttcggctggcagaagctatg
aagcgctatgggctgaatacaaaccatcggatcgtggtgtgcagcgagaa
tagcttgcagttcttcatgcccgtgttgggtgccctgttcatcggtgtgg
ctgtggcccagctaacgacatctacaacgagcgcgagctgctgaacagc
atgggcatcagccagcccaccgtcgtattcgtgagcaagaaagggctgca
aaagatcctcaacgtgcaaaagaagctaccgatcatacaaaagatcatca
tcatggatagcaagaccgactaccagggcttccaaagcatgtacaccttc
gtgacttcccatttgccacccggcttcaacgagtacgacttcgtgcccga
gagcttcgaccgggacaaaaccatcgccctgatcatgaacagtagtggca
gtaccggattgcccaagggcgtagccctaccgcaccgcaccgcttgtgtc
cgattcagtcatgcccgcgaccccatcttcggcaaccagatcatccccga
caccgctatcctcagcgtggtgccatttcaccacggcttcggcatgttca
ccacgctgggctacttgatctgcggctttcgggtcgtgctcatgtaccgc
ttcgaggaggagctattcttgcgcagcttgcaagactataagattcaatc
tgccctgctggtgcccacactatttagcttcttcgctaagagcactctca
tcgacaagtacgacctaagcaacttgcacgagatcgccagcggcggggcg
ccgctcagcaaggaggtaggtgaggccgtggccaaacgcttccacctacc
aggcatccgccagggctacggcctgacagaaacaaccagcgccattctga
tcacccccgaaggggacgacaagcctggcgcagtaggcaaggtggtgccc
ttcttcgaggctaaggtggtggacttggacaccggtaagacactgggtgt
gaaccagcgcggcgagctgtgcgtccgtggccccatgatcatgagcggct
acgttaacaaccccgaggctacaaacgctctcatcgacaaggacggctgg
ctgcacagcggcgacatcgcctactgggacgaggacgagcacttcttcat
cgtggaccggctgaagagcctgatcaaatacaagggctaccaggtagccc
cagccgaactggagagcatcctgctgcaacaccccaacatcttcgacgcc
ggggtcgccggcctgcccgacgacgatgccggcgagctgcccgccgcagt
cgtcgtgctggaacacggtaaaaccatgaccgagaaggagatcgtggact
atgtggccagccaggttacaaccgccaagaagctgcgcggtggtgttgtg
ttcgtggacgaggtgcctaaaggactgaccggcaagttggacgcccgcaa
gatccgcgagattctcattaaggccaagaagggcggcaagatcgccgtgt
aataattctagagtcggggcggccggccgcttcgagcagacatgataaga
tacattgatgagtttggacaaaccacaactagaatgcagtgaaaaaaatg
ctttatttgtgaaatttgtgatgctattgctttatttgtaaccattataa
gctgcaataaacaagttaacaacaacaattgcattcattttatgtttcag
gttcaggggaggtgtgggaggttttttaaagcaagtaaaacctctacaa
atgtggtaaaatcgataaggatccgtcgaccgatgcccttgagagccttc
aacccagtcagctccttccggtgggcgcggggcatgactatcgtcgccgc
acttatgactgtcttctttatcatgcaactcgtaggacaggtgccggcag
cgctcttccgcttcctcgctcactgactcgctgcgctcggtcgttcggct
gcggcgagcggtatcagctcactcaaaggcggtaatacggttatccacag
aatcaggggataacgcaggaaagaacatgtgagcaaaaagccagcaaaag
gccaggaaccgtaaaaaggccgcgttgctggcgtttttccataggctccg
cccccctgacgagcatcacaaaaatcgacgctcaagtcagaggtggcgaa
```

-continued

```
acccgacaggactataaagataccaggcgtttccccctggaagctccctc
gtgcgctctcctgttccgaccctgccgcttaccggatacctgtccgcctt
tctcccucgggaagcgtggcgcactcatagctcacgctgtaggtatctca
gttcggtgtaggtcgttcgctccaagctgggctgtgtgcacgaaccccc
gttcagcccgaccgctgcgccttatccggtaactatcgtcttgagtccaa
cccggtaagacacgacttatcgccactggcagcagccactggtaacagga
ttagcagagcgaggtatgtaggcggtgctacagagttcttgaagtggtgg
cctaactacggctacactagaagaacagtatttggtatctgcgctctgct
gaagccagttaccttcggaaaaagagttggtagctcttgatccggcaaac
aaaccaccgctggtagcggtggttttttttgtttgcaagcagcagattacg
cgcagaaaaaaaggatctcaagaagatcctttgatcttttctacggggtc
tgacgctcagtggaacgaaaactcacgttaagggatmggtcatgagatta
tcaaaaaggatcttcacctagatccttttaaattaaaaatgaagttttaa
atcaatctaaagtatatatgagtaaacttggtctgacagcggccgcaaat
gctaaaccactgcagtggttaccagtgcttgatcagtgaggcaccgatct
cagcgatctgcctatttcgttcgtccatagtggcctgactccccgtcgtg
tagatcactacgattcgtgagggcttaccatcaggccccagcgcagcaat
gatgccgcgagagccgcgttcaccggcccccgatttgtcagcaatgaacc
agccagcagggagggccgagcgaagaagtggtcctgctactttgtccgcc
tccatccagtctatgagctgctgtcgtgatgctagagtaagaagttcgcc
agtgagtagtttccgaagagttgtggccattgctactggcatcgtggtat
cacgctcgtcgttcggtatggcttcgttcaactctggttccagcggtca
agccgggtcacatgatcacccatattatgaagaaatgcagtcagctcctt
agggcctccgatcgttgtcagaagtaagttggccgcgcggtgttgtcgctca
tggtaatggcagcactacacaattctcttaccgtcatgccatccgtaaga
tgcttttccgtgaccggcgagtactcaaccaagtcgttttgtgagtagtg
tatacggcgaccaagctgctcttgcccggcgtctatacgggacaacaccg
cgccacatagcagtacutgaaagtgctcatcatcgggaatcgttcttcgg
ggcggaaagactcaaggatcttgccgctattgagatccagttcgatatag
cccactcttgcacccagttgatcttcagcatcttttactttcaccagcgt
ttcggggtgtgcaaaaacaggcaagcaaaatgccgcaaagaagggaatga
gtgcgacacgaaaatgttggatgctcatactcgtcctttttcaatattat
tgaagcatttatcagggttactagtacgtctctcaaggataagtaagtaa
tattaaggtacgggaggtattggacaggccgcaataaaatatctttatttt
tcattacatctgtgtgttggtttttgtgtgaatcgatagtactaacata
cgctctccatcaaaacaaaacgaaacaaaacaaactagcaaaataggctg
tccccagtgcaagtgcaggtgccagaacatttctctaagtaatattaagg
tacgggaggtattggacaggccgcaataaaatatctttattttcattaca
tctgtgtgttggtttttgtgtgaatc,
``` and pGL4.70

(SEQ ID NO:90)

```
ggcctaactggccggtacctgagctcgctagcctcgaggatatcaagatc
tggcctcggcggccaagcttggcaatccggtactgttggtaaagccacca
tggcttccaaggtgtacgaccccgagcaacgcaaacgcatgatcactggg
cctcagtggtgggctcgctgcaagcaaatgaacgtgctggactccttcat
caactactatgattccgagaagcacgccgagaacgccgtgatttttctgc
atggtaacgctgcctccagctacctgtggaggcacgtcgtgcctcacatc
gagcccgtggctagatgcatcatccctgatctgatcggaatgggtaagtc
cggcaagagcgggaatggctcatatcgcctcctggatcactacaagtacc
tcaccgcttggttcgagctgctgaaccttccaaagaaaatcatctttgtg
ggccacgactgggggcttgtctggccttcactactcctacgagcacca
agacaagatcaaggccatcgtccatgctgagagtgtcgtggacgtgatcg
agtcctgggacgagtggcctgacatcgaggaggatatcgccctgatcaag
agcgaagagggcgagaaaatggtgcttgagaataacttcttcgtcgagac
catgctcccaagcaagatcatgcggaaactggagcctgaggagttcgctg
cctacctggagccattcaaggagaagggcgaggttagacggcctaccctc
tcctggcctcgcgagatccctctcgttaagggaggcaagcccgacgtcgt
ccagattgtccgcaactacaacgcctaccttcgggccagcgacgatctgc
ctaagatgttcatcgagtccgaccctgggttcttttccaacgctattgtc
gagggagctaagaagttccctaacaccgagttcgtgaaggtgaagggcct
ccacttcagccaggaggacgctccagatgaaatgggtaagtacatcaaga
gcttcgtggagcgcgtgctgaagaacgagcagtaattctagagtcggggc
ggccggccgcttcgagcagacatgataagatacattgatgagtttggaca
aaccacaactagaatgcagtgaaaaaaatgctttatttgtgaaatttgtg
atgctattgctttatttgtaaccattataagctgcaataaacaagttaac
aacaacaattgcattcattttatgtttcaggttcaggggaggtgtggga
ggttttttaaagcaagtaaaacctctacaaatgtggtaaaatcgataagg
atccgtcgaccgatgcccttgagagccttcaacccagtcagctccttccg
gtgggcgcggggcatgactatcgtcgccgcacttatgactgtcttcttta
tcatgcaactcgtaggacaggtgccggcagcgctcttccgcttcctcgct
cactgactcgctgcgctcggtcgttcggctgcggcgagcggtatcagctc
actcaaaggcggtaatacggttatccacagaatcaggggataacgcagga
aagaacatgtgagcaaaaggccagcaaaaggccaggaaccgtaaaaaggc
cgcgttgctggcgtttttccataggctccgcccccctgacgagcatcaca
aaaatcgacgctcaagtcagaggtggcgaaacccgacaggactataaaga
taccaggcgtttccccctggaagctcctcgtgcgctctcctgttccgac
cctgccgcttaccggatacctgtccgcctttctcccttcgggaagcgtgg
cgctttctcatagctcacgctgtaggtatctcagttcggtgtaggtcgtt
cgctccaagctgggctgtgtgcacgaaccccccgttcagcccgaccgctg
cgccttatccggtaactatcgtcttgagtccaacccggtaagacacgact
```

-continued
```
tatcgccactggcagcagccactggtaacaggattagcagagcgaggtat
gtaggcggtgctacagagttcttgaagtggtggcctaactacggctacac
tagaagaacagtatttggtatctgcgctctgctgaagccagttaccttcg
gaaaaagagttggtagctcttgatccggcaaacaaaccaccgctggtagc
ggtggttttttgtttgcaagcagcagattacgcgcagaaaaaaggatc
tcaagaagatcctttgatcttttctacggggtctgacgctcagtggaacg
aaaactcacgttaagggattttggtcatgagattatcaaaaaggatcttc
acctagatccttttaaattaaaaatgaagttttaaatcaatctaaagtat
atatgagtaaacttggtctgacagcggccgcaaatgctaaaccactgcag
tggttaccagtgcttgatcagtgaggcaccgatctcagcgatctgcctat
ttcgttcgtccatagtggcctgactccccgtcgtgtagatcactacgatt
cgtgagggcttaccatcaggcccagcgcagcaatgatgccgcgagagcc
gcgttcaccggccccgatttgtcagcaatgaaccagccagcagggaggg
ccgagcgaagaagtggtcctgctactttgtccgcctccatccagtctatg
agctgctgtcgtgatgctagagtaagaagttcgccagtgagtagtttccg
aagagttgtggccattgctactggcatcgtggtatcacgctcgtcgttcg
gtatggcttcgttcaactctggttcccagcggtcaagccgggtcacatga
tcacccatattatgaagaaatgcagtcagctccttagggcctccgatcgt
tgtcagaagtaagttggccgcggtgttgtcgctcatggtaatggcagcac
tacacaattctcttaccgtcatgccatccgtaagatgcttttccgtgacc
ggcgagtactcaaccaagtcgttttgtgagtagtgtatacgcgaccaag
ctgctcttgcccggcgtctatacgggacaacaccgcgccacatagcagta
ctttgaaagtgctcatcatcgggaatcgttcttcggggcggaaagactca
aggatcttgccgctattgagatccagttcgatatagcccactcttgcacc
cagttgatcttcagcatcttttactttcaccagcgtttcggggtgtgcaa
aaacaggcaagcaaaatgccgcaaagaagggaatgagtgcgacacgaaaa
tgttggatgctcatactcgtcctttttcaatattattgaagcatttatca
gggttactagtacgtctctcaaggataagtaagtaatattaaggtacggg
aggtattggacaggccgcaataaaatatctttattttcattacatctgtg
tgttggttttttgtgtgaatcgatagtactaacatacgctctccatcaaa
acaaaacgaaacaaaacaaactagcaaaataggctgtccccagtgcaagt
gcaggtgccagaacatttctct.
```

The pGL4 backbone (NotI-NcoI) has the following sequence:

```
                                              (SEQ ID NO:74)
gcggccgcaaatgctaaaccactgcagtggttaccagtgcttgatcagtg
aggcaccgatctcagcgatctgcctatttcgttcgtccatagtggcctga
ctccccgtcgtgtagatcactacgattcgtgagggcttaccatcaggccc
cagcgcagcaatgatgccgcgagagccgcgttcaccggccccgatttgt
cagcaatgaaccagccagcagggagggccgagcgaagaagtggtcctgct
actttgtccgcctccatccagtctatgagctgctgtcgtgatgctagagt
aagaagttcgccagtgagtagtttccgaagagttgtggccattgctactg
gcatcgtggtatcacgctcgtcgttcggtatggcttcgttcaactctggt
tcccagcggtcaagccgggtcacatgatcacccatattatgaagaaatgc
agtcagctccttagggcctccgatcgttgtcagaagtaagttggccgcgg
tgttgtcgctcatggtaatggcagcactacacaattctcttaccgtcatg
ccatccgtaagatgcttttccgtgaccggcgagtactcaaccaagtcgtt
ttgtgagtagtgtatacgcgaccaagctgctcttgcccggcgtctatac
gggacaacaccgcgccacatagcagtactttgaaagtgctcatcatcggg
aatcgttcttcggggcggaaagactcaaggatcttgccgctattgagatc
cagttcgatatagcccactcttgcacccagttgatcttcagcatctttta
ctttcaccagcgtttcggggtgtgcaaaaacaggcaagcaaaatgccgca
aagaagggaatgagtgcgacacgaaaatgttggatgctcatactcgtcct
ttttcaatattattgaagcatttatcagggttactagtacgtctctcaag
gataagtaagtaatattaaggtacgggaggtattggacaggccgcaataa
aatatctttattttcattacatctgtgtgttggttttttgtgtgaatcga
tagtactaacatacgctctccatcaaaacaaaacgaaacaaaacaaacta
gcaaaataggctgtccccagtgcaagtgcaggtgccagaacatttctctg
gcctaactggccggtacctgagctcgctagcctcgaggatatcaagatct
ggcctcggcggccaagcttggcaatccggtactgttggtaaagccaccat
gg.
```

EXAMPLE 10

Summary of Sequences Removed in Synthetic Genes

Search Parameters:

TFBS searches were limited to vertebrate TF binding sites. Searches were performed by matrix family, i.e., the results show only the best match from a family for each site. MatInspector default parameters were used for the core and matrix similarity values (core similarity=0.75, matrix similarity=optimized), except for sequence MCS-1 (core similarity=1.00, matrix similarity=optimized).

Promoter module searches included all available promoter modules (vertebrate and others) and were performed using default parameters (optimized threshold or 80% of maximum score).

Splice site searches were performed for splice acceptor or donor consensus sequences.

TABLE 31

| Sequence | Matrix Library | TFBS (family matches) | Promoter modules | Splice sites (+ strand) |
|---|---|---|---|---|
| puro | (not applicable) | 62 | 5 | 0 |
| hpuro | (not applicable) | 68 | 4 | 1 |

TABLE 31-continued

| Sequence | Matrix Library | TFBS (family matches) | Promoter modules | Splice sites (+ strand) |
|---|---|---|---|---|
| hpuro1 | Ver 4.1 February 2004 | 4 | 2 | 1 |
| hpuro2 | Ver 4.1 February 2004 | 2 | 0 | 1 |
| Neo | (not applicable) | 53 | 0 | No data |
| hneo | (not applicable) | 61 | 2 | 3 |
| hneo-1 | Ver 3.1.2 June 2003 | No data | No data | No data |
| hneo-2 | Ver 3.1.2 June 2003 | No data | No data | No data |
| hneo-3 | Ver 3.1.2 June 2003 | 0 | 0 | 0 |
| hneo-4 | Ver 4.1 February 2004 | 7 | 1 | 0 |
| hneo-5 | Ver 4.1 February 2004 | 0 | 0 | 0 |
| Hyg | (not applicable) | 74 | 3 | No data |
| hhyg | (not applicable) | 94 | 4 | 6 |
| hhyg-1 | Ver 3.1.2 June 2003 | No data | No data | No data |
| hhyg-2 | Ver 3.1.2 June 2003 | No data | No data | No data |
| hhyg-3 | Ver 3.1.2 June 2003 | 3 | 0 | 0 |
| hHygro | Ver 3.3 August 2003 | 5 | 0 | 0 |
| hhyg-4 | Ver 3.3 August 2003 | 4 | 0 | 0 |
| Luc | (not applicable) | 213 | 11 | No data |
| Luc+ | (not applicable) | 189 | 7 | No data |
| hluc+ver2A1 | Ver 3.0 November 2002 | 110 | 7 | 6 |
| hluc+ver2A2 | Ver 3.0 November 2002 | No data | No data | No data |
| hluc+ver2A3 | Ver 3.0 November 2002 | 8 | No data | 0 |
| hluc+ver2A4 | Ver 3.0 November 2002 | No data | No data | No data |
| hluc+ver2A5 | Ver 3.0 November 2002 | No data | No data | No data |
| hluc+ver2A6 | Ver 3.0 November 2002 | 2 | 0 | 0 |
| hluc+ver2A6 | Ver 3.1.1 April 2003 | 4 | 0 | 0 |
| hluc+ver2A7 | Ver 3.1.1 April 2003 | 1 | 0 | 0 |
| hluc+ver2A8 | Ver 3.1.1 April 2003 | 1 | 0 | 0 |
| hluc+ver2B1 | Ver 3.0 November 2002 | 187 | 2 | 8 |
| hluc+ver2B2 | Ver 3.0 November 2002 | No data | No data | No data |
| hluc+ver2B3 | Ver 3.0 November 2002 | 35 | No data | 0 |
| hluc+ver2B4 | Ver 3.0 November 2002 | No data | No data | No data |
| hluc+ver2B5 | Ver 3.0 November 2002 | No data | No data | No data |
| hluc+ver2B6 | Ver 3.0 November 2002 | 2 | 0 | 0 |
| hluc+ver2B6 | Ver 3.1.1 April 2003 | 6 | 0 | 0 |
| hluc+ver2B7 | Ver 3.1.1 April 2003 | 2 | 0 | 0 |
| hluc+ver2B8 | Ver 3.1.1 April 2003 | 1 | 0 | 0 |
| hluc+ver2B9 | Ver 3.1.1 April 2003 | 1 | 0 | 0 |
| hluc+ver2B10 | Ver 3.1.1 April 2003 | 1 | 0 | 0 |
| MCS-1 | Ver 2.2 September 2001 | 14 | No data | (not applicable) |
| MCS-2 | Ver 2.2 September 2001 | 12 | No data | (not applicable) |
| MCS-3 | Ver 2.2 September 2001 | 0 | No data | (not applicable) |
| MCS-4 | Ver 2.3 February 2001 | 0 | 0 | (not applicable) |
| Bla | (not applicable) | No data | No data | (not applicable) |
| bla-1 | Ver 2.2 September 2001 | 94 | 1 | (not applicable) |
| bla-2 | Ver 2.3 February 2001 | 51 | No data | (not applicable) |
| bla-3 | Ver 2.3 February 2001 | 16 | No data | (not applicable) |
| bla-4 | Ver 2.3 February 2001 | 14 | No data | (not applicable) |
| bla-5 | Ver 2.3 February 2001 | 5 | 0 | (not applicable) |
| pGL4B-4NN | Ver 2.4 May 2002 | 11 | 0 | (not applicable) |
| pGL4B-4NN1 | Ver 2.4 May 2002 | 7 | No data | (not applicable) |
| pGL4B-4NN2 | Ver 2.4 May 2002 | 4 | 0 | (not applicable) |

TABLE 31-continued

| Sequence | Matrix Library | TFBS (family matches) | Promoter modules | Splice sites (+ strand) |
|---|---|---|---|---|
| pGL4B-4NN3 | Ver 2.4 May 2002 | 3 | 0 | (not applicable) |
| SpeI-NcoI-Ver2-Start | Ver 4.0 November 2003 | 34 | 1 | (not applicable) |
| SpeI-NcoI-Ver2 | Ver 4.0 November 2003 | 28 | 1 | (not applicable) |

Using the 5 sequences, i.e., hluc+ver2A1, bla-1, hneo-1, hpuro-1, hhyg-1 (humanized codon usage) for analysis, TFBS from the following families were found in 3 out 5 sequences:

V$AHRR (AHR-arnt heterodimers and AHR-related factors)
V$ETSF (Human and murine ETS 1 factors)
V&NFKB (Nuclear Factor Kappa B/c-rel)
V$VMYB (AMV-viral myb oncogene)
V$CDEF (Cell cycle regulators: Cell cycle dependent element)
V$HAND (bHLH transcription factor dimer of HAND2 and E12)
V$NRSF (Neuron-Restrictive Silencer Factor)
V$WHZF (Wingeg Helix and ZF5 binding sites)
V$CMYB (C-myb, cellular transcriptional activator)
V$MENI (Muscle INItiator)
V$P53F (p53 tumor suppr.-neg. regulat. of the tumor suppr. Rb)
V$ZF5F (ZF5 POZ domain zinc finger)
V$DEAF (Homolog to deformed epidermal autoregulatory factor-1 from *D. melanogaster*)
V$MYOD (MYOblast Determining factor)
V$PAX5 (PAX-5/PAX-9 B-cell-specific activating protein)
V$EGRF (EGR/nerve growth Factor Induced protein C & rel. fact.)
V$NEUR (NeuroD, Beta2, HLH domain)
V$REBV (Epstein-Barr virus transcription factor R);

TFBS from the following families were found in 4 out of 5 sequences:

V$ETSF (Human and murine ETS 1 factors)
V$CDEF (Cell cycle regulators: Cell cycle dependent element)
V$HAND (bHLH transcription factor dimer of HAND2 and E12)
V$NRSF (Neuron-Restrictive Silencer Factor)
V$PAX5 (PAX-5/PAX-9 B-cell-specific activating protein)
V$NEUR (NeuroD, Beta2, HLH domain); and TFBS from the following families were found in 5 out of 5 sequences:

V$PAX5 (PAX-5/PAX-9 B-cell-specific activating protein).

REFERENCES

Altschul et al., *Nucl. Acids Res.*, 25, 3389 (1997).
Aota et al., *Nucl. Acids Res.*, 16, 315 (1988).
Boshart et al., *Cell*, 41, 521 (1985).
Bronstein et al., *Cal. Biochem.*, 219, 169 (1994).
Corpet et al., *Nucl. Acids Res.*, 16, 881 (1988).
deWet et al., *Mol. Cell. Biol.*, 7, 725 (1987).
Dijkema et al., *EMBO J.*, 4, 761 (1985).
Faist and Meyer, *Nucl. Acids Res.*, 20, 26 (1992).
Gorman et al., *Proc. Natl. Acad. Sci. USA*, 79, 6777 (1982).
Higgins et al., *Gene*, 73, 237 (1985).
Higgins et al., *CABIOS*, 5, 151 (1989).
Huang et al., *CABIOS*, 8, 155 (1992).
Itolcik et al., *PNAS*, 94, 12410 (1997).
Johnson et al., *Mol. Reprod. Devel.*, 50, 377 (1998).
Jones et al., *Mol. Cell. Biol.*, 17, 6970 (1997).
Karlin and Altschul, *Proc. Natl. Acad. Sci. USA*, 87, 2264 (1990).
Karlin and Altschul, *Proc. Natl. Acad. Sci. USA*, 90, 5873 (1993).
Keller et al., *J. Cell Biol.*, 84, 3264 (1987).
Kim et al., *Gene*, 91, 217 (1990).
Lamb et al., *Mol. Reprod. Devel.*, 51, 218 (1998).
Mariatis et al., *Science*, 236, 1237 (1987).
Michael et al., *EMBO. J.*, 9, 481 (1990).
Mizushima and Nagata, *Nucl. Acids Res.*, 18, 5322 (1990).
Murray et al., *Nucl. Acids Res.*, 17, 477 (1989).
Myers and Miller, *CABIOS*, 4, 11 (1988).
Nakamura et al., *NAR*, 28:292 (2000).
Needleman and Wunsen, *J. Mol. Biol.*, 48, 443 (1970).
Pearson and Lipman, *Proc. Natl. Acad. Sci. USA*, 85, 2444 (1988).
Pearson et al., *Meth. Mol. Biol.*, 24, 307 (1994).
Sharp et al., *Nucl. Acids Res.*, 16, 8207 (1988).
Sharp et al., *Nucl. Acids Res.*, 15, 1281 (1987).
Smith and Waterman, *Adv. Appl. Math.*, 2, 482 (1981).
Stemmer et al., *Gene*, 164, 49 (1995).
Uetsuki et al., *J. Biol. Chem.*, 264, 5791 (1989).
Voss et al., *Trends Biochem. Sci.*, 11, 287 (1986).
Wada et al., *Nucl. Acids Res.*, 18, 2367 (1990).
Watson et al, eds. *Recombinant DNA: A Short Course*, Scientific American Books, W. H. Freeman and Company, New York (1983).
Wood, K. *Photochemistry and Photobiology*, 62, 662 (1995).
Wood, K. *Science* 244, 700 (1989)

All publications, patents and patent applications are incorporated herein by reference. While in the foregoing specification, this invention has been described in relation to certain preferred embodiments thereof, and many details have been set forth for purposes of illustration, it will be apparent to those skilled in the art that the invention is susceptible to additional embodiments and that certain of the details herein may be varied considerably without departing from the basic principles of the invention.

What is claimed is:

1. An isolated nucleic acid molecule comprising a synthetic nucleotide sequence having a coding region for a selectable polypeptide, wherein the synthetic nucleotide sequence has 90% or less nucleic acid sequence identity to a wild-type or parent nucleic acid sequence encoding a corresponding selectable polypeptide which, when expressed in a cell, confers resistance to puromycin, hygromycin-or neomycin, wherein the decreased sequence identity is a result of different codons in the synthetic nucleotide sequence relative to the codons in the wild-type or parent nucleic acid sequence, wherein the synthetic nucleotide sequence encodes a selectable polypeptide with at least 85% amino acid sequence identity to the corresponding selectable polypeptide encoded by the wild-type or parent nucleic acid sequence, wherein the synthetic nucleotide sequence has a reduced number of regulatory sequences including a reduced number of a combination of different vertebrate transcription factor binding sequences and of promoter modules relative to the number of regulatory sequences in a derivative of the wild-type or parent nucleic acid sequence in which native codons are replaced with high usage mammalian codons, as a result of selecting mammalian codons as the different codons so as to reduce the number of regulatory sequences, and wherein the synthetic nucleotide sequence, when expressed in a cell, confers resistance to puromycin, hygromycin or neomycin, wherein the synthetic nucleotide sequence has at least 90% or more nucleic acid sequence identity to SEQ ID NO:11, SEQ ID NO:71 or SEQ ID NO:73, or the complete complement thereof.

2. The isolated nucleic acid molecule of claim 1 wherein the regulatory sequences include transcription factor binding sequences, intron splice sites, poly(A) sites, promoter modules, and/or promoter sequences.

3. The isolated nucleic acid molecule of claim 1 wherein the nucleic acid molecule encodes a fusion of the selectable polypeptide with a luciferase.

4. The isolated nucleic acid molecule of claim 3 wherein the luciferase is a Renilla luciferase, a firefly luciferase or a click beetle luciferase.

5. The isolated nucleic acid molecule of claim 1 wherein the parent nucleic acid sequence is a wild-type neo, hyg, or pure sequence.

6. The isolated nucleic acid molecule of claim 1 wherein the parent nucleic acid sequence is SEQ ID NO:1, SEQ ID NO:6, or SEQ ID NO:15.

7. The isolated nucleic acid molecule of claim 1 wherein the synthetic nucleotide sequence comprises an open reading frame in SEQ ID NO:11, SEQ ID NO:71, or SEQ ID NO:73.

8. The isolated nucleic acid molecule of claim 1 wherein the synthetic nucleotide sequence has at least 10% fewer regulatory sequences.

9. The isolated nucleic acid molecule of claim 1 wherein the synthetic nucleotide sequence has an increased number of AGC seine-encoding codons, an increased number of ATC isoleucine-encoding codons, an increased number of CCC proline-encoding codons, and/or an increased number of ACC threonine-encoding codons.

10. The isolated nucleic acid molecule of claim 1 wherein the codons in the synthetic nucleotide sequence which differ encode the same amino acids as the corresponding codons in the parent nucleic acid sequence.

11. The isolated nucleic acid molecule of claim 1 wherein the nucleic acid molecule encodes a fusion of the selectable polypeptide with one or more other peptides or polypeptides, wherein at least the selectable polypeptide is encoded by the synthetic nucleic acid sequence.

12. The isolated nucleic acid molecule of claim 11 wherein one or more other peptides are peptides having protein destabilization sequences.

13. A plasmid comprising the nucleic acid molecule of claim 1.

14. The plasmid of claim 13 which further comprises a multiple cloning region.

15. The plasmid of claim 13 which further comprises an open reading frame of interest.

16. The plasmid of claim 13 which further comprises a promoter functional in a particular host cell operably linked to the synthetic nucleotide sequence.

17. The plasmid of claim 16 wherein the promoter is functional in a prokaryotic cells.

18. The plasmid of claim 16 wherein the promoter is functional in a eukaryotic cell.

19. The plasmid of claim 15 further comprising a promoter operably linked to the open reading frame of interest.

20. A synthetic nucleotide sequence of at least 100 nucleotides having a coding region for a selectable polypeptide which confers resistance to puromycin, hygromycin or neomycin, wherein the synthetic nucleotide sequence has 90% or less nucleic acid sequence identity to a corresponding region of a wild-type parent nucleic acid sequence for the selectable polypeptide, wherein the decreased sequence identity is a result of different codons in the synthetic nucleotide sequence relative to the codons in the corresponding region in the parent nucleic acid sequence, wherein the synthetic nucleotide sequence has a reduced number of regulatory sequences including a reduced number of a combination of different vertebrate transcription factor binding sequences and of promoter modules relative to the number of regulatory sequences in a derivative of the wild-type nucleic acid sequence in which native codons are replaced with high usage mammalian codons, as a result of selecting mammalian codons as the different codons so as to reduce the number of regulatory sequences, wherein the synthetic nucleotide sequence has at least 90% or more nucleic acid sequence identity to SEQ ID NO:11, SEQ ID NO:71 or SEQ ID NO:73, or the complete complement thereof.

21. An isolated nucleic acid molecule encoding a selectable polypeptide and comprising a synthetic nucleotide sequence of at least 100 nucleotides having a coding region for the selectable polypeptide when expressed in a cell, confers resistance to puromycin, hygromycin or neomycin, wherein the synthetic nucleotide sequence has 90% or less nucleic acid sequence identity to a corresponding region in a wild-type or parent nucleic acid sequence for the selectable polypeptide, wherein the decreased sequence identity is a result of different codons in the synthetic nucleotide sequence relative to the codons in the wild-type or parent nucleic acid sequence, wherein the synthetic nucleotide sequence encodes a region of the selectable polypeptide with at least 90% amino acid sequence identity to the corresponding region of the selectable polypeptide encoded by the wild-type or parent nucleic acid sequence, wherein the synthetic nucleotide sequence has a reduced number of regulatory sequences including a reduced number of a combination of different vertebrate transcription factor binding sequences and of promoter modules relative to the number of regulatory sequences in a derivative of the wild-type or parent nucleic acid sequence in which native codons are replaced with high usage mammalian codons, as a result of selecting mammalian codons as the different codons so as to reduce the number of regulatory sequences, and wherein the isolated nucleic acid molecule, when expressed in a cell, confers resistance to puromycin, hygromycin or neomycin, wherein the synthetic nucleotide sequence has at least 90% or more nucleic acid sequence identity to SEQ ID NO:11, SEQ ID NO:71 or SEQ ID NO:73, or the complete complement thereof.

22. The isolated nucleic acid molecule of claim 1 wherein the parent nucleic acid sequence has SEQ ID NO:1.

23. The isolated nucleic acid molecule of claim 1 wherein the parent nucleic acid sequence encodes SEQ ID NO:2.

24. An isolated nucleic acid molecule which has at least 90% nucleotide sequence identity to an open reading frame in any one of SEQ ID NO:11, SEQ ID NO:71, or SEQ ID NO:73, which open reading frame, when expressed in a cell, confers resistance to neomycin, or the complete complement thereof.

25. The isolated nucleic acid molecule of claim 24 which has any one of SEQ ID NO:11, SEQ ID NO:71, or SEQ ID NO:73, or the complete complement thereof.

26. The isolated nucleic acid molecule of claim 24 wherein the open reading frame has codons that are different than those in a wild-type parent nucleic acid sequence encoding a polypeptide that confers puromycin, hygromycin or neomycin resistance, which different codons reduce the number of different vertebrate transcription factor binding sequences and promoter modules.

27. The isolated nucleic acid molecule of claim 24 wherein the nucleic acid molecule encodes a fusion of one or more peptides or polypeptides with the polypeptide that confers neomycin resistance.

28. A plasmid comprising the isolated nucleic acid molecule of claim 24.

29. The plasmid of claim 28 which further comprises a multiple cloning region.

30. The plasmid of claim 28 which further comprises an open reading frame of interest.

31. The plasmid of claim 28 which further comprises a promoter functional in a particular host cell operably linked to the synthetic nucleotide sequence.

32. The plasmid of claim 31 wherein the promoter is functional in a eukaryotic cell.

33. The plasmid of claim 30 further comprising a promoter operably linked to the open reading frame of interest.

34. The isolated nucleic acid molecule of claim 26 wherein the parent nucleic acid sequence has SEQ ID NO: 1.

35. The isolated nucleic acid molecule of claim 1 or 21 wherein the synthetic nucleotide sequence has at least 90% or more nucleic acid sequence identity to SEQ ID NO:73 or the complete complement thereof.

36. The synthetic nucleotide sequence of claim 20 which has at least 90% or more nucleic acid sequence identity to SEQ ID NO:73 or the complete complement thereof.

* * * * *

SEQUENCE LISTING

<160> NUMBER OF SEQ ID NOS: 97

<210> SEQ ID NO 1
<211> LENGTH: 795
<212> TYPE: DNA
<213> ORGANISM: Unknown
<220> FEATURE:
<223> OTHER INFORMATION: Neo from neomycin gene from Promega's pCI-neo.

<400> SEQUENCE: 1

```
atgattgaac aagatggatt gcacgcaggt tctccggccg cttgggtgga gaggctattc      60
ggctatgact gggcacaaca gacaatcggc tgctctgatg ccgccgtgtt ccggctgtca     120
gcgcagggc gcccggttct ttttgtcaag accgacctgt ccggtgccct gaatgaactg     180
caggacgagg cagcgcggct atcgtggctg gccacgacgg gcgttccttg cgcagctgtg     240
ctcgacgttg tcactgaagc gggaagggac tggctgctat tgggcgaagt gccggggcag     300
gatctcctgt catctcacct tgctcctgcc gagaaagtat ccatcatggc tgatgcaatg     360
cggcggctgc atacgcttga tccggctacc tgcccattcg accaccaagc gaaacatcgc     420
atcgagcgag cacgtactcg gatggaagcc ggtcttgtcg atcaggatga tctggacgaa     480
gagcatcagg ggctcgcgcc agccgaactg ttcgccaggc tcaaggcgcg catgcccgac     540
ggcgaggatc tcgtcgtgac ccatggcgat gcctgcttgc cgaatatcat ggtggaaaat     600
ggccgctttt ctggattcat cgactgtggc cggctgggtg tggcggaccg ctatcaggac     660
atagcgttgg ctacccgtga tattgctgaa gagcttggcg gcgaatgggc tgaccgcttc     720
ctcgtgcttt acggtatcgc cgctcccgat tcgcagcgca tcgccttcta tcgccttctt     780
gacgagttct tctga                                                      795
```

<210> SEQ ID NO 2
<211> LENGTH: 264
<212> TYPE: PRT
<213> ORGANISM: Unknown
<220> FEATURE:
<223> OTHER INFORMATION: Neo from neomycin gene from Promega's pCI-neo.

<400> SEQUENCE: 2

```
Met Ile Glu Gln Asp Gly Leu His Ala Gly Ser Pro Ala Ala Trp Val
  1               5                  10                  15

Glu Arg Leu Phe Gly Tyr Asp Trp Ala Gln Gln Thr Ile Gly Cys Ser
             20                  25                  30

Asp Ala Ala Val Phe Arg Leu Ser Ala Gln Gly Arg Pro Val Leu Phe
         35                  40                  45

Val Lys Thr Asp Leu Ser Gly Ala Leu Asn Glu Leu Gln Asp Glu Ala
     50                  55                  60

Ala Arg Leu Ser Trp Leu Ala Thr Thr Gly Val Pro Cys Ala Ala Val
 65                  70                  75                  80

Leu Asp Val Val Thr Glu Ala Gly Arg Asp Trp Leu Leu Leu Gly Glu
                 85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140
```

```
Arg Thr Arg Met Glu Ala Gly Leu Val Asp Gln Asp Leu Asp Glu
145                 150                 155                 160

Glu His Gln Gly Leu Ala Pro Ala Glu Leu Phe Ala Arg Leu Lys Ala
            165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
            195                 200                 205

Cys Gly Arg Leu Gly Val Ala Asp Arg Tyr Gln Asp Ile Ala Leu Ala
            210                 215                 220

Thr Arg Asp Ile Ala Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
            245                 250                 255

Tyr Arg Leu Leu Asp Glu Phe Phe
            260
```

<210> SEQ ID NO 3
<211> LENGTH: 825
<212> TYPE: DNA
<213> ORGANISM: Artificial Sequence
<220> FEATURE:
<223> OTHER INFORMATION: A synthetic construct.

<400> SEQUENCE: 3

```
ccactcagtg gccaccatga tcgagcagga cggcctgcac gccggcagcc ccgccgcctg     60
ggtggagcgc ctgttcggct acgactgggc ccagcagacc atcggctgca gcgacgccgc    120
cgtgttccgc ctgagcgccc agggccgccc cgtgctgttc gtgaagaccg acctgagcgg    180
cgccctgaac gagctgcagg acgaggccgc ccgcctgagc tggctggcca ccaccggcgt    240
gccctgcgcc gccgtgctgg acgtggtgac cgaggccggc cgcgactggc tgctgctggg    300
cgaggtgccc ggccaggacc tgctgagcag ccacctggcc ccgccgaga aggtgagcat    360 catggccgac gccatgcgcc gcctgcacac cctggacccc gccacctgcc ccttcgacca    420
ccaggccaag caccgcatcg agcgcgcccg caccogcatg gaggccggcc tggtggacca    480
ggacgacctg gacgaggagc accagggcct ggccccgcc gagctgttcg cccgcctgaa    540
ggcccgcatg cccgacggcg aggacctggt ggtgacccac ggcgacgcct gcctgcccaa    600
catcatggtg gagaacggcc gcttcagcgg cttcatcgac tgcggccgcc tgggcgtggc    660
cgaccgctac caggacatcg ccctggccac ccgcgacatc gccgaggagc tgggcggcga    720
gtgggccgac cgcttcctgg tgctgtacgg catcgccgcc cccgacagcc agcgcatcgc    780
cttctaccgc ctgctggacg agttcttcta ataaccagtc tctgg                    825
```

<210> SEQ ID NO 4
<211> LENGTH: 825
<212> TYPE: DNA
<213> ORGANISM: Artificial Sequence
<220> FEATURE:
<223> OTHER INFORMATION: A synthetic construct.

<400> SEQUENCE: 4

```
ccactcagtg gccaccatga tcgagcagga cggcctgcac gccggcagcc ccgccgcctg     60
ggtggagcgc ctgttcggct acgactgggc ccagcagacc atcggctgca gcgacgccgc    120
cgtgttccgc ctgagcgccc agggccgccc cgtgctgttc gtgaagaccg acctgagcgg    180
cgccctgaac gagctgcagg acgaggccgc ccgcctgagc tggctggcca ccaccggcgt    240
```

```
gccctgcgcc gccgtgctgg acgtggtgac cgaggccggc cgcgactggc tgctgctggg    300
cgaggtgccc ggccaggacc tgctgagcag ccacctggcc cccgccgaga aggtgagcat    360
catggccgac gccatgcgcc gcctgcacac cctggacccc gccacctgcc ccttcgacca    420
ccaggccaag caccgcatcg agcgcgcccg cacccgcatg gaggccggcc tggtggacca    480
ggacgacctg gacgaggagc accagggcct ggccccgcc gagctgttcg cccgcctgaa    540
ggcccgcatg cccgacggcg aggacctggt ggtgacccac ggcgacgcct gcctgcccaa    600
catcatggtg gagaacggcc gcttcagcgg cttcatcgac tgcggccgcc tgggcgtggc    660
cgaccgctac caggacatcg ccctggccac ccgcgacatc gccgaggagc tgggcggcga    720
gtgggccgac cgcttcctgg tgctgtacgg catcgccgcc cccgacagcc agcgcatcgc    780
cttctaccgc ctgctggacg agttcttcta ataaccagtc tctgg                    825

<210> SEQ ID NO 5
<211> LENGTH: 818
<212> TYPE: DNA
<213> ORGANISM: Artificial Sequence
<220> FEATURE:
<223> OTHER INFORMATION: A synthetic construct.

<400> SEQUENCE: 5
cctgcaggcc accatgatcg aacaagacgg cctccatgct ggcagtcccg cagcttgggt     60
cgaacgcttg ttcgggtacg actgggccca gcagaccatc ggatgtagcg atgcggccgt    120
gttccgtcta agcgctcaag gccggccgt gctgttcgtg aagaccgacc tgagcggcgc    180
cctgaacgag cttcaagacg aggctgcccg cctgagctgg ctggccacca ccggtgtacc    240
ctgcgccgct gtgttggatg ttgtgaccga agccggccgg gactggctgc tgctgggcga    300
ggtccctggc caggatctgc tgagcagcca ccttgccccc gctgagaagg tttccatcat    360
ggccgatgca atgcggcgcc tgcacaccct ggaccccgct acatgcccct cgaccacca    420 ggctaagcat cggatcgagc gtgctcggac ccgcatggag gccggcctgg tggaccagga    480
cgacctggac gaggagcatc agggcctggc ccccgctgaa ctgttcgccc gcctgaaagc    540
ccgcatgccg gacggtgagg acctggttgt gacacatggt gatgcctgcc tccctaacat    600
catggtcgag aatggccgct ctccggctt catcgactgc ggtcgcctag agttgccga    660 ccgctaccag gacatcgccc tggccacccg cgacatcgct gaggagcttg gcggcgagtg    720
ggccgaccgc ttcttagtct tgtacggcat cgcagctccc gacagccagc gcatcgcctt    780
ctaccgcctg ctcgacgagt tcttttaatg agcttaag                             818

<210> SEQ ID NO 6
<211> LENGTH: 1024
<212> TYPE: DNA
<213> ORGANISM: Escherichia coli

<400> SEQUENCE: 6
atgaaaaagc ctgaactcac cgcgacgtct gtcgagaagt ttctgatcga aaagttcgac     60
agcgtctccg acctgatgca gctctcggag ggcgaagaat ctcgtgcttt cagcttcgat    120
gtaggagggc gtggatatgt cctgcgggta aatagctgcg ccgatggttt ctacaaagat    180
cgttatgttt atcggcactt tgcatcggcc gcgctcccga ttccggaagt gcttgacatt    240
ggggaattca gcgagagcct gacctattgc atctcccgcc gtgcacaggg tgtcacgttg    300
caagacctgc ctgaaaccga actgcccgct gttctgcagc cggtcgcgga ggccatggat    360
gcgatcgctg cggccgatct tagccagacg agcgggttcg gcccattcgg accgcaagga    420
```

-continued

```
atcggtcaat acactacatg gcgtgatttc atatgcgcga ttgctgatcc ccatgtgtat    480
cactggcaaa ctgtgatgga cgacaccgtc agtgcgtccg tcgcgcaggc tctcgatgag    540
ctgatgcttt gggccgagga ctgccccgaa gtccggcacc tcgtgcacgc ggatttcggc    600
tccaacaatg tcctgacgga caatggccgc ataacagcgg tcattgactg gagcgaggcg    660
atgttcgggg attcccaata cgaggtcgcc aacatcttct tctggaggcc gtggttggct    720
tgtatggagc agcagacgcg ctacttcgag cggaggcatc cggagcttgc aggatcgccg    780
cggctccggg cgtatatgct ccgcattggt cttgaccaac tctatcagag cttggttgac    840
ggcaatttcg atgatgcagc ttgggcgcag ggtcgatgcg acgcaatcgt ccgatccgga    900
gccgggactg tcgggcgtac acaaatcgcc cgcagaagcg cggccgtctg accgatggc    960 tgtgtagaag tactcgccga tagtggaaac cgacgcccca gcactcgtcc gagggcaaag   1020
gaat                                                                1024
```

<210> SEQ ID NO 7
<211> LENGTH: 341
<212> TYPE: PRT
<213> ORGANISM: Escherichia coli

<400> SEQUENCE: 7

```
Met Lys Lys Pro Glu Leu Thr Ala Thr Ser Val Glu Lys Phe Leu Ile
 1               5                  10                  15

Glu Lys Phe Asp Ser Val Ser Asp Leu Met Gln Leu Ser Glu Gly Glu
                20                  25                  30

Glu Ser Arg Ala Phe Ser Phe Asp Val Gly Gly Arg Gly Tyr Val Leu
            35                  40                  45

Arg Val Asn Ser Cys Ala Asp Gly Phe Tyr Lys Asp Arg Tyr Val Tyr
        50                  55                  60

Arg His Phe Ala Ser Ala Ala Leu Pro Ile Pro Glu Val Leu Asp Ile
65                  70                  75                  80

Gly Glu Phe Ser Glu Ser Leu Thr Tyr Cys Ile Ser Arg Arg Ala Gln
                85                  90                  95

Gly Val Thr Leu Gln Asp Leu Pro Glu Thr Glu Leu Pro Ala Val Leu
            100                 105                 110

Gln Pro Val Ala Glu Ala Met Asp Ala Ile Ala Ala Ala Asp Leu Ser
        115                 120                 125

Gln Thr Ser Gly Phe Gly Pro Phe Gly Pro Gln Gly Ile Gly Gln Tyr
    130                 135                 140

Thr Thr Trp Arg Asp Phe Ile Cys Ala Ile Ala Asp Pro His Val Tyr
145                 150                 155                 160

His Trp Gln Thr Val Met Asp Asp Thr Val Ser Ala Ser Val Ala Gln
                165                 170                 175

Ala Leu Asp Glu Leu Met Leu Trp Ala Glu Asp Cys Pro Glu Val Arg
            180                 185                 190

His Leu Val His Ala Asp Phe Gly Ser Asn Asn Val Leu Thr Asp Asn
        195                 200                 205

Gly Arg Ile Thr Ala Val Ile Asp Trp Ser Glu Ala Met Phe Gly Asp
    210                 215                 220

Ser Gln Tyr Glu Val Ala Asn Ile Phe Phe Trp Arg Pro Trp Leu Ala
225                 230                 235                 240

Cys Met Glu Gln Gln Thr Arg Tyr Phe Glu Arg Arg His Pro Glu Leu
                245                 250                 255
```

```
Ala Gly Ser Pro Arg Leu Arg Ala Tyr Met Leu Arg Ile Gly Leu Asp
            260                 265                 270

Gln Leu Tyr Gln Ser Leu Val Asp Gly Asn Phe Asp Asp Ala Ala Trp
        275                 280                 285

Ala Gln Gly Arg Cys Asp Ala Ile Val Arg Ser Gly Ala Gly Thr Val
    290                 295                 300

Gly Arg Thr Gln Ile Ala Arg Arg Ser Ala Ala Val Trp Thr Asp Gly
305                 310                 315                 320

Cys Val Glu Val Leu Ala Asp Ser Gly Asn Arg Arg Pro Ser Thr Arg
                325                 330                 335

Pro Arg Ala Lys Glu
            340

<210> SEQ ID NO 8
<211> LENGTH: 1056
<212> TYPE: DNA
<213> ORGANISM: Artificial Sequence
<220> FEATURE:
<223> OTHER INFORMATION: A synthetic construct.

<400> SEQUENCE: 8
ccactcagtg gccaccatga agaagcccga gctgaccgcc accagcgtgg agaagttcct      60
gatcgagaag ttcgacagcg tgagcgacct gatgcagctg agcgagggcg aggagagccg     120
cgccttcagc ttcgacgtgg cggccgcgg  ctacgtgctg cgcgtgaaca gctgcgccga     180
cggcttctac aaggaccgct acgtgtaccg ccacttcgcc agcgccgccc tgcccatccc     240
cgaggtgctg gacatcggcg agttcagcga gagcctgacc tactgcatca gccgccgcgc     300
ccagggcgtg accctgcagg acctgccgga gaccgagctg cccgccgtgc tgcagccggt     360
ggccgaggcc atggacgcca tcgccgccgc cgacctgagc cagaccagcg gcttcggccc     420
cttcggcccc cagggcatcg ccagtacac  cacctggcgc gacttcatct gcgccatcgc     480
cgacccccac gtgtaccact ggcagaccgt gatggacgac accgtgagcg ccagcgtggc     540
ccaggccctg gacgagctga tgctgtgggc cgaggactgc cccgaggtgc gccacctggt     600
gcacgccgac ttcggcagca caacgtgct  gaccgacaac ggccgcatca ccgccgtgat     660
cgactggagc gaggccatgt cggcgacag  ccagtacgag gtggccaaca tcttcttctg     720
gcgcccctgg ctggcctgca tggagcagca gacccgctac ttcgagcgcc gccaccccga     780
gctggccggc agccccgcc  tgcgcgccta catgctgcgc atcggcctgg accagctgta     840
ccagagcctg gtggacggca acttcgacga cgccgcctgg gcccagggcc gctgcgacgc     900
catcgtgcgc agcggcgccg gcaccgtggg ccgcacccag atcgcccgcc gcagcgccgc     960
cgtgtggacc gacggctgcg tggaggtgct ggccgacagc ggcaaccgcc gccccagcac    1020
ccgcccccgc gccaaggagt aataaccagc tcttgg                              1056

<210> SEQ ID NO 9
<211> LENGTH: 1056
<212> TYPE: DNA
<213> ORGANISM: Artificial Sequence
<220> FEATURE:
<223> OTHER INFORMATION: A synthetic construct.

<400> SEQUENCE: 9
ccactccgtg gccaccatga agaagcccga gctgaccgct accagcgttg aaaaatttct      60
catcgagaag ttcgacagtg tgagcgacct gatgcagttg tcgagggcg  aagagagccg     120 agccttcagc ttcgatgtcg gcggacgcgg ctatgtactg cgggtgaata gctgcgctga     180
```

| | |
|---|---:|
| tggcttctac aaagaccgct acgtgtaccg ccacttcgcc agcgctgcac tacccatccc | 240 |
| cgaagtgttg acatcggcg agttcagcga gagcctgaca tactgcatca gtagacgcgc | 300 |
| ccaaggcgtt actctccaag acctccccga acagagctg cctgctgtgt tacagcctgt | 360 |
| cgccgaagct atggatgcta ttgccgccgc cgacctcagt caaaccagcg gcttcggccc | 420 |
| attcgggccc caaggcatcg gccagtacac aacctggcgg gatttcattt gcgccattgc | 480 |
| tgatccccat gtctaccact ggcagaccgt gatggacgac accgtgtccg ccagcgtagc | 540 |
| tcaagccctg gacgaactga tgctgtgggc cgaagactgt cccgaggtgc gccacctcgt | 600 |
| ccatgccgac ttcggcagca caacgtcct gaccgacaac ggccgcatca ccgccgtaat | 660 |
| cgactggtcc gaagctatgt tcggggacag tcagtacgag gtggccaaca tcttcttctg | 720 |
| gcggccctgg ctggcttgca tggagcagca gactcgctac ttcgagcgcc ggcatcccga | 780 |
| gctggccgga gccctcgtc tgcgagccta catgctgcgc atcggcctgg atcagctcta | 840 |
| ccagagcctc gtggacggca acttcgacga tgctgcctgg gctcaaggcc gctgcgatgc | 900 |
| catcgtccgc agcggggccg gcaccgtcgg tcgcacacaa atcgctcgcc ggagcgccgc | 960 |
| cgtatggacc gacggctgcg tcgaggtgct ggccgacagc ggcaaccgcc ggcccagtac | 1020 |
| acgaccgcgc gctaaggagt agtaaccagg ctctgg | 1056 |

<210> SEQ ID NO 10
<211> LENGTH: 1048
<212> TYPE: DNA
<213> ORGANISM: Artificial Sequence
<220> FEATURE:
<223> OTHER INFORMATION: A synthetic construct.

<400> SEQUENCE: 10

| | |
|---|---:|
| cctgcaggcc accatgaaga agcccgagct gaccgctacc agcgttgaaa aatttctcat | 60 |
| cgagaagttc gacagtgtga gcgacctgat gcagttgtcg gagggcgaag agagccgagc | 120 |
| cttcagcttc gatgtcggcg gacgcggcta tgtactgcgg gtgaatagct gcgctgatgg | 180 |
| cttctacaaa gaccgctacg tgtaccgcca cttcgccagc gctgcactac ccatccccga | 240 |
| agtgttggac atcggcgagt tcagcgagag cctgacatac tgcatcagta gacgcgccca | 300 |
| aggcgttact ctccaagacc tccccgaaac agagctgcct gctgtgttac agcctgtcgc | 360 |
| cgaagctatg gatgctattg ccgccgccga cctcagtcaa accagcggct tcggcccatt | 420 |
| cgggccccaa ggcatcggcc agtacacaac ctggcgggat ttcatttgcg ccattgctga | 480 |
| tccccatgtc taccactggc agaccgtgat ggacgacacc gtgtccgcca gcgtagctca | 540 |
| agccctggac gaactgatgc tgtgggccga agactgtccc gaggtgcgcc acctcgtcca | 600 |
| tgccgacttc ggcagcaaca acgtcctgac cgacaacggc cgcatcaccg ccgtaatcga | 660 |
| ctggtccgaa gctatgttcg gggacagtca gtacgaggtg gccaacatct tcttctggcg | 720 |
| gccctggctg gcttgcatgg agcagcagac tcgctacttc gagcgccggc atcccgagct | 780 |
| ggccggcagc cctcgtctgc gagcctacat gctgcgcatc ggcctggatc agctctacca | 840 |
| gagcctcgtg gacggcaact tcgacgatgc tgcctgggct caaggccgct gcgatgccat | 900 |
| cgtccgcagc ggggccggca ccgtcggtcg cacacaaatc gctcgccgga gcgccgcgt | 960 |
| atggaccgac ggctgcgtcg aggtgctggc cgacagcggc aaccgccggc ccagtacacg | 1020 |
| accgcgcgct aaggagtagt aacttaag | 1048 |

<210> SEQ ID NO 11
<211> LENGTH: 1174
<212> TYPE: DNA
<213> ORGANISM: Artificial Sequence
<220> FEATURE:
<223> OTHER INFORMATION: A synthetic construct.

<400> SEQUENCE: 11

```
ggatccgttt gcgtattggg cgctcttccg ctgatctgcg cagcaccatg gcctgaaata      60
acctctgaaa gaggaacttg gttagctacc ttctgaggcg gaaagaacca gctgtggaat     120
gtgtgtcagt tagggtgtgg aaagtcccca ggctccccag caggcagaag tatgcaaagc     180
atgcatctca attagtcagc aaccaggtgt ggaaagtccc caggctcccc agcaggcaga     240
agtatgcaaa gcatgcatct caattagtca gcaaccatag tcccgccct aactccgccc      300
atcccgcccc taactccgcc cagttccgcc cattctccgc cccatggctg actaattttt     360
tttatttatg cagaggccga ggccgcctct gcctctgagc tattccagaa gtagtgagga     420
ggcttttttg gaggcctagg cttttgcaaa aagctcgatt cttctgacac tagcgccacc     480
atgaccgagt acaagcctac cgtgcgcctg gccactcgcg atgatgtgcc ccgcgccgtc     540
cgcactctgg ccgccgcttt cgccgactac cccgctaccc ggcacaccgt ggaccccgac     600
cggcacatcg agcgtgtgac agagttgcag gagctgttcc tgaccgcgt cgggctggac     660
atcggcaagg tgtgggtagc cgacgacggc gcggccgtgg ccgtgtggac taccccgag     720
agcgttgagg ccggcgccgt gttcgccgag atcggccccc gaatggccga gctgagcggc     780
agccgcctgg ccgcccagca gcaaatggag ggcctgcttg ccccccatcg tcccaaggag     840
cctgcctggt ttctggccac tgtaggagtg agcccgacc accagggcaa gggcttgggc      900
agcgccgtcg tgttgcccgg cgtagaggcc gccgaacgcg ccggtgtgcc cgcctttctc     960
gaaacaagcg caccaagaaa ccttccattc tacgagcgcc tgggcttcac cgtgaccgcc    1020
gatgtcgagg tgcccgaggg acctaggacc tggtgtatga cacgaaaacc tggcgcctaa    1080
tgatctagaa ccggtcatgg ccgcaataaa atatctttat tttcattaca tctgtgtgtt    1140
ggttttttgt gtgttcgaac tagatgctgt cgac                                1174
```

<210> SEQ ID NO 12
<211> LENGTH: 1776
<212> TYPE: DNA
<213> ORGANISM: Artificial Sequence
<220> FEATURE:
<223> OTHER INFORMATION: A synthetic construct.

<400> SEQUENCE: 12

```
atggcttcca aggtgtacga ccccgagcaa cgcaaacgca tgatcactgg gcctcagtgg      60
tgggctcgct gcaagcaaat gaacgtgctg gactccttca tcaactacta tgattccgag     120
aagcacgccg agaacgccgt gattttctg catggtaacg ctgcctccag ctacctgtgg     180
aggcacgtcg tgcctcacat cgagcccgtg gctagatgca tcatccctga tctgatcgga     240
atgggtaagt ccggcaagag cgggaatggc tcatatcgcc tcctggatca ctacaagtac     300
ctcaccgctt ggtcgagct gctgaacctt ccaaagaaaa tcatctttgt gggccacgac     360
tggggggctt gtctggcctt tcactactcc tacgagcacc aagacaagat caaggccatc     420
gtccatgctg agagtgtcgt ggacgtgatc gagtccgggg acgagtggcc tgacatcgag     480
gaggatatcg ccctgatcaa gagcgaagag ggcgagaaaa tggtgcttga gaataacttc     540
ttcgtcgaga ccatgctccc aagcaagatc atgcggaaac tggagcctga ggagttcgct     600
```

-continued

```
gcctacctgg agccattcaa ggagaagggc gaggttagac ggcctaccct ctcctggcct      660
cgcgagatcc ctctcgttaa gggaggcaag cccgacgtcg tccagattgt ccgcaactac      720
aacgcctacc ttcgggccag cgacgatctg cctaagatgt tcatcgagtc cgaccctggg      780
ttcttttcca acgctattgt cgagggagct aagaagttcc ctaacaccga gttcgtgaag      840
gtgaagggcc tccacttcag ccaggaggac gctccagatg aaatgggtaa gtacatcaag      900
agcttcgtgg agcgcgtgct gaagaacgag cagaccggtg tgggagcgg aggtggcgga      960 tcaggtggcg gaggctccgg agggattgaa caagatggat tgcacgcagg ttctccggcc     1020
gcttgggtgg agaggctatt cggctatgac tgggcacaac agacaatcgg ctgctctgat     1080
gccgccgtgt tccggctgtc agcgcagggg cgcccggttc tttttgtcaa gaccgacctg     1140
tccggtgccc tgaatgaact gcaggacgag cagcgcggc tatcgtggct ggccacgacg     1200
ggcgttcctt gcgcagctgt gctcgacgtt gtcactgaag cgggaaggga ctggctgcta     1260
ttgggcgaag tgccggggca ggatctcctg tcatctcacc ttgctcctgc cgagaaagta     1320
tccatcatgg ctgatgcaat gcggcggctg catacgcttg atccggctac ctgcccattc     1380
gaccaccaag cgaaacatcg catcgagcga gcacgtactc ggatggaagc cggtcttgtc     1440
gatcaggatg atctggacga agagcatcag gggctcgcgc cagccgaact gttcgccagg     1500
ctcaaggcgc gcatgcccga cggcgaggat ctcgtcgtga cccatggcga tgcctgcttg     1560
ccgaatatca tggtggaaaa tggccgcttt tctggattca tcgactgtgg ccggctgggt     1620
gtggcggacc gctatcagga catagcgttg gctacccgtg atattgctga agagcttggc     1680
ggcgaatggg ctgaccgctt cctcgtgctt tacggtatcg ccgctcccga ttcgcagcgc     1740
atcgccttct atcgccttct tgacgagttc ttctaa                               1776
```

<210> SEQ ID NO 13
<211> LENGTH: 1776
<212> TYPE: DNA
<213> ORGANISM: Artificial Sequence
<220> FEATURE:
<223> OTHER INFORMATION: A synthetic construct.

<400> SEQUENCE: 13

```
atgattgaac aagatggatt gcacgcaggt tctccggccg cttgggtgga gaggctattc       60
ggctatgact gggcacaaca gacaatcggc tgctctgatg ccgccgtgtt ccggctgtca      120
gcgcaggggc gcccggttct ttttgtcaag accgacctgt ccggtgccct gaatgaactg      180
caggacgagc agcgcggct atcgtggctg gccacgacgg gcgttccttg cgcagctgtg      240
ctcgacgttg tcactgaagc gggaagggac tggctgctat tgggcgaagt gccggggcag      300
gatctcctgt catctcacct tgctcctgcc gagaaagtat ccatcatggc tgatgcaatg      360
cggcggctgc atacgcttga tccggctacc tgcccattcg accaccaagc gaaacatcgc      420
atcgagcgag cacgtactcg gatggaagcc ggtcttgtcg atcaggatga tctggacgaa      480
gagcatcagg ggctcgcgcc agccgaactg ttcgccaggc tcaaggcgcg catgcccgac      540
ggcgaggatc tcgtcgtgac ccatggcgat gcctgcttgc cgaatatcat ggtggaaaat      600
ggccgctttt ctggattcat cgactgtggc cggctgggtg tggcggaccg ctatcaggac      660
atagcgttgc taccgtga tattgctgaa gagcttggcg gcgaatgggc tgaccgcttc      720
ctcgtgcttt acggtatcgc cgctcccgat tcgcagcgca tcgccttcta tcgccttctt      780
gacgagttct tctaccggtgg tgggagcgga ggtggcggat caggtggcgg aggctccgga      840
ggggcttcca aggtgtacga ccccgagcaa cgcaaacgca tgatcactgg gcctcagtgg      900
```

-continued

| | |
|---|---|
| tgggctcgct gcaagcaaat gaacgtgctg gactccttca tcaactacta tgattccgag | 960 |
| aagcacgccg agaacgccgt gattttctg catggtaacg ctgcctccag ctacctgtgg | 1020 |
| aggcacgtcg tgcctcacat cgagcccgtg gctagatgca tcatcccga tctgatcgga | 1080 |
| atgggtaagt ccggcaagag cgggaatggc tcatatcgcc tcctggatca ctacaagtac | 1140 |
| ctcaccgctt ggttcgagct gctgaacctt ccaaagaaaa tcatctttgt gggccacgac | 1200 |
| tgggggcttt gtctggcctt tcactactcc tacgagcacc aagacaagat caaggccatc | 1260 |
| gtccatgctg agagtgtcgt ggacgtgatc gagtcctggg acgagtggcc tgacatcgag | 1320 |
| gaggatatcg ccctgatcaa gagcgaagag ggcgagaaaa tggtgcttga gaataacttc | 1380 |
| ttcgtcgaga ccatgctccc aagcaagatc atgcggaaac tggagcctga ggagttcgct | 1440 |
| gcctacctgg agccattcaa ggagaagggc gaggttagac ggcctaccct ctcctggcct | 1500 |
| cgcgagatcc ctctcgttaa gggaggcaag cccgacgtcg tccagattgt ccgcaactac | 1560 |
| aacgcctacc ttcgggccag cgacgatctg cctaagatgt tcatcgagtc cgaccctggg | 1620 |
| ttcttttcca acgctattgt cgagggagct aagaagttcc ctaacaccga gttcgtgaag | 1680 |
| gtgaagggcc tccacttcag ccaggaggac gctccagatg aaatgggtaa gtacatcaag | 1740 |
| agcttcgtgg agcgcgtgct gaagaacgag cagtaa | 1776 |

<210> SEQ ID NO 14
<211> LENGTH: 1653
<212> TYPE: DNA
<213> ORGANISM: Artificial Sequence
<220> FEATURE:
<223> OTHER INFORMATION: A synthetic construct.

<400> SEQUENCE: 14

| | |
|---|---|
| atggccgatg ctaagaacat taagaagggc cctgctccct ctaccctct ggaggatggc | 60 |
| accgctggcg agcagctgca caaggccatg aagaggtatg ccctggtgcc tggcaccatt | 120 |
| gccttcaccg atgcccacat tgaggtggac atcacctatg ccgagtactt cgagatgtct | 180 |
| gtgcgcctgg ccgaggccat gaagaggtac ggcctgaaca ccaaccaccg catcgtggtg | 240 |
| tgctctgaga actctctgca gttcttcatg ccagtgctgg gcgccctgtt catcggagtg | 300 |
| gccgtggccc ctgctaacga catttacaac gagcgcgagc tgctgaacag catgggcatt | 360 |
| tctcagccta ccgtggtgtt cgtgtctaag aagggcctgc agaagatcct gaacgtgcag | 420 |
| aagaagctgc ctatcatcca gaagatcatc atcatggact ctaagaccga ctaccagggc | 480 |
| ttccagagca tgtacacatt cgtgacatct catctgcctc ctggcttcaa cgagtacgac | 540 |
| ttcgtgccag agtctttcga cagggacaaa accattgccc tgatcatgaa cagctctggg | 600 |
| tctaccggcc tgcctaaggg cgtggccctg cctcatcgca ccgcctgtgt gcgcttctct | 660 |
| cacgcccgcg acctattttt cggcaaccag atcatcccg acaccgctat tctgagcgtg | 720 |
| gtgccattcc accacggctt cggcatgttc accaccctgg ctacctgat tgcggctttt | 780 |
| cgggtggtgc tgatgtaccg cttcgaggag gagctgttcc tgcgcagcct gcaagactac | 840 |
| aaaattcagt ctgccctgct ggtgccaacc ctgttcagct tcttcgctaa gagcacctg | 900 |
| atcgacaagt acgacctgtc taacctgcac gagattgcct ctggcggcgc cccactgtct | 960 |
| aaggaggtgg cgaagccgt ggccaagcgc tttcatctgc caggcatccg ccagggctac | 1020 |
| ggcctgaccg agacaaccag cgccattctg attaccccag agggcgacga caagcctggc | 1080 |
| gccgtgggca agtggtgcc attcttcgag gccaaggtgg tggacctgga caccggcaag | 1140 |
| accctgggag tgaaccagcg cggcgagctg tgtgtgcgcg ccctatgat tatgtccggc | 1200 |

```
tacgtgaata accctgaggc cacaaacgcc ctgatcgaca aggacggctg gctgcactct    1260
ggcgacattg cctactggga cgaggacgag cacttcttca tcgtggaccg cctgaagtct    1320
ctgatcaagt acaagggcta ccaggtggcc ccagccgagc tggagtctat cctgctgcag    1380
caccctaaca ttttcgacgc cggagtggcc ggcctgcccg acgacgatgc cggcgagctg    1440
cctgccgccg tcgtcgtgct ggaacacggc aagaccatga ccgagaagga gatcgtggac    1500
tatgtggcca gccaggtgac aaccgccaag aagctgcgcg gcggagtggt gttcgtggac    1560
gaggtgccca agggcctgac cggcaagctg gacgcccgca agatccgcga gatcctgatc    1620
aaggctaaga aaggcggcaa gatcgccgtg taa                                 1653

<210> SEQ ID NO 15
<211> LENGTH: 597
<212> TYPE: DNA
<213> ORGANISM: Streptomyces sp.

<400> SEQUENCE: 15
atgaccgagt acaagcccac ggtgcgcctc gccacccgcg acgacgtccc ccgggccgta    60 cgcacccctcg ccgccgcgtt cgccgactac cccgccacgc gccacaccgt cgacccggac    120
cgccacatcg agcgggtcac cgagctgcaa gaactcttcc tcacgcgcgt cgggctcgac    180
atcggcaagg tgtgggtcgc ggacgacggc gccgcgtgg cggtctggac acgccggag    240 agcgtcgaag cggggggcggt gttcgccgag atcgcccgc gcatggccga gttgagcggt    300
tcccggctgg ccgcgcagca acagatggaa ggcctcctgg cgccgcaccg gcccaaggag    360
cccgcgtggt tcctggccac cgtcggcgtg tcgcccgacc accagggcaa gggtctgggc    420
agcgccgtcg tgctccccgg agtggaggcg gccgagcgcg ccggggtgcc cgccttcctg    480
gagacctccg cgccccgcaa cctccccttc tacgagcggc tcggcttcac cgtcaccgcc    540
gacgtcgagg tgcccgaagg accgcgcacc tggtgcatga cccgcaagcc cggtgcc       597

<210> SEQ ID NO 16
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 16
aaagccacca tggaggacgc caagaacatc aagaagggcc ccgcccccttt ctaccccctg    60 gaggacggca ccgccggcga gcagctgcac aaggccatga agcgctacgc cctggtgccc    120
ggcaccatcg ccttcaccga cgcccacatc gaggtggaca tcacctacgc cgagtacttc    180
gagatgagcg tgcgcctggc cgaggccatg aagcgctacg gcctgaacac caaccaccgc    240
atcgtggtgt gcagcgagaa cagcctgcag ttcttcatgc ccgtgctggg cgccctgttc    300
atcggcgtgg ccgtggcccc cgccaacgac atctacaacg agcgcgagct gctgaacagc    360
atgggcatca gccagcccac cgtggtgttc gtgagcaaga aaggcctgca gaagatcctg    420
aacgtgcaga gaagctgcc catcatccag aagatcatca tcatggacag caagaccgac    480
taccagggct tccagagcat gtacaccttc gtgaccagcc acctgccccc cggcttcaac    540
gagtacgact tcgtgcccga gagcttcgac cgcgacaaga ccatcgccct gatcatgaac    600
agcagcggca gcaccggcct gcccaagggc gtggccctgc ccaccgcac cgcctgcgtg    660 cgcttcagcc acgcccgcga ccccatcttc ggcaaccaga tcatccccga caccgccatc    720
ctgagcgtgg tgcccttcca ccacggcttc ggcatgttca ccaccctggg ctacctgatc    780
```

```
tgcggcttcc gcgtggtgct gatgtaccgc ttcgaggagg agctgttcct gcgcagcctg      840
caggactaca agatccagag cgccctgctg gtgcccaccc tgttcagctt cttcgccaag      900
agcaccctga tcgacaagta cgacctgagc aacctgcacg agatcgccag cggcggcgcc      960
cccctgagca aggaggtggg cgaggccgtg gccaagcgct tccacctgcc cggcatccgc     1020
cagggctacg gcctgaccga gaccaccagc gccatcctga tcaccccccga gggcgacgac    1080 aagcccggcg ccgtgggcaa ggtggtgccc ttcttcgagg ccaaggtggt ggacctggac     1140
accggcaaga ccctgggcgt gaaccagcgc ggcgagctgt gcgtgcgcgg ccccatgatc     1200
atgagcggct acgtgaacaa ccccgaggcc accaacgccc tgatcgacaa ggacggctgg     1260
ctgcacagcg gcgacatcgc ctactgggac gaggacgagc acttcttcat cgtggaccgc     1320
ctgaagagcc tgatcaagta caagggctac caggtggccc cgccgagct ggagagcatc      1380 ctgctgcagc accccaacat cttcgacgcc ggcgtggccg gcctgcccga cgacgacgcc    1440
ggcgagctgc ccgccgccgt ggtggtgctg agcacggca agaccatgac cgagaaggag      1500
atcgtggact acgtggccag ccaggtgacc accgccaaga agctgcgcgg cggcgtggtg     1560
ttcgtggacg aggtgcccaa gggcctgacc ggcaagctgg acgcccgcaa gatccgcgag    1620
atcctgatca aggccaagaa gggcggcaag atcgccgtgt aataattcta ga             1672

<210> SEQ ID NO 17
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 17
aaagccacca tggaggacgc caagaacatc aagaagggcc cagcgccatt ctaccccctg       60
gaggacggca ccgccggcga gcagctgcac aaggccatga gcgctacgc cctggtgccc      120 ggcaccatcg ccttcaccga cgcacatatc gaggtggaca tcacctacgc cgagtacttc     180
gagatgagcg ttcggctggc agaggctatg aagcgctatg gctgaacac caaccatcgc     240 atcgtggtgt gcagcgagaa cagcttgcag ttcttcatgc ccgtgttggg tgccctgttc    300
atcggcgtgg ctgtggcccc agctaacgac atctacaacg agcgcgagct gctgaacagc    360
atgggcatca gccagcccac cgtcgtattc gtgagcaaga aagggctgca aaagatcctg     420
aacgtgcaaa agaagctgcc catcatccaa aagatcatca tcatggacag caagaccgac    480
taccagggct tccaaagcat gtacaccttc gtgaccagcc atttgccgcc cggcttcaac     540
gagtacgact tcgtgcccga gagcttcgac cgcgacaaga ccatcgccct gatcatgaac    600
agtagtggca gtaccggctt acctaagggc gtggccctac cgcaccgcac cgcctgtgtc    660
cgattcagtc atgcccgcga ccccatcttc ggcaaccaga tcatccccga caccgctatc     720
ctgagcgtgg tgccatttca ccacggcttc ggcatgttca ccaccctggg ctacttgatc    780
tgcggcttcc gggtcgtgct gatgtaccgc ttcgaggagg agctattctt gcgcagcttg    840
caagactaca agattcaaag cgccctgctg gtgcccaccc tgttcagttt cttcgccaag    900
agcaccctga tcgacaagta cgacctgagc aacctgcacg agatcgccag cggcggcgcc    960
ccgctcagca aggaggtggg cgaggccgtg gccaagcgct tccacctgcc aggcatccgc   1020
cagggctacg gcctgaccga gacaaccagc gccattctga tcaccccccga ggggacgac    1080 aagcctggcg cagtaggcaa ggtggtgccc ttcttcgagg ctaaggtggt ggacctggac    1140
accggtaaaa ccctgggtgt gaaccagcgc ggcgagctgt gcgtccgtgg ccccatgatc    1200
```
atgagcggct acgttaacaa ccccgaggct acaaacgccc tgatcgacaa ggacggctgg    1260
ctgcacagcg gcgacatcgc ctactgggac gaggacgagc acttcttcat cgtggaccgg    1320
ctgaagagcc tgatcaaata caagggctac caggtagccc cagccgaact ggagagcatc    1380
ctgctgcagc accccaacat cttcgacgcc ggggtcgccg gcctgcccga cgacgatgcc    1440
ggcgagctgc ccgccgcagt cgtggtgctg gagcacggta aaaccatgac cgagaaggag    1500
atcgtggact atgtggccag ccaggttaca accgccaaga agctgcgcgg cggcgtggtg    1560
ttcgtggacg aggtgcctaa aggcctgacg ggcaagttgg acgcccgcaa gatccgcgag    1620
attctgatca aggccaagaa gggcggcaag atcgccgtgt aataattcta ga            1672

<210> SEQ ID NO 18
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 18
aaagccacca tggaagatgc caaaaacatt aagaagggcc cagcgccatt ctacccactg      60
gaggacggca ccgccggcga gcagctgcac aaagccatga gcgctacgc cctggtgccc     120 ggcaccatcg cctttaccga cgcacatatc gaggtggaca tcacctacgc cgagtacttc     180
gagatgagcg ttcggctggc agaggctatg aagcgctatg gctgaatac aaccatcgc     240 atcgtggtgt gcagcgagaa tagcttgcag ttcttcatgc ccgtgttggg tgccctgttc     300
atcggtgtgg ctgtggcccc agctaacgac atctacaacg agcgcgagct gctgaacagc     360
atgggcatca gccagcccac cgtcgtattc gtgagcaaga aagggctgca aaagatcctc     420
aacgtgcaaa agaagctacc gatcatacaa aagatcatca tcatggatag caagaccgac     480
taccagggct ccaaaagcat gtacaccttc gtgaccagcc atttgccacc cggcttcaac     540
gagtacgact tcgtgcccga gagcttcgac cgggacaaaa ccatcgccct gatcatgaac     600
agtagtggca gtaccggatt gcccaagggc gtagccctac cgcaccgcac cgcctgtgtc     660
cgattcagtc atgcccgcga ccccatcttc ggcaaccaga tcatcccga caccgctatc     720 ctcagcgtgg tgccatttca ccacggcttc ggcatgttca ccacgctggg ctacttgatc     780
tgcggctttc gggtcgtgct catgtaccgc ttcgaggagg agctattctt gcgcagcttg     840
caagactata agattcaaag cgccctgctg gtgcccacac tgttcagctt cttcgccaag     900
agcactctca tcgacaagta cgacctgagc aacctgcacg agatcgccag cggcggggcg     960
ccgctcagca aggaggtggg cgaggccgtg gccaagcgct tccacctacc aggcatccgc    1020
cagggctacg gcctgacaga aacaaccagc gccattctga tcaccccga aggggacgac    1080 aagcctggcg cagtaggcaa ggtggtgccc ttcttcgagg ctaaggtggt ggacttggac    1140
accggtaaga cctgggtgt gaaccagcgc ggcgagctgt gcgtccgtgg ccccatgatc    1200
atgagcggct acgttaacaa ccccgaggct acaaacgctc tcatcgacaa ggacggctgg    1260
ctgcacagcg gcgacatcgc ctactgggac gaggacgagc acttcttcat cgtggaccgg    1320
ctgaagagcc tgatcaaata caagggctac caggtagccc cagccgaact ggagagcatc    1380
ctgctgcaac accccaacat cttcgacgcc ggggtcgccg gcctgcccga cgacgatgcc    1440
ggcgagctgc ccgccgcagt cgtcgtgctg gagcacggta aaaccatgac cgagaaggag    1500
atcgtggact atgtggccag ccaggttaca accgccaaga agctgcgcgg tggtgttgtg    1560

```
ttcgtggacg aggtgcctaa aggcctgacg ggcaagttgg acgcccgcaa gatccgcgag   1620
attctcatta aggccaagaa gggcggcaag atcgccgtgt aataattcta ga           1672
```

<210> SEQ ID NO 19
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 19

```
aaagccacca tggaagatgc caaaaacatt aagaagggcc cagcgccatt ctacccactc     60
gaagacggca ccgccggcga gcagctgcac aaagccatga agcgctacgc cctggtgccc   120
ggcaccatcg cctttaccga cgcacatatc gaggtggaca ttacctacgc cgagtacttc   180
gagatgagcg ttcggctggc agaagctatg aagcgctatg gctgaacac caaccatcgc   240 atcgtggtgt gcagcgagaa tagcttgcag ttcttcatgc ccgtgttggg tgccctgttc   300
atcggtgtgg ctgtggcccc agctaacgac atctacaacg agcgcgagct gctgaacagc   360
atgggcatca gccagcccac cgtcgtattc gtgagcaaga aagggctgca aaagatcctc   420
aacgtgcaaa agaagctacc gatcatacaa aagatcatca tcatggatag caagaccgac   480
taccagggct ccaaagcat gtacaccttc gtgacttccc atttgccacc cggcttcaac   540
gagtacgact tcgtgcccga gagcttcgac cgggacaaaa ccatcgccct gatcatgaac   600
agtagtggca gtaccggatt gcccaagggc gtagccctac cgcaccgcac cgcttgtgtc   660
cgattcagtc atgcccgcga ccccatcttc ggcaaccaga tcatccccga caccgctatc   720
ctcagcgtgg tgccatttca ccacggcttc ggcatgttca ccacgctggg ctacttgatc   780
tgcggctttc gggtcgtgct catgtaccgc ttcgaggagg agctattctt gcgcagcttg   840
caagactata agattcaaag cgccctgctg gtgcccacac tgttcagttt cttcgccaag   900
agcactctca tcgacaagta cgacctaagc aacttgcacg agatcgccag cggcggggcg   960
ccgctcagca aggaggtggg cgaggccgtg gccaaacgct tccacctacc aggcatccgc  1020
cagggctacg gcctgacaga aacaaccagc gccattctga tcacccccga aggggacgac  1080
aagcctggcg cagtaggcaa ggtggtgccc ttcttcgagg ctaaggtggt ggacttggac  1140
accggtaaga cactgggtgt gaaccagcgc ggcgagctgt gcgtccgtgg ccccatgatc  1200
atgagcggct acgttaacaa ccccgaggct acaaacgctc tcatcgacaa ggacggctgg  1260
ctgcacagcg gcgacatcgc ctactgggac gaggacgagc acttcttcat cgtggaccgg  1320
ctgaagagcc tgatcaaata caagggctac caggtagccc cagccgaact ggagagcatc  1380
ctgctgcaac accccaacat cttcgacgcc ggggtcgccg gcctgcccga cgacgatgcc  1440
ggcgagctgc ccgccgcagt cgtcgtgctg gaacacggta aaaccatgac cgagaaggag  1500
atcgtggact atgtggccag ccaggttaca accgccaaga gctgcgcgg tggtgttgtg  1560 ttcgtggacg aggtgcctaa aggcctgacg ggcaagttgg acgcccgcaa gatccgcgag  1620
attctcatta aggccaagaa gggcggcaag atcgccgtgt aataattcta ga           1672
```

<210> SEQ ID NO 20
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 20

```
aaagccacca tggaagatgc caaaaacatt aagaagggcc cagcgccatt ctacccactc      60
gaagacggca ccgccggcga gcagctgcac aaagccatga agcgctacgc cctggtgccc     120
ggcaccatcg cctttaccga cgcacatatc gaggtggaca ttacctacgc cgagtacttc     180
gagatgagcg ttcggctggc agaagctatg aagcgctatg gctgaacaca caaccatcgg     240
atcgtggtgt gcagcgagaa tagcttgcag ttcttcatgc ccgtgtttgg gtgccctgttc    300
atcggtgtgg ctgtggcccc agctaacgac atctacaacg agcgcgagct gctgaacagc     360
atgggcatca gccagcccac cgtcgtattc gtgagcaaga aagggctgca aaagatcctc     420
aacgtgcaaa agaagctacc gatcatacaa aagatcatca tcatggatag caagaccgac     480
taccagggct tccaaagcat gtacaccttc gtgacttccc atttgccacc cggcttcaac     540
gagtacgact tcgtgcccga gagcttcgac cgggacaaaa ccatcgccct gatcatgaac     600
agtagtggca gtaccggatt gcccaagggc gtagccctac cgcaccgcac cgcttgtgtc     660
cgattcagtc atgcccgcga ccccatcttc ggcaaccaga tcatccccga caccgctatc     720
ctcagcgtgg tgccatttca ccacggcttc ggcatgttca ccacgctggg ctacttgatc     780
tgcggctttc gggtcgtgct catgtaccgc ttcgaggagg agctattctt gcgcagcttg     840
caagactata gattcaaag cgccctgctg gtgcccacac tgttcagttt cttcgctaag      900
agcactctca tcgacaagta cgacctaagc aacttgcacg agatcgccag cggcggggcg     960
ccgctcagca aggaggtggg cgaggccgtg gccaaacgct ccacctacc aggcatccgc     1020
cagggctacg gcctgacaga aacaaccagc gccattctga tcacccccga agggacgac    1080
aagcctggcg cagtaggcaa ggtggtgccc ttcttcgagg ctaaggtggt ggacttggac    1140
accggtaaga cactgggtgt gaaccagcgc ggcgagctgt gcgtccgtgg ccccatgatc    1200
atgagcggct acgttaacaa ccccgaggct acaaacgctc tcatcgacaa ggacggctgg    1260
ctgcacagcg gcgacatcgc ctactgggac gaggacgagc acttcttcat cgtggaccgg    1320
ctgaagagcc tgatcaaata caagggctac caggtagccc cagccgaact ggagagcatc    1380
ctgctgcaac accccaacat cttcgacgcc ggggtcgccg gcctgcccga cgacgatgcc    1440
ggcgagctgc ccgccgcagt cgtcgtgctg gaacacggta aaaccatgac cgagaaggag    1500
atcgtggact atgtggccag ccaggttaca accgccaaga agctgcgcgg tggtgttgtg    1560
ttcgtggacg aggtgcctaa aggcctgacg ggcaagttgg acgcccgcaa gatccgcgag    1620
attctcatta aggccaagaa gggcggcaag atcgccgtgt aataattcta ga            1672
```

<210> SEQ ID NO 21
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 21

```
aaagccacca tggaagatgc caaaaacatt aagaagggcc cagcgccatt ctacccactc      60
gaagacggca ccgccggcga gcagctgcac aaagccatga agcgctacgc cctggtgccc     120
ggcaccatcg cctttaccga cgcacatatc gaggtggaca ttacctacgc cgagtacttc     180
gagatgagcg ttcggctggc agaagctatg aagcgctatg gctgaatac aaaccatcgg      240
atcgtggtgt gcagcgagaa tagcttgcag ttcttcatgc ccgtgtttgg gtgccctgttc    300
atcggtgtgg ctgtggcccc agctaacgac atctacaacg agcgcgagct gctgaacagc     360
```

```
atgggcatca gccagcccac cgtcgtattc gtgagcaaga aagggctgca aaagatcctc      420
aacgtgcaaa agaagctacc gatcatacaa aagatcatca tcatggatag caagaccgac      480
taccagggct tccaaagcat gtacaccttc gtgacttccc atttgccacc cggcttcaac      540
gagtacgact tcgtgcccga gagcttcgac cgggacaaaa ccatcgccct gatcatgaac      600
agtagtggca gtaccggatt gcccaagggc gtagccctac cgcaccgcac cgcttgtgtc      660
cgattcagtc atgcccgcga ccccatcttc ggcaaccaga tcatcccccga caccgctatc      720 ctcagcgtgg tgccatttca ccacggcttc ggcatgttca ccacgctggg ctacttgatc      780
tgcggctttc gggtcgtgct catgtaccgc ttcgaggagg agctattctt gcgcagcttg      840
caagactata agattcaaag cgccctgctg gtgcccacac tgttcagttt cttcgctaag      900
agcactctca tcgacaagta cgacctaagc aacttgcacg agatcgccag cggcggggcg      960
ccgctcagca aggaggtagg tgaggccgtg gccaaacgct tccacctacc aggcatccgc     1020
cagggctacg gcctgacaga aacaaccagc gccattctga tcacccccga aggggacgac     1080
aagcctggcg cagtaggcaa ggtggtgccc ttcttcgagg ctaaggtggt ggacttggac     1140
accggtaaga cactgggtgt gaaccagcgc ggcgagctgt gcgtccgtgg ccccatgatc     1200
atgagcggct acgttaacaa ccccgaggct acaaacgctc tcatcgacaa ggacggctgg     1260
ctgcacagcg gcgacatcgc ctactgggac gaggacgagc acttcttcat cgtggaccgg     1320
ctgaagagcc tgatcaaata caagggctac caggtagccc agccgaact ggagagcatc     1380 ctgctgcaac accccaacat cttcgacgcc ggggtcgccg gcctgcccga cgacgatgcc     1440
ggcgagctgc ccgccgcagt cgtcgtgctg gaacacggta aaaccatgac cgagaaggag     1500
atcgtggact atgtggccag ccaggttaca accgccaaga gctgcgcgg tggtgttgtg     1560 ttcgtggacg aggtgcctaa aggcctgacg ggcaagttgg acgcccgcaa gatccgcgag     1620
attctcatta aggccaagaa gggcggcaag atcgccgtgt aataattcta ga            1672
```

<210> SEQ ID NO 22
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 22

```
aaagccacca tggaagatgc caaaaacatt aagaagggcc cagcgccatt ctacccactc       60
gaagacggga ccgccggcga gcagctgcac aaagccatga agcgctacgc cctggtgccc      120
ggcaccatcg cctttaccga cgcacatatc gaggtggaca ttacctacgc cgagtacttc      180
gagatgagcg ttcggctggc agaagctatg aagcgctatg gctgaatac aaaccatcgg      240 atcgtggtgt gcagcgagaa tagcttgcag ttcttcatgc ccgtgttggg tgccctgttc      300
atcggtgtgt ctgtggcccc agctaacgac atctacaacg agcgcgagct gctgaacagc      360
atgggcatca gccagcccac cgtcgtattc gtgagcaaga aagggctgca aaagatcctc      420
aacgtgcaaa agaagctacc gatcatacaa aagatcatca tcatggatag caagaccgac      480
taccagggct tccaaagcat gtacaccttc gtgacttccc atttgccacc cggcttcaac      540
gagtacgact tcgtgcccga gagcttcgac cgggacaaaa ccatcgccct gatcatgaac      600
agtagtggca gtaccggatt gcccaagggc gtagccctac cgcaccgcac cgcttgtgtc      660
cgattcagtc atgcccgcga ccccatcttc ggcaaccaga tcatcccccga caccgctatc      720 ctcagcgtgg tgccatttca ccacggcttc ggcatgttca ccacgctggg ctacttgatc      780
```

```
tgcggctttc gggtcgtgct catgtaccgc ttcgaggagg agctattctt gcgcagcttg     840
caagactata agattcaatc tgccctgctg gtgcccacac tatttagctt cttcgctaag     900
agcactctca tcgacaagta cgacctaagc aacttgcacg agatcgccag cggcggggcg     960
ccgctcagca aggaggtagg tgaggccgtg gccaaacgct tccacctacc aggcatccgc    1020
cagggctacg gcctgacaga aacaaccagc gccattctga tcaccccgga agggacgac     1080 aagcctggcg cagtaggcaa ggtggtgccc ttcttcgagg ctaaggtggt ggacttggac    1140
accggtaaga cactgggtgt gaaccagcgc ggcgagctgt gcgtccgtgg ccccatgatc    1200
atgagcggct acgttaacaa ccccgaggct acaaacgctc tcatcgacaa ggacggctgg    1260
ctgcacagcg gcgacatcgc ctactgggac gaggacgagc acttcttcat cgtggaccgg    1320
ctgaagagcc tgatcaaata caagggctac caggtagccc cagccgaact ggagagcatc    1380
ctgctgcaac accccaacat cttcgacgcc ggggtcgccg gcctgcccga cgacgatgcc    1440
ggcgagctgc ccgccgcagt cgtcgtgctg gaacacggta aaaccatgac cgagaaggag    1500
atcgtggact atgtggccag ccaggttaca accgccaaga agctgcgcgg tggtgttgtg    1560
ttcgtggacg aggtgcctaa aggcctgacg ggcaagttgg acgcccgcaa gatccgcgag    1620
attctcatta aggccaagaa gggcggcaag atcgccgtgt aataattcta ga            1672
```

<210> SEQ ID NO 23
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 23

```
aaagccacca tggaagatgc caaaaacatt aagaagggcc cagcgccatt ctacccactc      60
gaagacggga ccgccggcga gcagctgcac aaagccatga gcgctacgc cctggtgccc      120 ggcaccatcg cctttaccga cgcacatatc gaggtggaca ttacctacgc cgagtacttc     180
gagatgagcg ttcggctggc agaagctatg aagcgctatg gctgaatac aaaccatcgg      240 atcgtggtgt gcagcgagaa tagcttgcag ttcttcatgc ccgtgttggg tgccctgttc     300
atcggtgtgg ctgtggcccc agctaacgac atctacaacg agcgcgagct gctgaacagc     360
atgggcatca gccagcccac cgtcgtattc gtgagcaaga aagggctgca aagatcctc      420 aacgtgcaaa agaagctacc gatcatacaa aagatcatca tcatggatag caagaccgac     480
taccagggct tccaaagcat gtacaccttc gtgacttccc atttgccacc cggcttcaac     540
gagtacgact tcgtgcccga gagcttcgac cgggacaaaa ccatcgccct gatcatgaac     600
agtagtggca gtaccggatt gcccaagggc gtagccctac cgcaccgcac cgcttgtgtc     660
cgattcagtc atgcccgcga ccccatcttc ggcaaccaga tcatccccga caccgctatc     720
ctcagcgtgg tgccatttca ccacggcttc ggcatgttca ccacgctggg ctacttgatc     780
tgcggctttc gggtcgtgct catgtaccgc ttcgaggagg agctattctt gcgcagcttg     840
caagactata agattcaatc tgccctgctg gtgcccacac tatttagctt cttcgctaag     900
agcactctca tcgacaagta cgacctaagc aacttgcacg agatcgccag cggcggggcg     960
ccgctcagca aggaggtagg tgaggccgtg gccaaacgct tccacctacc aggcatccgc    1020
cagggctacg gcctgacaga aacaaccagc gccattctga tcaccccgga agggacgac     1080 aagcctggcg cagtaggcaa ggtggtgccc ttcttcgagg ctaaggtggt ggacttggac    1140
accggtaaga cactgggtgt gaaccagcgc ggcgagctgt gcgtccgtgg ccccatgatc    1200
```

| | | | | |
|---|---|---|---|---|
| atgagcggct | acgttaacaa | ccccgaggct | acaaacgctc | tcatcgacaa | ggacggctgg | 1260 |
| ctgcacagcg | gcgacatcgc | ctactgggac | gaggacgagc | acttcttcat | cgtggaccgg | 1320 |
| ctgaagagcc | tgatcaaata | caagggctac | caggtagccc | cagccgaact | ggagagcatc | 1380 |
| ctgctgcaac | accccaacat | cttcgacgcc | ggggtcgccg | gcctgcccga | cgacgatgcc | 1440 |
| ggcgagctgc | ccgccgcagt | cgtcgtgctg | aacacggta | aaaccatgac | cgagaaggag | 1500 |
| atcgtggact | atgtggccag | ccaggttaca | accgccaaga | agctgcgcgg | tggtgttgtg | 1560 |
| ttcgtggacg | aggtgcctaa | aggactgacc | ggcaagttgg | acgcccgcaa | gatccgcgag | 1620 |
| attctcatta | aggccaagaa | gggcggcaag | atcgccgtgt | aataattcta | ga | 1672 |

<210> SEQ ID NO 24
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 24

| | | | | | |
|---|---|---|---|---|---|
| aaagccacca | tggaggatgc | taagaatatt | aagaaggggc | tgctcccttt | ttatcctctg | 60 |
| gaggatggga | cagctgggga | gcagctgcat | aaggctatga | agagatatgc | tctggtgcct | 120 |
| gggacaattg | cttttacaga | tgctcatatt | gaggtggata | ttacatatgc | tgagtatttt | 180 |
| gagatgtctg | tgagactggc | tgaggctatg | aagagatatg | ggctgaatac | aaatcataga | 240 |
| attgtggtgt | gttctgagaa | ttctctgcag | ttttttatgc | ctgtgctggg | ggctctgttt | 300 |
| attggggtgg | ctgtggctcc | tgctaatgat | atttataatg | agagagagct | gctgaattct | 360 |
| atggggattt | ctcagcctac | agtggtgttt | gtgtctaaga | aggggctgca | gaagattctg | 420 |
| aatgtgcaga | gaagctgcc | tattattcag | aagattatta | ttatggattc | taagacagat | 480 |
| tatcaggggt | tcagtctat | gtatacattt | gtgacatctc | atctgcctcc | tgggtttaat | 540 |
| gagtatgatt | ttgtgcctga | gtcttttgat | agagataaga | caattgctct | gattatgaat | 600 |
| tcttctgggt | ctacagggct | gcctaagggg | gtggctctgc | tcatagaac | agcttgtgtg | 660 |
| agattttctc | atgctagaga | tcctattttt | gggaatcaga | ttattcctga | tacagctatt | 720 |
| ctgtctgtgg | tgccttttca | tcatgggttt | gggatgtta | caacactggg | gtatctgatt | 780 |
| tgtgggttta | gagtggtgct | gatgtataga | tttgaggagg | agctgtttct | gagatctctg | 840 |
| caggattata | agattcagtc | tgctctgctg | gtgcctacac | tgttttcttt | ttttgctaag | 900 |
| tctacactga | ttgataagta | tgatctgtct | aatctgcatg | agattgcttc | tgggggggct | 960 |
| cctctgtcta | aggaggtggg | ggaggctgtg | gctaagagat | tcatctgcc | tgggattaga | 1020 |
| caggggtatg | gctgacaga | gacaacatct | gctattctga | ttacacctga | ggggatgat | 1080 |
| aagcctgggg | ctgtggggaa | ggtggtgcct | ttttttgagg | ctaaggtggt | ggatctggat | 1140 |
| acagggaaga | cactgggggt | gaatcagaga | ggggagctgt | gtgtgagagg | gcctatgatt | 1200 |
| atgtctgggt | atgtgaataa | tcctgaggct | acaaatgctc | tgattgataa | ggatgggtgg | 1260 |
| ctgcattctg | gggatattgc | ttattgggat | gaggatgagc | attttttat | tgtggataga | 1320 |
| ctgaagtctc | tgattaagta | taaggggtat | caggtggctc | ctgctgagct | ggagtctatt | 1380 |
| ctgctgcagc | atcctaatat | ttttgatgct | ggggtggctg | gctgcctga | tgatgatgct | 1440 |
| ggggagctgc | ctgctgctgt | ggtggtgctg | gagcatggga | agacaatgac | agagaaggag | 1500 |
| attgtggatt | atgtggcttc | tcaggtgaca | acagctaaga | agctgagagg | ggggtggtg | 1560 | tttgtggatg aggtgcctaa ggggctgaca gggaagctgg atgctagaaa gattagagag    1620 attctgatta aggctaagaa gggggggaag attgctgtgt aataattcta ga             1672

<210> SEQ ID NO 25
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 25
aaagccacca tggaagatgc taaaaacatt aagaagggc ctgctccttt ctaccctctg      60
gaggatggga ctgccgggga gcagctgcat aaagctatga agcggtatgc tctggtgcca    120
ggcacaattg cgttcacgga tgctcacatt gaggtggaca ttacatacgc tgagtatttt    180
gagatgtcgg tgcggctggc tgaggctatg aagcgatatg gctgaatac aaaccataga    240 attgtagtgt gctctgagaa ctcgttgcag ttttttatgc ctgtgctggg ggctctcttc    300
atcggggtgg ctgtggctcc tgctaacgac atttacaatg agagagagct tttgaactcg    360
atggggattt ctcagcctac agtggtgttt gtgagtaaga aagggcttca aaagattctc    420
aatgtgcaaa agaagctgcc tattattcaa aagattatta ttatggactc taagacagac    480
taccaggggt tcagtctat gtatacattt gtgacatctc atctgcctcc tgggttcaac    540
gagtatgact ttgtgcccga gtctttcgac agagataaga caattgctct gattatgaat    600
tcatctgggt ctaccgggct gcctaagggt gtagctctgc cacatagaac agcttgtgtg    660 agatttctc atgctaggga ccctattttt gggaatcaga ttattcctga tactgctatt    720
ctgtcggttg tgcccttca tcatgggttt gggatgttta caacactggg ctacctgata    780
tgtgggttta gagtggtgct catgtatagg tttgaggagg agctttttt gcgctctctg    840 caagattata agattcagtc tgctctgctg gtgcctacac tgttttcttt ttttgctaag    900
tctaccctga tcgataagta tgatctgtcc aacctgcacg agattgcttc tgggggggct    960
cctctgtcta aggaggtagg tgaggctgtg gctaagcgct tcatctgcc tggaatcaga   1020 caggggtatg ggctaacaga aacaacatct gctattctga ttacaccaga ggggatgat   1080 aagcccgggg ctgtagggaa agtggtgccc tttttgaag ctaaagtagt tgatcttgat   1140
accggtaaga cactgggggt gaatcagcga ggggaactgt gtgtgagagg gcctatgatt   1200
atgtcggggt atgtgaacaa ccctgaggct acaaatgctc tgattgataa ggatgggtgg   1260
ctgcattcgg gcgatattgc ttactgggat gaggatgagc atttcttcat cgtggacaga   1320
ctgaagtcgt tgatcaaata taaggggtat caagtagctc ctgctgagct ggagtccatt   1380
ctgcttcaac atcctaacat tttcgatgct ggggtggctg gctgcctga tgatgatgct   1440 ggggagctgc ctgctgctgt agtggtgctg gagcacggta agacaatgac agagaaggag   1500
attgtggatt atgtggcttc acaagtgaca acagctaaga aactgagagg tggcgttgtg   1560
tttgtggatg aggtgcctaa agggctgaca ggcaagctgg atgctagaaa aattcgagag   1620
attctgatta aggctaagaa gggtggaaag attgctgtgt aatagttcta ga             1672

<210> SEQ ID NO 26
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 26

```
aaagccacca tggaagatgc taaaaacatt aagaaggggc ctgctccttt ctaccctctt      60
gaagatggga ctgctggcga gcaacttcac aaagctatga agcggtatgc tcttgtgcca     120
ggcacaattg cgttcacgga tgctcacatt gaggtggaca tcacatacgc tgagtatttt     180
gagatgtcgg tgcggctggc agaagctatg aagcgctatg ggctgaatac aaaccataga    240
attgtagtgt gcagtgagaa ctcgttgcag ttctttatgc ccgtgctggg ggctctcttc    300
atcggggtgg ctgtggctcc tgctaacgac atctacaacg agcgagagct gttgaactcg    360
atggggattt ctcagcctac agtggtgttt gtgagtaaga aagggcttca aaagattctc    420
aatgtgcaaa agaagctgcc tattattcaa aagattatta ttatggactc taagaccgac    480
taccagggggt ttcagtctat gtatacattt gtgacatctc atctgcctcc tggcttcaac    540
gagtacgact tcgtgcccga gtctttcgac agagataaga caattgctct gatcatgaat    600
tcatccgggt ctaccgggct gcctaagggt gtagctctgc cccatagaac agcttgtgtg    660
agattttctc atgctaggga ccctatttttt gggaatcaga ttattcctga cactgctatt    720
ctgtcggtgg tgcccttca tcatgggttt gggatgttta caacactggg ctacctaata    780
tgtgggttta gagtggtgct catgtatagg tttgaagaag agctgttctt acgctctttg    840
caagattata agattcagtc tgctctgctg gtgccaacac tattctcttt ttttgctaag    900
tctacgctca tagacaagta tgacttgtcc aacttgcacg agattgcttc tggcggagca    960
cctctgtcta aggaggtagg tgaggctgtg gctaagcgct tcatctgcc tggtatcaga   1020
cagggggtatg ggctaacaga aacaacatct gctattctga ttacaccaga gggggatgat   1080
aagcccgggg ctgtagggaa agtggtgccc tttttttgaag ccaaagtagt tgatcttgat   1140
accggtaaga cactaggggt gaaccagcgt ggtgaactgt gtgtgagagg gcctatgatt   1200
atgtcgggt acgttaacaa ccccgaagct acaaatgctc tgattgataa ggatggctgg   1260
ctgcattcgg gcgacattgc ttactgggat gaggatgagc atttcttcat cgtggacaga   1320
ctgaagtcgt tgatcaaata caaggggtat caagtagctc ctgctgagct ggaatccatt   1380
ctgcttcaac atcccaacat tttcgatgct ggggtggctg ggctgcctga tgatgatgct   1440
ggggagttgc ctgctgctgt agtggtgctt gagcacggta agacaatgac agagaaggag   1500
atcgtggatt atgtggcttc acaagtgaca acagctaaga aactgagagg tggcgttgtg   1560
tttgtggatg aggtgcctaa agggctcact ggcaagctgg atgctagaaa aattcgagag   1620
attctgatta aggctaagaa gggtggaaag attgctgtgt aatagttcta ga           1672
```

<210> SEQ ID NO 27
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 27

```
aaagccacca tggaagatgc taaaaacatt aagaaggggc ctgctccttt ctaccctctt      60
gaagatggga ctgctggcga gcaacttcac aaagctatga agcggtatgc tcttgtgcca    120
ggcacaattg cgttcacgga tgctcacatt gaggtggaca tcacatacgc tgagtatttt    180
gagatgtcgg tgcggctggc agaagctatg aagcgctatg ggctgaatac aaaccataga    240
attgtagtgt gcagtgagaa ctcgttgcag ttctttatgc ccgtgctggg ggctctcttc    300
atcggggtgg ctgtggctcc tgctaacgac atctacaacg agcgagagct gttgaactcg    360
```

```
atgggatct ctcagcctac agtggtgttt gtgagtaaga aagggcttca aaagattctc    420
aatgtgcaaa agaagctgcc tattattcaa aagattatta ttatggactc taagacagac    480
taccaggggt ttcagtccat gtatacattt gtgacatctc atctgcctcc tggcttcaac    540
gagtacgact tcgtgcccga gtctttcgac agagataaga caattgctct gatcatgaat    600
tcatccgggt ctaccgggct gcctaagggt gtagctctgc cccatcgaac agcttgtgtg    660
agattctctc atgccaggga cccgatcttt gggaatcaga ttattcctga cactgctatt    720
ctgtcggtgg tgcccttca tcatgggttt gggatgttta caacactggg atacctaata    780
tgtgggttta gagtggtgct catgtatagg tttgaagaag aactgttctt acgctctttg    840
caagattata agattcagtc tgctctgctg gtgccaacac tattctcttt ttttgctaag    900
tctacgctca tagacaagta tgacttgtcc aacttgcacg agattgcttc tggcggagca    960
cctctgtcta aggaggtagg tgaggctgtg gctaagcgct tcatctgcc tggtatcaga   1020
caggggtacg ggctaacaga aacaacttct gctattctga ttacaccaga gggcgatgac   1080
aagcccgggg ctgtagggaa agtggtgccc tttttttgaag ccaaagtagt tgatcttgat   1140
accggtaaga cactaggggt gaaccagcgt ggtgaactgt gtgtgcgggg ccctatgatt   1200
atgtcggggt acgttaacaa ccccgaagct acaaatgctc ttattgataa ggatggctgg   1260
ttgcattcgg gcgacattgc ctactgggat gaggatgagc atttcttcat cgtggacaga   1320
ctgaagtcgt tgatcaaata aaggggtat caagtagctc ctgctgagct ggaatccatt   1380
ctgcttcaac atccaaacat tttcgatgct ggggtggctg gctgcctga tgatgatgct   1440
ggagagttgc ctgctgctgt agtagtgctt gagcacggta agacaatgac agagaaggag   1500
atcgtggatt atgtggcttc acaagtgaca acagctaaga aactgagagg tggcgttgtg   1560
tttgtggatg aggtgcctaa agggctcact ggcaagctgg atgccagaaa aattcgagag   1620
attctcatta aggctaagaa gggtggaaag attgctgtgt aatagttcta ga           1672

<210> SEQ ID NO 28
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 28
aaagccacca tggaagatgc taaaaacatt aagaaggggc ctgctccctt ctaccctctt     60
gaagatggga ctgctggcga gcaacttcac aaagctatga agcggtatgc tcttgtgcca    120
ggcacaattg cgttcacgga tgctcacatt gaggtggaca tcacatacgc tgagtatttt    180
gagatgtcgt tgcggctggc agaagctatg aagcgctatg gctgaatac aaaccataga    240
attgtagtgt gcagtgagaa ctcgttgcag ttctttatgc ccgtgctggg ggctctcttc    300
atcggggtgg ctgtggctcc tgctaacgac atctacaacg agcgagagct gttgaactcg    360
atggggatct ctcagcctac agtggtgttt gtgagtaaga aagggcttca aaagattctc    420
aatgtgcaaa agaagctgcc tattatacaa aagattatta ttatggactc taagaccgac    480
taccaggggt ttcagtccat gtacacattt gtaacctctc atctgcctcc tggcttcaac    540
gagtacgact tcgtgcccga gtctttcgac agggacaaaa cgattgctct gatcatgaac    600
tcatccgggt ctaccgggct gcctaagggt gtagctctgc cccatcgaac agcttgtgtg    660
agattctctc atgccaggga cccgatcttt gggaatcaga ttattcctga cactgctatt    720
ctgtcggtgg tgcccttca tcatgggttt gggatgttca acactggg atacctcatt    780
```

```
tgcgggttta gagtggtgct catgtatagg tttgaagaag aactattcct acgctctttg    840
caagattata agattcagtc tgctctgctg gtgccaacac tattctcttt ttttgctaag    900
tctacgctca tagacaagta tgacttgtcc aacttgcacg agattgcttc tggcggagca    960
cctctgtcta aggaggtagg tgaggctgtg gctaagcgct ttcatctgcc tggtatcaga   1020
caggggtacg ggctaacaga aacaacttct gctattctga ttacaccaga gggcgatgac   1080
aaacccgggg ctgtagggaa agtggtgccc ttttttgaag ccaaagtagt tgatcttgat   1140
accggtaaga cactagggga gaaccagcgt ggtgaactgt gtgtgcgggg ccctatgatt   1200
atgtcggggt acgttaacaa ccccgaagct acaaatgctc ttattgataa ggatggctgg   1260
ttgcattcgg gcgacattgc ctactgggat gaggatgagc atttcttcat cgtggacaga   1320
ctgaagtcgt tgatcaaata caaggggtat caagtagctc ctgctgagct ggaatccatt   1380
ctgcttcaac atcctaacat tttcgatgct ggggtggctg ggctgcctga tgatgatgct   1440
ggagagttgc ctgctgctgt agtagtgctt gagcacggta agacaatgac agagaaggag   1500
atcgtggatt atgtggcttc acaagtgaca acagctaaga aactgagagg tggcgttgtg   1560
tttgtggatg aggtgcctaa agggctcact ggcaagctgg atgccagaaa aattcgagag   1620
attctcatta aggctaagaa gggtggaaag attgctgtgt aatagttcta ga           1672

<210> SEQ ID NO 29
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 29
aaagccacca tggaagatgc caaaaacatt aagaaggggc ctgctcccttc ctaccctctt    60 gaagatggga ctgctggcga gcaacttcac aaagctatga agcggtatgc tcttgtgcca   120
ggcacaattg cgttcacgga tgctcacatt gaagtagaca tcacatacgc tgagtatttt   180
gagatgtcgg tgcggctggc agaagctatg aagcgctatg ggctgaatac aaaccataga   240
attgtagtgt gcagtgagaa ctcgttgcag ttctttatgc ccgtgctggg ggctctcttc   300
atcggggtgg ctgtggctcc tgctaacgac atctacaacg agcgagagct gttgaactcg   360
atggggatct ctcagcctac agtggtgttt gtgagtaaga aagggcttca aaagattctc   420
aatgtgcaaa agaagctgcc tattatacaa aagattatta ttatggactc taagaccgac   480
taccaggggt ttcagtccat gtacacattt gtaacctctc atctgcctcc tggcttcaac   540
gagtacgact tcgtgcccga gtctttcgac agggacaaaa cgattgctct gatcatgaac   600
agctccgggt ctaccgggct gcctaagggt gtagctctgc cccatcgaac agcttgtgtg   660
agattctctc atgccaggga cccgatcttt ggaaaccaga tcatccctga cactgctatt   720
ctgtcggtgg tgccctttca tcatgggttt gggatgttca acacactggg atacctcatt   780
tgcgggttta gagtggtgct catgtatagg tttgaagaag aactattcct acgctctttg    840
caagattata agattcagtc tgctctgctg gtgccaacac tattctcttt ttttgctaag    900
tctacgctca tagacaagta tgacttgtcc aacttgcacg agattgcttc tggcggagca    960
cctctgtcta aggaggtagg tgaggctgtg gctaagcgct ttcatctgcc tggtatcaga   1020
caggggtacg ggctaacaga aacaacttct gctattctga ttacaccaga gggcgatgac   1080
aaacccgggg ctgtagggaa agtggtgccc ttttttgaag ccaaagtagt tgatcttgat   1140
accggtaaga cactagggga gaaccagcgt ggtgaactgt gtgtgcgggg ccctatgatt   1200
```

```
atgtcggggt acgttaacaa ccccgaagct acaaatgctc tcatagacaa ggacgggtgg   1260
cttcatagcg gcgacattgc ctactgggac gaggatgagc atttcttcat cgtggacaga   1320
ctgaagtcgt tgatcaaata caaggggtat caagtagctc ctgctgagct ggaatccatt   1380
ctgcttcaac accccaatat cttcgatgct ggggtggctg ggctgcctga tgatgatgct   1440
ggagagctgc ctgctgctgt agtagtgctt gagcacggta agacaatgac agagaaggag   1500
atcgtggatt atgtggcttc acaagtgaca acagctaaga aactgagagg tggcgttgtg   1560
tttgtggatg aggtgcctaa agggctcact ggcaagctgg atgccagaaa aattcgagag   1620
attctcatta aggctaagaa gggtggaaag attgctgtgt aatagttcta ga            1672

<210> SEQ ID NO 30
<211> LENGTH: 1056
<212> TYPE: DNA
<213> ORGANISM: Artificial Sequence
<220> FEATURE:
<223> OTHER INFORMATION: A synthetic construct.

<400> SEQUENCE: 30
ccactcagtg gccaccatga agaagcccga gctgaccgct accagcgttg agaagttcct     60
gatcgagaag ttcgacagcg tgagcgacct gatgcagtta agcgagggcg aggaaagccg    120
cgccttcagc ttcgatgtcg gcggacgcgg ctatgtactg cgggtgaata gctgcgctga    180
tggcttctac aaagaccgct acgtgtaccg ccacttcgcc agcgctgcac tgcccatccc    240
cgaggtgctg gacatcggcg agttcagcga gagcctgaca tactgcatca gccgccgcgc    300
tcaaggcgtg actctccaag acctgcccga gacagagctg cccgctgtgc tacagcctgt    360
cgccgaggct atggacgcta ttgccgccgc cgacctgagc cagaccagcg gcttcggccc    420
attcgggccc caaggcatcg gccagtacac cacctggcgc gacttcatct gcgccattgc    480
tgatccccat gtctaccact ggcagaccgt gatggacgac accgtgagcg ccagcgtagc    540
tcaagccctg gacgagctga tgctgtgggc cgaggactgc cccgaggtgc gccatctcgt    600
ccatgccgac ttcggcagca caacgtcct gaccgacaac ggccgcatca ccgccgtaat    660
cgactggagc gaggccatgt cggggacag tcagtacgag gtggccaaca tcttcttctg    720
gcggccctgg ctggcctgca tggagcagca aacccgctac ttcgagcgcc gccatcccga    780
gctggccggc agccccgtc tgcgagccta catgctgcgc atcggcctgg atcagctcta    840
ccagagcctc gtggacggca acttcgacga tgctgcctgg gctcaaggcc gctgcgatgc    900
catcgtccgc agcggggccg gcaccgtcgg tcgcacacaa atcgctcgcc ggagcgccgc    960
cgtatggacc gacggctgcg tcgaggtgct ggccgacagc ggcaaccgcc ggcccagtac   1020
acgaccgcgc gctaaggagt agtaaccagc tcttgg                              1056

<210> SEQ ID NO 31
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 31
aaagccacca tggaagatgc caaaaacatt aagaagggc ctgctccctt ctaccctctt     60
gaagatggga ctgctggcga gcaacttcac aaagctatga gcggtatgc tcttgtgcca    120 gggacaattg cgttcacgga tgctcacatt gaagtagaca tcacatacgc tgagtatttt    180
gagatgtcgg tgcggctggc agaagctatg aagcgctatg ggctgaatac aaaccataga    240
```

```
attgtagtgt gcagtgagaa ctcgttgcag ttctttatgc ccgtgctggg ggctctcttc      300
atcggggtgg ctgtggctcc tgctaacgac atctacaacg agcgagagct gttgaactcg      360
atggggatct ctcagcctac agtggtgttt gtgagtaaga aagggcttca aaagattctc      420
aatgtgcaaa agaagctacc gatcatacaa aagatcatca tcatggatag caagaccgac      480
taccaggggt ttcagtccat gtacacattt gtaacctctc atctgcctcc tggcttcaac      540
gagtacgact tcgtgcccga gtctttcgac agggacaaaa cgattgctct gatcatgaac      600
agctccgggt ctaccgggct gcctaagggt gtagctctgc cccatcgaac agcttgtgtg      660
agattctctc atgccaggga cccgatcttt ggaaaccaga tcatccctga cactgctatt      720
ctgtcggtgg tgccctttca tcatgggttt gggatgttca acactggga atacctcatt       780 tgcgggttta gagtggtgct catgtatagg tttgaagaag aactattcct acgctctttg      840
caagattata agattcagtc tgctctgctg gtgccaacac tattctcttt ttttgctaag      900
tctacgctca tagacaagta tgacttgtcc aacttgcacg agattgcttc tggcggagca      960
cctctgtcta aggaggtagg tgaggctgtg gctaagcgct tcatctgcc tggtatcaga     1020 cagggggtacg ggctaacaga aacaacttct gctattctga ttacaccaga gggcgatgac    1080
aaacctgggg ctgtagggaa agtggtgccc tttttgaag ccaaagtagt tgatcttgat      1140
accggtaaga cactagggt gaaccagcgt ggtgaactgt gtgtgcgggg ccctatgatt      1200
atgtcggggt acgttaacaa ccccgaagct acaaatgctc tcatagacaa ggacgggtgg    1260
cttcatagcg gcgacattgc ctactgggac gaggatgagc atttcttcat cgtggacaga    1320
ctgaagtcgt tgatcaaata caaggggtat caagtagctc ctgccgagct tgagtccatt    1380
ctgcttcaac accccaatat cttcgatgct ggggtggctg ggctgcctga tgatgatgct    1440
ggagagctgc ctgctgctgt agtagtgctt gagcatggta agacaatgac agagaaggag    1500
atcgtggatt atgtggcttc acaagtgaca acagctaaga aactccgagg tggcgttgtg    1560
tttgtggatg aggtgcctaa agggctcact ggcaagctgg atgccagaaa aattcgagag    1620
attctcatta aggctaagaa gggtggaaag attgctgtgt aatagttcta ga            1672
```

<210> SEQ ID NO 32
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 32

```
aaagccacca tggaagatgc caaaaacatt aagaaggggc ctgctccctt ctaccctctt       60
gaagatggga ctgctggcga gcaacttcac aaagctatga gcggtatgc tcttgtgcca      120 gggacaattg cgttcacgga tgctcacatt gaagtagaca tcacatacgc tgagtatttt      180
gagatgtcgg tgcggctggc agaagctatg aagcgctatg gctgaatac aaaccataga      240 attgtagtgt gcagtgagaa ctcgttgcag ttctttatgc ccgtgctggg ggctctcttc      300
attggggtgg ctgtggctcc tgctaatgac atctacaacg agcgagagct gttgaacagt      360
atggggatct ctcagcctac agtggtgttt gtgagtaaga aagggcttca aaagattctc      420
aatgtgcaaa agaagctacc gatcatacaa aagatcatca tcatggatag caagaccgac      480
taccaggggt ttcagtccat gtacacattt gtaacctctc atctgcctcc tggcttcaat      540
gagtatgact tcgtgcccga gtctttcgac agggacaaaa cgattgctct gatcatgaac      600
agcagtgggt ctaccgggct gcctaagggt gtagctctgc cccatcgaac agcttgtgtg      660
```

```
agattctctc atgccaggga cccgatcttt ggaaaccaga tcatccctga cactgctatt      720
ctgtcggtgg tgcccttca tcatgggttt ggatgttca caacactggg atacctcatt      780
tgcgggttta gagtggtgct catgtatagg tttgaagaag aactattcct acgctctttg      840
caagattata agattcagtc tgctctgctg gtgccaacac tattctcttt ttttgctaag      900
tctacgctca tagacaagta tgacttgtcc aacttgcacg agattgcttc tggcggagca      960
cctctgtcta aggaggtagg tgaggctgtg gctaagcgct ttcatctgcc tggtatcaga     1020
caggggtacg ggctaacaga aacaacttct gctattctga ttacaccaga gggcgatgac     1080
aaacctgggg ctgtagggaa agtggtgccc tttttgaag ccaaagtagt tgatcttgat     1140
accggtaaga cactaggggt gaaccagaga ggtgaattgt gtgtgagggg ccctatgatt     1200
atgtcggggt acgttaacaa ccccgaagct acaaatgctc tcatagacaa ggacgggtgg     1260
cttcatagtg gagatattgc ctactgggat gaagatgagc atttcttcat cgtggacaga     1320
ctgaagtcgt tgatcaaata caaggggtat caagtagctc ctgccgagct tgagtccatt     1380
ctgcttcaac accccaatat cttcgatgct ggggtggctg gctgcctga tgatgatgct     1440 ggagagctgc ctgctgctgt agtagtgctt gagcatggta agacaatgac agagaaggag     1500
atcgtggatt atgtggcttc acaagtgaca acagctaaga aactccgagg tggcgttgtg     1560
tttgtggatg aggtgcctaa agggctcact ggcaagctgg atgccagaaa aattcgagag     1620
attctcatta aggctaagaa gggtggaaag attgctgtgt aatagttcta ga            1672

<210> SEQ ID NO 33
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 33
aaagccacca tggaagatgc caaaaacatt aagaaggggc ctgctcccct ctaccctctt       60
gaagatggga ctgctggcga gcaacttcac aaagctatga gcggtatgc tcttgtgcca      120 gggacaattg cgttcacgga tgctcacatt gaagtagaca tcacatacgc tgagtatttt      180
gagatgtcgg tgcggctggc agaagctatg aagcgctatg gctgaatac aaaccataga      240 attgtagtgt gcagtgagaa ctcgttgcag ttctttatgc ccgtgctggg ggctctcttc      300 attgggtgg ctgtggctcc tgctaatgac atctacaacg agcgagagct gttgaacagt      360 atgggggatct ctcagcctac agtggtgttt gtgagtaaga aagggcttca aaagattctc      420
aatgtgcaaa agaagctacc gatcatacaa aagatcatca tcatggatag caagaccgac      480
taccaggggt ttcagtccat gtacacattt gtaacctctc atctgcctcc tggcttcaat      540
gagtatgact tcgtgcccga gtctttcgac agggacaaaa cgattgctct gatcatgaac      600
agcagtgggc taccggggct gcctaagggt gtagctctgc cccatcgaac agcttgtgtg      660
agattctctc atgccaggga cccgatcttt ggaaaccaga tcatccctga cactgctatt      720
ctgtcggtgg tgcccttca tcatgggttt ggatgttca caacactggg atacctcatt      780
tgcgggttta gagtggtgct catgtatagg tttgaagaag aactattcct acgctctttg      840
caagattata agattcagtc tgctctgctg gtgccaacac tattctcttt ttttgctaag      900
tctacgctca tagacaagta tgacttgtcc aacttgcacg agattgcttc tggcggagca      960
cctctgtcta aggaggtagg tgaggctgtg gctaagcgct ttcatctgcc tggtatcaga     1020
caggggtacg ggctaacaga aacaacttct gctattctga ttacaccaga gggcgatgac     1080
```

-continued

```
aaacctgggg ctgtagggaa agtggtgccc ttttttgaag ccaaagtagt tgatcttgat    1140
accggtaaga cactaggggt gaaccagaga ggtgaattgt gtgtgagggg ccctatgatt    1200 atgtcgggt acgttaacaa ccccgaagct acaaatgctc tcatagacaa ggacgggtgg    1260
cttcatagtg gagatattgc ctactgggat gaagatgagc atttcttcat cgtggacaga    1320
ctgaagtcgt tgatcaaata caaggggtat caagtagctc ctgccgagct tgagtccatt    1380
ctgcttcaac accccaatat cttcgatgct ggggtggctg gctgcctga tgatgatgct     1440 ggagagctgc ctgctgctgt agtagtgctt gagcatggta agacaatgac agagaaggag    1500
atcgtggatt atgtggcttc acaagtgaca acagctaaga aactccgagg tggcgttgtg    1560
tttgtggatg aggtgcctaa aggactcact ggcaagctgg atgccagaaa aattcgagag    1620
attctcatta aggctaagaa gggtggaaag attgctgtgt aatagttcta ga            1672

<210> SEQ ID NO 34
<211> LENGTH: 10
<212> TYPE: DNA
<213> ORGANISM: Artificial Sequence
<220> FEATURE:
<223> OTHER INFORMATION: A synthetic construct.

<400> SEQUENCE: 34
gccaccatga                                                            10

<210> SEQ ID NO 35
<211> LENGTH: 11
<212> TYPE: DNA
<213> ORGANISM: Artificial Sequence
<220> FEATURE:
<223> OTHER INFORMATION: A synthetic construct.
<220> FEATURE:
<221> NAME/KEY: misc_feature
<222> LOCATION: 4, 5, 6, 7, 8
<223> OTHER INFORMATION: n = A,T,C or G

<400> SEQUENCE: 35
ccannnnntg g                                                          11

<210> SEQ ID NO 36
<211> LENGTH: 25
<212> TYPE: DNA
<213> ORGANISM: Artificial Sequence
<220> FEATURE:
<223> OTHER INFORMATION: A synthetic construct.
<220> FEATURE:
<221> NAME/KEY: misc_feature
<222> LOCATION: 1, 2, 3, 4, 5, 9, 10, 11, 12, 13
<223> OTHER INFORMATION: n = A,T,C or G

<400> SEQUENCE: 36
nnnnnccann nnntggccac catgg                                           25

<210> SEQ ID NO 37
<211> LENGTH: 20
<212> TYPE: DNA
<213> ORGANISM: Artificial Sequence
<220> FEATURE:
<223> OTHER INFORMATION: A synthetic construct.
<220> FEATURE:
<221> NAME/KEY: misc_feature
<222> LOCATION: 10, 11, 12, 13, 14, 18, 19, 20
<223> OTHER INFORMATION: n = A,T,C or G

<400> SEQUENCE: 37
taataaccan nnnntggnnn                                                 20
```

<210> SEQ ID NO 38
<211> LENGTH: 825
<212> TYPE: DNA
<213> ORGANISM: Artificial Sequence
<220> FEATURE:
<223> OTHER INFORMATION: A synthetic construct.

<400> SEQUENCE: 38

```
ccactcagtg gccaccatga tcgagcagga cggcctccat gctggcagtc ccgcagcctg      60
ggtcgagcgc ttgttcgggt acgactgggc ccagcagacc atcggatgta gcgatgccgc     120
agtgttccgc ctgagcgctc aaggccggcc cgtgctgttc gtgaagaccg acctgagcgg     180
cgccctgaac gagcttcaag acgaggctgc ccgcctgagc tggctggcca ccaccggtgt     240
accctgcgcc gctgtgttgg atgttgtgac cgaagccggc cgcgactggc tgctgctggg     300
cgaggtgcct ggccaggacc tgctgagcag ccacctggcc cccgctgaga aggtgagcat     360
catggccgac gccatgcggc cctgcacac cctggacccc gctacatgcc ccttcgacca     420
ccaggctaag caccgcatcg agcgggctcg gacccgcatg gaggccggcc tggtggacca     480
ggacgacctg gacgaggagc accagggcct ggccccgct gaactgttcg cccgcctgaa     540
agcccgcatg ccggacggtg aggacctggt tgtgacacac ggcgacgcct gcctcctaa     600
catcatggtc gagaacgggc gcttctccgg cttcatcgac tgcggccgcc tgggcgttgc     660
cgaccgctac caggacatcg ccctggccac ccgcgacatc gccgaggagc tgggcggcga     720
gtgggccgac cgcttcctgg tcttgtacgg catcgcagct cccgacagcc agcgcatcgc     780
cttctaccgc ctgctggacg agttcttcta gtaaccaggc tctgg                    825
```

<210> SEQ ID NO 39
<211> LENGTH: 825
<212> TYPE: DNA
<213> ORGANISM: Artificial Sequence
<220> FEATURE:
<223> OTHER INFORMATION: A synthetic construct.

<400> SEQUENCE: 39

```
ccactccgtg gccaccatga tcgaacaaga cggcctccat gctggcagtc ccgcagcttg      60
ggtcgaacgc ttgttcgggt acgactgggc ccagcagacc atcggatgta gcgatgcggc     120
cgtgttccgt ctaagcgctc aaggccggcc cgtgctgttc gtgaagaccg acctgagcgg     180
cgccctgaac gagcttcaag acgaggctgc ccgcctgagc tggctggcca ccaccggtgt     240
accctgcgcc gctgtgttgg atgttgtgac cgaagccggc cgggactggc tgctgctggg     300
cgaggtccct ggccaggatc tgctgagcag ccaccttgcc cccgctgaga aggtttccat     360
catggccgat gcaatgcggc cctgcacac cctggacccc gctacatgcc ccttcgacca     420
ccaggctaag catcggatcg agcgtgctcg gacccgcatg gaggccggcc tggtggacca     480
ggacgacctg gacgaggagc atcagggcct ggccccgct gaactgttcg cccgcctgaa     540
agcccgcatg ccggacggtg aggacctggt tgtgacacat ggagatgcct gcctccctaa     600
catcatggtc gagaatggcc gcttctccgg cttcatcgac tgcggtcgcc taggagttgc     660
cgaccgctac caggacatcg ccctggccac ccgcgacatc gctgaggagc ttggcggcga     720
gtgggccgac cgcttcttag tcttgtacgg catcgcagct cccgacagcc agcgcatcgc     780
cttctaccgc ctgctcgacg agttcttta atgaccaggc tctgg                     825
```

<210> SEQ ID NO 40

<400> SEQUENCE: 40

000

<210> SEQ ID NO 41
<211> LENGTH: 861
<212> TYPE: DNA
<213> ORGANISM: Escherichia coli

<400> SEQUENCE: 41

| atgagtattc aacatttccg tgtcgccctt attcccttt ttgcggcatt ttgccttcct | 60 |
| gtttttgctc acccagaaac gctggtgaaa gtaaaagatg ctgaagatca gttgggtgca | 120 |
| cgagtgggtt acatcgaact ggatctcaac agcggtaaga tccttgagag ttttcgcccc | 180 |
| gaagaacgtt ttccaatgat gagcactttt aaagttctgc tatgtggcgc ggtattatcc | 240 |
| cgtattgacg ccgggcaaga gcaactcggt cgccgcatac actattctca gaatgacttg | 300 |
| gttgagtact caccagtcac agaaaagcat cttacggatg catgacagt aagagaatta | 360 |
| tgcagtgctg ccataaccat gagtgataac actgcggcca acttacttct gacaacgatc | 420 |
| ggaggaccga aggagctaac cgcttttttg cacaacatgg gggatcatgt aactcgcctt | 480 |
| gatcgttggg aaccggagct gaatgaagcc ataccaaacg acgagcgtga caccacgatg | 540 |
| cctgtagcaa tggcaacaac gttgcgcaaa ctattaactg gcgaactact tactctagct | 600 |
| tcccggcaac aattaataga ctggatggag gcggataaag ttgcaggacc acttctgcgc | 660 |
| tcggcccttc cggctggctg gtttattgct gataaatctg gagccggtga gcgtgggtct | 720 |
| cgcggtatca ttgcagcact ggggccagat ggtaagccct cccgtatcgt agttatctac | 780 |
| acgacgggga gtcaggcaac tatggatgaa cgaaatagac agatcgctga ataggtgcc | 840 |
| tcactgatta agcattggta a | 861 |

<210> SEQ ID NO 42
<211> LENGTH: 1056
<212> TYPE: DNA
<213> ORGANISM: Artificial Sequence
<220> FEATURE:
<223> OTHER INFORMATION: A synthetic construct.

<400> SEQUENCE: 42

| ccactccgtg gccaccatga agaagcccga gctgaccgct accagcgttg aaaaatttct | 60 |
| catcgagaag ttcgacagtg tgagcgacct gatgcagttg tcgagggcg aagagagccg | 120 |
| agccttcagc ttcgatgtcg gcggacgcgg ctatgtactg cgggtgaata gctgcgctga | 180 |
| tggcttctac aaagaccgct acgtgtaccg ccacttcgcc agcgctgcac tacccatccc | 240 |
| cgaagtgttg gacatcggcg agttcagcga gagcctgaca tactgcatca gtagacgcgc | 300 |
| ccaaggcgtt actctccaag acctccccga acagagctg cctgctgtgt tacagcctgt | 360 |
| cgccgaagct atggatgcta ttgccgccgc cgacctcagt caaaccagcg gcttcggccc | 420 |
| attcgggccc caaggcatcg gccagtacac aacctggcgg gatttcattt gcgccattgc | 480 |
| tgatccccat gtctaccact ggcagaccgt gatggacgac accgtgtccg ccagcgtagc | 540 |
| tcaagccctg gacgaactga tgctgtgggc gaagactgt cccgaggtgc gccacctcgt | 600 |
| ccatgccgac ttcggcagca acaacgtcct gaccgacaac ggccgcatca ccgccgtaat | 660 |
| cgactggagc gaggctatgt tcggggacag tcagtacgag gtggccaaca tcttcttctg | 720 |
| gcggccctgg ctggcttgca tggagcagca gactcgctac ttcgagcgcc ggcatccgga | 780 |

| | | |
|---|---|---|
| gctggccggc agccctcgtc tgcgagccta catgctgcgc atcggcctgg atcagctcta | 840 | |
| ccagagcctc gtggacggca acttcgacga tgctgcctgg gctcaaggcc gctgcgatgc | 900 | |
| catcgtccgc agcggggccg gcaccgtcgg tcgcacacaa atcgctcgcc ggagcgccgc | 960 | |
| cgtatggacc gacggctgcg tcgaggtgct ggccgacagc ggcaaccgcc ggcccagtac | 1020 | |
| acgaccgcgc gctaaggagt agtaaccagc tcttgg | 1056 | |

<210> SEQ ID NO 43
<211> LENGTH: 1653
<212> TYPE: DNA
<213> ORGANISM: Artificial Sequence
<220> FEATURE:
<223> OTHER INFORMATION: A synthetic construct.

<400> SEQUENCE: 43

| | | |
|---|---|---|
| atggaagacg ccaaaaacat aaagaaaggc ccggcgccat tctatccgct ggaagatgga | 60 | |
| accgctggag agcaactgca taaggctatg aagagatacg ccctggttcc tggaacaatt | 120 | |
| gcttttacag atgcacatat cgaggtggac atcacttacg ctgagtactt cgaaatgtcc | 180 | |
| gttcggttgg cagaagctat gaaacgatat gggctgaata caaatcacag aatcgtcgta | 240 | |
| tgcagtgaaa actctcttca attctttatg ccggtgttgg gcgcgttatt tatcggagtt | 300 | |
| gcagttgcgc ccgcgaacga catttataat gaacgtgaat tgctcaacag tatgggcatt | 360 | |
| tcgcagccta ccgtggtgtt cgtttccaaa aagggggttgc aaaaaatttt gaacgtgcaa | 420 | |
| aaaaagctcc caatcatcca aaaaattatt atcatggatt ctaaaacgga ttaccaggga | 480 | |
| tttcagtcga tgtacacgtt cgtcacatct catctacctc ccggttttaa tgaatacgat | 540 | |
| tttgtgccag agtccttcga tagggacaag acaattgcac tgatcatgaa ctcctctgga | 600 | |
| tctactggtc tgcctaaagg tgtcgctctg cctcatagaa ctgcctgcgt gagattctcg | 660 | |
| catgccagag atcctatttt tggcaatcaa atcattccgg atactgcgat tttaagtgtt | 720 | |
| gttccattcc atcacggttt tggaatgttt actacactcg gatatttgat atgtggattt | 780 | |
| cgagtcgtct taatgtatag atttgaagaa gagctgtttc tgaggagcct tcaggattac | 840 | |
| aagattcaaa gtgcgctgct ggtgccaacc ctattctcct tcttcgccaa agcactctg | 900 | |
| attgacaaat acgatttatc taatttacac gaaattgctt ctggtggcgc tcccctctct | 960 | |
| aaggaagtcg gggaagcggt tgccaagagg ttccatctgc caggtatcag gcaaggatat | 1020 | |
| ggctcactg agactacatc agctattctg attacacccg agggggatga taaaccgggc | 1080 | |
| gcggtcggta agttgttcc attttttgaa gcgaaggttg tggatctgga taccgggaaa | 1140 | |
| acgctgggcg ttaatcaaag aggcgaactg tgtgtgagag gtcctatgat tatgtccggt | 1200 | |
| tatgtaaaca atccggaagc gaccaacgcc ttgattgaca aggatggatg gctacattct | 1260 | |
| ggagacatag cttactggga cgaagacgaa cacttcttca tcgttgaccg cctgaagtct | 1320 | |
| ctgattaagt acaaaggcta tcaggtggct cccgctgaat ggaatccat cttgctccaa | 1380 | |
| caccccaaca tcttcgacgc aggtgtcgca ggtcttcccg acgatgacgc cggtgaactt | 1440 | |
| cccgccgccg ttgttgtttt ggagcacgga aagacgatga cggaaaaaga gatcgtggat | 1500 | |
| tacgtcgcca gtcaagtaac aaccgcgaaa aagttgcgcg gaggagttgt gtttgtggac | 1560 | |
| gaagtaccga aaggtcttac cggaaaactc gacgcaagaa aaatcagaga gatcctcata | 1620 | |
| aaggccaaga agggcggaaa gatcgccgtg taa | 1653 | |

<210> SEQ ID NO 44
<211> LENGTH: 1369
<212> TYPE: DNA
<213> ORGANISM: Artificial Sequence
<220> FEATURE:
<223> OTHER INFORMATION: A synthetic construct.

<400> SEQUENCE: 44

```
ggatccgttt gcgtattggg cgctcttccg ctgatctgcg cagcaccatg gcctgaaata      60
acctctgaaa gaggaacttg gttagctacc ttctgaggcg gaaagaacca gctgtggaat     120
gtgtgtcagt tagggtgtgg aaagtcccca ggctccccag caggcagaag tatgcaaagc     180
atgcatctca attagtcagc aaccaggtgt ggaaagtccc caggctcccc agcaggcaga     240
agtatgcaaa gcatgcatct caattagtca gcaaccatag tcccgcccct aactccgccc     300
atcccgcccc taactccgcc cagttccgcc cattctccgc cccatggctg actaattttt     360
tttatttatg cagaggccga ggccgcctct gcctctgagc tattccagaa gtagtgagga     420
ggcttttttg gaggcctagg cttttgcaaa aagctcgatt cttctgacac tagcgccacc     480
atgatcgaac aagacggcct ccatgctggc agtcccgcag cttgggtcga acgcttgttc     540
gggtacgact gggcccagca gaccatcgga tgtagcgatg cggccgtgtt ccgtctaagc     600
gctcaaggcc ggcccgtgct gttcgtgaag accgacctga gcggcgccct gaacgagctt     660
caagacgagg ctgcccgcct gagctggctg gccaccaccg gcgtaccctg cgccgctgtg     720
ttggatgttg tgaccgaagc cggccgggac tggctgctgc tgggcgaggt ccctggccag     780
gatctgctga gcagccacct tgccccgct gagaaggttt ctatcatggc cgatgcaatg     840
cggcgcctgc acaccctgga ccccgctacc tgccccttcg accaccaggc taagcatcgg     900
atcgagcgtg ctcggacccg catggaggcc ggcctggtgg accaggacga cctggacgag     960
gagcatcagg gcctggcccc cgctgaactg ttcgcccgac tgaaagcccg catgccggac    1020
ggtgaggacc tggttgtcac acacggagat gcctgcctcc ctaacatcat ggtcgagaat    1080
ggccgcttct ccggcttcat cgactgcggt cgcctaggag ttgccgaccg ctaccaggac    1140
atcgccctgg ccaccgcga catcgctgag gagcttggcg gcgagtgggc cgaccgcttc    1200
ttagtcttgt acggcatcgc agctcccgac agccagcgca tcgccttcta ccgcttgctc    1260
gacgagttct tttaatgatc tagaaccggt catggccgat aaaatatc tttatttca    1320 ttacatctgt gtgttggttt tttgtgtgtt cgaactagat gctgtcgac                 1369
```

<210> SEQ ID NO 45
<211> LENGTH: 1214
<212> TYPE: DNA
<213> ORGANISM: Artificial Sequence
<220> FEATURE:
<223> OTHER INFORMATION: A synthetic construct.

<400> SEQUENCE: 45

```
gcggccgcaa atgctaaacc actgcagtgg ttaccagtgc ttgatcagtg aggcaccgat      60
ctcagcgatc tgcctatttc gttcgtccat agtggcctga ctcccgtcg tgtagatcac     120 tacgattcgt gagggcttac catcaggccc cagcgcagca atgatgccgc gagagccgcg     180
ttcaccggcc cccgatttgt cagcaatgaa ccagccagca gggagggccg agcgaagaag     240
tggtcctgct actttgtccg cctccatcca gtctatgagc tgctgtcgtg atgctagagt     300
aagaagttcg ccagtgagta gtttccgaag agttgtggcc attgctactg gcatcgtggt     360
atcacgctcg tcgttcggta tggcttcgtt caactctggt tcccagcggt caagccgggt     420
```

```
cacatgatca cccatattat gaagaaatgc agtcagctcc ttagggcctc cgatcgttgt    480
cagaagtaag ttggccgcgg tgttgtcgct catggtaatg gcagcactac acaattctct    540
taccgtcatg ccatccgtaa gatgcttttc cgtgaccggc gagtactcaa ccaagtcgtt    600
ttgtgagtag tgtatacggc gaccaagctg ctcttgcccg gcgtctatac gggacaacac    660
cgcgccacat agcagtactt tgaaagtgct catcatcggg aatcgttctt cggggcggaa    720
agactcaagg atcttgccgc tattgagatc cagttcgata tagcccactc ttgcacccag    780
ttgatcttca gcatctttta ctttcaccag cgtttcgggg tgtgcaaaaa caggcaagca    840
aaatgccgca aagaagggaa tgagtgcgac acgaaaatgt tggatgctca tactcttcct    900
ttttcaatat gtttgcagca tttgtcaggg ttactagtac gtctctcttg agagaccgcg    960
atcgccacca tgtctaggta ggtagtaaac gaaagggctt aaaggcctaa gtggccctcg   1020
agtccagcct tgagttggtt gagtccaagt cacgtttgga gatctggtac cttacgcgta   1080
tgagggttga gtccaagtca cgtttggaga tctggtacct tacgcgtatg agctctacgt   1140
agctagcggc ctcggcggcc gaattcttgc gttcgaagct tggcaatccg gtactgttgg   1200
taaagccacc atgg                                                     1214

<210> SEQ ID NO 46
<211> LENGTH: 1522
<212> TYPE: DNA
<213> ORGANISM: Artificial Sequence
<220> FEATURE:
<223> OTHER INFORMATION: A synthetic construct.

<400> SEQUENCE: 46
gcggccgcaa atgctaaacc actgcagtgg ttaccagtgc ttgatcagtg aggcaccgat     60
ctcagcgatc tgcctatttc gttcgtccat agtggcctga ctccccgtcg tgtagatcac    120
tacgattcgt gagggcttac catcaggccc cagcgcagca atgatgccgc gagagccgcg    180
ttcaccggcc cccgatttgt cagcaatgaa ccagccagca gggagggccg agcgaagaag    240
tggtcctgct actttgtccg cctccatcca gtctatgagc tgctgtcgtg atgctagagt    300
aagaagttcg ccagtgagta gtttccgaag agttgtggcc attgctactg gcatcgtggt    360
atcacgctcg tcgttcggta tggcttcgtt caactctggt tcccagcggt caagccgggt    420
cacatgatca cccatattat gaagaaatgc agtcagctcc ttagggcctc cgatcgttgt    480
cagaagtaag ttggccgcgg tgttgtcgct catggtaatg gcagcactac acaattctct    540
taccgtcatg ccatccgtaa gatgcttttc cgtgaccggc gagtactcaa ccaagtcgtt    600
ttgtgagtag tgtatacggc gaccaagctg ctcttgcccg gcgtctatac gggacaacac    660
cgcgccacat agcagtactt tgaaagtgct catcatcggg aatcgttctt cggggcggaa    720
agactcaagg atcttgccgc tattgagatc cagttcgata tagcccactc ttgcacccag    780
ttgatcttca gcatctttta ctttcaccag cgtttcgggg tgtgcaaaaa caggcaagca    840
aaatgccgca aagaagggaa tgagtgcgac acgaaaatgt tggatgctca tactcttcct    900
ttttcaatat gtttgcagca tttgtcaggg ttactagtac gtctctcaag agatttgtgc    960
atacacagtg actcatactt tcaccaatac tttgcatttt ggataaatac tagacaactt   1020
tagaagtgaa ttatttatga ggttgtctta aaattaaaaa ttacaaagta ataaatcaca   1080
ttgtaatgta ttttgtgtga tacccagagg tttaaggcaa cctattactc ttatgctcct   1140
gaagtccaca attcacagtc ctgaactata atcttatctt tgtgattgct gagcaaattt   1200
gcagtataat ttcagtgctt ttaaattttg tcctgcttac tatttttcctt ttttatttgg   1260
```

```
gtttgatatg cgtgcacaga atggggcttc tattaaaata ttcttgagag accgcgatcg    1320
ccaccatgtc taggtaggta gtaaacgaaa gggcttaaag gcctaagtgg ccctcgagtc    1380
cagccttgag ttggttgagt ccaagtcacg tttggagatc tggtaccttg cgcgtatgag    1440
ctctacgtag ctagcggcct cggcggccga attcttgcgt tcgaagcttg gcaatccggt    1500
actgttggta aagccaccat gg                                             1522

<210> SEQ ID NO 47
<211> LENGTH: 1134
<212> TYPE: DNA
<213> ORGANISM: Artificial Sequence
<220> FEATURE:
<223> OTHER INFORMATION: A synthetic construct.

<400> SEQUENCE: 47
gcggccgcaa atgctaaacc actgcagtgg ttaccagtgc ttgatcagtg aggcaccgat     60
ctcagcgatc tgcctatttc gttcgtccat agtggcctga ctccccgtcg tgtagatcac    120
tacgattcgt gagggcttac catcaggccc cagcgcagca atgatgccgc gagagccgcg    180
ttcaccggcc cccgatttgt cagcaatgaa ccagccagca gggagggccg agcgaagaag    240
tggtcctgct actttgtccg cctccatcca gtctatgagc tgctgtcgtg atgctagagt    300
aagaagttcg ccagtgagta gtttccgaag agttgtggcc attgctactg gcatcgtggt    360
atcacgctcg tcgttcggta tggcttcgtt caactctggt tcccagcggt caagccgggt    420
cacatgatca cccatattat gaagaaatgc agtcagctcc ttagggcctc cgatcgttgt    480
cagaagtaag ttggccgcgg tgttgtcgct catggtaatg cagcactac acaattctct    540 taccgtcatg ccatccgtaa gatgcttttc cgtgaccggc gagtactcaa ccaagtcgtt    600
ttgtgagtag tgtatacggc gaccaagctg ctcttgcccg gcgtctatac gggacaacac    660
cgcgccacat agcagtactt tgaaagtgct catcatcggg aatcgttctt cggggcggaa    720
agactcaagg atcttgccgc tattgagatc cagttcgata tagcccactc ttgcacccag    780
ttgatcttca gcatcttta ctttccaccag cgtttcgggg tgtgcaaaaa caggcaagca    840
aaatgccgca aagaagggaa tgagtgcgac acgaaaatgt tggatgctca tactcgtcct    900
ttttcaatat tattgaagca tttatcaggg ttactagtac gtctctcaag agatttgtgc    960
atacacagtg actcatactt tcaccaatac tttgcatttt ggataaatac tagacaactt   1020
tagaagtgaa ttatttatga ggttgtctta aaattaaaaa ttacaaagta ataaatcaca   1080
ttgtaatgta ttttgtgtga tacccagagg tttaaggcaa cctattactc ttat         1134

<210> SEQ ID NO 48
<211> LENGTH: 319
<212> TYPE: DNA
<213> ORGANISM: Artificial Sequence
<220> FEATURE:
<223> OTHER INFORMATION: A synthetic construct.

<400> SEQUENCE: 48
actagtacgt ctctcaagga taagtaagta atattaaggt acgggaggta cttggagcgg     60
ccgcaataaa atatctttat tttcattaca tctgtgtgtt ggttttttgt gtgaatcgat    120
agtactaaca tacgctctcc atcaaaacaa aacgaaacaa acaaactag caaaataggc    180 tgtccccagt gcaagtgcag gtgccagaac atttctctgg cctaagtggc cggtaccgag    240
ctcgctagcc tcgaggatat cagatctggc ctcggcggcc aagcttggca atccggtact    300
gttggtaaag ccaccatgg                                                 319
```

<210> SEQ ID NO 49
<211> LENGTH: 320
<212> TYPE: DNA
<213> ORGANISM: Artificial Sequence
<220> FEATURE:
<223> OTHER INFORMATION: A synthetic construct.

<400> SEQUENCE: 49

```
actagtacgt ctctcaagga taagtaagta atattaaggt acgggaggta ttggacaggc      60
cgcaataaaa tatctttatt ttcattacat ctgtgtgttg gttttttgtg tgaatcgata     120
gtactaacat acgctctcca tcaaaacaaa acgaaacaaa acaaactagc aaaataggct     180
gtccccagtg caagtgcagg tgccagaaca tttctctggc ctaactggcc ggtacctgag     240
ctcgctagcc tcgaggatat caagatctgg cctcggcggc caagcttggc aatccggtac     300
tgttggtaaa gccaccatgg                                                  320
```

<210> SEQ ID NO 50
<211> LENGTH: 5
<212> TYPE: DNA
<213> ORGANISM: Artificial Sequence
<220> FEATURE:
<223> OTHER INFORMATION: A synthetic construct.

<400> SEQUENCE: 50

```
tataa                                                                    5
```

<210> SEQ ID NO 51
<211> LENGTH: 6
<212> TYPE: DNA
<213> ORGANISM: Artificial Sequence
<220> FEATURE:
<223> OTHER INFORMATION: A synthetic construct.

<400> SEQUENCE: 51

```
stratg                                                                   6
```

<210> SEQ ID NO 52
<211> LENGTH: 9
<212> TYPE: DNA
<213> ORGANISM: Artificial Sequence
<220> FEATURE:
<223> OTHER INFORMATION: A synthetic construct.
<220> FEATURE:
<221> NAME/KEY: misc_feature
<222> LOCATION: 4, 6, 7
<223> OTHER INFORMATION: n = A,T,C or G

<400> SEQUENCE: 52

```
mttncnnma                                                                9
```

<210> SEQ ID NO 53
<211> LENGTH: 5
<212> TYPE: DNA
<213> ORGANISM: Artificial Sequence
<220> FEATURE:
<223> OTHER INFORMATION: A synthetic construct.

<400> SEQUENCE: 53

```
tratg                                                                    5
```

<210> SEQ ID NO 54
<211> LENGTH: 38
<212> TYPE: DNA
<213> ORGANISM: Artificial Sequence
<220> FEATURE:
<223> OTHER INFORMATION: A synthetic construct.

<400> SEQUENCE: 54
gtactgagac gacgccagcc caagcttagg cctgagtg                              38

<210> SEQ ID NO 55
<211> LENGTH: 38
<212> TYPE: DNA
<213> ORGANISM: Artificial Sequence
<220> FEATURE:
<223> OTHER INFORMATION: A synthetic construct.

<400> SEQUENCE: 55
ggcatgagcg tgaactgact gaactagcgg ccgccgag                              38

<210> SEQ ID NO 56
<211> LENGTH: 24
<212> TYPE: DNA
<213> ORGANISM: Artificial Sequence
<220> FEATURE:
<223> OTHER INFORMATION: A synthetic construct.

<400> SEQUENCE: 56
ggatcccatg gtgaagcgtg agaa                                             24

<210> SEQ ID NO 57
<211> LENGTH: 21
<212> TYPE: DNA
<213> ORGANISM: Artificial Sequence
<220> FEATURE:
<223> OTHER INFORMATION: A synthetic construct.

<400> SEQUENCE: 57
ggatcccatg gtgaaacgcg a                                                21

<210> SEQ ID NO 58
<211> LENGTH: 31
<212> TYPE: DNA
<213> ORGANISM: Artificial Sequence
<220> FEATURE:
<223> OTHER INFORMATION: A synthetic construct.

<400> SEQUENCE: 58
ctagcttttt tttctagata atcatgaaga c                                     31

<210> SEQ ID NO 59
<211> LENGTH: 32
<212> TYPE: DNA
<213> ORGANISM: Artificial Sequence
<220> FEATURE:
<223> OTHER INFORMATION: A synthetic construct.

<400> SEQUENCE: 59
gcgtagccat ggtaaagcgt gagaaaaatg tc                                    32

<210> SEQ ID NO 60
<211> LENGTH: 33
<212> TYPE: DNA
<213> ORGANISM: Artificial Sequence
<220> FEATURE:
<223> OTHER INFORMATION: A synthetic construct.

<400> SEQUENCE: 60
ccgactctag attactaacc gccggccttc acc                                   33

<210> SEQ ID NO 61
<211> LENGTH: 54
<212> TYPE: DNA
<213> ORGANISM: Artificial Sequence
<220> FEATURE:
<223> OTHER INFORMATION: A synthetic construct.

<400> SEQUENCE: 61
caaaaagctt ggcattccgg tactgttggt aaagccacca tggtgaagcg agag     54

<210> SEQ ID NO 62
<211> LENGTH: 26
<212> TYPE: DNA
<213> ORGANISM: Artificial Sequence
<220> FEATURE:
<223> OTHER INFORMATION: A synthetic construct.

<400> SEQUENCE: 62
caattgttgt tgttaacttg tttatt     26

<210> SEQ ID NO 63

<400> SEQUENCE: 63

000

<210> SEQ ID NO 64

<400> SEQUENCE: 64

000

<210> SEQ ID NO 65
<211> LENGTH: 10
<212> TYPE: DNA
<213> ORGANISM: Artificial Sequence
<220> FEATURE:
<223> OTHER INFORMATION: A synthetic construct.

<400> SEQUENCE: 65
caccatggct     10

<210> SEQ ID NO 66
<211> LENGTH: 40
<212> TYPE: DNA
<213> ORGANISM: Artificial Sequence
<220> FEATURE:
<223> OTHER INFORMATION: A synthetic construct.

<400> SEQUENCE: 66
aaccatggct tccaaggtgt acgaccccga gcaacgcaaa     40

<210> SEQ ID NO 67
<211> LENGTH: 40
<212> TYPE: DNA
<213> ORGANISM: Artificial Sequence
<220> FEATURE:
<223> OTHER INFORMATION: A synthetic construct.

<400> SEQUENCE: 67
gctctagaat tactgctcgt tcttcagcac gcgctccacg     40

<210> SEQ ID NO 68
<211> LENGTH: 31
<212> TYPE: DNA
<213> ORGANISM: Artificial Sequence

```
<220> FEATURE:
<223> OTHER INFORMATION: A synthetic construct.

<400> SEQUENCE: 68
cgctagccat ggcttcgaaa gtttatgatc c                                      31

<210> SEQ ID NO 69
<211> LENGTH: 25
<212> TYPE: DNA
<213> ORGANISM: Artificial Sequence
<220> FEATURE:
<223> OTHER INFORMATION: A synthetic construct.

<400> SEQUENCE: 69
ggccagtaac tctagaatta ttgtt                                             25

<210> SEQ ID NO 70
<211> LENGTH: 1092
<212> TYPE: DNA
<213> ORGANISM: Artificial Sequence
<220> FEATURE:
<223> OTHER INFORMATION: A synthetic construct.

<400> SEQUENCE: 70
aagcttgcta gcgccaccat gaagaagccc gagctcaccg ctaccagcgt tgaaaaattt        60
ctcatcgaga agttcgacag tgtgagcgac ctgatgcagt tgtcggaggg cgaagagagc       120
cgagccttca gcttcgatgt cggcggacgg ggctatgtac tgcgggtgaa tagctgcgct       180
gatggcttct acaaagaccg ctacgtgtac cgccacttcg ccagcgctgc actacccatc       240
cccgaagtgt tggacatcgg cgagttcagc gagagcctga catactgcat cagtagacgc       300
gcccaaggcg ttactctcca agacctcccc gaaacagagc tgcctgctgt gttacagcct       360
gtcgccgaag ctatggatgc tattgccgcc gccgacctca gtcaaaccag cggcttcggc       420
ccattcgggc ccaaggcat cggccagtac acaacctggc gggatttcat ttgcgccatt       480
gctgatcccc atgtctacca ctggcagacc gtgatggacg acaccgtgtc cgccagcgta       540
gctcaagccc tggacgaact gatgctgtgg gccgaagact gtcccgaggt gcgccacctc       600
gtccatgccg acttcggcag caacaacgtc ctgaccgaca acggccgcat caccgccgta       660
atcgactggt ccgaagctat gttcggggac agtcagtacg aggtggccaa catcttcttc       720
tggcggccct ggctggcttg catggagcag cagactcgct acttcgagcg ccggcatccc       780
gagctggccg gcagccctcg tctgcgagcc tacatgctgc gcatcggcct ggatcagctc       840
taccagagcc tcgtggacgg caacttcgac gatgctgcct gggctcaagg ccgctgcgat       900
gccatcgtcc gcagcgggc cggcaccgtc ggtcgcacac aaatcgctcg ccggagcgcc       960
gccgtatgga ccgacggctg cgtcgaggtg ctggccgaca gcggcaaccg ccggcccagt      1020
acacgaccgc gcgctaagga gggtggcgga gggagcggtg gcggaggttc ctacgtatag      1080
tctagactcg ag                                                          1092

<210> SEQ ID NO 71
<211> LENGTH: 1093
<212> TYPE: DNA
<213> ORGANISM: Artificial Sequence
<220> FEATURE:
<223> OTHER INFORMATION: A synthetic construct.
```

<400> SEQUENCE: 71

```
aagcttgcta gcgccaccat gaagaagccc gagctcaccg ctaccagcgt tgaaaaattt      60
ctcatcgaga agttcgacag tgtgagcgac ctgatgcagt tgtcggaggg cgaagagagc     120
cgagccttca gcttcgatgt cggcggacgc ggctatgtac tgcgggtgaa tagctgcgct     180
gatggcttct acaaagaccg ctacgtgtac cgccacttcg ccagcgctgc actacccatc     240
cccgaagtgt tggacatcgg cgagttcagc gagagcctga catactgcat cagtagacgc     300
gcccaaggcg ttactctcca agacctcccc gaaacagagc tgcctgctgt gttacagcct     360
gtcgccgaag ctatgatgc tattgccgcc gccgacctca gtcaaaccag cggcttcggc      420
ccattcgggc ccaaggcat cggccagtac acaacctggc gggatttcat ttgcgccatt      480
gctgatcccc atgtctacca ctggcagacc gtgatggacg acaccgtgtc cgccagcgta     540
gctcaagccc tggacgaact gatgctgtgg gccgaagact gtcccgaggt cgccaccctc     600
gtccatgccg acttcggcag caacaacgtc ctgaccgaca acggccgcat caccgccgta     660
atcgactggt ccgaagctat gttcggggac agtcagtacg aggtggccaa catcttcttc     720
tggcggccct ggctggcttg catggagcag cagactcgct acttcgagcg ccggcatccc     780
gagctggccg gcagccctcg tctgcgagcc tacatgctgc gcatcggcct ggatcagctc     840
taccagagcc tcgtggacgg caacttcgac gatgctgcct gggctcaagg ccgctgcgat     900
gccatcgtcc gcagcggggc cggcaccgtc ggtcgcacac aaatcgctcg ccggagcgca     960
gccgtatgga ccgacggctg cgtcgaggtg ctggccgaca cggcaaccg ccggcccagt     1020
acacgaccgc gcgctaagga aggcggtgga ggtagtggtg gcggaggtag ctacgtataa    1080
ctctagactc gag                                                      1093
```

<210> SEQ ID NO 72
<211> LENGTH: 813
<212> TYPE: DNA
<213> ORGANISM: Artificial Sequence
<220> FEATURE:
<223> OTHER INFORMATION: A synthetic construct.

<400> SEQUENCE: 72

```
gctagcgcca ccatgatcga acaagacggc ctccatgctg gcagtcccgc agcttgggtc      60
gaacgcttgt tcgggtacga ctgggcccag cagaccatcg gatgtagcga tgcggccgtg     120
ttccgtctaa gcgctcaagg ccggcccgtg ctgttcgtga agaccgacct gagcggcgcc     180
ctgaacgagc ttcaagacga ggctgcccgc ctgagctggc tggccaccac cggtgtaccc     240
tgcgccgctg tgttggatgt tgtgaccgaa gccggccggg actggctgct gctgggcgag     300
gtccctggcc aggatctgct gagcagccac cttgccccg ctgagaaggt ttccatcatg      360
gccgatgcaa tgcggcgcct gcacaccctg accccgcta catgcccctt cgaccaccag     420
gctaagcatc ggatcgagcg tgctcggacc cgcatggagg ccggcctggt ggaccaggac     480
gacctggacg aggagcatca gggcctggcc ccgctgaac tgttcgcccg cctgaaagcc     540
cgcatgccgg acgtgagga cctggttgtg acacatggtg atgcctgcct ccctaacatc     600
atggtcgaga atggccgctt ctccggcttc atcgactgcg gtcgcctagg agttgccgac     660
cgctaccagg acatcgccct ggccaccgc gacatgctg aggagcttgg cggcgagtgg     720
gccgaccgct tcttagtctt gtacggcatc gcagctcccg acagccagcg catcgccttc     780
taccgcctgc tcgacgagtt cttttaatct aga                                  813
```

<210> SEQ ID NO 73
<211> LENGTH: 816
<212> TYPE: DNA
<213> ORGANISM: Artificial Sequence
<220> FEATURE:
<223> OTHER INFORMATION: A synthetic construct.

<400> SEQUENCE: 73

```
gctagcgcca ccatgatcga acaagacggc ctccatgctg gcagtcccgc agcttgggtc      60
gaacgcttgt tcgggtacga ctgggcccag cagaccatcg gatgtagcga tgcggccgtg     120
ttccgtctaa gcgctcaagg ccggcccgtg ctgttcgtga agaccgacct gagcggcgcc     180
ctgaacgagc ttcaagacga ggctgcccgc ctgagctggc tggccaccac cggcgtaccc     240
tgcgccgctg tgttggatgt tgtgaccgaa gccggccggg actggctgct gctgggcgag     300
gtccctggcc aggatctgct gagcagccac cttgcccccg ctgagaaggt ttctatcatg     360
gccgatgcaa tgcggcgcct gcacaccctg gaccccgcta cctgccccctt cgaccaccag     420
gctaagcatc ggatcgagcg tgctcggacc cgcatggagg ccggcctggt ggaccaggac     480
gacctggacg aggagcatca gggcctggcc ccgctgaac tgttcgcccg actgaaagcc      540
cgcatgccgg acggtgagga cctggttgtc acacacggag atgcctgcct ccctaacatc     600
atggtcgaga tggccgcttc ccggcttc atcgactgcg gtcgcctagg agttgccgac     660
cgctaccagg acatcgccct ggccacccgc gacatcgctg aggagcttgg cggcgagtgg     720
gccgaccgct tcttagtctt gtacggcatc gcagctcccg acagccagcg catcgccttc     780
taccgcttgc tcgacgagtt cttttaatga tctaga                               816
```

<210> SEQ ID NO 74
<211> LENGTH: 1252
<212> TYPE: DNA
<213> ORGANISM: Artificial Sequence
<220> FEATURE:
<223> OTHER INFORMATION: A synthetic construct.

<400> SEQUENCE: 74

```
gcggccgcaa atgctaaacc actgcagtgg ttaccagtgc ttgatcagtg aggcaccgat      60
ctcagcgatc tgcctatttc gttcgtccat agtggcctga ctccccgtcg tgtagatcac     120
tacgattcgt gagggcttac catcaggccc cagcgcagca atgatgccgc gagagccgcg     180
ttcaccggcc cccgatttgt cagcaatgaa ccagccagca gggagggccg agcgaagaag     240
tggtcctgct actttgtccg cctccatcca gtctatgagc tgctgtcgtg atgctagagt     300
aagaagttcg ccagtgagta gtttccgaag agttgtggcc attgctactg gcatcgtggt     360
atcacgctcg tcgttcggta tggcttcgtt caactctggt tcccagcggt caagccgggt     420
cacatgatca cccatattat gaagaaatgc agtcagctcc ttagggcctc cgatcgttgt     480
cagaagtaag ttggccgcgg tgttgtcgct catggtaatg gcagcactac acaattctct     540
taccgtcatg ccatccgtaa gatgcttttc cgtgaccggc gagtactcaa ccaagtcgtt     600
ttgtgagtag tgtatacggc gaccaagctg ctcttgcccg gcgtctatac gggacaacac     660
cgcgccacat agcagtactt tgaaagtgct catcatcggg aatcgttctt cggggcggaa     720
agactcaagg atcttgccgc tattgagatc cagttcgata tagcccactc ttgcacccag     780
ttgatcttca gcatcttta ctttcaccag cgtttcgggg tgtgcaaaaa caggcaagca     840
aaatgccgca agaagggaa tgagtgcgac acgaaaatgt tggatgctca tactcgtcct     900
ttttcaatat tattgaagca tttatcaggg ttactagtac gtctctcaag gataagtaag     960
```

-continued

```
taatattaag gtacgggagg tattggacag gccgcaataa aatatcttta ttttcattac      1020
atctgtgtgt tggtttttg tgtgaatcga tagtactaac atacgctctc catcaaaaca      1080
aaacgaaaca aaacaaacta gcaaaatagg ctgtccccag tgcaagtgca ggtgccagaa      1140
catttctctg gcctaactgg ccggtacctg agctcgctag cctcgaggat atcaagatct      1200
ggcctcggcg ccaagcttg gcaatccggt actgttggta aagccaccat gg              1252
```

<210> SEQ ID NO 75

<400> SEQUENCE: 75

000

<210> SEQ ID NO 76
<211> LENGTH: 228
<212> TYPE: DNA
<213> ORGANISM: Artificial Sequence
<220> FEATURE:
<223> OTHER INFORMATION: A synthetic construct.

<400> SEQUENCE: 76

```
actagtcgtc tctcttgaga gaccgcgatc gccaccatga taagtaagta atattaaata       60
agtaaggcct gagtggccct cgagccagcc ttgagttggt tgagtccaag tcacgtctgg      120
agatctggta cctacgcgtg agctctacgt agctagcggc ctcggcggcc gaattcttgc      180
gatctaagta agcttggcat tccggtactg ttggtaaagc caccatgg                  228
```

<210> SEQ ID NO 77
<211> LENGTH: 228
<212> TYPE: DNA
<213> ORGANISM: Artificial Sequence
<220> FEATURE:
<223> OTHER INFORMATION: A synthetic construct.

<400> SEQUENCE: 77

```
actagtacgt ctctcttgag agaccgcgat cgccaccatg ataagtaagt aatattaaat       60
aagtaaggcc tgagtggccc tcgagtccag ccttgagttg gttgagtcca agtcacgtct      120
ggagatctgg taccttacgc gtagagctct acgtagctag cggcctcggc ggccgaattc      180
ttgcgatcta agcttggcaa tccggtactg ttggtaaagc caccatgg                  228
```

<210> SEQ ID NO 78
<211> LENGTH: 230
<212> TYPE: DNA
<213> ORGANISM: Artificial Sequence
<220> FEATURE:
<223> OTHER INFORMATION: A synthetic construct.

<400> SEQUENCE: 78

```
actagtacgt ctctcttgag agaccgcgat cgcatgccta ggtaggtagt attagagcat       60
aggtagaggc ctaagtggcc ctcgagtcca gccttgagtt ggttgagtcc aagtcacgtc      120
tggagatctg gtaccttacg cgtatgagct ctacgtagct agcggcctcg gcggccgaat      180
tcttgcgatc taagcttggc aatccggtac tgttggtaaa gccaccatgg                230
```

<210> SEQ ID NO 79
<211> LENGTH: 234
<212> TYPE: DNA
<213> ORGANISM: Artificial Sequence
<220> FEATURE:
<223> OTHER INFORMATION: A synthetic construct.

<400> SEQUENCE: 79

```
actagtacgt ctctcttgag agaccgcgat cgccaccatg tctaggtagg tagtaaacga      60
aagggcttaa aggcctaagt ggccctcgag tccagccttg agttggttga gtccaagtca     120
cgtttggaga tctggtacct tacgcgtatg agctctacgt agctagcggc ctcggcggcc     180
gaattcttgc gatctaagct tggcaatccg gtactgttgg taaagccacc atgg          234
```

<210> SEQ ID NO 80
<211> LENGTH: 938
<212> TYPE: DNA
<213> ORGANISM: Artificial Sequence
<220> FEATURE:
<223> OTHER INFORMATION: A synthetic construct.

<400> SEQUENCE: 80

```
actagtaacc ctgataaatg cttcaataat attgaaaaag gaagagtatg agtattcaac      60
atttccgtgt cgcccttatt cccttttttg cggcattttg ccttcctgtt tttgctcacc     120
cagaaacgct ggtgaaagta aaagatgctg aagatcagtt gggtgcacga gtgggttaca     180
tcgaactgga tctcaacagc ggtaagatcc ttgagagttt cgccccgaa gaacgttttc      240
caatgatgag cacttttaaa gttctgctat gtggcgcggt attatcccgt attgacgccg     300
ggcaagagca actcggtcgc cgcatacact attctcagaa tgacttggtt gagtactcac     360
cagtcacaga aaagcatctt acggatggca tgacagtaag agaattatgc agtgctgcca     420
taaccatgag tgataacacc gcggccaact tacttctgac aacgatcgga ggaccgaagg     480
agctaaccgc ttttttgcac aacatggggg atcatgtaac tcgccttgat cgttgggaac     540
cggagctgaa tgaagccata ccaaacgacg agcgtgacac cacgatgcct gtagcaatgg     600
caacaacgtt gcgcaaacta ttaactggcg aactacttac tctagcttcc cggcaacaat     660
taatagactg gatggaggcg gataaagttg caggaccact tctgcgctcg gcccttccgg     720
ctggctggtt tattgctgat aaatctggag ccggtgagcg tggctctcgc ggtatcattg     780
cagcactggg gccagatggt aagccctccc gtatcgtagt tatctacacg acggggagtc     840
aggcaactat ggatgaacga aatagacaga tcgctgagat aggtgcctca ctgattaagc     900
attggtaacc actgcagtgg ttttccttt gcggccgc                             938
```

<210> SEQ ID NO 81
<211> LENGTH: 938
<212> TYPE: DNA
<213> ORGANISM: Artificial Sequence
<220> FEATURE:
<223> OTHER INFORMATION: A synthetic construct.

<400> SEQUENCE: 81

```
actagtaacc ctgataaatg ctgcaaacat attgaaaaag gaagagtatg agtattcaac      60
atttccgtgt cgcactcatt cccttctttg cggcattttg cttgcctgtt tttgcacacc     120
ccgaaacgct ggtgaaagta aaagatgctg aagatcaact gggtgcacga gtgggctata     180
tcgaactgga tctcaatagc ggtaagatcc ttgagagttt cgccccgaa gaacgttttc      240
caatgatgag cacttttaaa gttctgctat gtggcgcggt attatcccgt attgacgccg     300
ggcaagagca gctcggtcgc cgcatacact actcacagaa cgacttggtt gagtactcgc     360
cggtcacgga aaagcatctt acggatggca tgacagtaag agaattgtgt agtgctgcca     420
taaccatgag tgataacacc gcggccaact tacttctgac aacgatcgga ggccctaagg     480
agctgaccgc attttttgcac aacatggggg atcatgtaac ccggcttgat cgttgggaac     540
```

| | | |
|---|---|---|
| cggagctgaa cgaagccata ccgaacgacg agcgtgacac cacgatgcct gtagcaatgg | 600 | |
| caacaacgtt gcgcaaacta ctcactggcg aacttctcac tctagcatca cgacagcaac | 660 | |
| tcatagactg gatggaggcg ataaagttg caggaccact tctgcgctcg gcccttccgg | 720 | |
| ctggctggtt tatagctgat aaatccggtg ccggtgaacg cggctctcgc gggatcattg | 780 | |
| ctgcgctggg gccagatggt aagccctcac gaatcgtagt tatctacacg acggggagtc | 840 | |
| aggcaactat ggatgaacga aatagacaga tcgctgagat aggtgcctca ctgatcaagc | 900 | |
| actggtagcc actgcagtgg tttagctttt gcggccgc | 938 | |

<210> SEQ ID NO 82
<211> LENGTH: 938
<212> TYPE: DNA
<213> ORGANISM: Artificial Sequence
<220> FEATURE:
<223> OTHER INFORMATION: A synthetic construct.

<400> SEQUENCE: 82

| | | |
|---|---|---|
| actagtaacc ctgacaaatg ctgcaaacat attgaaaaag gaagagtatg agcatccaac | 60 | |
| attttcgtgt cgcactcatt cccttctttg cggcattttg cttgcctgtt tttgcacacc | 120 | |
| ccgaaacgct ggtgaaagta aaagatgctg aagatcaact gggtgcaaga gtgggctata | 180 | |
| tcgaactgga tctcaatagc ggcaagatcc ttgagtcttt cgccccgaa gaacgttttc | 240 | |
| cgatgatgag cacttttaaa gttctgctat gtggcgcggt gttgtcccgt atagacgccg | 300 | |
| ggcaagagca gcttggtcgc cgtatacact actcacaaaa cgacttggtt gagtactcgc | 360 | |
| cggtcacgga aaagcatctt acggatggca tgacggtaag agaattgtgt agtgctgcca | 420 | |
| ttaccatgag cgacaatacc gcggccaact tacttctgac aacgatcgga ggccctaagg | 480 | |
| agctgaccgc attttgcac aacatggggg atcatgtaac ccggcttgac cgctgggaac | 540 | |
| cggagctgaa cgaagccata ccgaacgacg agcgtgacac cacgatgcct gtagcaatgg | 600 | |
| caacaacgtt gcggaaacta ctcactggcg aacttctcac tctagcatca cgacagcagc | 660 | |
| tcatagactg gatggaggcg acaaagtag caggaccact tcttcgctcg gccctccctg | 720 | |
| ctggctggtt cattgctgat aaatccggtg ccggtgaacg cggctctcgc gggatcattg | 780 | |
| ctgcgctggg gcctgatggt aagccctcac gaatcgtagt aatctacacg acggggagtc | 840 | |
| aggccactat ggacgaacga aatagacaga tcgctgagat cggtgcctca ctgatcaagc | 900 | |
| actggtaacc actgcagtgg tttagcattt gcggccgc | 938 | |

<210> SEQ ID NO 83
<211> LENGTH: 938
<212> TYPE: DNA
<213> ORGANISM: Artificial Sequence
<220> FEATURE:
<223> OTHER INFORMATION: A synthetic construct.

<400> SEQUENCE: 83

| | | |
|---|---|---|
| actagtaacc ctgacaaatg ctgcaaacat attgaaaaag gaagagtatg agcatccaac | 60 | |
| attttcgtgt cgcactcatt cccttctttg cggcattttg cttgcctgtt tttgcacacc | 120 | |
| ccgaaacgct ggtgaaagta aaagatgctg aagatcaact gggtgcaaga gtgggctata | 180 | |
| tcgaactgga tctcaatagc ggcaagatcc ttgagtcttt ccgccccgaa gaacgttttc | 240 | |
| cgatgatgag cactttcaaa gtactgctat gtggcgcggt gttgtcccgt atagacgccg | 300 | |
| ggcaagagca gcttggtcgc cgtatacact actcacaaaa cgacttggtt gagtactcgc | 360 | |
| cggtcacgga aaagcatctt acggatggca tgacggtaag agaattgtgt agtgctgcca | 420 | |

```
ttaccatgag cgataatacc gcggccaact tacttctgac aacgatcgga ggccctaagg    480
agctgaccgc attttgcac aacatgggtg atcatgtgac ccggcttgac cgctgggaac    540
cggagctgaa cgaagccata ccgaacgacg agcgtgacac cacgatgcct gtagcaatgg    600
caacaactct tcggaaacta ctcactggcg aacttctcac tctagcatca cgacagcagc    660
tcatagactg gatggaggcg gacaaagtag caggaccact tcttcgctcg ccctccctg    720 ctggctggtt cattgctgat aaatctggag ccggtgagcg tggctctcgc ggtatcattg    780
ctgcgctggg gcctgatggt aagccctcac gaatcgtagt aatctacacg acggggagtc    840
aggccactat ggacgaacga aatagacaga tcgctgagat cggtgcctca ctgatcaagc    900
actggtaacc actgcagtgg tttagcattt gcggccgc                            938
```

<210> SEQ ID NO 84
<211> LENGTH: 938
<212> TYPE: DNA
<213> ORGANISM: Artificial Sequence
<220> FEATURE:
<223> OTHER INFORMATION: A synthetic construct.

<400> SEQUENCE: 84

```
actagtaacc ctgacaaatg ctgcaaacat attgaaaaag gaagagtatg agcatccaac     60
attttcgtgt cgcactcatt cccttctttg cggcattttg cttgcctgtt tttgcacacc    120
ccgaaacgct ggtgaaagta aaagatgctg aagatcaact gggtgcaaga gtgggctata    180
tcgaactgga tctcaatagc ggcaagatcc ttgagtcttt ccgccccgaa gaacgattcc    240
cgatgatgag cactttcaaa gtactgctat gtggcgcggt gttgtcccgt atagacgccg    300
ggcaagagca gcttggtcgc cgtatacact actcacaaaa cgacttggtt gagtactcgc    360
cggtcacgga aaagcatctt acggatggca tgacggtaag agaattgtgt agtgctgcca    420
ttaccatgag cgataatacc gcggccaact tacttctgac aacgatcgga ggccctaagg    480
agctgaccgc attttgcac aacatgggtg atcatgtgac ccggcttgac cgctgggaac    540
cggagctgaa cgaagccata ccgaacgacg agcgtgatac cacgatgcca gtagcaatgg    600
ccacaactct tcggaaacta ctcactggcg aacttctcac tctagcatca cgacagcagc    660
tcatagactg gatggaggcg gacaaagtag caggaccact tcttcgctcg ccctccctg    720 ctggctggtt cattgctgac aaatccggtg ccggtgaacg cggctctcgc ggcatcattg    780
ctgcgctggg gcctgatggt aagccctcac gaatcgtagt aatctacacg acggggagtc    840
aggccactat ggacgaacga aatagacaga tcgctgagat cggtgcctca ctgatcaagc    900
actggtaacc actgcagtgg tttagcattt gcggccgc                            938
```

<210> SEQ ID NO 85

<400> SEQUENCE: 85

000

<210> SEQ ID NO 86

<400> SEQUENCE: 86

000

<210> SEQ ID NO 87

<400> SEQUENCE: 87

000

<210> SEQ ID NO 88
<211> LENGTH: 1038
<212> TYPE: DNA
<213> ORGANISM: Artificial Sequence
<220> FEATURE:
<223> OTHER INFORMATION: A synthetic construct.

<400> SEQUENCE: 88

```
atgaagaagc ccgaactcac cgctaccagc gttgaaaaat ttctcatcga gaagttcgac      60
agtgtgagcg acctgatgca gttgtcggag ggcgaagaga gccgagcctt cagcttcgat     120
gtcggcggac gcggctatgt actgcgggtg aatagctgcg ctgatggctt ctacaaagac     180
cgctacgtgt accgccactt cgccagcgct gcactaccca tccccgaagt gttggacatc     240
ggcgagttca gcgagagcct gacatactgc atcagtagac gcgcccaagg cgttactctc     300
caagacctcc ccgaaacaga gctgcctgct gtgttacagc ctgtcgccga agctatggat     360
gctattgccg ccgccgacct cagtcaaacc agcggcttcg gcccattcgg ccccaaggc     420
atcggccagt acacaacctg gcgggatttc atttgcgcca ttgctgatcc ccatgtctac     480
cactggcaga ccgtgatgga cgacaccgtg tccgccagcg tagctcaagc cctggacgaa     540
ctgatgctgt gggccgaaga ctgtcccgag gtgcgccacc tcgtccatgc cgacttcggc     600
agcaacaacg tcctgaccga caacggccgc atcaccgccg taatcgactg gtccgaagct     660
atgttcgggg acagtcagta cgaggtggcc aacatcttct tctggcggcc ctggctggct     720
tgcatggagc agcagactcg ctacttcgag cgccggcatc ccgagctggc cggcagccct     780
cgtctgcgag cctacatgct gcgcatcggc ctggatcagc tctaccagag cctcgtggac     840
ggcaacttcg acgatgctgc ctgggctcaa ggccgctgcg atgccatcgt ccgcagcggg     900
gccggcaccg tcggtcgcac acaaatcgct cgccggagcg cagccgtatg gaccgacggc     960
tgcgtcgagg tgctggccga cagcggcaac cgccggccca gtacacgacc gcgcgctaag    1020
gaggtaggtc gagtttaa                                                  1038
```

<210> SEQ ID NO 89
<211> LENGTH: 4333
<212> TYPE: DNA
<213> ORGANISM: Artificial Sequence
<220> FEATURE:
<223> OTHER INFORMATION: A synthetic construct.

<400> SEQUENCE: 89

```
ggcctaactg gccggtacct gagctcgcta gcctcgagga tatcaagatc tggcctcggc      60
ggccaagctt ggcaatccgg tactgttggt aaagccacca tggaagatgc caaaaacatt     120
aagaagggcc cagcgccatt ctacccactc gaagacggga ccgccggcga gcagctgcac     180
aaagccatga gcgctacgc cctggtgccc ggcaccatcg cctttaccga cgcacatatc     240
gaggtggaca ttacctacgc cgagtacttc gagatgagcg ttcggctggc agaagctatg     300
aagcgctatg gctgaatac aaaccatcgg atcgtggtgt gcagcgagaa tagcttgcag     360
ttcttcatgc ccgtgttggg tgccctgttc atcggtgtgg ctgtggcccc agctaacgac     420
atctacaacg agcgcgagct gctgaacagc atgggcatca gccagcccac cgtcgtattc     480
gtgagcaaga aagggctgca aaagatcctc aacgtgcaaa agaagctacc gatcatacaa     540
```

```
aagatcatca tcatggatag caagaccgac taccagggct tccaaagcat gtacaccttc      600
gtgacttccc atttgccacc cggcttcaac gagtacgact tcgtgcccga gagcttcgac      660
cgggacaaaa ccatcgccct gatcatgaac agtagtggca gtaccggatt gcccaagggc      720
gtagccctac cgcaccgcac cgcttgtgtc cgattcagtc atgcccgcga ccccatcttc      780
ggcaaccaga tcatcccccga caccgctatc ctcagcgtgg tgccatttca ccacggcttc      840
ggcatgttca ccacgctggg ctacttgatc tgcggctttc gggtcgtgct catgtaccgc      900
ttcgaggagg agctattctt gcgcagcttg caagactata agattcaatc tgccctgctg      960
gtgcccacac tatttagctt cttcgctaag agcactctca tcgacaagta cgacctaagc     1020
aacttgcacg agatcgccag cggcggggcg ccgctcagca aggaggtagg tgaggccgtg     1080
gccaaacgct tccacctacc aggcatccgc cagggctacg gcctgacaga aacaaccagc     1140
gccattctga tcaccccccga aggggacgac aagcctggcg cagtaggcaa ggtggtgccc     1200
ttcttcgagg ctaaggtggt ggacttggac accggtaaga cactgggtgt gaaccagcgc     1260
ggcgagctgt gcgtccgtgg ccccatgatc atgagcggct acgttaacaa ccccgaggct     1320
acaaacgctc tcatcgacaa ggacggctgg ctgcacagcg cgacatcgc ctactgggac      1380 gaggacgagc acttcttcat cgtggaccgg ctgaagagcc tgatcaaata caagggctac     1440
caggtagccc cagccgaact ggagagcatc ctgctgcaac accccaacat cttcgacgcc     1500
ggggtcgccg gcctgcccga cgacgatgcc ggcgagctgc ccgccgcagt cgtcgtgctg     1560
gaacacggta aaaccatgac cgagaaggag atcgtggact atgtggccag ccaggttaca     1620
accgccaaga agctgcgcgg tggtgttgtg ttcgtggacg aggtgcctaa aggactgacc     1680
ggcaagttgg acgcccgcaa gatccgcgag attctcatta aggccaagaa gggcggcaag     1740
atcgccgtgt aataattcta gagtcggggc ggccggccgc ttcgagcaga catgataaga     1800
tacattgatg agtttggaca aaccacaact agaatgcagt gaaaaaaatg ctttatttgt     1860
gaaatttgtg atgctattgc tttatttgta accattataa gctgcaataa acaagttaac     1920
aacaacaatt gcattcattt tatgtttcag gttcaggggg aggtgtggga ggttttttaa     1980
agcaagtaaa acctctacaa atgtggtaaa atcgataagg atccgtcgac cgatgccctt     2040
gagagccttc aacccagtca gctccttccg gtgggcgcgg ggcatgacta tcgtcgccgc     2100
acttatgact gtcttcttta tcatgcaact cgtaggacag gtgccggcag cgctcttccg     2160
cttcctcgct cactgactcg ctgcgctcgg tcgttcggct gcggcgagcg gtatcagctc     2220
actcaaaggc ggtaatacgg ttatccacag aatcagggga taacgcagga agaacatgt     2280 gagcaaaagg ccagcaaaag gccaggaacc gtaaaaaggc cgcgttgctg gcgttttcc      2340 ataggctccg cccccctgac gagcatcaca aaaatcgacg ctcaagtcag aggtggcgaa     2400
acccgacagg actataaaga taccaggcgt ttccccctgg aagctccctc gtgcgctctc     2460
ctgttccgac cctgccgctt accggatacc tgtccgcctt tctcccttcg ggaagcgtgg     2520
cgctttctca tagctcacgc tgtaggtatc tcagttcggt gtaggtcgtt cgctccaagc     2580
tgggctgtgt gcacgaaccc cccgttcagc ccgaccgctg cgccttatcc ggtaactatc     2640
gtcttgagtc aacccggta agacacgact tatcgccact ggcagcagcc actggtaaca     2700
ggattagcag agcgaggtat gtaggcggtg ctacagagtt cttgaagtgg tggcctaact     2760
acggctacac tagaagaaca gtatttggta tctgcgctct gctgaagcca gttaccttcg     2820
gaaaaagagt tggtagctct tgatccggca aacaaaccac cgctggtagc ggtggttttt     2880
ttgtttgcaa gcagcagatt acgcgcagaa aaaaaggatc tcaagaagat cctttgatct     2940
```

| | |
|---|---|
| tttctacggg gtctgacgct cagtggaacg aaaactcacg ttaagggatt ttggtcatga | 3000 |
| gattatcaaa aaggatcttc acctagatcc ttttaaatta aaaatgaagt tttaaatcaa | 3060 |
| tctaaagtat atatgagtaa acttggtctg acagcggccg caaatgctaa accactgcag | 3120 |
| tggttaccag tgcttgatca gtgaggcacc gatctcagcg atctgcctat ttcgttcgtc | 3180 |
| catagtggcc tgactcccg tcgtgtagat cactacgatt cgtgagggct taccatcagg | 3240 |
| ccccagcgca gcaatgatgc cgcgagagcc gcgttcaccg gcccccgatt tgtcagcaat | 3300 |
| gaaccagcca gcagggaggg ccgagcgaag aagtggtcct gctactttgt ccgcctccat | 3360 |
| ccagtctatg agctgctgtc gtgatgctag agtaagaagt tcgccagtga gtagtttccg | 3420 |
| aagagttgtg gccattgcta ctggcatcgt ggtatcacgc tcgtcgttcg gtatggcttc | 3480 |
| gttcaactct ggttcccagc ggtcaagccg ggtcacatga tcacccatat tatgaagaaa | 3540 |
| tgcagtcagc tccttagggc ctccgatcgt tgtcagaagt aagttggccg cggtgttgtc | 3600 |
| gctcatggta atggcagcac tacacaattc tcttaccgtc atgccatccg taagatgctt | 3660 |
| ttccgtgacc ggcgagtact caaccaagtc gttttgtgag tagtgtatac ggcgaccaag | 3720 |
| ctgctcttgc ccggcgtcta tacgggacaa caccgcgcca catagcagta ctttgaaagt | 3780 |
| gctcatcatc gggaatcgtt cttcggggcg gaaagactca aggatcttgc cgctattgag | 3840 |
| atccagttcg atatagccca ctcttgcacc cagttgatct tcagcatctt ttactttcac | 3900 |
| cagcgtttcg gggtgtgcaa aaacaggcaa gcaaaatgcc gcaaagaagg gaatgagtgc | 3960 |
| gacacgaaaa tgttggatgc tcatactcgt ccttttttcaa tattattgaa gcatttatca | 4020 |
| gggttactag tacgtctctc aaggataagt aagtaatatt aaggtacggg aggtattgga | 4080 |
| caggccgcaa taaatatct ttattttcat tacatctgtg tgttggtttt tgtgtgaat | 4140 |
| cgatagtact aacatacgct ctccatcaaa acaaaacgaa acaaaacaaa ctagcaaaat | 4200 |
| aggctgtccc cagtgcaagt gcaggtgcca gaacatttct ctaagtaata ttaaggtacg | 4260 |
| ggaggtattg gacaggccgc aataaaatat ctttattttc attacatctg tgtgttggtt | 4320 |
| ttttgtgtga atc | 4333 |

<210> SEQ ID NO 90
<211> LENGTH: 3522
<212> TYPE: DNA
<213> ORGANISM: Artificial Sequence
<220> FEATURE:
<223> OTHER INFORMATION: A synthetic construct.

<400> SEQUENCE: 90

| | |
|---|---|
| ggcctaactg gccggtacct gagctcgcta gcctcgagga tatcaagatc tggcctcggc | 60 |
| ggccaagctt ggcaatccgg tactgttggt aaagccacca tggcttccaa ggtgtacgac | 120 |
| cccgagcaac gcaaacgcat gatcactggg cctcagtggt gggctcgctg caagcaaatg | 180 |
| aacgtgctgg actccttcat caactactat gattccgaga agcacgccga gaacgccgtg | 240 |
| attttctgc atggtaacgc tgcctccagc tacctgtgga ggcacgtcgt gcctcacatc | 300 |
| gagcccgtgg ctagatgcat catccctgat ctgatcggaa tgggtaagtc cggcaagagc | 360 |
| gggaatggct catatcgcct cctggatcac tacaagtacc tcaccgcttg gttcgagctg | 420 |
| ctgaaccttc caaagaaaat catctttgtg ggccacgact gggggggcttg tctggccttt | 480 |
| cactactcct acgagcacca agacaagatc aaggccatcg tccatgctga gagtgtcgtg | 540 |
| gacgtgatcg agtcctggga cgagtggcct gacatcgagg aggatatcgc cctgatcaag | 600 |
| agcgaagagg gcgagaaaat ggtgcttgag ataacttct tcgtcgagac catgctccca | 660 |

```
agcaagatca tgcggaaact ggagcctgag gagttcgctg cctacctgga gccattcaag    720
gagaagggcg aggttagacg gcctaccctc tcctggcctc gcgagatccc tctcgttaag    780
ggaggcaagc ccgacgtcgt ccagattgtc cgcaactaca acgcctacct tcgggccagc    840
gacgatctgc ctaagatgtt catcgagtcc gaccctgggt tcttttccaa cgctattgtc    900
gagggagcta agaagttccc taacaccgag ttcgtgaagg tgaagggcct ccacttcagc    960
caggaggacg ctccagatga aatgggtaag tacatcaaga gcttcgtgga gcgcgtgctg   1020
aagaacgagc agtaattcta gagtcggggc ggccggccgc ttcgagcaga catgataaga   1080
tacattgatg agtttggaca aaccacaact agaatgcagt gaaaaaaatg ctttatttgt   1140
gaaatttgtg atgctattgc tttatttgta accattataa gctgcaataa acaagttaac   1200
aacaacaatt gcattcattt tatgtttcag gttcaggggg aggtgtggga ggttttttaa   1260
agcaagtaaa acctctacaa atgtggtaaa atcgataagg atccgtcgac cgatgccctt   1320
gagagccttc aacccagtca gctccttccg gtgggcgcgg ggcatgacta tcgtcgccgc   1380
acttatgact gtcttcttta tcatgcaact cgtaggacag gtgccggcag cgctcttccg   1440
cttcctcgct cactgactcg ctgcgctcgg tcgttcggct gcggcgagcg gtatcagctc   1500
actcaaaggc ggtaatacgg ttatccacag aatcagggga taacgcagga agaacatgt   1560
gagcaaaagg ccagcaaaag gccaggaacc gtaaaaaggc cgcgttgctg gcgttttttcc   1620
ataggctccg cccccctgac gagcatcaca aaaatcgacg ctcaagtcag aggtggcgaa   1680
acccgacagg actataaaga taccaggcgt ttccccctgg aagctccctc gtgcgctctc   1740
ctgttccgac cctgccgctt accggatacc tgtccgcctt tctcccttcg ggaagcgtgg   1800
cgctttctca tagctcacgc tgtaggtatc tcagttcggt gtaggtcgtt cgctccaagc   1860
tgggctgtgt gcacgaaccc cccgttcagc ccgaccgctg cgccttatcc ggtaactatc   1920
gtcttgagtc caacccggta agacacgact tatcgccact ggcagcagcc actggtaaca   1980
ggattagcag agcgaggtat gtaggcggtg ctacagagtt cttgaagtgg tggcctaact   2040
acggctacac tagaagaaca gtatttggta tctgcgctct gctgaagcca gttaccttcg   2100
gaaaaagagt tggtagctct tgatccggca aacaaaccac cgctggtagc ggtggttttt   2160
ttgtttgcaa gcagcagatt acgcgcagaa aaaaaggatc tcaagaagat cctttgatct   2220
tttctacggg gtctgacgct cagtggaacg aaaactcacg ttaagggatt ttggtcatga   2280
gattatcaaa aaggatcttc acctagatcc ttttaaatta aaaatgaagt tttaaatcaa   2340
tctaaagtat atatgagtaa acttggtctg acagcggccg caaatgctaa accactgcag   2400
tggttaccag tgcttgatca gtgaggcacc gatctcagcg atctgcctat ttcgttcgtc   2460
catagtggcc tgactccccg tcgtgtagat cactacgatt cgtgagggct taccatcagg   2520
ccccagcgca gcaatgatgc cgcgagagcc gcgttcaccg gccccgatt tgtcagcaat   2580
gaaccagcca gcagggaggg ccgagcgaag aagtggtcct gctactttgt ccgcctccat   2640
ccagtctatg agctgctgtc gtgatgctag agtaagaagt tcgccagtga gtagtttccg   2700
aagagttgtg gccattgcta ctggcatcgt ggtatcacgc tcgtcgttcg gtatggcttc   2760
gttcaactct ggttcccagc ggtcaagccg ggtcacatga tcacccatat tatgaagaaa   2820
tgcagtcagc tccttagggc ctccgatcgt tgtcagaagt aagttggccg cggtgttgtc   2880
gctcatggta atggcagcac tacacaattc tcttaccgtc atgccatccg taagatgctt   2940
ttccgtgacc ggcgagtact caaccaagtc gttttgtgag tagtgtatac ggcgaccaag   3000
ctgctcttgc ccggcgtcta tacgggacaa caccgcgcca catagcagta ctttgaaagt   3060
```

| | |
|---|---|
| gctcatcatc gggaatcgtt cttcggggcg gaaagactca aggatcttgc cgctattgag | 3120 |
| atccagttcg atatagccca ctcttgcacc cagttgatct tcagcatctt ttactttcac | 3180 |
| cagcgtttcg gggtgtgcaa aaacaggcaa gcaaaatgcc gcaaagaagg gaatgagtgc | 3240 |
| gacacgaaaa tgttggatgc tcatactcgt cctttttcaa tattattgaa gcatttatca | 3300 |
| gggttactag tacgtctctc aaggataagt aagtaatatt aaggtacggg aggtattgga | 3360 |
| caggccgcaa taaatatct ttattttcat tacatctgtg tgttggtttt ttgtgtgaat | 3420 |
| cgatagtact aacatacgct ctccatcaaa acaaaacgaa acaaaacaaa ctagcaaaat | 3480 |
| aggctgtccc cagtgcaagt gcaggtgcca gaacatttct ct | 3522 |

<210> SEQ ID NO 91
<211> LENGTH: 621
<212> TYPE: DNA
<213> ORGANISM: Artificial Sequence
<220> FEATURE:
<223> OTHER INFORMATION: A synthetic construct.

<400> SEQUENCE: 91

| | |
|---|---|
| gctagcgcca ccatgaccga gtacaagccc accgtgcgcc tggccacccg cgacgacgtg | 60 |
| ccccgcgccg tgcgcaccct ggccgccgcc ttcgccgact accccgccac ccgccacacc | 120 |
| gtggaccccg accgccacat cgagcgcgtg accgagctgc aggagctgtt cctgaccccg | 180 |
| gtgggcctgg acatcggcaa ggtgtgggtg gccgacgacg gcgccgccgt ggccgtgtgg | 240 |
| accacccccg agagcgtgga ggccggcgcc gtgttcgccg agatcggccc ccgcatggcc | 300 |
| gagctgagcg gcagccgcct ggccgcccag cagcagatgg agggcctgct ggcccccac | 360 |
| cgccccaagg agcccgcctg gttcctggcc accgtgggcg tgagccccga ccaccagggc | 420 |
| aagggcctgg gcagcgccgt ggtgctgccc ggcgtggagg ccgccgagcg cgccggcgtg | 480 |
| cccgccttcc tggagaccag cgccccccgc aacctgccct tctacgagcg cctgggcttc | 540 |
| accgtgaccg ccgacgtgga ggtgcccgag ggccccccgca cctggtgcat gacccgcaag | 600 |
| cccggcgcct aatgatctag a | 621 |

<210> SEQ ID NO 92
<211> LENGTH: 621
<212> TYPE: DNA
<213> ORGANISM: Artificial Sequence
<220> FEATURE:
<223> OTHER INFORMATION: A synthetic construct.

<400> SEQUENCE: 92

| | |
|---|---|
| gctagcgcca ccatgaccga gtacaagcct accgtgcgcc tggccactcg cgatgatgtg | 60 |
| ccccgcgccg tccgcactct ggccgccgct ttcgccgact accccgctac ccggcacacc | 120 |
| gtggaccccg accggcacat cgagcgtgtg acagagttgc aggagctgtt cctgacccgc | 180 |
| gtcgggctgg acatcggcaa ggtgtgggta gccgacgacg gcgcggccgt ggccgtgtgg | 240 |
| actaccccg agagcgttga ggccggcgcc gtgttcgccg atcggccc ccgaatggcc | 300 |
| gagctgagcg gcagccgcct ggccgcccag cagcaaatgg agggcctgct tgcccccat | 360 |
| cgtcccaagg agcccgcctg gtttctggcc actgtaggag tgagccccga ccaccagggc | 420 |
| aagggcttgg gcagcgccgt cgtgttgccc ggcgtagagg ccgccgaacg cgccggtgtg | 480 |
| cccgcctttc tggagacaag cgctccgcgt aaccttccat tctacgagcg cctgggcttc | 540 |
| accgtgaccg ccgatgtcga ggtgcccgag ggaccccgga cctggtgcat gactcgcaag | 600 |
| cctggcgcct aatgatctag a | 621 |

<210> SEQ ID NO 93
<211> LENGTH: 621
<212> TYPE: DNA
<213> ORGANISM: Artificial Sequence
<220> FEATURE:
<223> OTHER INFORMATION: A synthetic construct.

<400> SEQUENCE: 93

| gctagcgcca | ccatgaccga | gtacaagcct | accgtgcgcc | tggccactcg | cgatgatgtg | 60 |
| cccccgcgccg | tccgcactct | ggccgccgct | ttcgccgact | accccgctac | ccggcacacc | 120 |
| gtggaccccg | accggcacat | cgagcgtgtg | acagagttgc | aggagctgtt | cctgaccccgc | 180 |
| gtcgggctgg | acatcggcaa | ggtgtgggta | ccgacgacg | cgcggccgt | ggccgtgtgg | 240 |
| actaccccg | agagcgttga | ggccggcgcc | gtgttcgccg | agatcggccc | ccgaatggcc | 300 |
| gagctgagcg | gcagccgcct | ggccgcccag | cagcaaatgg | agggcctgct | tgcccccat | 360 |
| cgtcccaagg | agcctgcctg | gtttctggcc | actgtaggag | tgagccccga | ccaccagggc | 420 |
| aagggcttgg | gcagcgccgt | cgtgttgccc | ggcgtagagg | ccgccgaacg | cgccggtgtg | 480 |
| cccgccttc | tcgaaacaag | cgcaccaaga | aaccttccat | tctacgagcg | cctgggcttc | 540 |
| accgtgaccg | ccgatgtcga | ggtgcccgag | ggacctagga | cctggtgtat | gacacgaaaa | 600 |
| cctggcgcct | aatgatctag | a |  |  |  | 621 |

<210> SEQ ID NO 94
<211> LENGTH: 1672
<212> TYPE: DNA
<213> ORGANISM: Artificial Sequence
<220> FEATURE:
<223> OTHER INFORMATION: A synthetic construct.

<400> SEQUENCE: 94

| aaagccacca | tggaagatgc | caaaaacatt | aagaaggggc | ctgctcccctt | ctaccctctt | 60 |
| gaagatggga | ctgctggcga | gcaacttcac | aaagctatga | agcggtatgc | tcttgtgcca | 120 |
| gggacaattg | cgttcacgga | tgctcacatt | gaagtagaca | tcacatacgc | tgagtatttt | 180 |
| gagatgtcgg | tgcggctggc | agaagctatg | aagcgctatg | gctgaatac | aaaccataga | 240 |
| attgtagtgt | gcagtgagaa | ctcgttgcag | ttctttatgc | ccgtgctggg | ggctctcttc | 300 |
| atcggggtgg | ctgtggctcc | tgctaacgac | atctacaacg | agcgagagct | gttgaactcg | 360 |
| atggggatct | ctcagcctac | agtggtgttt | gtgagtaaga | aagggcttca | aaagattctc | 420 |
| aatgtgcaaa | agaagctgcc | tattatacaa | aagattatta | ttatggactc | taagacagac | 480 |
| taccagggt | ttcagtccat | gtacacattt | gtaacctctc | atctgcctcc | tggcttcaac | 540 |
| gagtacgact | tcgtgcccga | gtctttcgac | agggacaaaa | cgattgctct | gatcatgaac | 600 |
| agctccgggt | ctaccgggct | gcctaagggt | gtagctctgc | cccatcgaac | agcttgtgtg | 660 |
| agattctctc | atgccaggga | cccgatcttt | ggaaaccaga | tcatccctga | cactgctatt | 720 |
| ctgtcggtgg | tgccctttca | tcatgggttt | ggatgttca | caacactggg | ataccctcatt | 780 |
| tgcgggttta | gagtggtgct | catgtatagg | tttgaagaag | aactattcct | acgctctttg | 840 |
| caagattata | agattcagtc | tgctctgctg | gtgccaacac | tattctcttt | ttttgctaag | 900 |
| tctacgctca | tagacaagta | tgacttgtcc | aacttgcacg | agattgcttc | tggcggagca | 960 |
| cctctgtcta | aggaggtagg | tgaggctgtg | gctaagcgct | tcatctgcc | tggtatcaga | 1020 |
| caggggtacg | gctaacaga | aacaacttct | gctattctga | ttacaccaga | gggcgatgac | 1080 |
| aaacccgggg | ctgtagggaa | agtggtgccc | tttttgaag | ccaaagtagt | tgatcttgat | 1140 |

| | |
|---|---|
| accggtaaga cactaggggt gaaccagcgt ggtgaactgt gtgtgcgggg ccctatgatt | 1200 |
| atgtcggggt acgttaacaa ccccgaagct acaaatgctc tcatagacaa ggacgggtgg | 1260 |
| cttcatagcg gcgacattgc ctactgggac gaggatgagc atttcttcat cgtggacaga | 1320 |
| ctgaagtcgt tgatcaaata caaggggtat caagtagctc ctgccgagct tgagtccatt | 1380 |
| ctgcttcaac accccaatat cttcgatgct ggggtggctg gctgcctga tgatgatgct | 1440 |
| ggagagctgc ctgctgctgt agtagtgctt gagcatggta agacaatgac agagaaggag | 1500 |
| atcgtggatt atgtggcttc acaagtgaca acagctaaga aactccgagg tggcgttgtg | 1560 |
| tttgtggatg aggtgcctaa agggctcact ggcaagctgg atgccagaaa aattcgagag | 1620 |
| attctcatta aggctaagaa gggtggaaag attgctgtgt aatagttcta ga | 1672 |

<210> SEQ ID NO 95
<211> LENGTH: 1166
<212> TYPE: DNA
<213> ORGANISM: Artificial Sequence
<220> FEATURE:
<223> OTHER INFORMATION: A synthetic construct.

<400> SEQUENCE: 95

| | |
|---|---|
| gcggccgcaa atgctaaacc actgcagtgg ttaccagtgc ttgatcagtg aggcaccgat | 60 |
| ctcagcgatc tgtctatttc gttcgtccat agtggcctga ctcccgtcg tgtagattac | 120 |
| tacgattcgt gagggcttac catcaggccc cagcgcagca atgatgccgc gagagccgcg | 180 |
| ttcaccggca ccggatttgt cagcaatgaa ccagccagca gggagggccg agcgaagaag | 240 |
| tggtcctgct actttgtccg cctccatcca gtctatgagc tgctgtcgtg atgctagagt | 300 |
| gagaagttcg ccagtgagta gtttccgaag agttgtggcc attgctactg catcgtggt | 360 |
| atcacgctcg tcgttcggta tggcttcgtt cagctccggt tcccagcggt caagccgggt | 420 |
| cacatgatca cccatgttgt gcaaaaatgc ggtcagctcc ttagggcctc cgatcgttgt | 480 |
| cagaagtaag ttggccgcgg tattatcgct catggtaatg gcagcactac acaattctct | 540 |
| taccgtcatg ccatccgtaa gatgcttttc cgtgaccggc gagtactcaa ccaagtcgtt | 600 |
| ttgtgagtag tgtatacggc gaccaagctg ctcttgcccg gcgtctatac gggacaacac | 660 |
| cgcgccacat agcagtactt tgaaagtgct catcatcggg aatcgttctt cggggcggaa | 720 |
| agactcaagg atcttgccgc tattgagatc cagttcgata tagcccactc ttgcacccag | 780 |
| ttgatcttca gcatctttta ctttcaccag cgtttcgggg tgtgcaaaaa caggcaagca | 840 |
| aaatgccgca agaagggaa tgagtgcgac acgaaaatgt tggatgctca tactcttcct | 900 |
| ttttcaatat gttttgcagca tttgtcaggg ttactagtac gtctctcttg agagaccgcg | 960 |
| atcgccacca tgtctaggta ggtagtaaac gaaagggctt aaaggcctaa gtggccctcg | 1020 |
| agtccagcct tgagttggtt gagtccaagt cacgtttgga gatctggtac cttacgcgta | 1080 |
| tgagctctac gtagctagcg gcctcggcgg ccgaattctt gcgatctaag cttggcaatc | 1140 |
| cggtactgtt ggtaaagcca ccatgg | 1166 |

<210> SEQ ID NO 96
<211> LENGTH: 1166
<212> TYPE: DNA
<213> ORGANISM: Artificial Sequence
<220> FEATURE:
<223> OTHER INFORMATION: A synthetic construct.

<400> SEQUENCE: 96

```
gcggccgcaa atgctaaacc actgcagtgg ttaccagtgc ttgatcagtg aggcaccgat      60
ctcagcgatc tgtctatttc gttcgtccat agtggcctga ctccccgtcg tgtagattac     120
tacgattcgt gagggcttac catcaggccc cagcgcagca atgatgccgc gagagccgcg     180
ttcaccggcc cccgatttgt cagcaatgaa ccagccagca gggagggccg agcgaagaag     240
tggtcctgct actttgtccg cctccatcca gtctatgagc tgctgtcgtg atgctagagt     300
aagaagttcg ccagtgagta gtttccgaag agttgtggcc attgctactg gcatcgtggt     360
atcacgctcg tcgttcggta tggcttcgtt caactccggt tcccagcggt caagccgggt     420
cacatgatca cccatgttgt gcaaaaatgc ggtcagctcc ttagggcctc cgatcgttgt     480
cagaagtaag ttggccgcgg tgttgtcgct catggtaatg gcagcactac acaattctct     540
taccgtcatg ccatccgtaa gatgcttttc cgtgaccggc gagtactcaa ccaagtcgtt     600
ttgtgagtag tgtatacggc gaccaagctg ctcttgcccg cgtctatac gggacaacac      660
cgcgccacat agcagtactt tgaaagtgct catcatcggg aatcgttctt cggggcggaa     720
agactcaagg atcttgccgc tattgagatc cagttcgata tagcccactc ttgcacccag     780
ttgatcttca gcatctttta cttctaccag cgtttcgggg tgtgcaaaaa caggcaagca    840
aaatgccgca aagaagggaa tgagtgcgac acgaaaatgt tggatgctca tactcttcct     900
ttttcaatat gtttgcagca tttgtcaggg ttactagtac gtctctcttg agagaccgcg     960
atcgccacca tgtctaggta ggtagtaaac gaaagggctt aaaggcctaa gtggccctcg    1020
agtccagcct tgagttggtt gagtccaagt cacgtttgga gatctggtac cttacgcgta    1080
tgagctctac gtagctagcg gcctcggcgg ccgaattctt gcgttcgaag cttggcaatc    1140
cggtactgtt ggtaaagcca ccatgg                                          1166
```

<210> SEQ ID NO 97
<211> LENGTH: 1166
<212> TYPE: DNA
<213> ORGANISM: Artificial Sequence
<220> FEATURE:
<223> OTHER INFORMATION: A synthetic construct.

<400> SEQUENCE: 97

```
gcggccgcaa atgctaaacc actgcagtgg ttaccagtgc ttgatcagtg aggcaccgat      60
ctcagcgatc tgcctatttc gttcgtccat agtggcctga ctccccgtcg tgtagatcac     120
tacgattcgt gagggcttac catcaggccc cagcgcagca atgatgccgc gagagccgcg     180
ttcaccggcc cccgatttgt cagcaatgaa ccagccagca gggagggccg agcgaagaag     240
tggtcctgct actttgtccg cctccatcca gtctatgagc tgctgtcgtg atgctagagt     300
aagaagttcg ccagtgagta gtttccgaag agttgtggcc attgctactg gcatcgtggt     360
atcacgctcg tcgttcggta tggcttcgtt caactctggt tcccagcggt caagccgggt     420
cacatgatca cccatgttgt gcaaaaatgc ggtcagctcc ttagggcctc cgatcgttgt     480
cagaagtaag ttggccgcgg tgttgtcgct catggtaatg gcagcactac acaattctct     540
taccgtcatg ccatccgtaa gatgcttttc cgtgaccggc gagtactcaa ccaagtcgtt     600
ttgtgagtag tgtatacggc gaccaagctg ctcttgcccg cgtctatac gggacaacac      660
cgcgccacat agcagtactt tgaaagtgct catcatcggg aatcgttctt cggggcggaa     720
agactcaagg atcttgccgc tattgagatc cagttcgata tagcccactc ttgcacccag     780
ttgatcttca gcatctttta cttctaccag cgtttcgggg tgtgcaaaaa caggcaagca    840
```

```
aaatgccgca aagaagggaa tgagtgcgac acgaaaatgt tggatgctca tactcttcct     900
ttttcaatat gtttgcagca tttgtcaggg ttactagtac gtctctcttg agagaccgcg     960
atcgccacca tgtctaggta ggtagtaaac gaaagggctt aaaggcctaa gtggccctcg    1020
agtccagcct tgagttggtt gagtccaagt cacgtttgga gatctggtac cttacgcgta    1080
tgagctctac gtagctagcg gcctcggcgg ccgaattctt gcgttcgaag cttggcaatc    1140
cggtactgtt ggtaaagcca ccatgg                                         1166
```